US011357865B2

(12) United States Patent
Rushworth et al.

(10) Patent No.: US 11,357,865 B2
(45) Date of Patent: Jun. 14, 2022

(54) COMPOSITIONS CONTAINING NUCLEIC ACID NANOPARTICLES WITH MODULAR FUNCTIONALITY

(71) Applicant: Sixfold Bioscience Ltd., London (GB)

(72) Inventors: James Luke Rushworth, London (GB); George William Foot, Dorchester (GB); Anna Perdrix Rosell, London (GB); Zuzanna Aleksandra Brzosko, London (GB)

(73) Assignee: Sixfold Bioscience Ltd., London (GB)

( * ) Notice: Subject to any disclaimer, the term of this patent is extended or adjusted under 35 U.S.C. 154(b) by 0 days.

(21) Appl. No.: 17/241,920

(22) Filed: Apr. 27, 2021

(65) Prior Publication Data
US 2021/0330810 A1 Oct. 28, 2021

Related U.S. Application Data

(60) Provisional application No. 63/015,735, filed on Apr. 27, 2020.

(51) Int. Cl.
*A61K 47/69* (2017.01)
*A61K 47/22* (2006.01)
*A61K 47/26* (2006.01)
*C12N 15/113* (2010.01)
*C12N 15/115* (2010.01)

(52) U.S. Cl.
CPC .......... *A61K 47/6929* (2017.08); *A61K 47/22* (2013.01); *A61K 47/26* (2013.01); *C12N 15/113* (2013.01); *C12N 15/115* (2013.01); *C12N 2310/14* (2013.01); *C12N 2310/16* (2013.01); *C12N 2310/3519* (2013.01)

(58) Field of Classification Search
CPC ............ C12N 2310/14; C12N 2310/15; C12N 2310/16; C12N 2310/53; C12N 2310/3519; C12N 2310/322; C12N 15/11; C12N 15/111; C12N 15/112; C12N 15/113; C12N 15/115; C12N 2320/30; C12N 2320/32; C12Q 1/68; A61P 35/00; A61K 51/12
USPC ..................... 435/6.1, 91.1, 91.31, 455, 458; 514/44 A; 536/23.1, 24.5
See application file for complete search history.

(56) References Cited

U.S. PATENT DOCUMENTS

| 4,166,452 A | 9/1979 | Generales, Jr. |
| 4,256,108 A | 3/1981 | Theeuwes |
| 4,265,874 A | 5/1981 | Bonsen et al. |
| 6,214,841 B1 | 4/2001 | Jackson et al. |
| 7,655,787 B2 | 2/2010 | Guo et al. |
| 7,842,793 B2 | 11/2010 | Rothemund |
| 8,058,069 B2 | 11/2011 | Yaworski et al. |
| 8,088,912 B2 | 1/2012 | Guo et al. |
| 8,163,291 B2 | 4/2012 | Chang et al. |
| 8,883,994 B2 | 11/2014 | Wang et al. |
| 8,916,696 B2 | 12/2014 | Rossi et al. |
| 8,932,593 B2 | 1/2015 | Chang et al. |
| 9,176,122 B2 | 11/2015 | Burnette |
| 9,228,207 B2 | 1/2016 | Liu et al. |
| 9,297,013 B2 | 3/2016 | Guo |
| 9,388,418 B2 | 7/2016 | Rossi et al. |
| 9,412,955 B2 | 8/2016 | Thompson et al. |
| 9,732,337 B2 | 8/2017 | Shapiro et al. |
| 10,300,148 B2 | 5/2019 | Lee et al. |
| 10,301,621 B2 | 5/2019 | Shapiro et al. |
| 2003/0232877 A1 | 12/2003 | Sikorski et al. |
| 2005/0260651 A1 | 11/2005 | Calias et al. |
| 2006/0147924 A1 | 7/2006 | Ramsing et al. |
| 2006/0228300 A1 | 10/2006 | Chang et al. |
| 2006/0228357 A1 | 10/2006 | Chang et al. |
| 2009/0004644 A1 | 1/2009 | Kiel et al. |
| 2009/0124571 A1 | 5/2009 | Morvan et al. |
| 2009/0191225 A1 | 7/2009 | Chang et al. |
| 2010/0003753 A1 | 1/2010 | Guo |
| 2010/0016409 A1 | 1/2010 | Mngling et al. |
| 2010/0240732 A1 | 9/2010 | Gilboa |
| 2011/0008251 A1 | 1/2011 | Chang et al. |
| 2011/0143417 A1 | 6/2011 | Chang et al. |
| 2011/0263526 A1 | 10/2011 | Satyam |
| 2012/0196346 A1 | 8/2012 | Chang et al. |
| 2012/0263648 A1 | 10/2012 | Shapiro et al. |
| 2013/0022538 A1 | 1/2013 | Rossi et al. |

(Continued)

FOREIGN PATENT DOCUMENTS

EP 1992632 A1 11/2008
WO 2002016596 A2 2/2002

(Continued)

OTHER PUBLICATIONS

Li et al (Nano Today, vol. 10 No. No. 5, pp. 631-655 (2015)) (Year: 2015).*

(Continued)

*Primary Examiner* — Jane J Zara

(74) *Attorney, Agent, or Firm* — Brown Rudnick LLP

(57) ABSTRACT

The invention provides compositions containing cargo molecules attached to elements that improve the function of the cargo molecules in the body of a subject. The compositions are useful for therapeutic and diagnostic purposes. Furthermore, the invention outlines ways in which these compositions can be produced; the core molecule can be functionalized, via bioorthogonal click chemistry, in such a way as to impart modular characteristics. This functionalization simultaneously allows for loading of biologically relevant cargo and provides stabilization to the overall structure of the molecule.

20 Claims, 53 Drawing Sheets

Specification includes a Sequence Listing.

(56) References Cited

U.S. PATENT DOCUMENTS

| | | |
|---|---|---|
| 2013/0209514 A1 | 8/2013 | Gilboa et al. |
| 2014/0179758 A1 | 6/2014 | Guo |
| 2014/0221253 A1 | 8/2014 | Johnston et al. |
| 2015/0086584 A1 | 3/2015 | Gilboa et al. |
| 2015/0166998 A1 | 6/2015 | Rossi et al. |
| 2015/0232883 A1 | 8/2015 | Dahlman et al. |
| 2015/0359907 A1 | 12/2015 | Getts et al. |
| 2016/0032292 A1 | 2/2016 | Storici et al. |
| 2016/0051693 A1 | 2/2016 | Getts et al. |
| 2016/0145348 A1 | 5/2016 | Stephan |
| 2016/0208245 A1 | 7/2016 | Ahn et al. |
| 2016/0237142 A1 | 8/2016 | Olichon et al. |
| 2017/0057415 A1 | 3/2017 | Line et al. |
| 2017/0079916 A1 | 3/2017 | Khan et al. |
| 2017/0121708 A1 | 5/2017 | Shapiro et al. |
| 2017/0175122 A1 | 6/2017 | Guo et al. |
| 2017/0209599 A1 | 7/2017 | Getts et al. |
| 2017/0306335 A1 | 10/2017 | Zhang et al. |
| 2017/0312299 A1 | 11/2017 | Getts et al. |
| 2017/0349894 A1 | 12/2017 | Dahlman et al. |
| 2018/0028686 A1 | 2/2018 | Brinker et al. |
| 2018/0185417 A1 | 7/2018 | Joly et al. |
| 2021/0046105 A1* | 2/2021 | Peviani ............. A61K 49/1824 |

FOREIGN PATENT DOCUMENTS

| | | |
|---|---|---|
| WO | 2005003293 A2 | 1/2005 |
| WO | 2005110489 A2 | 11/2005 |
| WO | 2006107617 A2 | 10/2006 |
| WO | 2006107786 A2 | 10/2006 |
| WO | 2007016507 A2 | 2/2007 |
| WO | 2008039254 A9 | 8/2008 |
| WO | 2008120016 A1 | 10/2008 |
| WO | 2009046104 A1 | 4/2009 |
| WO | 2010017544 A2 | 2/2010 |
| WO | 2010144295 A1 | 12/2010 |
| WO | 2010148085 A1 | 12/2010 |
| WO | 2012022945 A1 | 2/2012 |
| WO | 2012094586 A2 | 7/2012 |
| WO | 2012170372 A2 | 12/2012 |
| WO | 2013075132 A1 | 5/2013 |
| WO | 2013075140 A1 | 5/2013 |
| WO | 2013142255 A2 | 9/2013 |
| WO | 2014039809 A2 | 3/2014 |
| WO | 2014121050 A1 | 8/2014 |
| WO | 2014153394 A1 | 9/2014 |
| WO | 2015042101 A1 | 3/2015 |
| WO | 2015171827 A1 | 11/2015 |
| WO | 2015177520 A1 | 11/2015 |
| WO | 2015196146 A2 | 12/2015 |
| WO | 2016124765 A1 | 8/2016 |
| WO | 2016144755 A1 | 9/2016 |
| WO | 2016145003 A1 | 9/2016 |
| WO | 2016145005 A1 | 9/2016 |
| WO | 2016168784 A2 | 10/2016 |
| WO | 2016201129 A1 | 12/2016 |
| WO | 2017139758 A1 | 8/2017 |
| WO | 2017143150 A1 | 8/2017 |
| WO | 2017143156 A1 | 8/2017 |
| WO | 2017143171 A1 | 8/2017 |
| WO | 2017147557 A1 | 8/2017 |
| WO | 2017176894 A1 | 10/2017 |
| WO | 2017189978 A1 | 11/2017 |
| WO | 2017197009 A1 | 11/2017 |
| WO | 2018/118587 A1 | 6/2018 |

OTHER PUBLICATIONS

Lee et al (Oncotarget, vol. 6, No. 17, pp. 14766-14776(2015)) (Year: 2015).*

Khaled et al (Nano Lett. vol. 5, No. 9, pp. 1797-1808 (2005)) (Year: 2005).*

Gaithier et al (Eur. J. Org. Chem., 2019, pp. 5636-5645 (2019)) (Year: 2019).*

Ma, D (Nanoscale, vol. 6 pp. 6415-6425 (2014)). (Year: 2014).*

Wu, 2017, A Fusion Receptor as a Safety Switch, Detection, and Purification Biomarker for Adoptive Transferred T Cells, Mol Ther. 25(10):2270-2279.

Xu, 2018, Favorable Biodistribution, Specific Targeting and Conditional Endosomal Escape of RNA Nanoparticles in Cancer Therapy, Cancer Lett. 414:57-70.

Ye, 2018, Engineering chimeric antigen receptor-T cells for cancer treatment, MoL Cancer. 17(1):32 [16 pages].

Zhou, 2015, Cell-Specific RNA Aptamer against Human CCR5 Specifically Targets HIV-1 Susceptible Cells and Inhibits HIV-1 Infectivity, Chemistry & Biology 22(3):379-390.

Zumrut, 2016, Ligand-guided selection of aptamers against T-cell Receptorcluster of differentiation 3 (TCR-CD3) expressed on Jurkat. E6 cells, Anal Biochem. 512:1-7.

Milton, 2015, Nuclease resistant oligonucleotides with cell penetrating properties, Chem Commun (Camb). 51(19):4044-47.

Misak, 2014, Albumin-based nanocomposite spheres for advanced drug delivery systems, Biotechnol J. 9(1):163-70.

Morsut, 2016, Engineering customized cell sensing and response behaviors using synthetic notch receptors, Cell. 164:780-91.

Moss, 2019, Lipid Nanoparticles for Delivery of Therapeutic RNA Oligonucleotides, Mol. Pharmaceutics. 16(6):2265-2277.

Nair, 2014, Multivalent N-Acetylgalactosamine-Conjugated siRNA Localizes in Hepatocytes and Elicits Robust RNAi-Mediated Gene Silencing, J. Am. Chem. Soc., 136(49):6958-16961.

O'Brien, 2012, Elacytarabine has single-agent activity in patients with advanced acute myeloid leukaemia, Br. J. Haematol. 158(5):581-588.

O'Keefe, 2013, siRNAs and shRNAs: Tools for Protein Knockdown by Gene Silencing, Mater Methods. 3:197 [13 pages].

Oh, 2018, Cloaking nanoparticles with protein corona shield for targeted drug delivery, Nat Commun. 9(1):4548 [9 pages].

Oishi, 2005, Lactosylated poly(ethylene glycol)-siRNA conjugate through acid-labile beta-thiopropionate linkage to construct pH-sensitive polyion complex micelles achieving enhanced gene silencing in hepatoma cells, J Am Chem Soc. 127(6):1624-1625.

Okada, 2011, Novel complementary peptides to target molecules, Anticancer Res. 31(7):2511-6.

Olejniczak, 2007, 2'-deoxyadenosine bearing hydrophobic carborane pharmacophore, Nucleosides Nucleotides Nucleic Acids 26(10-12):1611-1613.

Painter, 2004, Design and development of oral drugs for the prophylaxis and treatment of smallpox infection, Trends Biotechnol. 22(8):423-427.

Paredes, 2011, RNA labeling, conjugation and ligation, Methods. 54(2); 251-259.

Pramod, 2015, Real-Time Drug Release Analysis of Enzyme and pH Responsive Polysaccharide Nanovesicles, J Phys Chem B. 119(33):10511-10523.

Prhavc, 2003, 2'-O-[2-[2-(N,N-dimethylamino)ethoxy]ethyl] modified oligonucleotides: symbiosis of charge interaction factors and stereoelectronic effects, Org Lett. 5(12):2017-20.

Pyka, 2014, Diels-alder cycloadditions on synthetic RNA in mammalian cells, Bioconjug. Chem. 25:1438-1443.

Rajeev, 2015, Hepatocyte-Specific Delivery of siRNAs Conjugated to Novel Non-nucleosidic Trivalent N-Acetylgalactosamine Elicits Robust Gene Silencing in Vivo, ChemBioChem. 16:903-908.

Recchia, 2006, Retroviral vector integration deregulates gene expression but has no consequence on the biology and function of transplanted T cells. Proc. Natl. Acad. Sci. U.S.A. 103(5):1457-1462.

Rose, 2002, Enhancement of nucleoside cytotoxicity through nucleotide prodrugs, J. Med. Chem. 45:4505-4512.

Rose, 2017, Rapidly inducible Cas9 and DSB-ddPCR to probe editing kinetics, Nat. Methods, 14:891-896.

Rostovtsev, 2002, A stepwise huisgen cycloaddition process: Copper(I)-catalyzed regioselective "ligation" of azides and terminal alkynes, Angew. Chemie—Int. Ed. 41:2596-2599.

Samanta, 2016, Nanoparticles and DNA—a powerful and growing functional combination in bionanotechnology, Nanoscale. 8(17):9037-9095.

(56) References Cited

OTHER PUBLICATIONS

Santos-Cancel, 2017, Collagen Membranes with Ribonuclease Inhibitors for Long-Term Stability of Electrochemical Aptamer-Based Sensors Employing RNA, Anal Chem. 89(10):5598-5604.
Schoch, 2010, Post-Synthetic Modification of DNA by Inverse-Electron-Demand Diels-Alder Reaction, J. Am. Chem. Soc. 132:8846-8847.
Senel, 2019, Applications of Lipidic and Polymeric Nanoparticles for siRNA Delivery, Intech Open. (16 pages).
Shen, 2016, Screening of efficient polymers for siRNA delivery in a library of hydrophobically modified polyethyleneimines, Journal of Materials Chemistry B. 4(39):6468-6474.
Shin, 2018, Recent Advances in RNA Therapeutics and RNA Delivery Systems Based on Nanoparticles, Adv. Therap 1(7):1800065 [27 pages].
Shu, 2011, Assembly of Multifunctional Phi29 pRNA Nanoparticles for Specific Delivery of SiRNA and other Therapeutics to Targeted Cells, Methods. 54(2):204-214.
Shu, 2013, Fabrication of pRNA nanoparticles to deliver therapeutic RNAs and bioactive compounds into tumor cells, Nat Protoc. 8(9):1635-59.
Shum, 2013, Nucleic Acid Aptamers as Potential Therapeutic and Diagnostic Agents for Lymphoma, J Cancer Ther. 4(4):872-890.
Singh, 2019, CRISPR/Cas9 guided genome and epigenome engineering and its therapeutic applications in immune mediated diseases, Semin Cell Dev Biol; 96:32-43 doi 10.1016/j.semcdb.2019.05.007. Epub Jun. 20, 2019. [12 pages].
Smith, 2016, Chimeric antigen receptor (CAR) T cell therapy for malignant cancers:Summary and perspective, J. Cellular Immnother. 2(2):59-68.
Sorek, 2013, CRISPR-Mediated Adaptive Immune Systems in Bacteria and Archaea, Ann. Rev, Biochem., 82:237-266.
Sparvath, 2017, Computer-Aided Design of RNA Origami Structures. In:Ke Y., Wang P. (eds) 3D DNA Nanostructure. Methods in Molecular Biology. vol. 1500 [30 pages].
Straathof, 2005, An inducible caspase 9 safety switch for T-cell therapy, Blood. 105(11):4247-4254.
Stuparu, 2016, Thiol-epoxy "click" chemistry: Application in preparation and postpolymerization modification of polymers, J. Polym. Sci. Part A Polym. Chem. 54(19)3057-3070.
Sun, 2016, Factors influencing the nuclear targeting ability of nuclear localization signals, J Drug Target. 24(10):927-933.
Swider, 2015, Synthesis, biological activity and structural study of new benzotriazole-based protein kinase CK2 inhibitors, RSC Adv., 5:72482-72494.
Tobias, 2004, Synthesis and biological evaluation of a cytarabine phosphoramidate prodrug, Mol. Pharm. 1(2):112-116.
Todorovic, 2019, Fluorescent Isoindole Crosslink (FlICk) Chemistry: A Rapid, User-friendly Stapling Reaction, Angew. Chemie Int. Ed. 58(40):14120-14124.
Tornøe, 2002, [1,2,3]-Triazoles by regiospecific copper(I)-catalyzed 1,3-dipolar cycloadditions of terminal alkynes to azides, J. Org. Chem. 67:3057-3064.
Van Der Oost, 2014, CRISPR-based adaptive and heritable immunity in prokaryotes, Trends in Biochemical Sciences, 34(8):401-407.
Van Loenen, 2013, Multicistronic vector encoding optimized safety switch for adoptive therapy with T-cell receptormodified T cells, Gene Ther. 20(8):861-7.
Varenikov, 2019, Organotitanium Nucleophiles in Asymmetric Cross-Coupling Reaction: Stereoconvergent Synthesis of Chiral a-CF 3 Thioethers, J. Am. Chem. Soc. 141(28):10994-10999.
Vinogradova, 2015, Organometallic palladium reagents for cysteine bioconjugation, Nature. 526(7575):687-691.
Wada, 2018, Cholesterol-GaINAc Dual Conjugation Strategy for Reducing Renal Distribution of Antisense Oligonucleotides, Nucleic Acid Ther. 28(1):50-57.
Wang, 2013. RNA-DNA hybrid origami:folding of a long RNA single strand into complex nanostructures using short DNA helper strands, Chem Commun (Camb). 49(48):5462-4.
Winz, 2018, Site-specific one-pot triple click labeling for DNA and RNA, Chem. Commun. 54:11781-11784.
Wipf, 1996, Synthesis of chemoreversible prodrugs of ara-C with variable time-release profiles. Biological evaluation of their apoptotic activity, Bioorg. Med. Chem. 4(10)1585-1596.
Wojtczak, 2008, "Chemical Ligation": A versatile method for nucleoside modification with boron clusters, Chemistry 14(34):10675-10682.
Hostetler, 2009, Alkoxyalkyl prodrugs of acyclic nucleoside phosphonates enhance oral antiviral activity and reduce toxicity: current state of the art, Antiviral Res. 82(2):A84-A98.
Hu, 2013, Polyprodrug amphiphiles: Hierarchical assemblies for shape-regulated cellular internalization trafficking, and drug delivery, J. Am. Chem. Soc., 135(46):17617-17629.
Huang, 2016, Delivery of Therapeutics Targeting the mRNABinding Protein HuR Using 3DNA Nanocarriers Suppresses Ovarian Tumor Growth, Cancer Res. 76(6):1549-59.
Humphreys, 2019, Plasma and Liver Protein Binding of N-Acetylgalactosamine-Conjugated Small Interfering RNA, Drug Metab Dispos. 47(10):1174-1182.
Icten, 2015, Dropwise additive manufacturing of pharmaceutical products for melt-based dosage forms, J Pharm Sci. 104(5):1641-9.
International Search Report and Written Opinion dated Jul. 23, 2019, for International Patent Application PCT/IB2019/000209 with International filing date Mar. 1, 2019 (21 pages).
Jain, 2018, MicroRNAs Enable mRNA Therapeutics to Selectively Program Cancer Cells to Self-Destruct, Nucleic Acid Ther. 28(5):285-296.
Jakiela, 2014, Generation of Nanoliter Droplets on Demand at Hundred-Hz Frequencies, Micromachines. 5(4):1002-1011.
Janas, 2017, Impact of Oligonucleotide Structure, Chemistry, and Delivery Method on In Vitro Cytotoxicity, Nucleic Acid Ther. 27(1):11-22.
Jasinski, 2017, Advancement of the Emerging Field of RNA Nanotechnology, ACS Nano. 11(2):1142-1164.
Juliano, 2015, Cellular uptake and intracellular trafficking of oligonucleotides, Adv Drug Deliv Rev. 87:35-45.
Kariko, 2008, Incorporation of pseudouridine into mRNA yields superior nonimmunogenic vector with increased translational capacity and biological stability, Mol Ther. 16(11):1833-40.
Kariko, 2011, Generating the optimal mRNA for therapy: HPLC purification eliminates immune activation and improves translation of nucleoside-modified, protein-encoding mRNA, Nucleic Acids Res. 39(21):e142 [10 pages].
Kettler, 2014, Cellular uptake of nanoparticles as determined by particle properties, experimental conditions, and cell type, Environ Toxicol Chem. 33(3):481-92.
Khaled, 2005, Controllable Self-Assembly of Nanoparticles for Specific Delivery of Multiple Therapeutic Molecules to Cancer Cells Using RNA Nanotechnology, Nano Lett. 5(9):1797-1808.
Khaleghi, 2012, A caspase 8-based suicide switch induces apoptosis in nanobody-directed chimeric receptor expressing T cells, International journal of hematology 95(4):434-44.
Kienast, 2013, Ang-2-VEGF-A CrossMab, a Novel Bispecific Human IgG1 Antibody Blocking VEGF-A and Ang-2 Functions Simultaneously, Mediates Potent Antitumor, Antiangiogenic, and Antimetastatic Efficacy, Clin Cancer Res. 19(24):6730-40.
Kiliszek, 2017, Stabilization of RNA hairpins using non-nucleotide linkers and circularization, Nucleic Acids Res. 45(10), 9 pages.
Kim, 2015, Self-assembled Messenger RNA Nanoparticles (mRNA-NPs) for Efficient Gene Expression, Sci Rep. 5:12737 [9 pages].
Klein, 2001, The kink-turn: a new RNA secondary structure motif, EMBO J. 20(15):4214-4221.
Knouse, 2018, Unlocking P(V): Reagents for chiral phosphorothioate synthesis, Science. 361(6408):1234-1238.
Kock, 2014,, Disulfide reshuffling triggers the release of a thiol-free anti-HIV agent to make up fast-acting, potent macromolecular prodrugs, Chem. Commun. 50:14498-14500.
Kollaschinski, 2020, Efficient DNA Click Reaction Replaces Enzymatic Ligation, Bioconjug. Chem., 31:507-512.
Krissanaprasit, 2019, Genetically Encoded, Functional Single-Strand RNA Origami: Anticoagulant, Adv Mater. 31(21):e1808262 [7 pages].

(56) References Cited

OTHER PUBLICATIONS

Kurrikoff, 2016, Recent in vivo advances in cell-penetrating peptide-assisted drug delivery, Expert Opin Drug Deliv. 13(3):373-87.
Kölmel, 2017, Oximes and Hydrazones in Bioconjugation: Mechanism and Catalysis, Chem. Rev. 117(15):10358-10376.
Lee, 2003, A potent and highly selective inhibitor of human a-1,3-fucosyltransferase via click chemistry, J. Am. Chem. Soc. 125(32):9588-9589.
Lee, 2015, RNA nanoparticle as a vector for targeted siRNA delivery into glioblastoma mouse model, Oncotarget 6(17):14766-14776.
Li, 2008, Selecting aptamers for a glycoprotein through the incorporation of the boronic acid moiety, J. Am. Chem. Soc. 130(38):12636-12638.
Li, 2015, RNA as a stable polymer to build controllable and defined nanostructures for material and biomedical applications, Nano Today. 10(5):631-655.
Li, 2016, Controllable Self-assembly of RNA Tetrahedrons with Precise Shape and Size for Cancer Targeting, Adv Mater. 28(34):7501-7507.
Lietard, 2008, New strategies for cyclization and bicyclization of oligonucleotides by click chemistry assisted by microwaves, J. Org. Chem. 73(1):191-200.
Lin, 2007, Design and synthesis of boronic-acid-labeled thymidine triphosphate for incorporation into DNA, Nucleic Acids Res. 35(4):1222-1229.
Liu, 2015, Cancer targeted therapeutics: From molecules to drug delivery vehicles, J Control Release. 219:632-643.
Liu, 2019, Biocompatible SuFEx Click Chemistry: Thionyl Tetrafluoride (SOF 4)-Derived Connective Hubs for Bioconjugation to DNA and Proteins, Angew. Chemie—Int. Ed.8029-8033.
Lonn, 2016, Enhancing Endosomal Escape for Intracellular Delivery of Macromolecular Biologic Therapeutics, Sci Rep. 6:32301 [9 pages].
Lowe, 2014, Thiol-ene "click" reactions and recent applications in polymer and materials synthesis: A first update, Polym. Chem. 5:4820-4870.
Lowe, 2014, Thiol-yne 'click'/coupling chemistry and recent applications in polymer and materials synthesis and modification, Polymer (Guildf). 55:5517-5549.
Ludek, 2006, Divergent synthesis and biological evaluation of carbocyclic a-, iso-and 3'-epi-nucleosides and their lipophilic nucleotide prodrugs, Synthesis, 8:1313-1324.
Luong, 2010, pH-Sensitive, N-ethoxybenzylimidazole (NEBI) bifunctional crosslinkers enable triggered release of therapeutics from drug delivery carriers, Org. Biomol. Chem., 8(22):5105-5109.
Ma, 2014, Enhancing endosomal escape for nanoparticle mediated siRNA delivery, Nanoscale. 6(12):6415-25.
Ma, 2018, Design and synthesis of ortho-phthalaldehyde phosphoramidite for single-step, rapid, efficient and chemoselective coupling of DNA with proteins under physiological conditions, Chem. Commun. 54:9434-9437.
Maier, 2012, Acid-labile traceless click linker for protein transduction, J Am Chem Soc. 134(24); 10169-10173.
Makarova, 2011, Evolution and classification of the CRISPR-Cas systems, Nat. Rev. Microbiol, 9:467-477.
McGuigan, 1989, Synthesis and biological evaluation of some phosphate triester derivatives of the anti-viral drug AraA, Nucleic Acids Res. 17(15):6065-6075.
McGuigan, 1992, Aryl phosphate derivatives of AZT retain activity against HIV1 in cell lines which are resistant to the action of AZT, Antiviral Res. 17(4):311-321.
Meier, 1998, Chemistry and anti-herpes simplex virus type 1 evaluation of cyclo Sal-nucleotides of acyclic nucleoside analogues, Antivir. Chem. Chemother. 9(5):389-402.
Meier, 2006, Application of the cycloSal prodrug approach for improving the biological potential of phosphorylated biomolecules, Antiviral Res. 71(2-3):282-292.
Miah, 1998, 2',3'-Anhydrouridine. A useful synthetic intermediate, J. Chem. Soc.—Perkin Trans. 19:3277-3283.
Miersch, 2012, Synthetic antibodies: concepts, potential and practical considerations, Methods. 57(4):486-98.
Afonin, 2011, Design and self-assembly of siRNA-functionalized RNA nanoparticles for use in automated nanomedicine, Nat Protoc. 6(12):2022-2034.
Afonin, 2012, Co-transcriptional Assembly of Chemically Modified RNA Nanoparticles Functionalized with siRNAs, Nano Lett. 12(10):5192-5195.
Afonin, 2014, Multifunctional RNA Nanoparticles, Nano Lett. 14(10):5662-71.
Afonin, 2016, The Use of Minimal RNA Toeholds to Trigger the Activation of Multiple Functionalities, Nano Lett. 16:1746-1753.
Agard, 2006, Comparative study of bioorthogonal reactions with azides., ACS Chem. Biol. 11644-648.
Alomari, 2015, Personalised dosing: Printing a dose of one's own medicine, Int J Pharm. 494(2):568-577.
Andrukh, 2011, Wire-in-a-nozzle as a new droplet-on-demand electrogenerator, Langmuir. 27(6):3206-10.
Arumugam, 2011, Enterotypes of the human gut microbiome, Nature. 473(7346):174-180.
Axup, 2012, Synthesis of site-specific antibody-drug conjugates using unnatural amino acids, Proc. Natl. Acad. Sci. U. S. A. 109:16101-16106.
Balzarini, 1996, Mechanism of anti-HIV action of masked alaninyl d4T-MP derivatives, Proc. Natl. Acad. Sci. 93(14):7295-7299.
Benzaria, 1996, Synthesis, in vitro antiviral evaluation, and stability studies of bis (S-acyl-2-thioethyl) ester derivatives of 9-[2-(phosphonomethoxy) ethyl] adenine (PMEA) as potential PMEA prodrugs with improved oral bioavailability, J. Med. Chem. 39(25):4958-4965.
Bhuniya, 2014, An activatable theranostic for targeted cancer therapy and imaging, Angew. Chemie—Int. Ed. 53:4469-4474.
Binzel, 2016, Specific Delivery of MiRNA for High Efficient Inhibition of Prostate Cancer by RNA Nanotechnology, Mol Ther. 24(7):1267-77.
Birkholz, 2018, Multi-functional DNA nanostructures that puncture and remodel lipid membranes into hybrid materials, Nat. Commun. 9(1)1521, 12 pages.
Blencowe, 2011, Self-immolative linkers in polymeric delivery systems, Polym. Chem. 2:773-790.
Boyer, 2006, Synthesis and characterization of a novel liver-targeted prodrug of cytosine-1-ß-D-arabinofuranoside monophosphate for the treatment of hepatocellular carcinoma, J. Med. Chem. 49(26)7711-7720.
Bryden, 2018, Impact of cathepsin B-sensitive triggers and hydrophilic linkers on: In vitro efficacy of novel site-specific antibody-drug conjugates, Org. Biomol. Chem. 16:1882-1889.
Burke, 2011, Elacytarabine-lipid vector technology overcoming drug resistance in acute myeloid leukemia, Expert Opin. Invest. Drugs 20(12):1707-1715.
Burns, 2014, Membrane-spanning DNA nanopores with cytotoxic effect, Angew. Chemie—Int. Ed. 53:12466-12470.
Cao, 2016, An easy and efficient inducible CRISPR/Cas9 platform with improved specificity for multiple gene targeting, Nucleic Acids Res. 14(19):e149 [10 pages].
Chan, 2017, Exploiting the Protein Corona from Cell Lysate on DNA Functionalized Gold Nanoparticles for Enhanced mRNA Translation, ACS Appl. Mater. Interfaces. 9:10408-10417.
Chen, 2018, A compound chimeric antigen receptor strategy for targeting multiple myeloma, Leukemia. 32:402-412.
Chou, 2007, Phosphoramidate pronucleotides: a comparison of the phosphoramidase substrate specificity of human and *Escherichia coli* histidine triad nucleotide binding proteins, Mol. Pharm. 4(2):208-217.
Chworos, 2004, Building Programmable Jigsaw Puzzles with RNA, Science. 306(5704):2068-72.
Ciceri, 2009, Infusion of suicide gene-engineered donor lymphocytes after family haploidentical haemopoietic stem-cell transplantation for leukaemia (the TK007 trial): a non-randomised phase I-II study, Lancet Oncol. 10:489-500.
Congiatu, 2007, Molecular modelling studies on the binding of some protides to the putative human phosphoramidase Hint1, Nucleosides Nucleotides Nucleic Acids 26(8-9):1121-1124.

(56) References Cited

OTHER PUBLICATIONS

Deglane, 2006, Impact of the guanidinium group on hybridization and cellular uptake of cationic oligonucleotides, Chembiochem, 7(4):684-92.
Diehl, 2016, Click and chemically triggered declick reactions through reversible amine and thiol coupling via a conjugate acceptor, Nat. Chem. 8:968-973.
Dominguez, 2016, Beyond editing: repurposing CRISPR-Cas9 for precision genome regulation and interrogation, Nat. Rev. Cell Biol. 17(1):5-15.
Douglas, 2012, A Logic-Gated Nanorobot for Targeted Transport of Molecular Payloads, Science. 335(6070):831-4.
Dowdy, 2018, GalNAc-SiRNA Conjugates: Leading the Way for Delivery of RNAi Therapeutics. Nucleic Acid Ther., 28(3):109-118.
El-Sagheer, 2012, Click nucleic acid ligation: Applications in biology and nanotechnology, Acc. Chem. Res. 45:1258-1267.
Elzoghby, 2012, Albumin-based nanoparticles as potential controlled release drug delivery systems, J Control Release. 157(2):168-82.
Endo, 2014, Preparation of chemically modified RNA origami nanostructures, Chemistry. 20(47):15330-3.
Erion, 2005, Liver-targeted drug delivery using HepDirect prodrugs, J. Pharmacol. Exp. Ther. 312(2):554-560.
Fan, 2008, Development of a drop-on-demand droplet generator for one-drop-fill technology, Sensors and Actuators A, Physical 147(2,3):649-655.
Fan, 2015, Bispecific antibodies and their applications, Journal of Hematology & Oncology. 8:130; [14 pages].
Gargett, 2014, The inducible caspase-9 suicide gene system as a "safety switch" to limit on-target, off-tumor toxicities of chimeric antigen receptor T cells, Front. Pharmacol. 5:235; [7 pages].
Garrett, 2011, Archaeal CRISPR-based immune systems: exchangeable functional modules, Trends in Microbiol, 19(11):549-556.
Gauthier, 2019, Conjugation of Small Molecules to RNA Using a Reducible Disulfide Linker Attached at the 2'-OH Position through a Carbamate Function, European J. Org. Chem., 2019(33):5636-5645.
Geary, 2011, Promoting RNA helical stacking via A-minor junctions, Nucleic Acids Res. 39(3):1066-1080.
Geary, 2014, A single-stranded architecture for cotranscriptional folding of RNA nanostructures, Science. 345(6198):799-804.
Gilleron, 2013, Image-based analysis of lipid nanoparticle-mediated siRNA delivery, intracellular trafficking and endosomal escape, Nat Biotechnol. 31(7):638-46.
Gujrati, 2016, Multifunctional pH-Sensitive Amino Lipids for siRNA Delivery, Bioconjug Chem. 27(1):19-35.
Guo, 2011, Nanoparticles Escaping RES and Endosome: Challenges for siRNA Delivery for Cancer Therapy, J. Nanomaterials. (742895) (12 pages).
Guo, 2017, Size, Shape, and Sequence-Dependent Immunogenicity of RNA Nanoparticles, Mol Ther Nucleic Acids. (9):399-408.
Halman, 2017, Functionally-interdependent shape-switching nanoparticles with controllable properties, Nucleic Acids Research. 45(4):2210-2220.
Han, 2017, Single-stranded DNA and RNA origami, Science. 358(6369):2648; [12 pages].
Hensarling, 2011, Thiol-isocyanate "click" reactions: Rapid development of functional polymeric surfaces, Polym. Chem., 2011(2): 88-90.
Hoeprich, 2003, Bacterial virus phi29 pRNA as a hammerhead ribozyme escort to destroy hepatitis B virus, Gene Ther. 10:1258-1267.

\* cited by examiner (S-acyl-2-thioethyl) ester derivative of 9-[2-(phosphonomethoxy) ethyl] adenine HepDirect octadecyloxyethyl cyclic cidofovir

SEQUENCE LISTING

```
<160> NUMBER OF SEQ ID NOS: 106

<210> SEQ ID NO 1
<211> LENGTH: 4
<212> TYPE: PRT
<213> ORGANISM: Artificial
<220> FEATURE:
<223> OTHER INFORMATION: Synthetic

<400> SEQUENCE: 1

Gly Trp Trp Gly
1
```

```
<210> SEQ ID NO 2
<211> LENGTH: 6
<212> TYPE: PRT
<213> ORGANISM: Artificial
<220> FEATURE:
<223> OTHER INFORMATION: Synthetic

<400> SEQUENCE: 2

Cys His Gly Trp Trp Gly
1               5

<210> SEQ ID NO 3
<211> LENGTH: 9
<212> TYPE: PRT
<213> ORGANISM: Artificial
<220> FEATURE:
<223> OTHER INFORMATION: Synthetic

<400> SEQUENCE: 3

Cys His Gly Trp Trp Gly Leu Leu Leu
1               5

<210> SEQ ID NO 4
<211> LENGTH: 7
<212> TYPE: PRT
<213> ORGANISM: Artificial
<220> FEATURE:
<223> OTHER INFORMATION: Synthetic

<400> SEQUENCE: 4

Gly Trp Trp Gly Leu Leu Leu
1               5

<210> SEQ ID NO 5
<211> LENGTH: 8
<212> TYPE: PRT
<213> ORGANISM: Artificial
<220> FEATURE:
<223> OTHER INFORMATION: Synthetic

<400> SEQUENCE: 5

Cys Gly Trp Trp Gly Leu Leu Leu
1               5

<210> SEQ ID NO 6
<211> LENGTH: 9
<212> TYPE: PRT
<213> ORGANISM: Artificial
<220> FEATURE:
<223> OTHER INFORMATION: Synthetic

<400> SEQUENCE: 6

His Cys Gly Trp Trp Gly Leu Leu Leu
1               5

<210> SEQ ID NO 7
<211> LENGTH: 8
<212> TYPE: PRT
<213> ORGANISM: Artificial
<220> FEATURE:
<223> OTHER INFORMATION: Synthetic

<400> SEQUENCE: 7

His Gly Trp Trp Gly Leu Leu Leu
1               5
```

<210> SEQ ID NO 8
<211> LENGTH: 5
<212> TYPE: PRT
<213> ORGANISM: Artificial
<220> FEATURE:
<223> OTHER INFORMATION: Synthetic

<400> SEQUENCE: 8

Cys Gly Trp Trp Gly
1               5

<210> SEQ ID NO 9
<211> LENGTH: 5
<212> TYPE: PRT
<213> ORGANISM: Artificial
<220> FEATURE:
<223> OTHER INFORMATION: Synthetic

<400> SEQUENCE: 9

His Gly Trp Trp Gly
1               5

<210> SEQ ID NO 10
<211> LENGTH: 9
<212> TYPE: PRT
<213> ORGANISM: Artificial
<220> FEATURE:
<223> OTHER INFORMATION: Synthetic

<400> SEQUENCE: 10

Cys Gly Phe Trp Phe Gly Leu Leu Leu
1               5

<210> SEQ ID NO 11
<211> LENGTH: 8
<212> TYPE: PRT
<213> ORGANISM: Artificial
<220> FEATURE:
<223> OTHER INFORMATION: Synthetic

<400> SEQUENCE: 11

Gly Phe Trp Phe Gly Leu Leu Leu
1               5

<210> SEQ ID NO 12
<211> LENGTH: 10
<212> TYPE: PRT
<213> ORGANISM: Artificial
<220> FEATURE:
<223> OTHER INFORMATION: Synthetic

<400> SEQUENCE: 12

His Cys Gly Phe Trp Phe Gly Leu Leu Leu
1               5                   10

<210> SEQ ID NO 13
<211> LENGTH: 9
<212> TYPE: PRT
<213> ORGANISM: Artificial
<220> FEATURE:
<223> OTHER INFORMATION: Synthetic

<400> SEQUENCE: 13

His Gly Phe Trp Phe Gly Leu Leu Leu
1               5

```
<210> SEQ ID NO 14
<211> LENGTH: 6
<212> TYPE: PRT
<213> ORGANISM: Artificial
<220> FEATURE:
<223> OTHER INFORMATION: Synthetic

<400> SEQUENCE: 14

Cys Gly Phe Trp Phe Gly
1               5

<210> SEQ ID NO 15
<211> LENGTH: 6
<212> TYPE: PRT
<213> ORGANISM: Artificial
<220> FEATURE:
<223> OTHER INFORMATION: Synthetic

<400> SEQUENCE: 15

His Gly Phe Trp Phe Gly
1               5

<210> SEQ ID NO 16
<211> LENGTH: 5
<212> TYPE: PRT
<213> ORGANISM: Artificial
<220> FEATURE:
<223> OTHER INFORMATION: Synthetic

<400> SEQUENCE: 16

Gly Phe Trp Phe Gly
1               5

<210> SEQ ID NO 17
<211> LENGTH: 7
<212> TYPE: PRT
<213> ORGANISM: Artificial
<220> FEATURE:
<223> OTHER INFORMATION: Synthetic

<400> SEQUENCE: 17

His Cys Gly Phe Trp Phe Gly
1               5

<210> SEQ ID NO 18
<211> LENGTH: 6
<212> TYPE: PRT
<213> ORGANISM: Artificial
<220> FEATURE:
<223> OTHER INFORMATION: Synthetic

<400> SEQUENCE: 18

His Cys Gly Trp Trp Gly
1               5

<210> SEQ ID NO 19
<211> LENGTH: 4
<212> TYPE: PRT
<213> ORGANISM: Artificial
<220> FEATURE:
<223> OTHER INFORMATION: Synthetic

<400> SEQUENCE: 19

Cys Leu Leu Leu
1

<210> SEQ ID NO 20
```

```
<400> SEQUENCE: 20

000

<210> SEQ ID NO 21
<211> LENGTH: 5
<212> TYPE: PRT
<213> ORGANISM: Artificial
<220> FEATURE:
<223> OTHER INFORMATION: Synthetic

<400> SEQUENCE: 21

His Cys Leu Leu Leu
1               5

<210> SEQ ID NO 22
<211> LENGTH: 9
<212> TYPE: PRT
<213> ORGANISM: Artificial
<220> FEATURE:
<223> OTHER INFORMATION: Synthetic

<400> SEQUENCE: 22

Cys Gly Phe Trp Phe Gly Leu Leu Leu
1               5

<210> SEQ ID NO 23

<400> SEQUENCE: 23

000

<210> SEQ ID NO 24
<211> LENGTH: 9
<212> TYPE: PRT
<213> ORGANISM: Artificial
<220> FEATURE:
<223> OTHER INFORMATION: Synthetic

<400> SEQUENCE: 24

His Gly Phe Trp Phe Gly Leu Leu Leu
1               5

<210> SEQ ID NO 25
<211> LENGTH: 10
<212> TYPE: PRT
<213> ORGANISM: Artificial
<220> FEATURE:
<223> OTHER INFORMATION: Synthetic

<400> SEQUENCE: 25

Cys His Gly Phe Trp Phe Gly Leu Leu Leu
1               5                   10

<210> SEQ ID NO 26
<211> LENGTH: 10
<212> TYPE: PRT
<213> ORGANISM: Artificial
<220> FEATURE:
<223> OTHER INFORMATION: Synthetic

<400> SEQUENCE: 26

His Cys Gly Phe Trp Phe Gly Leu Leu Leu
1               5                   10

<210> SEQ ID NO 27
```

```
<211> LENGTH: 8
<212> TYPE: PRT
<213> ORGANISM: Artificial
<220> FEATURE:
<223> OTHER INFORMATION: Synthetic

<400> SEQUENCE: 27

Gly Phe Trp Phe Gly Leu Leu Leu
1               5

<210> SEQ ID NO 28
<211> LENGTH: 5
<212> TYPE: PRT
<213> ORGANISM: Artificial
<220> FEATURE:
<223> OTHER INFORMATION: Synthetic

<400> SEQUENCE: 28

Gly Phe Trp Phe Gly
1               5

<210> SEQ ID NO 29
<211> LENGTH: 6
<212> TYPE: PRT
<213> ORGANISM: Artificial
<220> FEATURE:
<223> OTHER INFORMATION: Synthetic

<400> SEQUENCE: 29

Cys Gly Phe Trp Phe Gly
1               5

<210> SEQ ID NO 30
<211> LENGTH: 7
<212> TYPE: PRT
<213> ORGANISM: Artificial
<220> FEATURE:
<223> OTHER INFORMATION: Synthetic

<400> SEQUENCE: 30

Cys His Gly Phe Trp Phe Gly
1               5

<210> SEQ ID NO 31
<211> LENGTH: 7
<212> TYPE: PRT
<213> ORGANISM: Artificial
<220> FEATURE:
<223> OTHER INFORMATION: Synthetic

<400> SEQUENCE: 31

His Cys Gly Phe Trp Phe Gly
1               5

<210> SEQ ID NO 32
<211> LENGTH: 6
<212> TYPE: PRT
<213> ORGANISM: Artificial
<220> FEATURE:
<223> OTHER INFORMATION: Synthetic

<400> SEQUENCE: 32

His Gly Phe Trp Phe Gly
1               5

<210> SEQ ID NO 33
<211> LENGTH: 7
```

```
<212> TYPE: PRT
<213> ORGANISM: Artificial
<220> FEATURE:
<223> OTHER INFORMATION: Synthetic

<400> SEQUENCE: 33

Gly Trp Tyr Trp Met Asp Leu
1               5

<210> SEQ ID NO 34
<211> LENGTH: 8
<212> TYPE: PRT
<213> ORGANISM: Artificial
<220> FEATURE:
<223> OTHER INFORMATION: Synthetic

<400> SEQUENCE: 34

Cys Gly Trp Tyr Trp Met Asp Leu
1               5

<210> SEQ ID NO 35
<211> LENGTH: 8
<212> TYPE: PRT
<213> ORGANISM: Artificial
<220> FEATURE:
<223> OTHER INFORMATION: Synthetic

<400> SEQUENCE: 35

His Gly Trp Tyr Trp Met Asp Leu
1               5

<210> SEQ ID NO 36
<211> LENGTH: 9
<212> TYPE: PRT
<213> ORGANISM: Artificial
<220> FEATURE:
<223> OTHER INFORMATION: Synthetic

<400> SEQUENCE: 36

His Cys Gly Trp Tyr Trp Met Asp Leu
1               5

<210> SEQ ID NO 37
<211> LENGTH: 9
<212> TYPE: PRT
<213> ORGANISM: Artificial
<220> FEATURE:
<223> OTHER INFORMATION: Synthetic

<400> SEQUENCE: 37

Cys His Gly Trp Tyr Trp Met Asp Leu
1               5

<210> SEQ ID NO 38
<211> LENGTH: 10
<212> TYPE: PRT
<213> ORGANISM: Artificial
<220> FEATURE:
<223> OTHER INFORMATION: Synthetic

<400> SEQUENCE: 38

Cys Gly Trp Tyr Trp Met Asp Leu Leu Leu
1               5                   10

<210> SEQ ID NO 39
<211> LENGTH: 11
<212> TYPE: PRT
```

```
<213> ORGANISM: Artificial
<220> FEATURE:
<223> OTHER INFORMATION: Synthetic

<400> SEQUENCE: 39

His Cys Gly Trp Tyr Trp Met Asp Leu Leu Leu
1               5                   10

<210> SEQ ID NO 40
<211> LENGTH: 10
<212> TYPE: PRT
<213> ORGANISM: Artificial
<220> FEATURE:
<223> OTHER INFORMATION: Synthetic

<400> SEQUENCE: 40

His Gly Trp Tyr Trp Met Asp Leu Leu Leu
1               5                   10

<210> SEQ ID NO 41
<211> LENGTH: 11
<212> TYPE: PRT
<213> ORGANISM: Artificial
<220> FEATURE:
<223> OTHER INFORMATION: Synthetic

<400> SEQUENCE: 41

Cys His Gly Trp Tyr Trp Met Asp Leu Leu Leu
1               5                   10

<210> SEQ ID NO 42
<211> LENGTH: 9
<212> TYPE: PRT
<213> ORGANISM: Artificial
<220> FEATURE:
<223> OTHER INFORMATION: Synthetic

<400> SEQUENCE: 42

Gly Trp Tyr Trp Met Asp Leu Leu Leu
1               5

<210> SEQ ID NO 43
<211> LENGTH: 7
<212> TYPE: PRT
<213> ORGANISM: Artificial
<220> FEATURE:
<223> OTHER INFORMATION: Synthetic

<400> SEQUENCE: 43

Phe Phe Leu Ile Pro Lys Gly
1               5

<210> SEQ ID NO 44
<211> LENGTH: 8
<212> TYPE: PRT
<213> ORGANISM: Artificial
<220> FEATURE:
<223> OTHER INFORMATION: Synthetic

<400> SEQUENCE: 44

Cys Phe Phe Leu Ile Pro Lys Gly
1               5

<210> SEQ ID NO 45
<211> LENGTH: 9
<212> TYPE: PRT
<213> ORGANISM: Artificial
```

```
<220> FEATURE:
<223> OTHER INFORMATION: Synthetic

<400> SEQUENCE: 45

His Cys Phe Phe Leu Ile Pro Lys Gly
1               5

<210> SEQ ID NO 46
<211> LENGTH: 9
<212> TYPE: PRT
<213> ORGANISM: Artificial
<220> FEATURE:
<223> OTHER INFORMATION: Synthetic

<400> SEQUENCE: 46

Cys His Phe Phe Leu Ile Pro Lys Gly
1               5

<210> SEQ ID NO 47
<211> LENGTH: 8
<212> TYPE: PRT
<213> ORGANISM: Artificial
<220> FEATURE:
<223> OTHER INFORMATION: Synthetic

<400> SEQUENCE: 47

His Phe Phe Leu Ile Pro Lys Gly
1               5

<210> SEQ ID NO 48
<211> LENGTH: 10
<212> TYPE: PRT
<213> ORGANISM: Artificial
<220> FEATURE:
<223> OTHER INFORMATION: Synthetic

<400> SEQUENCE: 48

Phe Phe Leu Ile Pro Lys Gly Leu Leu Leu
1               5                   10

<210> SEQ ID NO 49
<211> LENGTH: 11
<212> TYPE: PRT
<213> ORGANISM: Artificial
<220> FEATURE:
<223> OTHER INFORMATION: Synthetic

<400> SEQUENCE: 49

Cys Phe Phe Leu Ile Pro Lys Gly Leu Leu Leu
1               5                   10

<210> SEQ ID NO 50
<211> LENGTH: 12
<212> TYPE: PRT
<213> ORGANISM: Artificial
<220> FEATURE:
<223> OTHER INFORMATION: Synthetic

<400> SEQUENCE: 50

His Cys Phe Phe Leu Ile Pro Lys Gly Leu Leu Leu
1               5                   10

<210> SEQ ID NO 51
<211> LENGTH: 12
<212> TYPE: PRT
<213> ORGANISM: Artificial
<220> FEATURE:
```

```
<223> OTHER INFORMATION: Synthetic

<400> SEQUENCE: 51

Cys His Phe Phe Leu Ile Pro Lys Gly Leu Leu Leu
1               5                   10

<210> SEQ ID NO 52
<211> LENGTH: 11
<212> TYPE: PRT
<213> ORGANISM: Artificial
<220> FEATURE:
<223> OTHER INFORMATION: Synthetic

<400> SEQUENCE: 52

His Phe Phe Leu Ile Pro Lys Gly Leu Leu Leu
1               5                   10

<210> SEQ ID NO 53
<211> LENGTH: 4
<212> TYPE: PRT
<213> ORGANISM: Artificial
<220> FEATURE:
<223> OTHER INFORMATION: Synthetic

<400> SEQUENCE: 53

Cys His Tyr Phe
1

<210> SEQ ID NO 54
<211> LENGTH: 5
<212> TYPE: PRT
<213> ORGANISM: Artificial
<220> FEATURE:
<223> OTHER INFORMATION: Synthetic

<400> SEQUENCE: 54

His Cys His Tyr Phe
1               5

<210> SEQ ID NO 55

<400> SEQUENCE: 55

000

<210> SEQ ID NO 56
<211> LENGTH: 5
<212> TYPE: PRT
<213> ORGANISM: Artificial
<220> FEATURE:
<223> OTHER INFORMATION: Synthetic

<400> SEQUENCE: 56

Cys His His Tyr Phe
1               5

<210> SEQ ID NO 57
<211> LENGTH: 6
<212> TYPE: PRT
<213> ORGANISM: Artificial
<220> FEATURE:
<223> OTHER INFORMATION: Synthetic

<400> SEQUENCE: 57

His Tyr Phe Leu Leu Leu
1               5
```

<210> SEQ ID NO 58
<211> LENGTH: 7
<212> TYPE: PRT
<213> ORGANISM: Artificial
<220> FEATURE:
<223> OTHER INFORMATION: Synthetic

<400> SEQUENCE: 58

Cys His Tyr Phe Leu Leu Leu
1               5

<210> SEQ ID NO 59
<211> LENGTH: 7
<212> TYPE: PRT
<213> ORGANISM: Artificial
<220> FEATURE:
<223> OTHER INFORMATION: Synthetic

<400> SEQUENCE: 59

His His Tyr Phe Leu Leu Leu
1               5

<210> SEQ ID NO 60
<211> LENGTH: 8
<212> TYPE: PRT
<213> ORGANISM: Artificial
<220> FEATURE:
<223> OTHER INFORMATION: Synthetic

<400> SEQUENCE: 60

His Cys His Tyr Phe Leu Leu Leu
1               5

<210> SEQ ID NO 61
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 2' fluorine
<220> FEATURE:
<221> NAME/KEY: misc_feature
<222> LOCATION: (5)..(6)
<223> OTHER INFORMATION: 2' fluorine
<220> FEATURE:
<221> NAME/KEY: misc_feature
<222> LOCATION: (8)..(8)
<223> OTHER INFORMATION: 2' fluorine
<220> FEATURE:
<221> NAME/KEY: misc_feature
<222> LOCATION: (14)..(14)
<223> OTHER INFORMATION: 2' fluorine
<220> FEATURE:
<221> NAME/KEY: misc_feature
<222> LOCATION: (18)..(18)
<223> OTHER INFORMATION: 2' fluorine

<400> SEQUENCE: 61
gcaauuacau gagcgagcat t                                      21

<210> SEQ ID NO 62
<211> LENGTH: 21
<212> TYPE: DNA
<213> ORGANISM: Artificial
<220> FEATURE:
<223> OTHER INFORMATION: Synthetic
<220> FEATURE:

-continued

```
<221> NAME/KEY: misc_feature
<222> LOCATION: (1)..(1)
<223> OTHER INFORMATION: 5' thiol
<220> FEATURE:
<221> NAME/KEY: misc_feature
<222> LOCATION: (2)..(2)
<223> OTHER INFORMATION: 2' fluorine
<220> FEATURE:
<221> NAME/KEY: misc_feature
<222> LOCATION: (5)..(6)
<223> OTHER INFORMATION: 2' fluorine
<220> FEATURE:
<221> NAME/KEY: misc_feature
<222> LOCATION: (8)..(8)
<223> OTHER INFORMATION: 2' fluorine
<220> FEATURE:
<221> NAME/KEY: misc_feature
<222> LOCATION: (14)..(14)
<223> OTHER INFORMATION: 2' fluorine
<220> FEATURE:
<221> NAME/KEY: misc_feature
<222> LOCATION: (18)..(18)
<223> OTHER INFORMATION: 2' fluorine

<400> SEQUENCE: 62
gcaauuacau gagcgagcat t                                              21

<210> SEQ ID NO 63
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5' amino
<220> FEATURE:
<221> NAME/KEY: misc_feature
<222> LOCATION: (2)..(2)
<223> OTHER INFORMATION: 2' fluorine
<220> FEATURE:
<221> NAME/KEY: misc_feature
<222> LOCATION: (5)..(6)
<223> OTHER INFORMATION: 2' fluorine
<220> FEATURE:
<221> NAME/KEY: misc_feature
<222> LOCATION: (8)..(8)
<223> OTHER INFORMATION: 2' fluorine
<220> FEATURE:
<221> NAME/KEY: misc_feature
<222> LOCATION: (14)..(14)
<223> OTHER INFORMATION: 2' fluorine
<220> FEATURE:
<221> NAME/KEY: misc_feature
<222> LOCATION: (18)..(18)
<223> OTHER INFORMATION: 2' fluorine

<400> SEQUENCE: 63
gcaauuacau gagcgagcat t                                              21

<210> SEQ ID NO 64
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5' Cy3
<220> FEATURE:
<221> NAME/KEY: misc_feature
<222> LOCATION: (2)..(2)
<223> OTHER INFORMATION: 2' fluorine
```

```
<220> FEATURE:
<221> NAME/KEY: misc_feature
<222> LOCATION: (5)..(6)
<223> OTHER INFORMATION: 2' fluorine
<220> FEATURE:
<221> NAME/KEY: misc_feature
<222> LOCATION: (8)..(8)
<223> OTHER INFORMATION: 2' fluorine
<220> FEATURE:
<221> NAME/KEY: misc_feature
<222> LOCATION: (14)..(14)
<223> OTHER INFORMATION: 2' fluorine
<220> FEATURE:
<221> NAME/KEY: misc_feature
<222> LOCATION: (18)..(18)
<223> OTHER INFORMATION: 2' fluorine

<400> SEQUENCE: 64
gcaauuacau gagcgagcat t                                               21

<210> SEQ ID NO 65
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5' Cy7
<220> FEATURE:
<221> NAME/KEY: misc_feature
<222> LOCATION: (2)..(2)
<223> OTHER INFORMATION: 2' fluorine
<220> FEATURE:
<221> NAME/KEY: misc_feature
<222> LOCATION: (5)..(6)
<223> OTHER INFORMATION: 2' fluorine
<220> FEATURE:
<221> NAME/KEY: misc_feature
<222> LOCATION: (8)..(8)
<223> OTHER INFORMATION: 2' fluorine
<220> FEATURE:
<221> NAME/KEY: misc_feature
<222> LOCATION: (14)..(14)
<223> OTHER INFORMATION: 2' fluorine
<220> FEATURE:
<221> NAME/KEY: misc_feature
<222> LOCATION: (18)..(18)
<223> OTHER INFORMATION: 2' fluorine

<400> SEQUENCE: 65
gcaauuacau gagcgagcat t                                               21

<210> SEQ ID NO 66
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5' PEG5-tetrazine
<220> FEATURE:
<221> NAME/KEY: misc_feature
<222> LOCATION: (2)..(2)
<223> OTHER INFORMATION: 2' fluorine
<220> FEATURE:
<221> NAME/KEY: misc_feature
<222> LOCATION: (5)..(6)
<223> OTHER INFORMATION: 2' fluorine
<220> FEATURE:
<221> NAME/KEY: misc_feature
<222> LOCATION: (8)..(8)
```

```
<223> OTHER INFORMATION: 2' fluorine
<220> FEATURE:
<221> NAME/KEY: misc_feature
<222> LOCATION: (14)..(14)
<223> OTHER INFORMATION: 2' fluorine
<220> FEATURE:
<221> NAME/KEY: misc_feature
<222> LOCATION: (18)..(18)
<223> OTHER INFORMATION: 2' fluorine

<400> SEQUENCE: 66
gcaauuacau gagcgagcat t                                              21

<210> SEQ ID NO 67
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5' PEG4-azide
<220> FEATURE:
<221> NAME/KEY: misc_feature
<222> LOCATION: (2)..(2)
<223> OTHER INFORMATION: 2' fluorine
<220> FEATURE:
<221> NAME/KEY: misc_feature
<222> LOCATION: (5)..(6)
<223> OTHER INFORMATION: 2' fluorine
<220> FEATURE:
<221> NAME/KEY: misc_feature
<222> LOCATION: (8)..(8)
<223> OTHER INFORMATION: 2' fluorine
<220> FEATURE:
<221> NAME/KEY: misc_feature
<222> LOCATION: (14)..(14)
<223> OTHER INFORMATION: 2' fluorine
<220> FEATURE:
<221> NAME/KEY: misc_feature
<222> LOCATION: (18)..(18)
<223> OTHER INFORMATION: 2' fluorine

<400> SEQUENCE: 67
gcaauuacau gagcgagcat t                                              21

<210> SEQ ID NO 68
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (2)..(2)
<223> OTHER INFORMATION: 2' fluorine
<220> FEATURE:
<221> NAME/KEY: misc_feature
<222> LOCATION: (5)..(6)
<223> OTHER INFORMATION: 2' fluorine
<220> FEATURE:
<221> NAME/KEY: misc_feature
<222> LOCATION: (8)..(8)
<223> OTHER INFORMATION: 2' fluorine
<220> FEATURE:
<221> NAME/KEY: misc_feature
<222> LOCATION: (14)..(14)
<223> OTHER INFORMATION: 2' fluorine
<220> FEATURE:
<221> NAME/KEY: misc_feature
<222> LOCATION: (18)..(18)
<223> OTHER INFORMATION: 2' fluorine
<220> FEATURE:
<221> NAME/KEY: misc_feature
```

```
<222> LOCATION: (21)..(21)
<223> OTHER INFORMATION: 3' thiol

<400> SEQUENCE: 68
gcaauuacau gagcgagcat t                                              21

<210> SEQ ID NO 69
<211> LENGTH: 21
<212> TYPE: DNA
<213> ORGANISM: Artificial
<220> FEATURE:
<223> OTHER INFORMATION: Synthetic

<400> SEQUENCE: 69
ugcucgcuca uguaauugcg g                                              21

<210> SEQ ID NO 70
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2' fluorine
<220> FEATURE:
<221> NAME/KEY: misc_feature
<222> LOCATION: (3)..(5)
<223> OTHER INFORMATION: 2' fluorine
<220> FEATURE:
<221> NAME/KEY: misc_feature
<222> LOCATION: (7)..(9)
<223> OTHER INFORMATION: 2' fluorine
<220> FEATURE:
<221> NAME/KEY: misc_feature
<222> LOCATION: (11)..(11)
<223> OTHER INFORMATION: 2' fluorine
<220> FEATURE:
<221> NAME/KEY: misc_feature
<222> LOCATION: (13)..(13)
<223> OTHER INFORMATION: 2' fluorine
<220> FEATURE:
<221> NAME/KEY: misc_feature
<222> LOCATION: (16)..(17)
<223> OTHER INFORMATION: 2' fluorine
<220> FEATURE:
<221> NAME/KEY: misc_feature
<222> LOCATION: (19)..(19)
<223> OTHER INFORMATION: 2' fluorine

<400> SEQUENCE: 70
ugcucgcuca uguaauugcg g                                              21

<210> SEQ ID NO 71
<211> LENGTH: 42
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5' amino
<220> FEATURE:
<221> NAME/KEY: misc_feature
<222> LOCATION: (2)..(2)
<223> OTHER INFORMATION: 2' fluorine
<220> FEATURE:
<221> NAME/KEY: misc_feature
<222> LOCATION: (5)..(6)
<223> OTHER INFORMATION: 2' fluorine
<220> FEATURE:
```

```
<221> NAME/KEY: misc_feature
<222> LOCATION: (8)..(8)
<223> OTHER INFORMATION: 2' fluorine
<220> FEATURE:
<221> NAME/KEY: misc_feature
<222> LOCATION: (10)..(10)
<223> OTHER INFORMATION: 2' fluorine
<220> FEATURE:
<221> NAME/KEY: misc_feature
<222> LOCATION: (14)..(14)
<223> OTHER INFORMATION: 2' fluorine
<220> FEATURE:
<221> NAME/KEY: misc_feature
<222> LOCATION: (18)..(18)
<223> OTHER INFORMATION: 2' fluorine
<220> FEATURE:
<221> NAME/KEY: misc_feature
<222> LOCATION: (25)..(25)
<223> OTHER INFORMATION: 2' fluorine
<220> FEATURE:
<221> NAME/KEY: misc_feature
<222> LOCATION: (28)..(29)
<223> OTHER INFORMATION: 2' fluorine
<220> FEATURE:
<221> NAME/KEY: misc_feature
<222> LOCATION: (31)..(31)
<223> OTHER INFORMATION: 2' fluorine
<220> FEATURE:
<221> NAME/KEY: misc_feature
<222> LOCATION: (33)..(33)
<223> OTHER INFORMATION: 2' fluorine
<220> FEATURE:
<221> NAME/KEY: misc_feature
<222> LOCATION: (37)..(37)
<223> OTHER INFORMATION: 2' fluorine
<220> FEATURE:
<221> NAME/KEY: misc_feature
<222> LOCATION: (41)..(41)
<223> OTHER INFORMATION: 2' fluorine

<400> SEQUENCE: 71
gcaauuacau gagcgagcat tttgcaauua caugagcgag ca                              42

<210> SEQ ID NO 72
<211> LENGTH: 42
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5' PEG5-tetrazine
<220> FEATURE:
<221> NAME/KEY: misc_feature
<222> LOCATION: (2)..(2)
<223> OTHER INFORMATION: 2' fluorine
<220> FEATURE:
<221> NAME/KEY: misc_feature
<222> LOCATION: (5)..(6)
<223> OTHER INFORMATION: 2' fluorine
<220> FEATURE:
<221> NAME/KEY: misc_feature
<222> LOCATION: (8)..(8)
<223> OTHER INFORMATION: 2' fluorine
<220> FEATURE:
<221> NAME/KEY: misc_feature
<222> LOCATION: (10)..(10)
<223> OTHER INFORMATION: 2' fluorine
<220> FEATURE:
<221> NAME/KEY: misc_feature
<222> LOCATION: (14)..(14)
<223> OTHER INFORMATION: 2' fluorine
<220> FEATURE:
<221> NAME/KEY: misc_feature
<222> LOCATION: (18)..(18)
<223> OTHER INFORMATION: 2' fluorine
```

```
<220> FEATURE:
<221> NAME/KEY: misc_feature
<222> LOCATION: (25)..(25)
<223> OTHER INFORMATION: 2' fluorine
<220> FEATURE:
<221> NAME/KEY: misc_feature
<222> LOCATION: (28)..(29)
<223> OTHER INFORMATION: 2' fluorine
<220> FEATURE:
<221> NAME/KEY: misc_feature
<222> LOCATION: (31)..(31)
<223> OTHER INFORMATION: 2' fluorine
<220> FEATURE:
<221> NAME/KEY: misc_feature
<222> LOCATION: (33)..(33)
<223> OTHER INFORMATION: 2' fluorine
<220> FEATURE:
<221> NAME/KEY: misc_feature
<222> LOCATION: (37)..(37)
<223> OTHER INFORMATION: 2' fluorine
<220> FEATURE:
<221> NAME/KEY: misc_feature
<222> LOCATION: (41)..(41)
<223> OTHER INFORMATION: 2' fluorine

<400> SEQUENCE: 72
gcaauuacau gagcgagcat tttgcaauua caugagcgag ca                              42

<210> SEQ ID NO 73
<211> LENGTH: 42
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5' amino
<220> FEATURE:
<221> NAME/KEY: misc_feature
<222> LOCATION: (2)..(2)
<223> OTHER INFORMATION: 2' fluorine
<220> FEATURE:
<221> NAME/KEY: misc_feature
<222> LOCATION: (5)..(6)
<223> OTHER INFORMATION: 2' fluorine
<220> FEATURE:
<221> NAME/KEY: misc_feature
<222> LOCATION: (8)..(8)
<223> OTHER INFORMATION: 2' fluorine
<220> FEATURE:
<221> NAME/KEY: misc_feature
<222> LOCATION: (10)..(10)
<223> OTHER INFORMATION: 2' fluorine
<220> FEATURE:
<221> NAME/KEY: misc_feature
<222> LOCATION: (14)..(14)
<223> OTHER INFORMATION: 2' fluorine
<220> FEATURE:
<221> NAME/KEY: misc_feature
<222> LOCATION: (18)..(18)
<223> OTHER INFORMATION: 2' fluorine
<220> FEATURE:
<221> NAME/KEY: misc_feature
<222> LOCATION: (21)..(21)
<223> OTHER INFORMATION: cross-linked to residue 22 by disulfide bond
<220> FEATURE:
<221> NAME/KEY: misc_feature
<222> LOCATION: (22)..(22)
<223> OTHER INFORMATION: cross-linked to residue 21 by disulfide bond
<220> FEATURE:
<221> NAME/KEY: misc_feature
<222> LOCATION: (25)..(25)
<223> OTHER INFORMATION: 2' fluorine
<220> FEATURE:
<221> NAME/KEY: misc_feature
<222> LOCATION: (28)..(29)
```

```
<223> OTHER INFORMATION: 2' fluorine
<220> FEATURE:
<221> NAME/KEY: misc_feature
<222> LOCATION: (31)..(31)
<223> OTHER INFORMATION: 2' fluorine
<220> FEATURE:
<221> NAME/KEY: misc_feature
<222> LOCATION: (33)..(33)
<223> OTHER INFORMATION: 2' fluorine
<220> FEATURE:
<221> NAME/KEY: misc_feature
<222> LOCATION: (37)..(37)
<223> OTHER INFORMATION: 2' fluorine
<220> FEATURE:
<221> NAME/KEY: misc_feature
<222> LOCATION: (41)..(41)
<223> OTHER INFORMATION: 2' fluorine

<400> SEQUENCE: 73
gcaauuacau gagcgagcat tttgcaauua caugagcgag ca                              42

<210> SEQ ID NO 74
<211> LENGTH: 42
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5' PEG5-tetrazine
<220> FEATURE:
<221> NAME/KEY: misc_feature
<222> LOCATION: (2)..(2)
<223> OTHER INFORMATION: 2' fluorine
<220> FEATURE:
<221> NAME/KEY: misc_feature
<222> LOCATION: (5)..(6)
<223> OTHER INFORMATION: 2' fluorine
<220> FEATURE:
<221> NAME/KEY: misc_feature
<222> LOCATION: (8)..(8)
<223> OTHER INFORMATION: 2' fluorine
<220> FEATURE:
<221> NAME/KEY: misc_feature
<222> LOCATION: (10)..(10)
<223> OTHER INFORMATION: 2' fluorine
<220> FEATURE:
<221> NAME/KEY: misc_feature
<222> LOCATION: (14)..(14)
<223> OTHER INFORMATION: 2' fluorine
<220> FEATURE:
<221> NAME/KEY: misc_feature
<222> LOCATION: (18)..(18)
<223> OTHER INFORMATION: 2' fluorine
<220> FEATURE:
<221> NAME/KEY: misc_feature
<222> LOCATION: (21)..(21)
<223> OTHER INFORMATION: cross-linked to residue 22 by disulfide bond
<220> FEATURE:
<221> NAME/KEY: misc_feature
<222> LOCATION: (22)..(22)
<223> OTHER INFORMATION: cross-linked to residue 21 by disulfide bond
<220> FEATURE:
<221> NAME/KEY: misc_feature
<222> LOCATION: (25)..(25)
<223> OTHER INFORMATION: 2' fluorine
<220> FEATURE:
<221> NAME/KEY: misc_feature
<222> LOCATION: (28)..(29)
<223> OTHER INFORMATION: 2' fluorine
<220> FEATURE:
<221> NAME/KEY: misc_feature
<222> LOCATION: (31)..(31)
<223> OTHER INFORMATION: 2' fluorine
<220> FEATURE:
<221> NAME/KEY: misc_feature
```

<222> LOCATION: (33)..(33)
<223> OTHER INFORMATION: 2' fluorine
<220> FEATURE:
<221> NAME/KEY: misc_feature
<222> LOCATION: (37)..(37)
<223> OTHER INFORMATION: 2' fluorine
<220> FEATURE:
<221> NAME/KEY: misc_feature
<222> LOCATION: (41)..(41)
<223> OTHER INFORMATION: 2' fluorine

<400> SEQUENCE: 74
gcaauuacau gagcgagcat tttgcaauua caugagcgag ca                    42

<210> SEQ ID NO 75
<211> LENGTH: 48
<212> TYPE: DNA
<213> ORGANISM: Artificial
<220> FEATURE:
<223> OTHER INFORMATION: Synthetic
<220> FEATURE:
<221> NAME/KEY: misc_feature
<223> OTHER INFORMATION: 5' Cy5
<220> FEATURE:
<221> NAME/KEY: misc_feature
<222> LOCATION: (4)..(4)
<223> OTHER INFORMATION: 2' fluorine
<220> FEATURE:
<221> NAME/KEY: misc_feature
<222> LOCATION: (8)..(10)
<223> OTHER INFORMATION: 2' fluorine
<220> FEATURE:
<221> NAME/KEY: misc_feature
<222> LOCATION: (13)..(14)
<223> OTHER INFORMATION: 2' fluorine
<220> FEATURE:
<221> NAME/KEY: misc_feature
<222> LOCATION: (16)..(17)
<223> OTHER INFORMATION: 2' fluorine
<220> FEATURE:
<221> NAME/KEY: misc_feature
<222> LOCATION: (19)..(19)
<223> OTHER INFORMATION: 2' fluorine
<220> FEATURE:
<221> NAME/KEY: misc_feature
<222> LOCATION: (29)..(29)
<223> OTHER INFORMATION: 2' fluorine
<220> FEATURE:
<221> NAME/KEY: misc_feature
<222> LOCATION: (31)..(32)
<223> OTHER INFORMATION: 2' fluorine
<220> FEATURE:
<221> NAME/KEY: misc_feature
<222> LOCATION: (37)..(38)
<223> OTHER INFORMATION: 2' fluorine
<220> FEATURE:
<221> NAME/KEY: misc_feature
<222> LOCATION: (43)..(44)
<223> OTHER INFORMATION: 2' fluorine
<220> FEATURE:
<221> NAME/KEY: misc_feature
<222> LOCATION: (46)..(48)
<223> OTHER INFORMATION: 2' fluorine

<400> SEQUENCE: 75
ggacggauuu aaucgccgua gaaaagcaug ucaaagccgg aaccgucc              48

<210> SEQ ID NO 76
<211> LENGTH: 74
<212> TYPE: DNA
<213> ORGANISM: Artificial
<220> FEATURE:
<223> OTHER INFORMATION: Synthetic
<220> FEATURE:
<221> NAME/KEY: misc_feature

```
<222> LOCATION: (1)..(1)
<223> OTHER INFORMATION: 2' fluorine
<220> FEATURE:
<221> NAME/KEY: misc_feature
<222> LOCATION: (5)..(5)
<223> OTHER INFORMATION: 2' fluorine
<220> FEATURE:
<221> NAME/KEY: misc_feature
<222> LOCATION: (7)..(7)
<223> OTHER INFORMATION: 2' fluorine
<220> FEATURE:
<221> NAME/KEY: misc_feature
<222> LOCATION: (9)..(9)
<223> OTHER INFORMATION: 2' fluorine
<220> FEATURE:
<221> NAME/KEY: misc_feature
<222> LOCATION: (11)..(12)
<223> OTHER INFORMATION: 2' fluorine
<220> FEATURE:
<221> NAME/KEY: misc_feature
<222> LOCATION: (16)..(16)
<223> OTHER INFORMATION: 2' fluorine
<220> FEATURE:
<221> NAME/KEY: misc_feature
<222> LOCATION: (18)..(19)
<223> OTHER INFORMATION: 2' fluorine
<220> FEATURE:
<221> NAME/KEY: misc_feature
<222> LOCATION: (21)..(26)
<223> OTHER INFORMATION: 2' fluorine
<220> FEATURE:
<221> NAME/KEY: misc_feature
<222> LOCATION: (30)..(30)
<223> OTHER INFORMATION: 2' fluorine
<220> FEATURE:
<221> NAME/KEY: misc_feature
<222> LOCATION: (34)..(36)
<223> OTHER INFORMATION: 2' fluorine
<220> FEATURE:
<221> NAME/KEY: misc_feature
<222> LOCATION: (39)..(40)
<223> OTHER INFORMATION: 2' fluorine
<220> FEATURE:
<221> NAME/KEY: misc_feature
<222> LOCATION: (42)..(43)
<223> OTHER INFORMATION: 2' fluorine
<220> FEATURE:
<221> NAME/KEY: misc_feature
<222> LOCATION: (45)..(45)
<223> OTHER INFORMATION: 2' fluorine
<220> FEATURE:
<221> NAME/KEY: misc_feature
<222> LOCATION: (53)..(53)
<223> OTHER INFORMATION: 2' fluorine
<220> FEATURE:
<221> NAME/KEY: misc_feature
<222> LOCATION: (55)..(55)
<223> OTHER INFORMATION: 2' fluorine
<220> FEATURE:
<221> NAME/KEY: misc_feature
<222> LOCATION: (57)..(58)
<223> OTHER INFORMATION: 2' fluorine
<220> FEATURE:
<221> NAME/KEY: misc_feature
<222> LOCATION: (63)..(64)
<223> OTHER INFORMATION: 2' fluorine
<220> FEATURE:
<221> NAME/KEY: misc_feature
<222> LOCATION: (69)..(70)
<223> OTHER INFORMATION: 2' fluorine
<220> FEATURE:
<221> NAME/KEY: misc_feature
<222> LOCATION: (72)..(74)
<223> OTHER INFORMATION: 2' fluorine

<400> SEQUENCE: 76
cgagcguaua ucggacacug uuuuuuggac ggauuuaauc gccguagaaa agcaugucaa    60
```
agccggaacc gucc 74

```
<210> SEQ ID NO 77
<211> LENGTH: 74
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5' amino
<220> FEATURE:
<221> NAME/KEY: misc_feature
<222> LOCATION: (1)..(1)
<223> OTHER INFORMATION: 2' fluorine
<220> FEATURE:
<221> NAME/KEY: misc_feature
<222> LOCATION: (5)..(5)
<223> OTHER INFORMATION: 2' fluorine
<220> FEATURE:
<221> NAME/KEY: misc_feature
<222> LOCATION: (7)..(7)
<223> OTHER INFORMATION: 2' fluorine
<220> FEATURE:
<221> NAME/KEY: misc_feature
<222> LOCATION: (9)..(9)
<223> OTHER INFORMATION: 2' fluorine
<220> FEATURE:
<221> NAME/KEY: misc_feature
<222> LOCATION: (11)..(12)
<223> OTHER INFORMATION: 2' fluorine
<220> FEATURE:
<221> NAME/KEY: misc_feature
<222> LOCATION: (16)..(16)
<223> OTHER INFORMATION: 2' fluorine
<220> FEATURE:
<221> NAME/KEY: misc_feature
<222> LOCATION: (18)..(19)
<223> OTHER INFORMATION: 2' fluorine
<220> FEATURE:
<221> NAME/KEY: misc_feature
<222> LOCATION: (21)..(26)
<223> OTHER INFORMATION: 2' fluorine
<220> FEATURE:
<221> NAME/KEY: misc_feature
<222> LOCATION: (30)..(30)
<223> OTHER INFORMATION: 2' fluorine
<220> FEATURE:
<221> NAME/KEY: misc_feature
<222> LOCATION: (34)..(36)
<223> OTHER INFORMATION: 2' fluorine
<220> FEATURE:
<221> NAME/KEY: misc_feature
<222> LOCATION: (39)..(40)
<223> OTHER INFORMATION: 2' fluorine
<220> FEATURE:
<221> NAME/KEY: misc_feature
<222> LOCATION: (42)..(43)
<223> OTHER INFORMATION: 2' fluorine
<220> FEATURE:
<221> NAME/KEY: misc_feature
<222> LOCATION: (45)..(45)
<223> OTHER INFORMATION: 2' fluorine
<220> FEATURE:
<221> NAME/KEY: misc_feature
<222> LOCATION: (53)..(53)
<223> OTHER INFORMATION: 2' fluorine
<220> FEATURE:
<221> NAME/KEY: misc_feature
<222> LOCATION: (55)..(55)
<223> OTHER INFORMATION: 2' fluorine
<220> FEATURE:
<221> NAME/KEY: misc_feature
<222> LOCATION: (57)..(58)
<223> OTHER INFORMATION: 2' fluorine
<220> FEATURE:
<221> NAME/KEY: misc_feature
```

```
<222> LOCATION: (63)..(64)
<223> OTHER INFORMATION: 2' fluorine
<220> FEATURE:
<221> NAME/KEY: misc_feature
<222> LOCATION: (69)..(70)
<223> OTHER INFORMATION: 2' fluorine
<220> FEATURE:
<221> NAME/KEY: misc_feature
<222> LOCATION: (72)..(74)
<223> OTHER INFORMATION: 2' fluorine

<400> SEQUENCE: 77
cgagcguaua ucggacacug uuuuuuggac ggauuuaauc gccguagaaa agcaugucaa      60
agccggaacc gucc                                                       74

<210> SEQ ID NO 78
<211> LENGTH: 74
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5' PEG5-tetrazine
<220> FEATURE:
<221> NAME/KEY: misc_feature
<222> LOCATION: (1)..(1)
<223> OTHER INFORMATION: 2' fluorine
<220> FEATURE:
<221> NAME/KEY: misc_feature
<222> LOCATION: (5)..(5)
<223> OTHER INFORMATION: 2' fluorine
<220> FEATURE:
<221> NAME/KEY: misc_feature
<222> LOCATION: (7)..(7)
<223> OTHER INFORMATION: 2' fluorine
<220> FEATURE:
<221> NAME/KEY: misc_feature
<222> LOCATION: (9)..(9)
<223> OTHER INFORMATION: 2' fluorine
<220> FEATURE:
<221> NAME/KEY: misc_feature
<222> LOCATION: (11)..(12)
<223> OTHER INFORMATION: 2' fluorine
<220> FEATURE:
<221> NAME/KEY: misc_feature
<222> LOCATION: (16)..(16)
<223> OTHER INFORMATION: 2' fluorine
<220> FEATURE:
<221> NAME/KEY: misc_feature
<222> LOCATION: (18)..(19)
<223> OTHER INFORMATION: 2' fluorine
<220> FEATURE:
<221> NAME/KEY: misc_feature
<222> LOCATION: (21)..(26)
<223> OTHER INFORMATION: 2' fluorine
<220> FEATURE:
<221> NAME/KEY: misc_feature
<222> LOCATION: (30)..(30)
<223> OTHER INFORMATION: 2' fluorine
<220> FEATURE:
<221> NAME/KEY: misc_feature
<222> LOCATION: (34)..(36)
<223> OTHER INFORMATION: 2' fluorine
<220> FEATURE:
<221> NAME/KEY: misc_feature
<222> LOCATION: (39)..(40)
<223> OTHER INFORMATION: 2' fluorine
<220> FEATURE:
<221> NAME/KEY: misc_feature
<222> LOCATION: (42)..(43)
<223> OTHER INFORMATION: 2' fluorine
<220> FEATURE:
<221> NAME/KEY: misc_feature
<222> LOCATION: (45)..(45)
```

```
<223> OTHER INFORMATION: 2' fluorine
<220> FEATURE:
<221> NAME/KEY: misc_feature
<222> LOCATION: (53)..(53)
<223> OTHER INFORMATION: 2' fluorine
<220> FEATURE:
<221> NAME/KEY: misc_feature
<222> LOCATION: (55)..(55)
<223> OTHER INFORMATION: 2' fluorine
<220> FEATURE:
<221> NAME/KEY: misc_feature
<222> LOCATION: (57)..(58)
<223> OTHER INFORMATION: 2' fluorine
<220> FEATURE:
<221> NAME/KEY: misc_feature
<222> LOCATION: (63)..(64)
<223> OTHER INFORMATION: 2' fluorine
<220> FEATURE:
<221> NAME/KEY: misc_feature
<222> LOCATION: (69)..(70)
<223> OTHER INFORMATION: 2' fluorine
<220> FEATURE:
<221> NAME/KEY: misc_feature
<222> LOCATION: (72)..(74)
<223> OTHER INFORMATION: 2' fluorine

<400> SEQUENCE: 78
cgagcguaua ucggacacug uuuuuuggac ggauuuaauc gccguagaaa agcaugucaa    60
agccggaacc gucc                                                     74

<210> SEQ ID NO 79
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: 6-maleimidohexanoic acid conjugated to
      N-terminus

<400> SEQUENCE: 79

Gly Phe Trp Phe Gly
1               5

<210> SEQ ID NO 80
<211> LENGTH: 23
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: 6-maleimidohexanoic acid conjugated to
      N-terminus

<400> SEQUENCE: 80

Gly Leu Phe Gly Ala Ile Ala Gly Phe Ile Glu Asn Gly Trp Glu Gly
1               5                   10                  15

Met Ile Asp Gly Trp Tyr Gly
            20

<210> SEQ ID NO 81
<211> LENGTH: 23
<212> TYPE: PRT
<213> ORGANISM: Artificial
<220> FEATURE:
<223> OTHER INFORMATION: Synthetic
<220> FEATURE:
```

```
<221> NAME/KEY: MOD_RES
<222> LOCATION: (1)..(1)
<223> OTHER INFORMATION: 6-maleimidohexanoic acid conjugated to
      N-terminus

<400> SEQUENCE: 81

Gly Leu Phe Glu Ala Ile Glu Gly Phe Ile Glu Asn Gly Trp Glu Gly
1               5                   10                  15

Met Ile Asp Gly Trp Tyr Gly
            20

<210> SEQ ID NO 82
<211> LENGTH: 14
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: 6-maleimidohexanoic acid conjugated to
      N-terminus

<400> SEQUENCE: 82

Leu Ala Glu Ala Leu Ala Glu Ala Leu Glu Ala Leu Ala Ala
1               5                   10

<210> SEQ ID NO 83
<211> LENGTH: 30
<212> TYPE: PRT
<213> ORGANISM: Artificial
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: 6-maleimidohexanoic acid conjugated to
      N-terminus

<400> SEQUENCE: 83

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 84
<211> LENGTH: 47
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (7)..(10)
<223> OTHER INFORMATION: 2' fluorine
<220> FEATURE:
<221> NAME/KEY: misc_feature
<222> LOCATION: (12)..(13)
<223> OTHER INFORMATION: 2' fluorine
<220> FEATURE:
<221> NAME/KEY: misc_feature
<222> LOCATION: (15)..(15)
<223> OTHER INFORMATION: 2' fluorine
<220> FEATURE:
<221> NAME/KEY: misc_feature
<222> LOCATION: (20)..(20)
<223> OTHER INFORMATION: 2' fluorine
<220> FEATURE:
<221> NAME/KEY: misc_feature
<222> LOCATION: (23)..(24)
<223> OTHER INFORMATION: 2' fluorine
```

```
<220> FEATURE:
<221> NAME/KEY: misc_feature
<222> LOCATION: (28)..(29)
<223> OTHER INFORMATION: 2' fluorine
<220> FEATURE:
<221> NAME/KEY: misc_feature
<222> LOCATION: (31)..(33)
<223> OTHER INFORMATION: 2' fluorine
<220> FEATURE:
<221> NAME/KEY: misc_feature
<222> LOCATION: (36)..(37)
<223> OTHER INFORMATION: 2' fluorine
<220> FEATURE:
<221> NAME/KEY: misc_feature
<222> LOCATION: (39)..(47)
<223> OTHER INFORMATION: 2' fluorine

<400> SEQUENCE: 84
gggaaacucu gucgugggac ggucagacug uucaaccacu ccucuuc          47

<210> SEQ ID NO 85
<211> LENGTH: 47
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5' thiol
<220> FEATURE:
<221> NAME/KEY: misc_feature
<222> LOCATION: (7)..(10)
<223> OTHER INFORMATION: 2' fluorine
<220> FEATURE:
<221> NAME/KEY: misc_feature
<222> LOCATION: (12)..(13)
<223> OTHER INFORMATION: 2' fluorine
<220> FEATURE:
<221> NAME/KEY: misc_feature
<222> LOCATION: (15)..(15)
<223> OTHER INFORMATION: 2' fluorine
<220> FEATURE:
<221> NAME/KEY: misc_feature
<222> LOCATION: (20)..(20)
<223> OTHER INFORMATION: 2' fluorine
<220> FEATURE:
<221> NAME/KEY: misc_feature
<222> LOCATION: (23)..(24)
<223> OTHER INFORMATION: 2' fluorine
<220> FEATURE:
<221> NAME/KEY: misc_feature
<222> LOCATION: (28)..(29)
<223> OTHER INFORMATION: 2' fluorine
<220> FEATURE:
<221> NAME/KEY: misc_feature
<222> LOCATION: (31)..(33)
<223> OTHER INFORMATION: 2' fluorine
<220> FEATURE:
<221> NAME/KEY: misc_feature
<222> LOCATION: (36)..(37)
<223> OTHER INFORMATION: 2' fluorine
<220> FEATURE:
<221> NAME/KEY: misc_feature
<222> LOCATION: (39)..(47)
<223> OTHER INFORMATION: 2' fluorine

<400> SEQUENCE: 85
gggaaacucu gucgugggac ggucagacug uucaaccacu ccucuuc          47

<210> SEQ ID NO 86
<211> LENGTH: 47
<212> TYPE: DNA
<213> ORGANISM: Artificial
<220> FEATURE:
```

```
<223> OTHER INFORMATION: Synthetic
<220> FEATURE:
<221> NAME/KEY: misc_feature
<222> LOCATION: (1)..(1)
<223> OTHER INFORMATION: 5' norborene
<220> FEATURE:
<221> NAME/KEY: misc_feature
<222> LOCATION: (7)..(10)
<223> OTHER INFORMATION: 2' fluorine
<220> FEATURE:
<221> NAME/KEY: misc_feature
<222> LOCATION: (12)..(13)
<223> OTHER INFORMATION: 2' fluorine
<220> FEATURE:
<221> NAME/KEY: misc_feature
<222> LOCATION: (15)..(15)
<223> OTHER INFORMATION: 2' fluorine
<220> FEATURE:
<221> NAME/KEY: misc_feature
<222> LOCATION: (20)..(20)
<223> OTHER INFORMATION: 2' fluorine
<220> FEATURE:
<221> NAME/KEY: misc_feature
<222> LOCATION: (23)..(24)
<223> OTHER INFORMATION: 2' fluorine
<220> FEATURE:
<221> NAME/KEY: misc_feature
<222> LOCATION: (28)..(29)
<223> OTHER INFORMATION: 2' fluorine
<220> FEATURE:
<221> NAME/KEY: misc_feature
<222> LOCATION: (31)..(33)
<223> OTHER INFORMATION: 2' fluorine
<220> FEATURE:
<221> NAME/KEY: misc_feature
<222> LOCATION: (36)..(37)
<223> OTHER INFORMATION: 2' fluorine
<220> FEATURE:
<221> NAME/KEY: misc_feature
<222> LOCATION: (39)..(47)
<223> OTHER INFORMATION: 2' fluorine

<400> SEQUENCE: 86
gggaaacucu gucgugggac ggucagacug uucaaccacu ccucuuc        47

<210> SEQ ID NO 87
<211> LENGTH: 67
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2' fluorine
<220> FEATURE:
<221> NAME/KEY: misc_feature
<222> LOCATION: (4)..(4)
<223> OTHER INFORMATION: 2' fluorine
<220> FEATURE:
<221> NAME/KEY: misc_feature
<222> LOCATION: (6)..(8)
<223> OTHER INFORMATION: 2' fluorine
<220> FEATURE:
<221> NAME/KEY: misc_feature
<222> LOCATION: (11)..(11)
<223> OTHER INFORMATION: 2' fluorine
<220> FEATURE:
<221> NAME/KEY: misc_feature
<222> LOCATION: (13)..(13)
<223> OTHER INFORMATION: 2' fluorine
<220> FEATURE:
<221> NAME/KEY: misc_feature
<222> LOCATION: (15)..(15)
<223> OTHER INFORMATION: 2' fluorine
<220> FEATURE:
<221> NAME/KEY: misc_feature
```

```
<222> LOCATION: (17)..(19)
<223> OTHER INFORMATION: 2' fluorine
<220> FEATURE:
<221> NAME/KEY: misc_feature
<222> LOCATION: (27)..(30)
<223> OTHER INFORMATION: 2' fluorine
<220> FEATURE:
<221> NAME/KEY: misc_feature
<222> LOCATION: (32)..(33)
<223> OTHER INFORMATION: 2' fluorine
<220> FEATURE:
<221> NAME/KEY: misc_feature
<222> LOCATION: (35)..(35)
<223> OTHER INFORMATION: 2' fluorine
<220> FEATURE:
<221> NAME/KEY: misc_feature
<222> LOCATION: (40)..(40)
<223> OTHER INFORMATION: 2' fluorine
<220> FEATURE:
<221> NAME/KEY: misc_feature
<222> LOCATION: (43)..(44)
<223> OTHER INFORMATION: 2' fluorine
<220> FEATURE:
<221> NAME/KEY: misc_feature
<222> LOCATION: (48)..(49)
<223> OTHER INFORMATION: 2' fluorine
<220> FEATURE:
<221> NAME/KEY: misc_feature
<222> LOCATION: (51)..(53)
<223> OTHER INFORMATION: 2' fluorine
<220> FEATURE:
<221> NAME/KEY: misc_feature
<222> LOCATION: (56)..(57)
<223> OTHER INFORMATION: 2' fluorine
<220> FEATURE:
<221> NAME/KEY: misc_feature
<222> LOCATION: (59)..(67)
<223> OTHER INFORMATION: 2' fluorine

<400> SEQUENCE: 87
caguguccga uauacgcucg gggaaacucu gucgugggac ggucagacug uucaaccacu    60
ccucuuc                                                              67

<210> SEQ ID NO 88
<211> LENGTH: 47
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (16)..(16)
<223> OTHER INFORMATION: 2' fluorine
<220> FEATURE:
<221> NAME/KEY: misc_feature
<222> LOCATION: (20)..(20)
<223> OTHER INFORMATION: 2' fluorine
<220> FEATURE:
<221> NAME/KEY: misc_feature
<222> LOCATION: (23)..(23)
<223> OTHER INFORMATION: 2' fluorine
<220> FEATURE:
<221> NAME/KEY: misc_feature
<222> LOCATION: (25)..(26)
<223> OTHER INFORMATION: 2' fluorine
<220> FEATURE:
<221> NAME/KEY: misc_feature
<222> LOCATION: (28)..(28)
<223> OTHER INFORMATION: 2' fluorine
<220> FEATURE:
<221> NAME/KEY: misc_feature
<222> LOCATION: (30)..(33)
<223> OTHER INFORMATION: 2' fluorine
<220> FEATURE:
<221> NAME/KEY: misc_feature
<222> LOCATION: (30)..(33)
```

```
<223> OTHER INFORMATION: 2' fluorine
<220> FEATURE:
<221> NAME/KEY: misc_feature
<222> LOCATION: (36)..(38)
<223> OTHER INFORMATION: 2' fluorine
<220> FEATURE:
<221> NAME/KEY: misc_feature
<222> LOCATION: (40)..(44)
<223> OTHER INFORMATION: 2' fluorine
<220> FEATURE:
<221> NAME/KEY: misc_feature
<222> LOCATION: (47)..(47)
<223> OTHER INFORMATION: 2' fluorine

<400> SEQUENCE: 88
gggaaagaag aggaguggac gguacugugu uucaaccugu cucugac                47

<210> SEQ ID NO 89
<211> LENGTH: 47
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5' thiol
<220> FEATURE:
<221> NAME/KEY: misc_feature
<222> LOCATION: (16)..(16)
<223> OTHER INFORMATION: 2' fluorine
<220> FEATURE:
<221> NAME/KEY: misc_feature
<222> LOCATION: (20)..(20)
<223> OTHER INFORMATION: 2' fluorine
<220> FEATURE:
<221> NAME/KEY: misc_feature
<222> LOCATION: (23)..(23)
<223> OTHER INFORMATION: 2' fluorine
<220> FEATURE:
<221> NAME/KEY: misc_feature
<222> LOCATION: (25)..(26)
<223> OTHER INFORMATION: 2' fluorine
<220> FEATURE:
<221> NAME/KEY: misc_feature
<222> LOCATION: (28)..(28)
<223> OTHER INFORMATION: 2' fluorine
<220> FEATURE:
<221> NAME/KEY: misc_feature
<222> LOCATION: (30)..(33)
<223> OTHER INFORMATION: 2' fluorine
<220> FEATURE:
<221> NAME/KEY: misc_feature
<222> LOCATION: (36)..(38)
<223> OTHER INFORMATION: 2' fluorine
<220> FEATURE:
<221> NAME/KEY: misc_feature
<222> LOCATION: (40)..(44)
<223> OTHER INFORMATION: 2' fluorine
<220> FEATURE:
<221> NAME/KEY: misc_feature
<222> LOCATION: (47)..(47)
<223> OTHER INFORMATION: 2' fluorine

<400> SEQUENCE: 89
gggaaagaag aggaguggac gguacugugu uucaaccugu cucugac                47

<210> SEQ ID NO 90
<211> LENGTH: 47
<212> TYPE: DNA
<213> ORGANISM: Artificial
<220> FEATURE:
<223> OTHER INFORMATION: Synthetic
<220> FEATURE:
<221> NAME/KEY: misc_feature
```

```
<222> LOCATION: (1)..(1)
<223> OTHER INFORMATION: 5' DBCO-serinol
<220> FEATURE:
<221> NAME/KEY: misc_feature
<222> LOCATION: (16)..(16)
<223> OTHER INFORMATION: 2' fluorine
<220> FEATURE:
<221> NAME/KEY: misc_feature
<222> LOCATION: (20)..(20)
<223> OTHER INFORMATION: 2' fluorine
<220> FEATURE:
<221> NAME/KEY: misc_feature
<222> LOCATION: (23)..(23)
<223> OTHER INFORMATION: 2' fluorine
<220> FEATURE:
<221> NAME/KEY: misc_feature
<222> LOCATION: (25)..(26)
<223> OTHER INFORMATION: 2' fluorine
<220> FEATURE:
<221> NAME/KEY: misc_feature
<222> LOCATION: (28)..(28)
<223> OTHER INFORMATION: 2' fluorine
<220> FEATURE:
<221> NAME/KEY: misc_feature
<222> LOCATION: (30)..(33)
<223> OTHER INFORMATION: 2' fluorine
<220> FEATURE:
<221> NAME/KEY: misc_feature
<222> LOCATION: (36)..(38)
<223> OTHER INFORMATION: 2' fluorine
<220> FEATURE:
<221> NAME/KEY: misc_feature
<222> LOCATION: (40)..(44)
<223> OTHER INFORMATION: 2' fluorine
<220> FEATURE:
<221> NAME/KEY: misc_feature
<222> LOCATION: (47)..(47)
<223> OTHER INFORMATION: 2' fluorine

<400> SEQUENCE: 90
gggaaagaag aggaguggac gguacugugu uucaaccugu cucugac       47

<210> SEQ ID NO 91
<211> LENGTH: 67
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2' fluorine
<220> FEATURE:
<221> NAME/KEY: misc_feature
<222> LOCATION: (4)..(4)
<223> OTHER INFORMATION: 2' fluorine
<220> FEATURE:
<221> NAME/KEY: misc_feature
<222> LOCATION: (6)..(8)
<223> OTHER INFORMATION: 2' fluorine
<220> FEATURE:
<221> NAME/KEY: misc_feature
<222> LOCATION: (11)..(11)
<223> OTHER INFORMATION: 2' fluorine
<220> FEATURE:
<221> NAME/KEY: misc_feature
<222> LOCATION: (13)..(13)
<223> OTHER INFORMATION: 2' fluorine
<220> FEATURE:
<221> NAME/KEY: misc_feature
<222> LOCATION: (15)..(15)
<223> OTHER INFORMATION: 2' fluorine
<220> FEATURE:
<221> NAME/KEY: misc_feature
<222> LOCATION: (17)..(19)
<223> OTHER INFORMATION: 2' fluorine
<220> FEATURE:
```

```
<221> NAME/KEY: misc_feature
<222> LOCATION: (36)..(36)
<223> OTHER INFORMATION: 2' fluorine
<220> FEATURE:
<221> NAME/KEY: misc_feature
<222> LOCATION: (40)..(40)
<223> OTHER INFORMATION: 2' fluorine
<220> FEATURE:
<221> NAME/KEY: misc_feature
<222> LOCATION: (43)..(43)
<223> OTHER INFORMATION: 2' fluorine
<220> FEATURE:
<221> NAME/KEY: misc_feature
<222> LOCATION: (45)..(46)
<223> OTHER INFORMATION: 2' fluorine
<220> FEATURE:
<221> NAME/KEY: misc_feature
<222> LOCATION: (48)..(48)
<223> OTHER INFORMATION: 2' fluorine
<220> FEATURE:
<221> NAME/KEY: misc_feature
<222> LOCATION: (50)..(53)
<223> OTHER INFORMATION: 2' fluorine
<220> FEATURE:
<221> NAME/KEY: misc_feature
<222> LOCATION: (56)..(58)
<223> OTHER INFORMATION: 2' fluorine
<220> FEATURE:
<221> NAME/KEY: misc_feature
<222> LOCATION: (60)..(64)
<223> OTHER INFORMATION: 2' fluorine
<220> FEATURE:
<221> NAME/KEY: misc_feature
<222> LOCATION: (67)..(67)
<223> OTHER INFORMATION: 2' fluorine

<400> SEQUENCE: 91
caguguccga uauacgcucg gggaaagaag aggaguggac gguacugugu uucaaccugu      60
cucugac                                                                67

<210> SEQ ID NO 92
<211> LENGTH: 47
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (8)..(8)
<223> OTHER INFORMATION: 2' fluorine
<220> FEATURE:
<221> NAME/KEY: misc_feature
<222> LOCATION: (11)..(11)
<223> OTHER INFORMATION: 2' fluorine
<220> FEATURE:
<221> NAME/KEY: misc_feature
<222> LOCATION: (13)..(13)
<223> OTHER INFORMATION: 2' fluorine
<220> FEATURE:
<221> NAME/KEY: misc_feature
<222> LOCATION: (16)..(16)
<223> OTHER INFORMATION: 2' fluorine
<220> FEATURE:
<221> NAME/KEY: misc_feature
<222> LOCATION: (20)..(20)
<223> OTHER INFORMATION: 2' fluorine
<220> FEATURE:
<221> NAME/KEY: misc_feature
<222> LOCATION: (23)..(23)
<223> OTHER INFORMATION: 2' fluorine
<220> FEATURE:
<221> NAME/KEY: misc_feature
<222> LOCATION: (25)..(25)
<223> OTHER INFORMATION: 2' fluorine
<220> FEATURE:
<221> NAME/KEY: misc_feature
```

```
<222> LOCATION: (27)..(28)
<223> OTHER INFORMATION: 2' fluorine
<220> FEATURE:
<221> NAME/KEY: misc_feature
<222> LOCATION: (31)..(33)
<223> OTHER INFORMATION: 2' fluorine
<220> FEATURE:
<221> NAME/KEY: misc_feature
<222> LOCATION: (36)..(38)
<223> OTHER INFORMATION: 2' fluorine
<220> FEATURE:
<221> NAME/KEY: misc_feature
<222> LOCATION: (40)..(40)
<223> OTHER INFORMATION: 2' fluorine
<220> FEATURE:
<221> NAME/KEY: misc_feature
<222> LOCATION: (43)..(43)
<223> OTHER INFORMATION: 2' fluorine

<400> SEQUENCE: 92
gggaaagcag uguagcggac ggugugucag uucaacccac gacagag         47

<210> SEQ ID NO 93
<211> LENGTH: 67
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2' fluorine
<220> FEATURE:
<221> NAME/KEY: misc_feature
<222> LOCATION: (4)..(4)
<223> OTHER INFORMATION: 2' fluorine
<220> FEATURE:
<221> NAME/KEY: misc_feature
<222> LOCATION: (6)..(8)
<223> OTHER INFORMATION: 2' fluorine
<220> FEATURE:
<221> NAME/KEY: misc_feature
<222> LOCATION: (11)..(11)
<223> OTHER INFORMATION: 2' fluorine
<220> FEATURE:
<221> NAME/KEY: misc_feature
<222> LOCATION: (13)..(13)
<223> OTHER INFORMATION: 2' fluorine
<220> FEATURE:
<221> NAME/KEY: misc_feature
<222> LOCATION: (15)..(15)
<223> OTHER INFORMATION: 2' fluorine
<220> FEATURE:
<221> NAME/KEY: misc_feature
<222> LOCATION: (17)..(19)
<223> OTHER INFORMATION: 2' fluorine
<220> FEATURE:
<221> NAME/KEY: misc_feature
<222> LOCATION: (28)..(28)
<223> OTHER INFORMATION: 2' fluorine
<220> FEATURE:
<221> NAME/KEY: misc_feature
<222> LOCATION: (31)..(31)
<223> OTHER INFORMATION: 2' fluorine
<220> FEATURE:
<221> NAME/KEY: misc_feature
<222> LOCATION: (33)..(33)
<223> OTHER INFORMATION: 2' fluorine
<220> FEATURE:
<221> NAME/KEY: misc_feature
<222> LOCATION: (36)..(36)
<223> OTHER INFORMATION: 2' fluorine
<220> FEATURE:
<221> NAME/KEY: misc_feature
<222> LOCATION: (40)..(40)
<223> OTHER INFORMATION: 2' fluorine
<220> FEATURE:
```

```
<221> NAME/KEY: misc_feature
<222> LOCATION: (43)..(43)
<223> OTHER INFORMATION: 2' fluorine
<220> FEATURE:
<221> NAME/KEY: misc_feature
<222> LOCATION: (45)..(45)
<223> OTHER INFORMATION: 2' fluorine
<220> FEATURE:
<221> NAME/KEY: misc_feature
<222> LOCATION: (47)..(48)
<223> OTHER INFORMATION: 2' fluorine
<220> FEATURE:
<221> NAME/KEY: misc_feature
<222> LOCATION: (51)..(53)
<223> OTHER INFORMATION: 2' fluorine
<220> FEATURE:
<221> NAME/KEY: misc_feature
<222> LOCATION: (56)..(58)
<223> OTHER INFORMATION: 2' fluorine
<220> FEATURE:
<221> NAME/KEY: misc_feature
<222> LOCATION: (60)..(60)
<223> OTHER INFORMATION: 2' fluorine
<220> FEATURE:
<221> NAME/KEY: misc_feature
<222> LOCATION: (63)..(63)
<223> OTHER INFORMATION: 2' fluorine

<400> SEQUENCE: 93
caguguccga uauacgcucg gggaaagcag uguagcggac ggugugucag uucaacccac    60
gacagag                                                              67

<210> SEQ ID NO 94
<211> LENGTH: 67
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2' fluorine
<220> FEATURE:
<221> NAME/KEY: misc_feature
<222> LOCATION: (4)..(4)
<223> OTHER INFORMATION: 2' fluorine
<220> FEATURE:
<221> NAME/KEY: misc_feature
<222> LOCATION: (6)..(8)
<223> OTHER INFORMATION: 2' fluorine
<220> FEATURE:
<221> NAME/KEY: misc_feature
<222> LOCATION: (11)..(11)
<223> OTHER INFORMATION: 2' fluorine
<220> FEATURE:
<221> NAME/KEY: misc_feature
<222> LOCATION: (13)..(13)
<223> OTHER INFORMATION: 2' fluorine
<220> FEATURE:
<221> NAME/KEY: misc_feature
<222> LOCATION: (15)..(15)
<223> OTHER INFORMATION: 2' fluorine
<220> FEATURE:
<221> NAME/KEY: misc_feature
<222> LOCATION: (17)..(19)
<223> OTHER INFORMATION: 2' fluorine
<220> FEATURE:
<221> NAME/KEY: misc_feature
<222> LOCATION: (28)..(28)
<223> OTHER INFORMATION: 2' fluorine
<220> FEATURE:
<221> NAME/KEY: misc_feature
<222> LOCATION: (31)..(31)
<223> OTHER INFORMATION: 2' fluorine
<220> FEATURE:
<221> NAME/KEY: misc_feature
```

```
<222> LOCATION: (33)..(33)
<223> OTHER INFORMATION: 2' fluorine
<220> FEATURE:
<221> NAME/KEY: misc_feature
<222> LOCATION: (36)..(36)
<223> OTHER INFORMATION: 2' fluorine
<220> FEATURE:
<221> NAME/KEY: misc_feature
<222> LOCATION: (40)..(40)
<223> OTHER INFORMATION: 2' fluorine
<220> FEATURE:
<221> NAME/KEY: misc_feature
<222> LOCATION: (43)..(43)
<223> OTHER INFORMATION: 2' fluorine
<220> FEATURE:
<221> NAME/KEY: misc_feature
<222> LOCATION: (45)..(45)
<223> OTHER INFORMATION: 2' fluorine
<220> FEATURE:
<221> NAME/KEY: misc_feature
<222> LOCATION: (47)..(48)
<223> OTHER INFORMATION: 2' fluorine
<220> FEATURE:
<221> NAME/KEY: misc_feature
<222> LOCATION: (51)..(53)
<223> OTHER INFORMATION: 2' fluorine
<220> FEATURE:
<221> NAME/KEY: misc_feature
<222> LOCATION: (56)..(58)
<223> OTHER INFORMATION: 2' fluorine
<220> FEATURE:
<221> NAME/KEY: misc_feature
<222> LOCATION: (60)..(60)
<223> OTHER INFORMATION: 2' fluorine
<220> FEATURE:
<221> NAME/KEY: misc_feature
<222> LOCATION: (63)..(63)
<223> OTHER INFORMATION: 2' fluorine

<400> SEQUENCE: 94
caguguccga uauacgcucg gggaaagcag uguagcggac ggugugucag uucaacccac      60
gacagag                                                               67

<210> SEQ ID NO 95
<211> LENGTH: 47
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (8)..(9)
<223> OTHER INFORMATION: 2' fluorine
<220> FEATURE:
<221> NAME/KEY: misc_feature
<222> LOCATION: (15)..(15)
<223> OTHER INFORMATION: 2' fluorine
<220> FEATURE:
<221> NAME/KEY: misc_feature
<222> LOCATION: (20)..(20)
<223> OTHER INFORMATION: 2' fluorine
<220> FEATURE:
<221> NAME/KEY: misc_feature
<222> LOCATION: (23)..(25)
<223> OTHER INFORMATION: 2' fluorine
<220> FEATURE:
<221> NAME/KEY: misc_feature
<222> LOCATION: (29)..(33)
<223> OTHER INFORMATION: 2' fluorine
<220> FEATURE:
<221> NAME/KEY: misc_feature
<222> LOCATION: (36)..(37)
<223> OTHER INFORMATION: 2' fluorine
<220> FEATURE:
<221> NAME/KEY: misc_feature
<222> LOCATION: (39)..(40)
```

<223> OTHER INFORMATION: 2' fluorine
<220> FEATURE:
<221> NAME/KEY: misc_feature
<222> LOCATION: (42)..(42)
<223> OTHER INFORMATION: 2' fluorine
<220> FEATURE:
<221> NAME/KEY: misc_feature
<222> LOCATION: (44)..(45)
<223> OTHER INFORMATION: 2' fluorine
<220> FEATURE:
<221> NAME/KEY: misc_feature
<222> LOCATION: (47)..(47)
<223> OTHER INFORMATION: 2' fluorine

<400> SEQUENCE: 95
gggaaaguca gagacaggac ggucuagguc uucaaccgcu acacugc    47

<210> SEQ ID NO 96
<211> LENGTH: 47
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5' thiol
<220> FEATURE:
<221> NAME/KEY: misc_feature
<222> LOCATION: (8)..(9)
<223> OTHER INFORMATION: 2' fluorine
<220> FEATURE:
<221> NAME/KEY: misc_feature
<222> LOCATION: (15)..(15)
<223> OTHER INFORMATION: 2' fluorine
<220> FEATURE:
<221> NAME/KEY: misc_feature
<222> LOCATION: (20)..(20)
<223> OTHER INFORMATION: 2' fluorine
<220> FEATURE:
<221> NAME/KEY: misc_feature
<222> LOCATION: (23)..(25)
<223> OTHER INFORMATION: 2' fluorine
<220> FEATURE:
<221> NAME/KEY: misc_feature
<222> LOCATION: (29)..(33)
<223> OTHER INFORMATION: 2' fluorine
<220> FEATURE:
<221> NAME/KEY: misc_feature
<222> LOCATION: (36)..(37)
<223> OTHER INFORMATION: 2' fluorine
<220> FEATURE:
<221> NAME/KEY: misc_feature
<222> LOCATION: (39)..(40)
<223> OTHER INFORMATION: 2' fluorine
<220> FEATURE:
<221> NAME/KEY: misc_feature
<222> LOCATION: (42)..(42)
<223> OTHER INFORMATION: 2' fluorine
<220> FEATURE:
<221> NAME/KEY: misc_feature
<222> LOCATION: (44)..(45)
<223> OTHER INFORMATION: 2' fluorine
<220> FEATURE:
<221> NAME/KEY: misc_feature
<222> LOCATION: (47)..(47)
<223> OTHER INFORMATION: 2' fluorine

<400> SEQUENCE: 96
gggaaaguca gagacaggac ggucuagguc uucaaccgcu acacugc    47

<210> SEQ ID NO 97
<211> LENGTH: 47
<212> TYPE: DNA
<213> ORGANISM: Artificial

```
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5' amino
<220> FEATURE:
<221> NAME/KEY: misc_feature
<222> LOCATION: (8)..(9)
<223> OTHER INFORMATION: 2' fluorine
<220> FEATURE:
<221> NAME/KEY: misc_feature
<222> LOCATION: (15)..(15)
<223> OTHER INFORMATION: 2' fluorine
<220> FEATURE:
<221> NAME/KEY: misc_feature
<222> LOCATION: (20)..(20)
<223> OTHER INFORMATION: 2' fluorine
<220> FEATURE:
<221> NAME/KEY: misc_feature
<222> LOCATION: (23)..(25)
<223> OTHER INFORMATION: 2' fluorine
<220> FEATURE:
<221> NAME/KEY: misc_feature
<222> LOCATION: (29)..(33)
<223> OTHER INFORMATION: 2' fluorine
<220> FEATURE:
<221> NAME/KEY: misc_feature
<222> LOCATION: (36)..(37)
<223> OTHER INFORMATION: 2' fluorine
<220> FEATURE:
<221> NAME/KEY: misc_feature
<222> LOCATION: (39)..(40)
<223> OTHER INFORMATION: 2' fluorine
<220> FEATURE:
<221> NAME/KEY: misc_feature
<222> LOCATION: (42)..(42)
<223> OTHER INFORMATION: 2' fluorine
<220> FEATURE:
<221> NAME/KEY: misc_feature
<222> LOCATION: (44)..(45)
<223> OTHER INFORMATION: 2' fluorine
<220> FEATURE:
<221> NAME/KEY: misc_feature
<222> LOCATION: (47)..(47)
<223> OTHER INFORMATION: 2' fluorine

<400> SEQUENCE: 97
gggaaaguca gagacaggac ggucuagguc uucaaccgcu acacugc            47

<210> SEQ ID NO 98
<211> LENGTH: 47
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5' DBCO-serinol
<220> FEATURE:
<221> NAME/KEY: misc_feature
<222> LOCATION: (8)..(9)
<223> OTHER INFORMATION: 2' fluorine
<220> FEATURE:
<221> NAME/KEY: misc_feature
<222> LOCATION: (15)..(15)
<223> OTHER INFORMATION: 2' fluorine
<220> FEATURE:
<221> NAME/KEY: misc_feature
<222> LOCATION: (20)..(20)
<223> OTHER INFORMATION: 2' fluorine
<220> FEATURE:
<221> NAME/KEY: misc_feature
<222> LOCATION: (23)..(25)
<223> OTHER INFORMATION: 2' fluorine
<220> FEATURE:
```

<221> NAME/KEY: misc_feature
<222> LOCATION: (29)..(33)
<223> OTHER INFORMATION: 2' fluorine
<220> FEATURE:
<221> NAME/KEY: misc_feature
<222> LOCATION: (36)..(37)
<223> OTHER INFORMATION: 2' fluorine
<220> FEATURE:
<221> NAME/KEY: misc_feature
<222> LOCATION: (39)..(40)
<223> OTHER INFORMATION: 2' fluorine
<220> FEATURE:
<221> NAME/KEY: misc_feature
<222> LOCATION: (42)..(42)
<223> OTHER INFORMATION: 2' fluorine
<220> FEATURE:
<221> NAME/KEY: misc_feature
<222> LOCATION: (44)..(45)
<223> OTHER INFORMATION: 2' fluorine
<220> FEATURE:
<221> NAME/KEY: misc_feature
<222> LOCATION: (47)..(47)
<223> OTHER INFORMATION: 2' fluorine

<400> SEQUENCE: 98
gggaaaguca gagacaggac ggucuagguc uucaaccgcu acacugc        47

<210> SEQ ID NO 99
<211> LENGTH: 47
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5' norbornene
<220> FEATURE:
<221> NAME/KEY: misc_feature
<222> LOCATION: (8)..(9)
<223> OTHER INFORMATION: 2' fliuorine
<220> FEATURE:
<221> NAME/KEY: misc_feature
<222> LOCATION: (15)..(15)
<223> OTHER INFORMATION: 2' fliuorine
<220> FEATURE:
<221> NAME/KEY: misc_feature
<222> LOCATION: (20)..(20)
<223> OTHER INFORMATION: 2' fliuorine
<220> FEATURE:
<221> NAME/KEY: misc_feature
<222> LOCATION: (23)..(25)
<223> OTHER INFORMATION: 2' fliuorine
<220> FEATURE:
<221> NAME/KEY: misc_feature
<222> LOCATION: (29)..(33)
<223> OTHER INFORMATION: 2' fliuorine
<220> FEATURE:
<221> NAME/KEY: misc_feature
<222> LOCATION: (36)..(37)
<223> OTHER INFORMATION: 2' fliuorine
<220> FEATURE:
<221> NAME/KEY: misc_feature
<222> LOCATION: (39)..(40)
<223> OTHER INFORMATION: 2' fliuorine
<220> FEATURE:
<221> NAME/KEY: misc_feature
<222> LOCATION: (42)..(42)
<223> OTHER INFORMATION: 2' fliuorine
<220> FEATURE:
<221> NAME/KEY: misc_feature
<222> LOCATION: (44)..(45)
<223> OTHER INFORMATION: 2' fliuorine
<220> FEATURE:
<221> NAME/KEY: misc_feature
<222> LOCATION: (47)..(47)
<223> OTHER INFORMATION: 2' fliuorine

<400> SEQUENCE: 99
gggaaaguca gagacaggac ggucuagguc uucaaccgcu acacugc                    47

<210> SEQ ID NO 100
<211> LENGTH: 67
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2' fluorine
<220> FEATURE:
<221> NAME/KEY: misc_feature
<222> LOCATION: (4)..(4)
<223> OTHER INFORMATION: 2' fluorine
<220> FEATURE:
<221> NAME/KEY: misc_feature
<222> LOCATION: (6)..(8)
<223> OTHER INFORMATION: 2' fluorine
<220> FEATURE:
<221> NAME/KEY: misc_feature
<222> LOCATION: (11)..(11)
<223> OTHER INFORMATION: 2' fluorine
<220> FEATURE:
<221> NAME/KEY: misc_feature
<222> LOCATION: (13)..(13)
<223> OTHER INFORMATION: 2' fluorine
<220> FEATURE:
<221> NAME/KEY: misc_feature
<222> LOCATION: (15)..(15)
<223> OTHER INFORMATION: 2' fluorine
<220> FEATURE:
<221> NAME/KEY: misc_feature
<222> LOCATION: (17)..(19)
<223> OTHER INFORMATION: 2' fluorine
<220> FEATURE:
<221> NAME/KEY: misc_feature
<222> LOCATION: (28)..(29)
<223> OTHER INFORMATION: 2' fluorine
<220> FEATURE:
<221> NAME/KEY: misc_feature
<222> LOCATION: (35)..(35)
<223> OTHER INFORMATION: 2' fluorine
<220> FEATURE:
<221> NAME/KEY: misc_feature
<222> LOCATION: (40)..(40)
<223> OTHER INFORMATION: 2' fluorine
<220> FEATURE:
<221> NAME/KEY: misc_feature
<222> LOCATION: (43)..(45)
<223> OTHER INFORMATION: 2' fluorine
<220> FEATURE:
<221> NAME/KEY: misc_feature
<222> LOCATION: (49)..(53)
<223> OTHER INFORMATION: 2' fluorine
<220> FEATURE:
<221> NAME/KEY: misc_feature
<222> LOCATION: (56)..(57)
<223> OTHER INFORMATION: 2' fluorine
<220> FEATURE:
<221> NAME/KEY: misc_feature
<222> LOCATION: (59)..(60)
<223> OTHER INFORMATION: 2' fluorine
<220> FEATURE:
<221> NAME/KEY: misc_feature
<222> LOCATION: (62)..(62)
<223> OTHER INFORMATION: 2' fluorine
<220> FEATURE:
<221> NAME/KEY: misc_feature
<222> LOCATION: (64)..(65)
<223> OTHER INFORMATION: 2' fluorine
<220> FEATURE:
<221> NAME/KEY: misc_feature
<222> LOCATION: (67)..(67)

<223> OTHER INFORMATION: 2' fluorine

<400> SEQUENCE: 100
caguguccga uauacgcucg gggaaaguca gagacaggac ggucuagguc uucaaccgcu    60
acacugc    67

<210> SEQ ID NO 101
<211> LENGTH: 58
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (7)..(8)
<223> OTHER INFORMATION: 2' fluorine
<220> FEATURE:
<221> NAME/KEY: misc_feature
<222> LOCATION: (12)..(13)
<223> OTHER INFORMATION: 2' fluorine
<220> FEATURE:
<221> NAME/KEY: misc_feature
<222> LOCATION: (18)..(18)
<223> OTHER INFORMATION: 2' fluorine
<220> FEATURE:
<221> NAME/KEY: misc_feature
<222> LOCATION: (20)..(20)
<223> OTHER INFORMATION: 2' fluorine
<220> FEATURE:
<221> NAME/KEY: misc_feature
<222> LOCATION: (23)..(23)
<223> OTHER INFORMATION: 2' fluorine
<220> FEATURE:
<221> NAME/KEY: misc_feature
<222> LOCATION: (25)..(26)
<223> OTHER INFORMATION: 2' fluorine
<220> FEATURE:
<221> NAME/KEY: misc_feature
<222> LOCATION: (30)..(30)
<223> OTHER INFORMATION: 2' fluorine
<220> FEATURE:
<221> NAME/KEY: misc_feature
<222> LOCATION: (33)..(35)
<223> OTHER INFORMATION: 2' fluorine
<220> FEATURE:
<221> NAME/KEY: misc_feature
<222> LOCATION: (38)..(39)
<223> OTHER INFORMATION: 2' fluorine
<220> FEATURE:
<221> NAME/KEY: misc_feature
<222> LOCATION: (43)..(44)
<223> OTHER INFORMATION: 2' fluorine
<220> FEATURE:
<221> NAME/KEY: misc_feature
<222> LOCATION: (47)..(47)
<223> OTHER INFORMATION: 2' fluorine
<220> FEATURE:
<221> NAME/KEY: misc_feature
<222> LOCATION: (49)..(49)
<223> OTHER INFORMATION: 2' fluorine
<220> FEATURE:
<221> NAME/KEY: misc_feature
<222> LOCATION: (51)..(52)
<223> OTHER INFORMATION: 2' fluorine
<220> FEATURE:
<221> NAME/KEY: misc_feature
<222> LOCATION: (58)..(58)
<223> OTHER INFORMATION: 2' fluorine

<400> SEQUENCE: 101
gggaaacuag auuggaacac aguauuggac agucugauug gacugacaca uuggagac    58

<210> SEQ ID NO 102
<211> LENGTH: 58

```
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5' Cy3
<220> FEATURE:
<221> NAME/KEY: misc_feature
<222> LOCATION: (7)..(8)
<223> OTHER INFORMATION: 2' fluorine
<220> FEATURE:
<221> NAME/KEY: misc_feature
<222> LOCATION: (12)..(13)
<223> OTHER INFORMATION: 2' fluorine
<220> FEATURE:
<221> NAME/KEY: misc_feature
<222> LOCATION: (18)..(18)
<223> OTHER INFORMATION: 2' fluorine
<220> FEATURE:
<221> NAME/KEY: misc_feature
<222> LOCATION: (20)..(20)
<223> OTHER INFORMATION: 2' fluorine
<220> FEATURE:
<221> NAME/KEY: misc_feature
<222> LOCATION: (23)..(23)
<223> OTHER INFORMATION: 2' fluorine
<220> FEATURE:
<221> NAME/KEY: misc_feature
<222> LOCATION: (25)..(26)
<223> OTHER INFORMATION: 2' fluorine
<220> FEATURE:
<221> NAME/KEY: misc_feature
<222> LOCATION: (30)..(30)
<223> OTHER INFORMATION: 2' fluorine
<220> FEATURE:
<221> NAME/KEY: misc_feature
<222> LOCATION: (33)..(35)
<223> OTHER INFORMATION: 2' fluorine
<220> FEATURE:
<221> NAME/KEY: misc_feature
<222> LOCATION: (38)..(39)
<223> OTHER INFORMATION: 2' fluorine
<220> FEATURE:
<221> NAME/KEY: misc_feature
<222> LOCATION: (43)..(44)
<223> OTHER INFORMATION: 2' fluorine
<220> FEATURE:
<221> NAME/KEY: misc_feature
<222> LOCATION: (47)..(47)
<223> OTHER INFORMATION: 2' fluorine
<220> FEATURE:
<221> NAME/KEY: misc_feature
<222> LOCATION: (49)..(49)
<223> OTHER INFORMATION: 2' fluorine
<220> FEATURE:
<221> NAME/KEY: misc_feature
<222> LOCATION: (51)..(52)
<223> OTHER INFORMATION: 2' fluorine
<220> FEATURE:
<221> NAME/KEY: misc_feature
<222> LOCATION: (58)..(58)
<223> OTHER INFORMATION: 2' fluorine

<400> SEQUENCE: 102
gggaaacuag auuggaacac aguauuggac agucugauug gacugacaca uuggagac     58

<210> SEQ ID NO 103
<211> LENGTH: 58
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
```

<223> OTHER INFORMATION: 5' Cy7
<220> FEATURE:
<221> NAME/KEY: misc_feature
<222> LOCATION: (7)..(8)
<223> OTHER INFORMATION: 2' fluorine
<220> FEATURE:
<221> NAME/KEY: misc_feature
<222> LOCATION: (12)..(13)
<223> OTHER INFORMATION: 2' fluorine
<220> FEATURE:
<221> NAME/KEY: misc_feature
<222> LOCATION: (18)..(18)
<223> OTHER INFORMATION: 2' fluorine
<220> FEATURE:
<221> NAME/KEY: misc_feature
<222> LOCATION: (20)..(20)
<223> OTHER INFORMATION: 2' fluorine
<220> FEATURE:
<221> NAME/KEY: misc_feature
<222> LOCATION: (23)..(23)
<223> OTHER INFORMATION: 2' fluorine
<220> FEATURE:
<221> NAME/KEY: misc_feature
<222> LOCATION: (25)..(26)
<223> OTHER INFORMATION: 2' fluorine
<220> FEATURE:
<221> NAME/KEY: misc_feature
<222> LOCATION: (30)..(30)
<223> OTHER INFORMATION: 2' fluorine
<220> FEATURE:
<221> NAME/KEY: misc_feature
<222> LOCATION: (33)..(35)
<223> OTHER INFORMATION: 2' fluorine
<220> FEATURE:
<221> NAME/KEY: misc_feature
<222> LOCATION: (38)..(39)
<223> OTHER INFORMATION: 2' fluorine
<220> FEATURE:
<221> NAME/KEY: misc_feature
<222> LOCATION: (43)..(44)
<223> OTHER INFORMATION: 2' fluorine
<220> FEATURE:
<221> NAME/KEY: misc_feature
<222> LOCATION: (47)..(47)
<223> OTHER INFORMATION: 2' fluorine
<220> FEATURE:
<221> NAME/KEY: misc_feature
<222> LOCATION: (49)..(49)
<223> OTHER INFORMATION: 2' fluorine
<220> FEATURE:
<221> NAME/KEY: misc_feature
<222> LOCATION: (51)..(52)
<223> OTHER INFORMATION: 2' fluorine
<220> FEATURE:
<221> NAME/KEY: misc_feature
<222> LOCATION: (58)..(58)
<223> OTHER INFORMATION: 2' fluorine

<400> SEQUENCE: 103
gggaaacuag auuggaacac aguauuggac agucugauug gacugacaca uuggagac        58

<210> SEQ ID NO 104
<211> LENGTH: 57
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5' amino
<220> FEATURE:
<221> NAME/KEY: misc_feature
<222> LOCATION: (7)..(8)
<223> OTHER INFORMATION: 2' fluorine
<220> FEATURE:
<221> NAME/KEY: misc_feature

```
<222> LOCATION: (12)..(13)
<223> OTHER INFORMATION: 2' fluorine
<220> FEATURE:
<221> NAME/KEY: misc_feature
<222> LOCATION: (18)..(18)
<223> OTHER INFORMATION: 2' fluorine
<220> FEATURE:
<221> NAME/KEY: misc_feature
<222> LOCATION: (20)..(20)
<223> OTHER INFORMATION: 2' fluorine
<220> FEATURE:
<221> NAME/KEY: misc_feature
<222> LOCATION: (23)..(23)
<223> OTHER INFORMATION: 2' fluorine
<220> FEATURE:
<221> NAME/KEY: misc_feature
<222> LOCATION: (25)..(26)
<223> OTHER INFORMATION: 2' fluorine
<220> FEATURE:
<221> NAME/KEY: misc_feature
<222> LOCATION: (30)..(30)
<223> OTHER INFORMATION: 2' fluorine
<220> FEATURE:
<221> NAME/KEY: misc_feature
<222> LOCATION: (33)..(35)
<223> OTHER INFORMATION: 2' fluorine
<220> FEATURE:
<221> NAME/KEY: misc_feature
<222> LOCATION: (38)..(39)
<223> OTHER INFORMATION: 2' fluorine
<220> FEATURE:
<221> NAME/KEY: misc_feature
<222> LOCATION: (43)..(44)
<223> OTHER INFORMATION: 2' fluorine
<220> FEATURE:
<221> NAME/KEY: misc_feature
<222> LOCATION: (47)..(47)
<223> OTHER INFORMATION: 2' fluorine
<220> FEATURE:
<221> NAME/KEY: misc_feature
<222> LOCATION: (49)..(49)
<223> OTHER INFORMATION: 2' fluorine
<220> FEATURE:
<221> NAME/KEY: misc_feature
<222> LOCATION: (51)..(52)
<223> OTHER INFORMATION: 2' fluorine

<400> SEQUENCE: 104
gggaaacuag auuggaacac aguauuggac agucugauug gacugacaca uuggaga          57

<210> SEQ ID NO 105
<211> LENGTH: 58
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (4)..(4)
<223> OTHER INFORMATION: 2' O-propargyl
<220> FEATURE:
<221> NAME/KEY: misc_feature
<222> LOCATION: (7)..(8)
<223> OTHER INFORMATION: 2' fluorine
<220> FEATURE:
<221> NAME/KEY: misc_feature
<222> LOCATION: (12)..(13)
<223> OTHER INFORMATION: 2' fluorine
<220> FEATURE:
<221> NAME/KEY: misc_feature
<222> LOCATION: (18)..(18)
<223> OTHER INFORMATION: 2' fluorine
<220> FEATURE:
<221> NAME/KEY: misc_feature
<222> LOCATION: (20)..(20)
<223> OTHER INFORMATION: 2' fluorine
<220> FEATURE:
```

<221> NAME/KEY: misc_feature
<222> LOCATION: (23)..(23)
<223> OTHER INFORMATION: 2' fluorine
<220> FEATURE:
<221> NAME/KEY: misc_feature
<222> LOCATION: (25)..(26)
<223> OTHER INFORMATION: 2' fluorine
<220> FEATURE:
<221> NAME/KEY: misc_feature
<222> LOCATION: (30)..(30)
<223> OTHER INFORMATION: 2' fluorine
<220> FEATURE:
<221> NAME/KEY: misc_feature
<222> LOCATION: (33)..(35)
<223> OTHER INFORMATION: 2' fluorine
<220> FEATURE:
<221> NAME/KEY: misc_feature
<222> LOCATION: (38)..(39)
<223> OTHER INFORMATION: 2' fluorine
<220> FEATURE:
<221> NAME/KEY: misc_feature
<222> LOCATION: (43)..(44)
<223> OTHER INFORMATION: 2' fluorine
<220> FEATURE:
<221> NAME/KEY: misc_feature
<222> LOCATION: (47)..(47)
<223> OTHER INFORMATION: 2' fluorine
<220> FEATURE:
<221> NAME/KEY: misc_feature
<222> LOCATION: (49)..(49)
<223> OTHER INFORMATION: 2' fluorine
<220> FEATURE:
<221> NAME/KEY: misc_feature
<222> LOCATION: (51)..(52)
<223> OTHER INFORMATION: 2' fluorine
<220> FEATURE:
<221> NAME/KEY: misc_feature
<222> LOCATION: (58)..(58)
<223> OTHER INFORMATION: 2' fluorine

<400> SEQUENCE: 105
gggaaacuag auuggaacac aguauuggac agucugauug gacugacaca uuggagac    58

<210> SEQ ID NO 106
<211> LENGTH: 57
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (4)..(4)
<223> OTHER INFORMATION: 2' O-propargyl
<220> FEATURE:
<221> NAME/KEY: misc_feature
<222> LOCATION: (7)..(8)
<223> OTHER INFORMATION: 2' fluorine
<220> FEATURE:
<221> NAME/KEY: misc_feature
<222> LOCATION: (9)..(9)
<223> OTHER INFORMATION: 2' O-propargyl
<220> FEATURE:
<221> NAME/KEY: misc_feature
<222> LOCATION: (12)..(13)
<223> OTHER INFORMATION: 2' fluorine
<220> FEATURE:
<221> NAME/KEY: misc_feature
<222> LOCATION: (16)..(16)
<223> OTHER INFORMATION: 2' O-propargyl
<220> FEATURE:
<221> NAME/KEY: misc_feature
<222> LOCATION: (18)..(18)
<223> OTHER INFORMATION: 2' fluorine
<220> FEATURE:
<221> NAME/KEY: misc_feature
<222> LOCATION: (20)..(20)
<223> OTHER INFORMATION: 2' fluorine

```
<220> FEATURE:
<221> NAME/KEY: misc_feature
<222> LOCATION: (21)..(21)
<223> OTHER INFORMATION: 2' O-propargyl
<220> FEATURE:
<221> NAME/KEY: misc_feature
<222> LOCATION: (23)..(23)
<223> OTHER INFORMATION: 2' fluorine
<220> FEATURE:
<221> NAME/KEY: misc_feature
<222> LOCATION: (25)..(26)
<223> OTHER INFORMATION: 2' fluorine
<220> FEATURE:
<221> NAME/KEY: misc_feature
<222> LOCATION: (30)..(30)
<223> OTHER INFORMATION: 2' fluorine
<220> FEATURE:
<221> NAME/KEY: misc_feature
<222> LOCATION: (31)..(31)
<223> OTHER INFORMATION: 2' O-propargyl
<220> FEATURE:
<221> NAME/KEY: misc_feature
<222> LOCATION: (33)..(35)
<223> OTHER INFORMATION: 2' fluorine
<220> FEATURE:
<221> NAME/KEY: misc_feature
<222> LOCATION: (38)..(39)
<223> OTHER INFORMATION: 2' fluorine
<220> FEATURE:
<221> NAME/KEY: misc_feature
<222> LOCATION: (42)..(42)
<223> OTHER INFORMATION: 2' O-propargyl
<220> FEATURE:
<221> NAME/KEY: misc_feature
<222> LOCATION: (43)..(44)
<223> OTHER INFORMATION: 2' fluorine
<220> FEATURE:
<221> NAME/KEY: misc_feature
<222> LOCATION: (46)..(46)
<223> OTHER INFORMATION: 2' O-propargyl
<220> FEATURE:
<221> NAME/KEY: misc_feature
<222> LOCATION: (47)..(47)
<223> OTHER INFORMATION: 2' fluorine
<220> FEATURE:
<221> NAME/KEY: misc_feature
<222> LOCATION: (49)..(49)
<223> OTHER INFORMATION: 2' fluorine
<220> FEATURE:
<221> NAME/KEY: misc_feature
<222> LOCATION: (51)..(52)
<223> OTHER INFORMATION: 2' fluorine
<220> FEATURE:
<221> NAME/KEY: misc_feature
<222> LOCATION: (55)..(55)
<223> OTHER INFORMATION: 2' O-propargyl
<220> FEATURE:
<221> NAME/KEY: misc_feature
<222> LOCATION: (58)..(58)
<223> OTHER INFORMATION: 2' fluorine

<400> SEQUENCE: 106
gggaaacuag auuggaacac aguauuggac agucugauug gacugacaca uuggaga         57
```

COMPOSITIONS CONTAINING NUCLEIC ACID NANOPARTICLES WITH MODULAR FUNCTIONALITY

CROSS-REFERENCE TO RELATED APPLICATIONS

This application claims the benefit of, and priority to, U.S. Provisional Patent Application No. 63/015,735, filed Apr. 27, 2020, the contents of which are incorporated by reference.

FIELD OF THE INVENTION

The invention relates generally to therapeutic compositions that include nucleic acid nanoparticles for delivery of cargo and methods of using the same.

SEQUENCE LISTING

The present application incorporates by reference a Sequence Listing in electronic format. The sequence listing is provided as the field entitled "SIX-003/01US_Sequence_Listing.txt", created on Feb. 11, 2022 and is 52 kilobytes size.

BACKGROUND

Over the last decade, much effort has focused on the development of nucleic acid nanoparticles as vehicles for delivery of therapeutics against a wide range of diseases (e.g. anti-neoplastic agents to treat cancer). However, therapies based on nucleic acid nanoparticles are plagued by a variety of problems that have yet to be overcome. Many promising therapeutic agents are biological macromolecules that need to be delivered intact to the right cells in the body, internalized by those cells, and then transported to a specific intracellular site, and nucleic acid nanoparticles are often unable to perform one or more of those functions. Furthermore, current early stage oligonucleotide-based therapies have been designed specifically for a given indication. When changing the design of a nanoparticle, one needs to take various factors into account, such as stability, ease of synthesis and its potential behaviour in a biological environment. It is not practical, therefore, to continuously change the design of a nanoparticle.

SUMMARY

This invention provides compositions for delivery of cargo to targeted cells, such as cancer cells, using a nanoparticle, e.g. nucleic acid (DNA, RNA, PNA, LNA, GNA, TNA) nanoparticle, linked to one or more cargoes via several different types of linkage. The nucleic acid nanoparticles, such as RNA nanoparticles, serve both as structural scaffolds for the delivery of the cargo to target cells within the body and as functional regulators that preserve activity of the cargo en route to its target, promote its activity upon arrival, and/or inhibit its activity at off-target sites.

The compositions of the invention are useful for treating a variety of disorders, including cancer. Examples of the mechanisms of action include degrading mRNA, blocking DNA replication, promoting apoptosis, and tagging cells for destruction by the immune system. Because compositions of the invention allow activity of agents to be triggered in targeted cells but blocked in other cells, they are well-suited for delivery of potentially hazardous cargo, such as chemotherapeutics.

The nanoparticle compositions have a modular design, which is achieved via the use of bioorthogonal click chemistry (FIG. 1). These reactions are used for both ligation and stabilisation. "Click Chemistry" encompasses any reaction that is high yielding, wide in scope and creates little to no by-product. Any by-product that is created should be easily removed. This invention incorporates several different linkages that are widely regarded as "click chemistry" and these are discussed herein. Briefly these include, but are not limited to, copper (I)-catalyzed alkyne-azide cycloaddition (CuAAC), strain-promoted alkyne-azide cycloaddition (SPAAC), ruthenium-catalysed azide-alkyne cycloaddition (RuAAC), inverse electron demand Diels-Alder reaction (IEDDA), Sulfur Fluoride Exchange (SuFEx), strain-promoted alkyne-nitrone cycloaddition (SPANC), hydrazone/oxime ether formation, thiol-ene radical reaction, thiol-yne radical reaction, thiol-Michael addition reaction, thiol-isocyanate reaction, thiol-epoxide click reaction, nucleophilic ring opening reactions (spring-loaded reactions), traceless Staudinger ligation.

The modular design in the present invention allows for a highly stable core scaffold. When an additional functionality needs to be added to the delivery system, this can be clicked on rather than having to redesign the entire nucleic acid nanoparticle. Many current generation nucleic acid nanoparticles utilize DNA/RNA toeholds to promote the association of DNA/RNA hybrids and this often requires in silico design of the components that will associate with the core scaffold (K. A. Afonin et al. The Use of Minimal RNA Toeholds to Trigger the Activation of Multiple Functionalities, Nano Lett. 16 (2016) 1746-1753. https://doi.org/10.1021/acs.nanolett.5b04676.). The modular design of the present invention allows for easier attachment of cargo molecules, which therefore leads to a significant reduction in time associated with the development process, as less optimisation is required in sequence design. The modular design also leads to greater reproducibility in synthesis and assembly and less batch-to-batch variation.

In addition to the advantages outlined above, the modular design also allows for increased cargo capacity and higher therapeutic payload. The alternating attachment sites allow for the conjugation of multiple unique therapeutic modalities, and also allow for the attachment of greater amounts of therapeutic payload per nanoparticle, thereby generating more efficacious combination therapies. For example, a hexameric RNA nanostructure structure can be limited to six attachment sites for siRNA therapeutic cargo molecules using previously documented toehold conjugation strategies (K. A. Afonin et al. Multifunctional RNA nanoparticles, Nano Lett. 14 (2014) 5662-5671. https://doi.org/10.1021/nl502385k). As described herein, using click chemistry, instead of toehold conjugation, would increase the available attachment sites on a similar hexameric structure, leading to increased loading capacity of cargo molecules.

The use of bioorthogonal click chemistry also allows for the ability to attach multiple cargo molecules to nucleic acid nanoparticles. In one embodiment, this could include more than one of the same cargo molecule conjugated to the nanoparticle. In another embodiment this could include multiple cargo molecules that undertake a different biological function conjugated to the nanoparticle. The composition could include multiple variations of siRNA molecules, aptamers, chemotherapeutics, cytotoxic nucleosides and endosomal escape molecules conjugated to the same nucleic acid nanoparticle. This versatility allows for greater flexibility in the design and manufacture of nanoparticles for diagnostic or therapeutic purposes.

Cargo molecules may also be attached to each other in "combinatorial chains", whereby each cargo molecule is attached to another via a reversible or irreversible linker. This concept will allow for even higher therapeutic loading. In one embodiment, two or more siRNAs comprising the same sequence are linked to form a homomultimer for increased silencing potency and enhanced cellular uptake per ligand-receptor interaction. In another embodiment, two or more siRNAs comprising different sequences that target the same mRNA are linked, thereby forming single-gene-targeting heteromultimers that allow for a greater target sequence coverage (including splice variants, untranslated regions) for more complete knockdown and increased phenotypic penetrance to decrease the impact of off-target effects. In another embodiment, two or more siRNAs comprising different sequences that target different mRNAs are linked to form heteromultimers for combinatorial silencing of multiple genes. By using such multi-gene-targeting heteromultimers as combination therapies, synergistic therapeutic effects can be achieved, especially for more complex diseases that cannot efficiently be treated with single-targeting siRNAs. In yet another embodiment, a linear homo- or heteromultimeric chain of siRNA is further conjugated to additional cargo molecules such as N-Acetylgalactosamine (GalNAc) for cell type-specific targeting to hepatocytes. In one embodiment the combinatorial chains are attached to a nucleic acid nanoparticle. One or more combinatorial chains may be attached to each nanoparticle In another embodiment, the combinatorial chains are independent of a core nanoparticle.

The nucleic acid nanoparticle may include a component conjugated to a nucleic acid in the nanoparticle. The component may be conjugated to a T position of a nucleic acid in the nucleic acid nanoparticle. The component may be conjugated to a base of a nucleic acid in the nucleic acid nanoparticle. The component may be conjugated to the 5' terminus of an oligonucleotide. The component may be conjugated to the 3' terminus of an oligonucleotide. The component may be conjugated to a phosphorus-containing linkage of nucleotides in the nucleic acid nanoparticle. The phosphorus-containing linkage may be a 3-(2-nitrophenyl)-propyl phosphoramidite linkage, a 3-phenylpropyl phosphoramidite linkage, an alkyl phosphorothioate linkage, an aminobutyl phosphoramidite linkage, an aryl phosphorothioate linkage, a dimethylamino phosphoramidite linkage, a guanidinobutylphosphoramidate linkage, or a phosphorothioate linkage.

In one embodiment the present invention comprises ligating together one of the positions described on the modified nucleotide or phosphoramidite above with a suitable coupling partner. For CuAAC, SPAAC and RuAAC, said method comprises reacting an alkyne group with an azide group to form a triazole linkage. For IEDDA, said method comprises reacting a 1,2,4,5-tetrazine with an olefin to form a dihydropyridazine, which might be further oxidised to the corresponding pyridazine. For SuFEx, said method comprises reacting a sulfonyl fluoride with a nucleophile to form the substituted product. For SPANC, said method comprises reacting a dibenzocyclooctyne with a nitrone to give an N-alkylated isoxazoline. For hydrazone formation, said method comprises reacting a hydrazine with a carbonyl to give a hydrazone. For oxime ether formation, said method comprises reacting a hydroxylamine with a carbonyl. For the thiol-ene radical reaction, thiol-yne radical reaction, thiol-isocyanate reaction, thiol-epoxide click reaction, said methods comprise reacting a thiol with the appropriate coupling partner. For nucleophilic ring opening reactions, said method comprises reacting a nucleophile with an appropriate strained electrophile to generate the desired attachment. For traceless Staudinger ligation, said method comprises reacting a phosphine (i.e. (diphenylphosphino) methanethiol) with a thioester to form the desired attachment.

In addition to using the chemistries outlined above to attach one or more cargo molecules, it may also be used to stabilise nucleotide strands in the nanoparticle. Thermodynamic stabilisation with the use of click chemistry, particularly CuAAC, has been shown in the art (see WO 2008/120016). This composition will use a combination of the methods above to stabilise the nucleic acid nanoparticle structure (FIG. 2).

In another embodiment, the nucleic acid nanoparticle might be constructed from oligonucleotides that are ligated via click chemistry or chemical ligation. Such oligonucleotide-based structures are known in the art (WO 2015/177520; US2017/057415; M. Kollaschinski et al., Efficient DNA Click Reaction Replaces Enzymatic Ligation, Bioconjug. Chem. 31 (2020) 507-512. https://doi.org/10.1021/acs.bioconjchem.9b00805.).

In another embodiment, the present invention comprises a nucleic acid nanoparticle, whereby individual oligonucleotide strands have pendant moieties that can be coupled with an external agent to generate a fluorophore.

The composition may include fluorogenic click moieties that can be used to visualise and monitor nanoparticle assembly and cellular uptake. This might include fluorescent isoindole crosslink (FlICk) chemistry. Such functionality could be incorporated via amine- or thiol-modified nucleotides. This could then act as a staple or attachment site for cargo.

The composition may include any combination of the above modifications. Alternative click reactions may be coupled with fluorophore-generating reactions.

The composition may include multiple RNA molecules. For example, the composition may contain 1, 2, 3, 4, 5, 6, 7, 8, 9, 10, 11, 12, or more RNA molecules.

The nucleic acid nanoparticle may include an aptamer.

The nucleic acid nanoparticle may be an RNA nanoparticle, a DNA nanoparticle, or a particle that contains both RNA and DNA.

The self-assembled construct may take the form of any number of morphologies including, but not limited to, a trimer, tetramer, pentamer or hexamer.

In another embodiment, the nucleic acid nanoparticle may be a duplex of RNA molecules with multiple biorthogonal click attachments. These may or may not be attached to cargo via a stimuli-responsive linker. The core strand could be RNA, DNA, mRNA, siRNA or another type of oligonucleotide therapeutic (FIG. 3). Various cargo molecules could be attached, including cytotoxic drugs (I), RNA/siRNA (II), targeting moieties (e.g. aptamers) (III), endosomal escape molecules (IV) and fluorophores (V). These moieties may or may not be attached via a stimuli-responsive linker (VI).

In another aspect, the invention provides compositions that include a cargo molecule and an element that is linked to the cargo molecule to promote a biological activity of the cargo molecule in a subject, such as a stimuli-responsive linker (FIG. 4).

The cargo molecule may be, or include, an RNA molecule, DNA molecule, peptide, polypeptide, protein, cytotoxic drug or any combination thereof. The RNA molecule may be mRNA molecule, a lnRNA molecule, a miRNA molecule, a siRNA molecule, or a shRNA molecule. The cargo molecule may be, or may encode, a CRISPR component. The cargo molecule may be, or may encode, a chimeric antigen receptor.

In addition to using therapeutically redundant RNA scaffolds, the core scaffold could be modified to incorporate several functionalities to enhance its therapeutic effect. The core nanoscaffold could, for instance, be modified to promote cellular uptake and endosomal escape thereby increasing cytoplasmic availability of the cargo.

DETAILED DESCRIPTION

Figure 1:
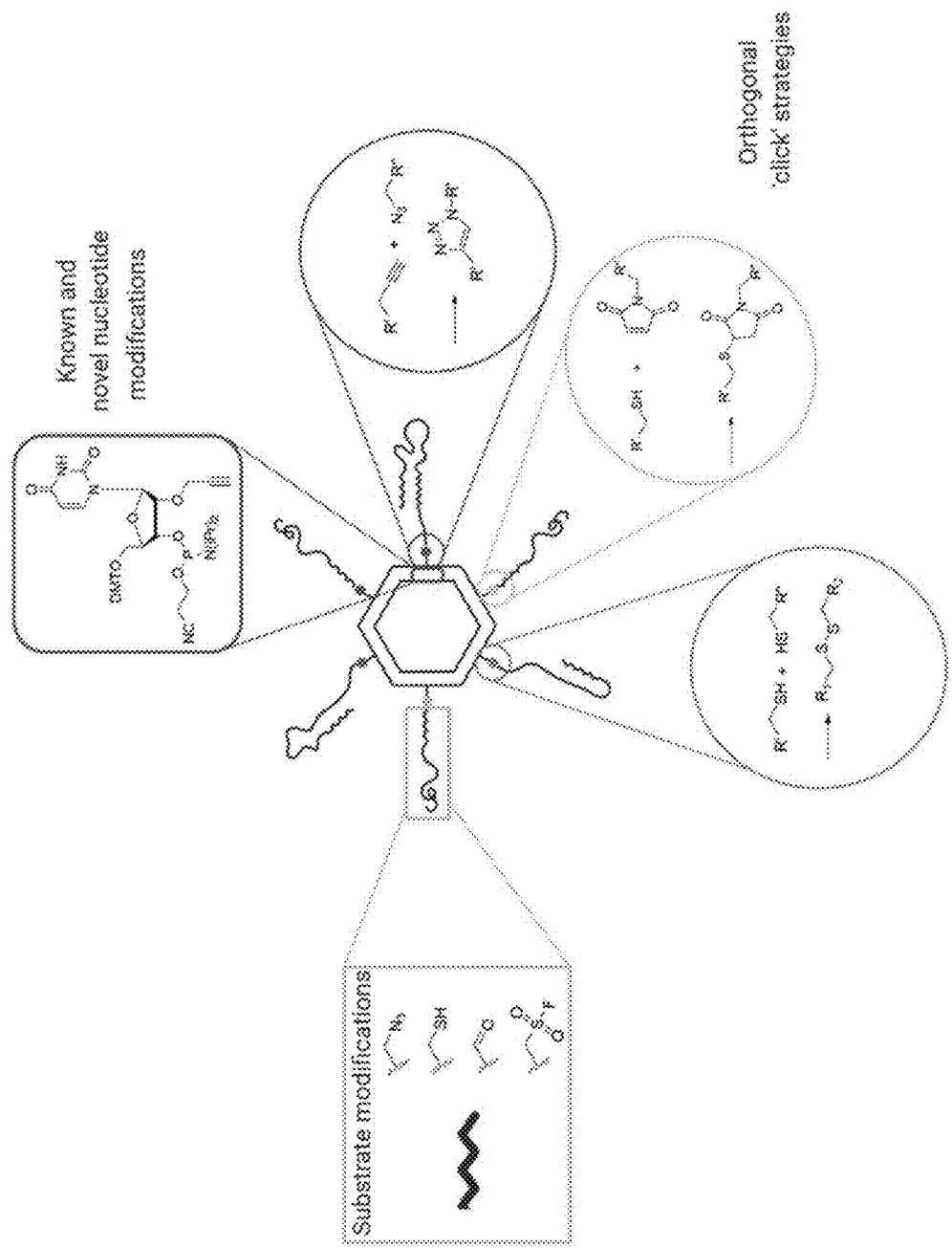
FIG. 1 is a schematic showing a simplified hexameric nucleic acid nanoparticle with modular click-based functionality. Orthogonal click handles can be incorporated onto known and novel nucleotides.

The invention provides a broad range of compositions that allow delivery of cargo to cells. These compositions are decorated with reactive sites that allow for the interchangeable attachment of cargo. Examples of cargo include mRNA molecules that allow expression of exogenous polypeptides in target cells, other types of RNA molecules that permit regulation of gene expression in target cells, and other types of therapeutic or diagnostic agents. The compositions of the invention may modify the cell-specificity, cell internalization potential, therapeutic efficacy of biological molecules and reduce off-target effects.

Nanoparticles, Including Nucleic Acid Nanoparticles

In certain embodiments, compositions of the invention include nanoparticles. As used herein, "nanoparticle" refers to particles having dimensions that are measured on the nanometer scale. For example, a nanoparticle may have a diameter, length, width, or depth of from 1 to 1000 nm.

RNA nanoparticles are formed from the ordered arrangement of individual RNA molecules, which have defined secondary structures. RNA molecules form a variety of structural motifs, such as pseudoknots, kissing hairpins, and hairpin loops, 3-way and 4-way junctions, that affect both the geometry of the molecule and its ability to form stable interactions with other RNA molecules via base pairing. Typically, individual RNA molecules have double-stranded regions that result from intramolecular base pairing and single-stranded regions that can form base pairs with other RNA molecules or can otherwise bind to other types of molecules.

Various RNA nanostructures having ordered two-dimensional or three-dimensional structures are known, including, for example and without limitation, nanoarrays, nanocages, nanocubes, nanoprisms, nanorings, nanoscaffolds, and nanotubes. Nanorings may be symmetric or asymmetric structures that include 3, 4, 5, 6, 7, 8, or more RNA molecules arrayed around an axis. Thus, nanorings may be trimers, tetramers, pentamers, hexamers, heptamers, octamers, or higher-numbered polymers. Nanorings may be circular, triangular, square, pentagonal, hexagonal, heptagonal, octagonal, or otherwise polygonal in shape. Other types of RNA nanoparticles, such as sheets, cages, dendrimers and clusters, are also possible and within the scope of the invention. "Nanoscaffold" refers generally to a nanostructure to which other molecules can be attached. RNA nanoparticles of various structural arrangements are described in, for example, WO 2005/003,293; WO 2007/016,507; WO 2008/039,254; WO 2010/148,085; WO 2012/170,372; WO 2015/042,101; WO 2015/196,146; WO 2016/168,784; and WO 2017/197,009, the contents of each of which are incorporated herein by reference.

Nucleic acid nanoparticles may contain naturally-occurring nucleotides, or they may contain chemically-modified nucleotides. Chemically-modified nucleotides are known in the art and described in, for example, WO 2018/118587, the contents of which are incorporated herein by reference. For example and without limitation, nucleic acid nanoparticles, therapeutics and aptamers may contain one or more of a 2' fluoro, 2' O-methyl, 2-thiouridine, 2'-O-methoxyethyl, 2'-amine, 5-methoxyuridine, pseudouridine, 5-methylcytidine, N1-methyl-pseudouridine, locked nucleic acid (LNA), morpholino, and phosphorothioate modification. Other modified nucleotides include 5caC, 5fC, 5hoC, 5hmC, 5meC/5fu, 5meC/5moU, 5meC/thG, 5moC, 5meC/5camU, 5meC, ψ, 5meC/ψ, 5moC/5moU, 5moC/5meU, 5hmC/5meU, me1ψ, 5meC/me1ψ, 5moU, 5camU, m6A, 5hmC/ψ, 5moC/ψ, me6DAP, me4C, 5fu, 5-methoxyuridine, 2-aminoadenine, 2-thiocytosine, 2-thiothymine, 2-thiouracil, 3-methyladenine, 4-thiouracil, 5,6-dehydrouracil, 5-allylcytosine, 5-allyluracil, 5-aminoallylcytosine, 5-aminoallyluracil, 5-bromouracil, 5-ethynylcytosine, 5-ethynyluracil, 5-fluorouracil, 5-hydroxymethylcytosine, 5-hydroxymethyluracil, 5-iodouracil, 5-methylcytosine, 5-methyluracil, 5-propynylcytosine, 5-propynylcytosine, 5-propynyluracil, 5-propynyluracil, 6-O-methylguanine, 6-thioguanine, 7-deaza-8-azaguanine, 7-deazaadenine, 7-deazaguanine, 7-deazaguanine, 8-oxoadenine, 8-oxoguanine, 5-methylcytidine, pseudouridine, inosine, 2'-O-methyladenosine, 2'-O-methylcytidine, 2'-O-methylguanosine, 2'-O-methyluridine, 2'49-methyl-pseudouridine, 2'49-methyl 3'-phosphorothioate adenosine, 2'-O-methyl 3'-phosphorothioate cytidine, 2'49-methyl 3'-phosphorothioate guanosine, 2'-O-methyl 3'-phosphorothioate uridine, a conformationally-restricted nucleotide, and 2'-O-methyl 3'-phosphorothioate pseudouridine.

The nucleic acids of the nanoparticles may contain sugar modifications. For example and without limitation, the nucleic acids of the nanoparticles may contain one or more of 2'-O-(2-methoxyethyl) (2'MOE), 2'-methoxy (2'OMe), 2'-fluoro (2'F), 2'-O-acetalesters, 2-guanidinomethyl-2-ethylbutyryloxymethyl (GMEBuOM), 2-amino-2-methylpropionyloxymethyl (AMPrOM), 2-aminomethyl-2-ethylbutyryloxymethyl (AMEBuOM), 2'-O-Pivaloyloxymethyl (PivOM), 2' amino locked nucleic acids (LNA) modified with amines or peptides mentioned above, 2'-O—[N,N-dimethylamino)ethoxy]ethyl, 2'-N—[N,N-dimethylamino)ethoxy]ethyl, 2'-N-imidazolacetyamide, 2'-O-[3-(guanidinium)propyl], 2'-N-[3-(guanidinium)propyl], 2'-O-[3-(guanidinium)ethyl], 2'-N-[3-(guanidinium)ethyl], 2'-O—(N-(aminoethyl)carbamoyl)methyl, 2'-N—(N-(aminoethyl)carbamoyl)methyl, 2'-O—[N-(2-((2-aminoethyl)amino)ethyl)]acetamide, 2'-N—[N-(2-((2-aminoethyl)amino)ethyl]acetamide, 2'-N-2,2,3,3,4,4,5,5,6,6,7,7,8,8,8-pentadecafluorooctanamide, 2'-N-imidazolacetamide, 2'-O-imidazole methyl, 2'-N-guanidylbenzylamide, and 4'-C-guanidinincarbohydrazidomethyl, 2'-O-imidazolemethyl, 2'-N-imidazolemethylamine ethyl.

Click Chemistry

Click chemistry was developed to provide a simple method to join organic molecules together to afford products in high yields and under mild conditions. The reaction between an azide and alkyne to form a disubstituted 1,2,3-triazole was originally reported separately by Meldal and co-workers (C. W. Tornøe et al. [1,2,3]-Triazoles by regiospecific copper(I)-catalyzed 1,3-dipolar cycloadditions of terminal alkynes to azides, J. Org. Chem. 67 (2002) 3057-3064. https://doi.org/10.1021/jo011148j.) and Sharpless and co-workers (V. V. Rostovtsev et al. A stepwise huisgen cycloaddition process: Copper(I)-catalyzed regioselective "ligation" of azides and terminal alkynes, Angew. Chemie—Int. Ed. 41 (2002) 2596-2599. https://doi.org/10.1002/1521-3773(20020715)41:14<2596::AID-ANIE2596>3.0.CO; 2-4.). Since then, the reaction has emerged as one of the most important conjugation reactions due to its simplicity and use of mild conditions.

Figure 5:
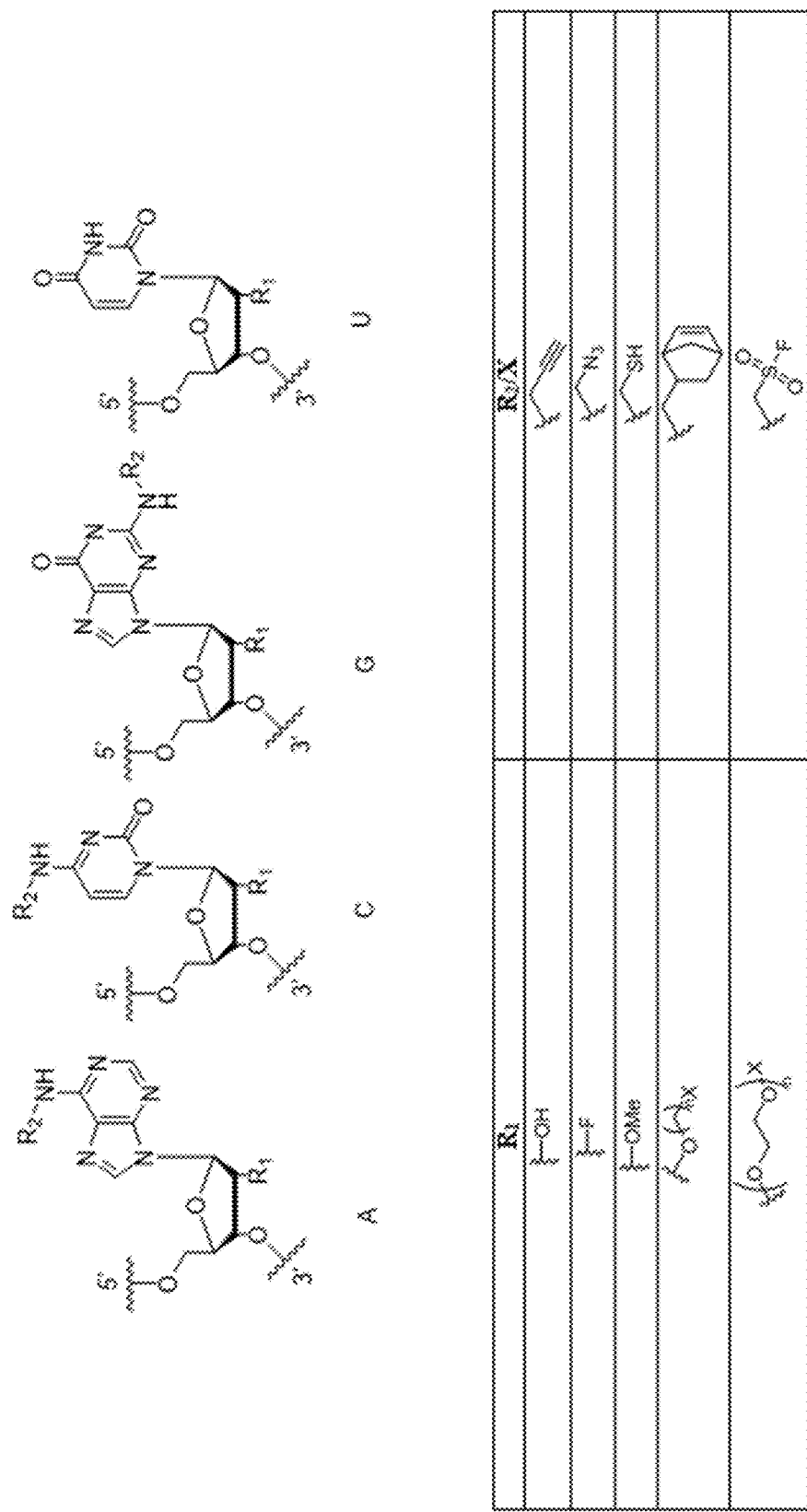
FIG. 5 is a table outlining possible 2' modification of DNA/RNA used within the nucleic acid nanoparticles.

Nanoparticles may contain any alkyne-bearing moiety. This could be via a chemically or enzymatically modified nucleotide. Alkyne-modified nucleotides are known in the art and described in, for example, WO/2017/189978. Alkyne-modified nucleotides may be modified on the sugar, at the 2' position, or on the nucleotide base. For example, and without limitation, the sugar-modified nucleic acid nanoparticles may contain one or more of 4-amino-1-((2R, 3R,4R,5R)-4-hydroxy-5-(hydroxymethyl)-3-(prop-2-yn-1-yloxy)tetrahydrofuran-2-yl)pyrimidin-2(1H)-one (2'O alkyne C), 1-((2R,3R,4R,5R)-4-hydroxy-5-(hydroxymethyl)-3-(prop-2-yn-1-yloxy)tetrahydrofuran-2-yl)pyrimidine-2,4(1H,3H)-dione (2'O alkyne U), (2R,3R,4R,5R)-5-(6-amino-9H-purin-9-yl)-2-(hydroxymethyl)-4-(prop-2-yn-1-yloxy)tetrahydrofuran-3-ol (2'O alkyne A), 2-amino-9-((2R,3R,4R,5R)-4-hydroxy-5-(hydroxymethyl)-3-(prop-2-yn-1-yloxy)tetrahydrofuran-2-yl)-1,9-dihydro-6H-purin-6-one (2' 0 alkyne G). Additional $CH_2$ or ethylene glycol groups may also be added between the alkyne moiety and the $CH_2$ moiety. Ethylene glycol units may also be used instead of methylene (FIG. 5).

Alkyne-modified nucleotides, where the modification appears on the base, may contain one or more of (2R,3S, 4R,5R)-2-(hydroxymethyl)-5-(6-(prop-2-yn-1-ylamino)-9H-purin-9-yl)tetrahydrofuran-3,4-diol (N6 propargyl A), 1-((2R,3R,4S,5R)-3,4-dihydroxy-5-(hydroxymethyl)tetrahydrofuran-2-yl)-4-(prop-2-yn-1-ylamino)pyrimidin-2(1H)-one (N4 propargyl C), 9-((2R,3R,4S,5R)-3,4-dihydroxy-5-(hydroxymethyl)tetrahydrofuran-2-yl)-2-(prop-2-yn-1-ylamino)-1,9-dihydro-6H-purin-6-one (N2 propargyl G), 1-((2R,3R,4S,5R)-3,4-dihydroxy-5-(hydroxymethyl)tetrahydrofuran-2-yl)-3-(prop-2-yn-1-yl)pyrimidine-2,4(1H, 3H)-dione (N3 propargyl U).

Figure 7:
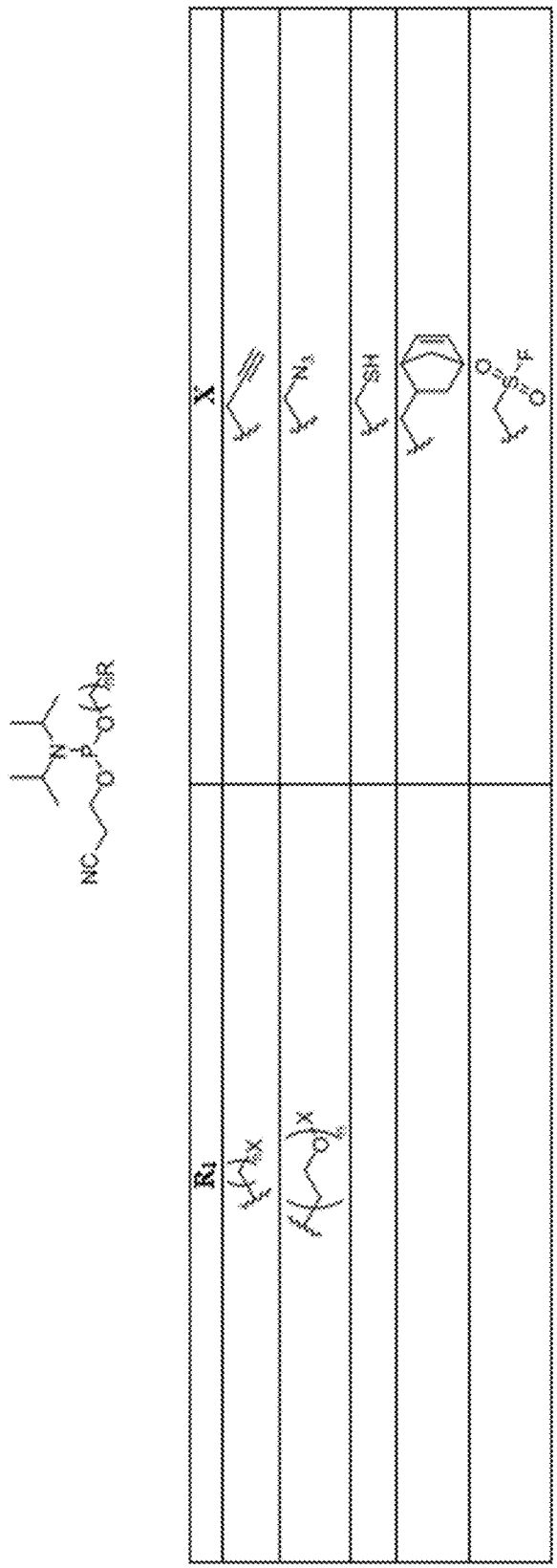
FIG. 7 is a table showing possible phosphoramidite modifications that allow for bioorthogonal click chemistry.

Nanoparticles may contain an alkyne-modified phosphate that is incorporated at the 5' or 3' end of the oligonucleotide sequence (FIG. 7). Such phosphoramidites are described in the art, for example, in US2009124571. These may include, but not limited to, 2-cyanoethyl prop-2-yn-1-yl diisopropylphosphoramidite and any methylene extensions between the phosphorus centre and alkyne moiety. Ethylene glycol units may also be used instead of methylene.

Nanoparticles may contain any azide-bearing moiety. This could be via a chemically or enzymatically modified nucleotide. Alkyne-modified nucleotides may be modified on the sugar, at the 2' position, or on the nucleotide base. For example, and without limitation, the sugar-modified nucleic acid nanoparticles may contain one or more of (2R,3R,4R, 5R)-5-(6-amino-9H-purin-9-yl)-4-(azidomethoxy)-2-(hydroxymethyl)tetrahydrofuran-3-ol, 4-amino-1-((2R,3R,4R, 5R)-3-(azidomethoxy)-4-hydroxy-5 (hydroxymethyl) tetrahydrofuran-2-yl)pyrimidin-2(1H)-one, 2-amino-9-((2R, 3R,4R,5R)-3-(azidomethoxy)-4-hydroxy-5-(hydroxymethyl)tetrahydrofuran-2-yl)-1,9-dihydro-6H-purin-6-one (N2 azido G), 1-((2R,3R,4R,5R)-3-(azidomethoxy)-4-hydroxy-5-(hydroxymethyl)tetrahydrofuran-2-yl)pyrimidine-2,4(1H,3H)-dione.

Figure 6:
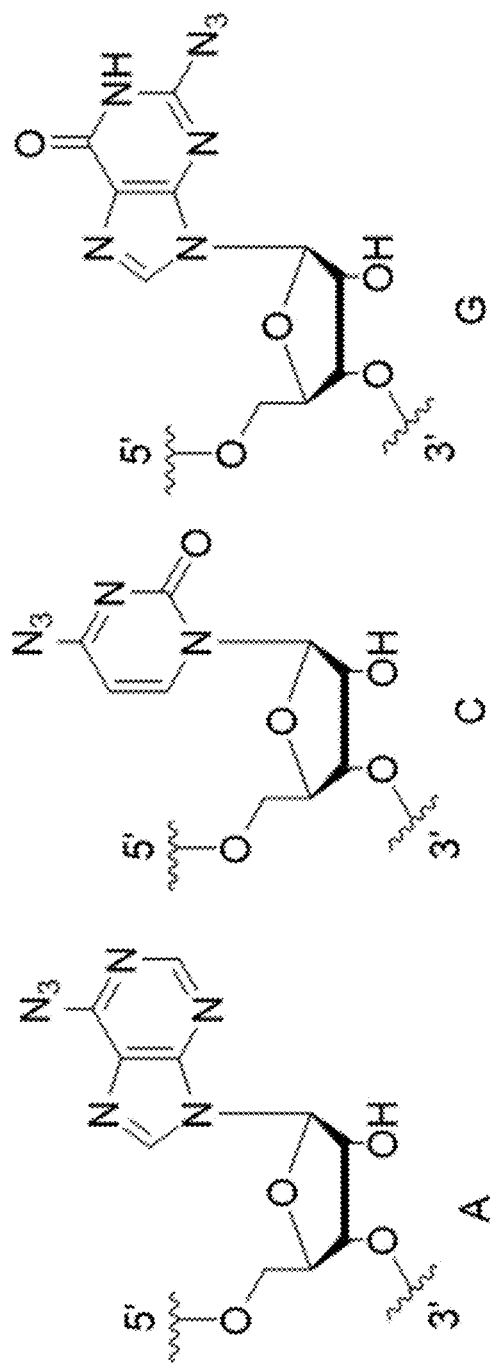
FIG. 6 shows structural modifications of RNA nucleotides. These have been modified with an azide on the base.

Azide modifications of the nucleotide base are known in the art and are described, for example, in US 2006/0147924. Base-modified azido compounds may contain, but not limited to, one or more of (2R,3R,4S,5R)-2-(6-azido-9H-purin-9-yl)-5-(hydroxymethyl)tetrahydrofuran-3,4-diol (N6 azido A), 4-azido-1-((2R,3R,4S,5R)-3,4-dihydroxy-5-(hydroxymethyl)tetrahydrofuran-2-yl)pyrimidin-2(1H)-one (N4 azido C), 2-azido-9-((2R,3R,4S,5R)-3,4-dihydroxy-5-(hydroxymethyl)tetrahydrofuran-2-yl)-1,9-dihydro-6H-purin-6-one (N2 azido G) (FIG. 6).

Nanoparticles may contain an azide-modified phosphate that is incorporated at the 5' or 3' end of the oligonucleotide sequence. These may include, but are not limited to azidomethyl (2-cyanoethyl) diisopropylphosphoramidite and any methylene extensions between the phosphorus centre and azide moiety. Ethylene glycol units may also be used instead of methylene.

Due to potential toxicity concerns with trace copper, copper-free azide-alkyne cycloadditions have become increasingly popular for biologically relevant molecules in the literature. Strain-promoted azide-alkyne cycloaddition (SPAAC) is a convenient way around this issue. Instead of using Cu(I) to activate the alkyne, the alkyne is introduced in a strained cyclooctyne derivative (N. J. Agard et al. Comparative study of bioorthogonal reactions with azides, ACS Chem. Biol. 1 (2006) 644-648. https://doi.org/10.1021/cb6003228.). The desire to relieve this ring strain drives the reaction with an azide. This approach has been used for post-synthetic labelling of oligonucleotide-azide derivatives (M. L. Winz. Site-specific one-pot triple click labeling for DNA and RNA, Chem. Commun. 54 (2018) 11781-11784. https://doi.org/10.1039/c8cc04520h.) and can be applied as part of the modular design in the present invention. Azide modified nucleotides can be incorporated into the nucleic acid nanoparticle. Assembled constructs can then be tagged with cyclooctyne-labelled substrates.

Figure 8:
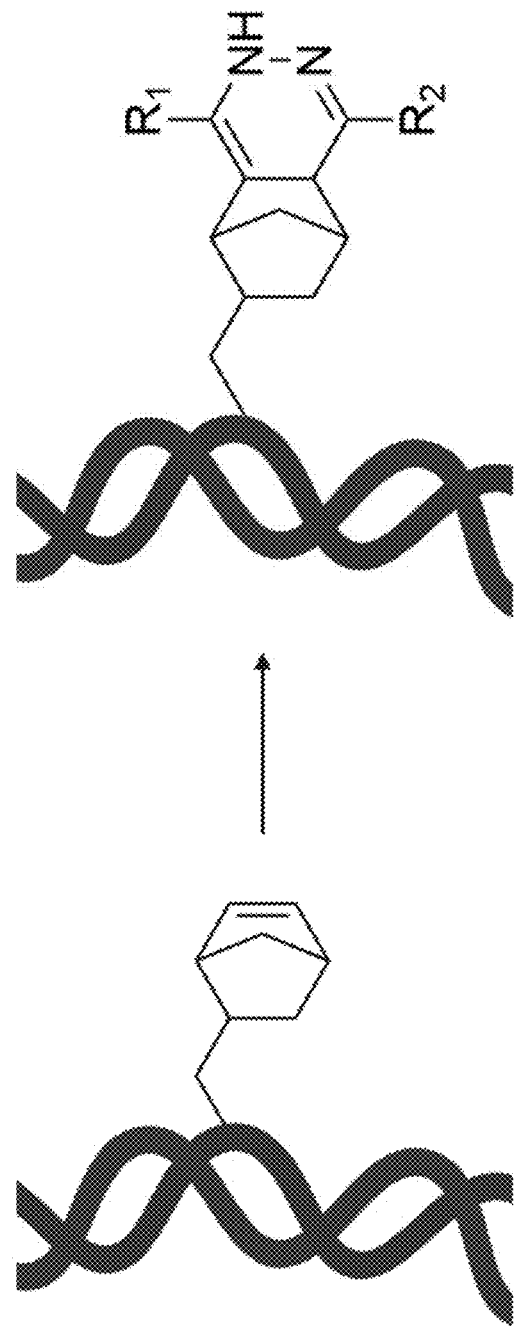
FIG. 8 is a schematic showing an inverse electron demand Diels Alder reaction on an oligonucleotide.

Inverse electron demand Diels Alder has been established as one of the most robust click chemistries for biomolecule conjugation and has been used for post-synthetic labelling of DNA and RNA (J. Schoch et al. Post-Synthetic Modification of DNA by Inverse-Electron-Demand Diels-Alder Reaction, J. Am. Chem. Soc. 132 (2010) 8846-8847. https://doi.org/10.1021/ja102871p.); (A. M. Pyka et al. Diels-alder cycloadditions on synthetic RNA in mammalian cells, Bioconjug. Chem. 25 (2014) 1438-1443. https://doi.org/10.1021/bc500302y.). The contents of which are incorporated herein by reference. This cycloaddition reaction proceeds rapidly, without the use of transition metals, and allows efficient functionalization of oligonucleotides at room temperature (FIG. 8).

Nanoparticles may contain any norbornene (bicyclo[2.2.1]hept-2-ene) moiety. This could be via a chemically or enzymatically modified nucleotide. Norbornene-modified nucleotides may be modified on the sugar, at the 2' position, or on the nucleotide base. For example, and without limitation, the sugar-modified nucleic acid nanoparticles may contain one or more of (2R,3R,4R,5R)-5-(6-amino-9H-purin-9-yl)-4-(bicyclo[2.2.1]hept-5-en-2-ylmethoxy)-2-(hydroxymethyl)tetrahydrofuran-3-ol, 4-amino-1-((2R,3R,4R,5R)-3-(bicyclo[2.2.1]hept-5-en-2-ylmethoxy)-4-hydroxy-5-(hydroxymethyl)tetrahydrofuran-2-yl)pyrimidin-2(1H)-one, 1-((2R,3R,4R,5R)-3-(bicyclo[2.2.1]hept-5-en-2-ylmethoxy)-4-hydroxy-5-(hydroxymethyl)tetrahydrofuran-2-yl)pyrimidine-2,4(1H,3H)-dione (FIG. 5).

Nanoparticles may contain a norbornene-modified phosphate that is incorporated at the 5' end of the oligonucleotide sequence. These may include, but are not limited to azidomethyl bicyclo[2.2.1]hept-5-en-2-ylmethyl (2-cyanoethyl) diisopropylphosphoramidite, which is described in the art (J. Schoch et al. Post-Synthetic Modification of DNA by Inverse-Electron-Demand Diels-Alder Reaction, J. Am. Chem. Soc. 132 (2010) 8846-8847. https://doi.org/10.1021/ja102871p.) and any methylene extensions between the phosphorus centre and azide moiety. Ethylene glycol units may also be used instead of methylene (FIG. 7).

Nanoparticles may contain any thiol moiety. This could be via a chemically modified nucleotide (FIG. 5). Thiol-modified nucleotides may be modified on the sugar, at the 2' position, or on the nucleotide base. For example, and without limitation, the sugar-modified nucleic acid nanoparticles may contain one or more of (2R,3R,4R,5R)-5-(6-amino-9H-purin-9-yl)-2-(hydroxymethyl)-4-(2-mercaptoethoxy)tetrahydrofuran-3-ol (thiol A), 4-amino-1-((2R,3R,4R,5R)-4-hydroxy-5-(hydroxymethyl)-3-(2 mercaptoethoxy) tetrahydrofuran-2-yl)pyrimidin-2(1H)-one (thiol C), 2-amino-9-((2R,3R,4R,5R)-4-hydroxy-5-(hydroxymethyl)-3-(2-mercaptoethoxy)tetrahydrofuran-2-yl)-1,9-dihydro-6H-purin-6-one (thiol G), 1-((2R,3R,4R,5R)-4-hydroxy-5-(hydroxymethyl)-3-(2-mercaptoethoxy)tetrahydrofuran-2-yl)pyrimidine-2,4(1H,3H)-dione (thiol U). Any number of methylene extensions are possible between the sugar and the sulphur atom. Ethylene glycol units may also be used instead of methylene and combinations of the above may be used.

Figure 9:
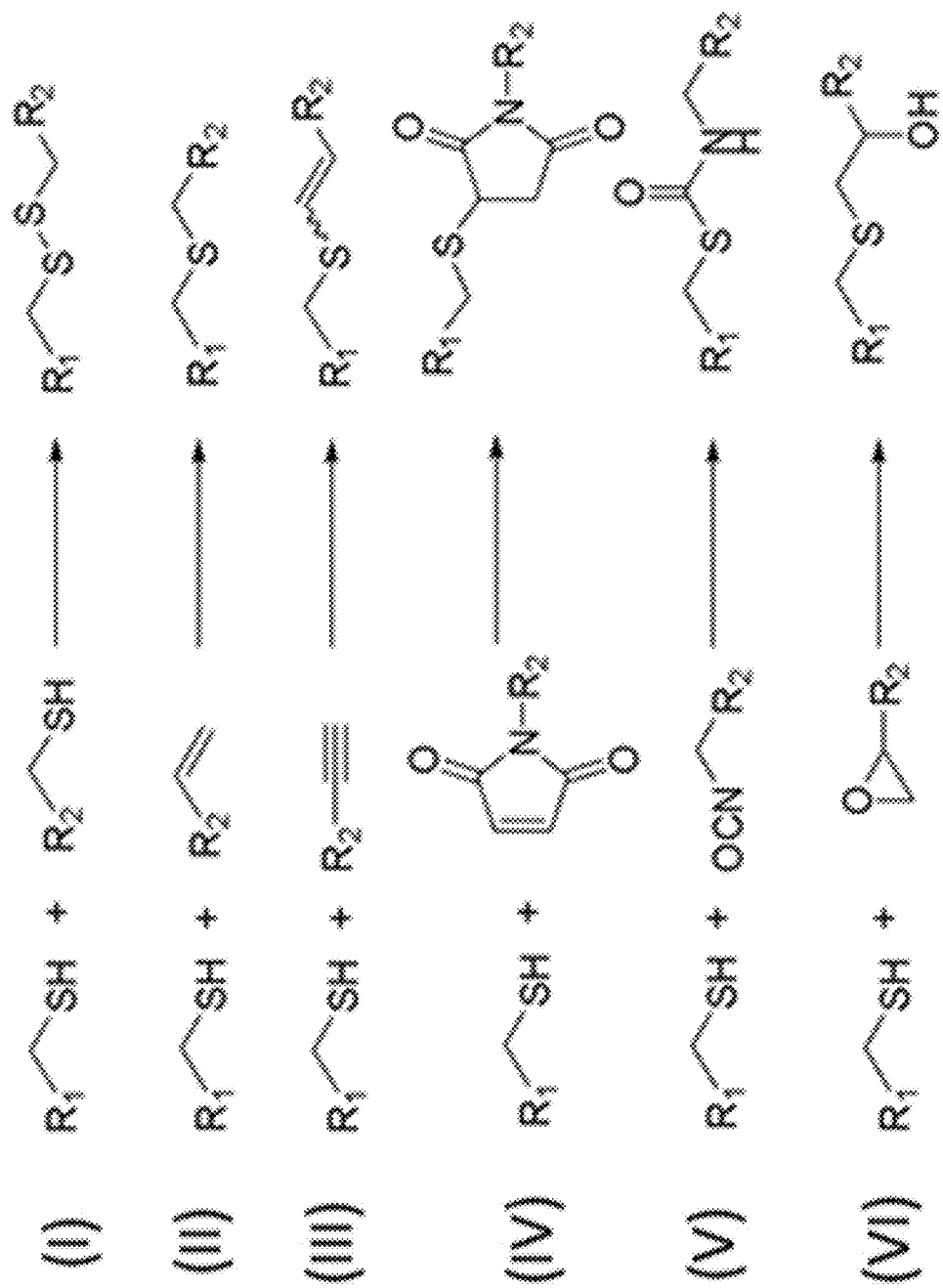
FIG. 9 is a schematic showing possible click reactions that can be carried out with thiol-modified oligonucleotides. These include disulphide (I), thiol-ene (II), thiol-yne (III), thiol-maleimide (IV), thiol-isocyanate (V) and thiol-epoxy (VI).
Figure 10:
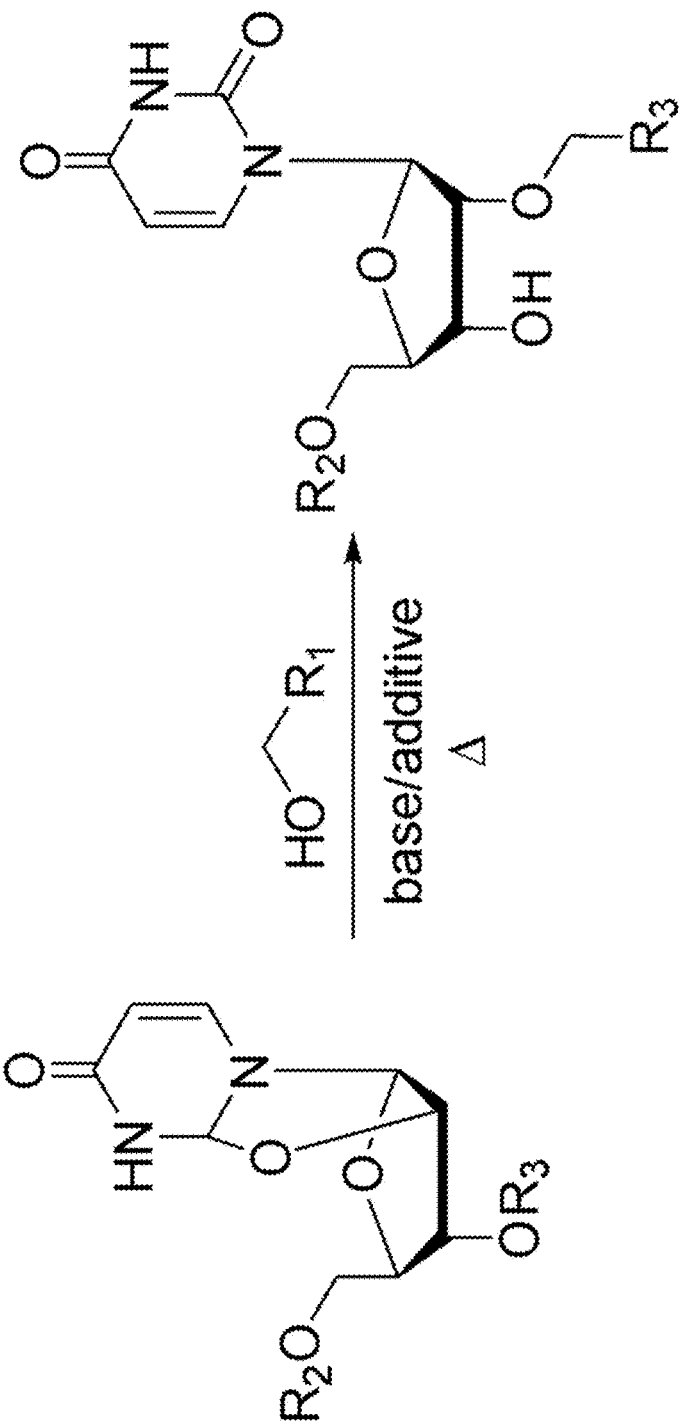
FIG. 10 is a schematic showing optimisation of the nucleophilic ring opening of 2,2'-anhydro-1-β-D-arabinofuranosyl)uracil with a range of nucleophiles.

Possible conjugation reactions with sulfur-modified nucleotides include disulphide formation (F. Gauthier et al. Conjugation of Small Molecules to RNA Using a Reducible Disulfide Linker Attached at the 2'-OH Position through a Carbamate Function, European J. Org. Chem. 2019 (2019) 5636-5645. https://doi.org/10.1002/ejoc.201900740.), thiol-ene radical reaction (A. B. Lowe, Thiol-ene "click" reactions and recent applications in polymer and materials synthesis: A first update, Polym. Chem. 5 (2014) 4820-4870. https://doi.org/10.1039/c4py00339j.), thiol-yne radical reaction ([1] A. B. Lowe, Thiol-yne 'click'/coupling chemistry and recent applications in polymer and materials synthesis and modification, Polymer (Guildf). 55 (2014) 5517-5549. https://doi.org/10.1016/j.polymer.2014.08.015.), thiol-Michael addition (R. M. Hensarling, Thiol-isocyanate "click" reactions: Rapid development of functional polymeric surfaces, Polym. Chem. 2 (2011) 88-90. https://doi.org/10.1039/c0py00292e.), thiol-isocyanate (R. M. Hensarling, Thiol-isocyanate "click" reactions: Rapid development of functional polymeric surfaces, Polym. Chem. 2 (2011) 88-90. https://doi.org/10.1039/c0py00292e.) or thiol-epoxide ring opening (M. C. Stuparu, Thiol-epoxy "click" chemistry: Application in preparation and postpolymerization modification of polymers, J. Polym. Sci. Part A Polym. Chem. 54 (2016) 3057-3070. https://doi.org/10.1002/pola.28195.) (FIG. 9).

Nanoparticles may contain any amine moiety. This could be via a chemically or enzymatically modified nucleotide or phosphoramidite. Amine-modified nucleotides may be modified on the sugar, at the 2' position, or on the nucleotide base. For example, and without limitation, the sugar-modified nucleic acid nanoparticles may contain one or more of (2R,3R,4R,5R)-5-(6-amino-9H-purin-9-yl)-4-(2-aminoethoxy)-2-(hydroxymethyl)tetrahydrofuran-3-ol (amino A), 4-amino-1-(2R,3R,4R,5R)-3-(2-aminoethoxy)-4-hydroxy-5-(hydroxymethyl)tetrahydrofuran-2-yl)pyrimidin-2(1H)-one (amino C), 2-amino-9-((2R,3R,4R,5R)-3-(2-aminoethoxy)-4-hydroxy-5-(hydroxymethyl)tetrahydrofuran-2-yl)-1,9-dihydro-6H-purin-6-one (amino G), 1-((2R,3R,4R,5R)-3-(2-aminoethoxy)-4-hydroxy-5-(hydroxymethyl) tetrahydrofuran-2-yl)pyrimidine-2,4(1H,3H)-dione. Any number of methylene extensions are possible between the sugar and the amino group. Ethylene glycol units may also be used instead of methylene (FIG. 5).

Thionyl tetrafluoride (SON has emerged as a highly biocompatible click chemistry handle. Sharpless and coworkers recently developed a range of combinatorial DNA tags with this handle (F. Liu et al. Biocompatible SuFEx Click Chemistry: Thionyl Tetrafluoride (SOF 4)-Derived Connective Hubs for Bioconjugation to DNA and Proteins, Angew. Chemie—Int. Ed. (2019) 8029-8033. https://doi.org/10.1002/anie.201902489.). For the current invention, any nucleophile-modified oligonucleotide strand will react with an $SOF_4$ group, hence any SuFEx modification will take place on the substrate to be attached to the construct.

Thionyl tetrafluoride handle may be conjugated to a molecule with another click functionality.

In addition to conventional click chemistries, direct covalent attachment may be achieved by, for example, thiol arylation using palladium complexes (E. V. Vinogradova et al., Organometallic palladium reagents for cysteine bioconjugation, Nature. 526 (2015) 687-691. https://doi.org/10.1038/nature15739.), oxime ligation (J. Y. Axup et al. Synthesis of site-specific antibody-drug conjugates using unnatural amino acids, Proc. Natl. Acad. Sci. U.S.A 109 (2012) 16101-16106. https://doi.org/10.1073/pnas.1211023109.), hydrazone formation (D. K. Kölmel et al., Oximes and Hydrazones in Bioconjugation: Mechanism and Catalysis, Chem. Rev. 117 (2017) 10358-10376. https://doi.org/10.1021/acs.chemrev.7b00090.) or via a cathepsin B-responsive linker (F. Bryden et al., Impact of cathepsin B-sensitive triggers and hydrophilic linkers on: In vitro efficacy of novel site-specific antibody-drug conjugates, Org. Biomol. Chem. 16 (2018) 1882-1889. https://doi.org/10.1039/c7ob02780j.).

Use of Click Chemistry to Generate Covalently-Stabilized Structures

Click chemistry has been widely used as a ligation strategy in the formation of oligonucleotides; the materials generated by replacing the phosphate backbone with a triazole, for example, have high thermodynamic stability and increased resistance to enzymatic degradation (A. H. El-Sagheer et al. Click nucleic acid ligation: Applications in biology and nanotechnology, Acc. Chem. Res. 45 (2012) 1258-1267. https://doi.org/10.1021/ar200321n.). The current invention utilises this principle to confer higher stability to the nucleic acid nanoparticle.

Figure 2:
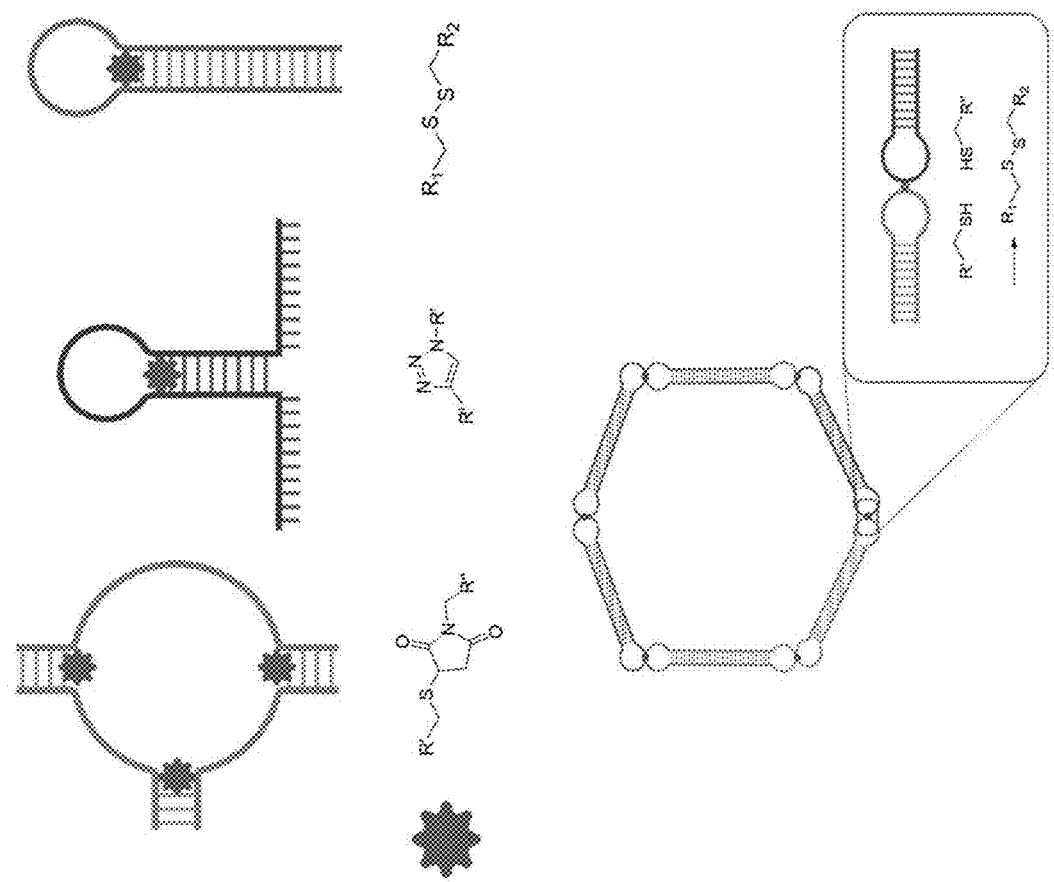
FIG. 2 is a schematic showing the use of bioorthogonal click chemistry to stabilise nucleic acid nanoparticles.
Figure 3:
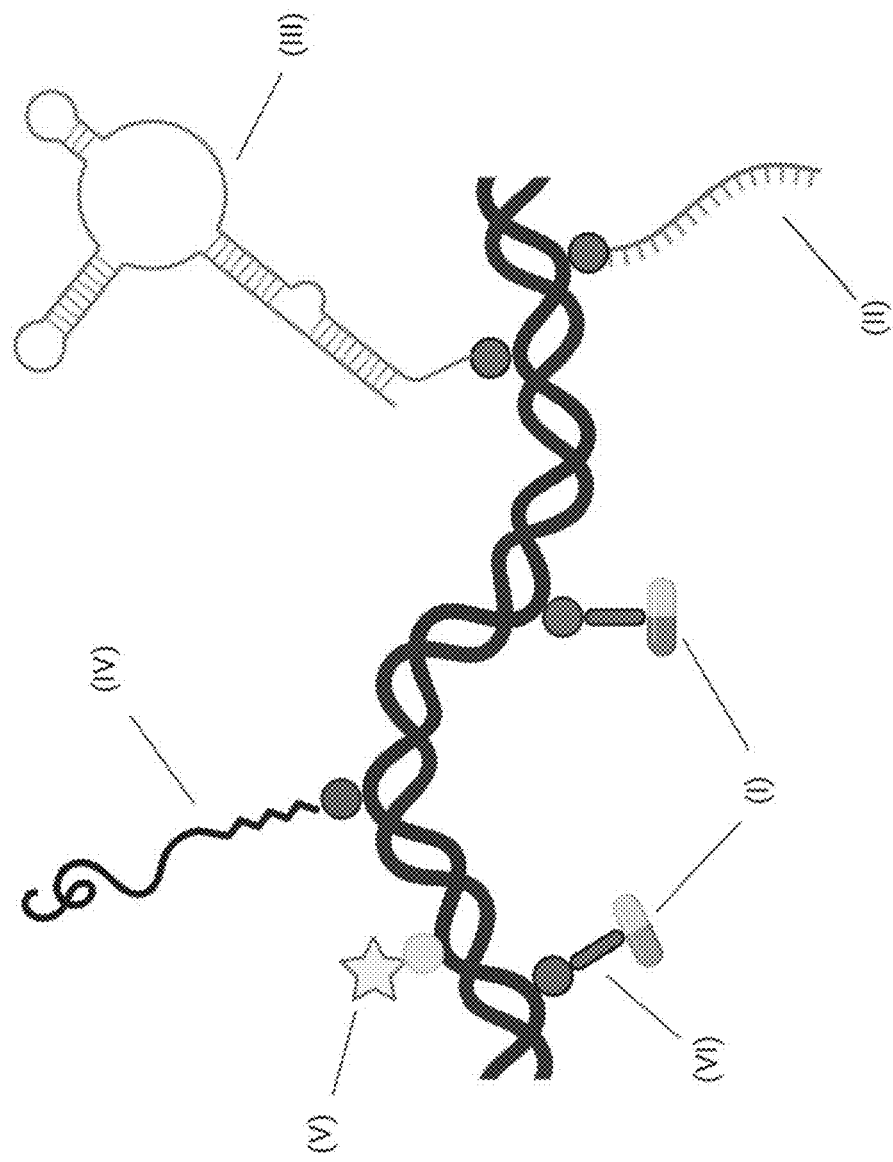
FIG. 3 is a schematic showing double-stranded RNA as a delivery vehicle without the requirement for additional assembly into nanostructures such as hexamers. Various cargo molecules are shown to be directly attached, including cytotoxic drugs (I), RNA/siRNA (II), targeting moieties (e.g. aptamers) (III), endosomal escape molecules (IV) and fluorophores (V). These moieties may or may not be attached via a stimuli-responsive linker (VI).
Figure 4:
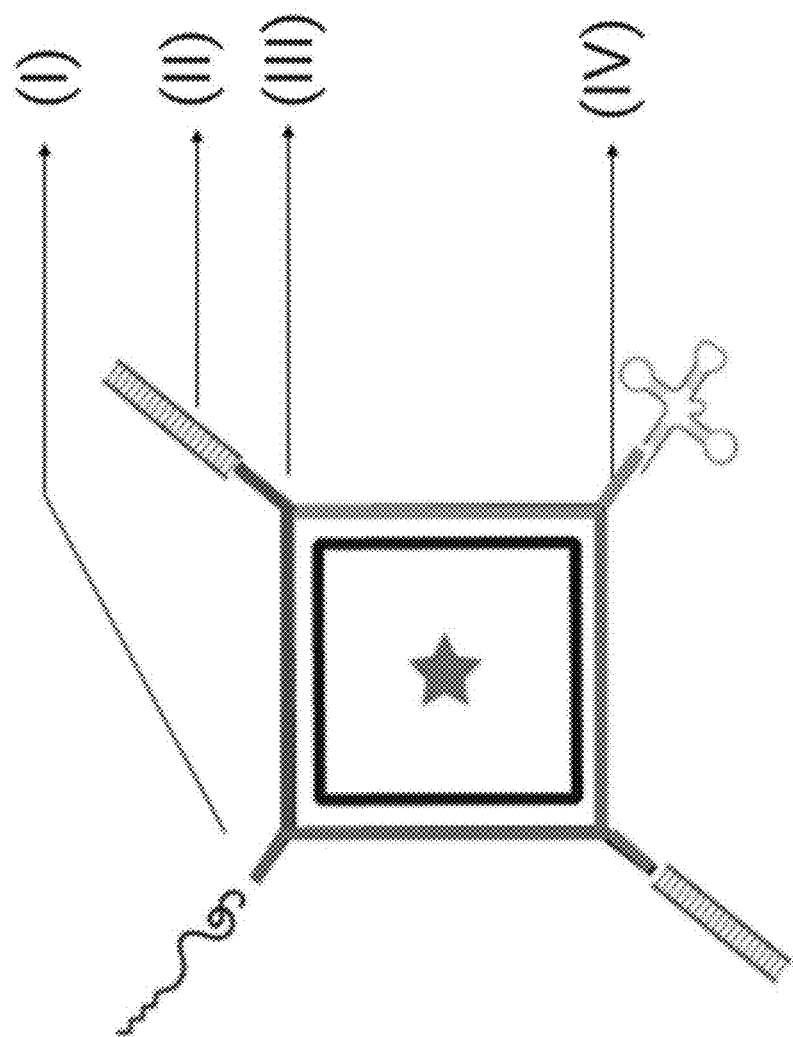
FIG. 4 is a schematic showing a tetrameric nucleic acid nanoparticle with cargo conjugated via bioorthogonal click chemistry. Click chemistries shown include alkyne-azide (I) of an siRNA (II) and disulphide attachments (III). Hybridization of targeting molecules such as aptamers (IV) is also possible.

Nanoparticles may contain click moieties at pseudoknots, kissing hairpins, and hairpin loops, 3-way and 4-way junctions (FIG. 2). These modifications may also be interspersed throughout the duplex and may be present in place of the phosphate backbone at various points throughout each nucleic acid strand.

Hairpins and other circular higher order structures might also be formed via click chemistry. The 1,3-dipolar cycloaddition between an alkyne and azide to generate a hairpin stem composed of G-C and C-G base pairs has been shown in the art (A. Kiliszek et al. Stabilization of RNA hairpins using non-nucleotide linkers and circularization, Nucleic Acids Res. 45 (2017) 4-12. https://doi.org/10.1093/nar/gkx122.). This methodology may be used in the present invention to generate a circular structure. On-resin synthesis of oligonucleotides might also be used to generate cyclic structures (J. Lietard et al. New strategies for cyclization and bicyclization of oligonucleotides by click chemistry assisted by microwaves, J. Org. Chem. 73 (2008) 191-200. https://doi.org/10.1021/jo702177c.).

Method for Functionalized Nucleotide Production 2,2'-Anhydro-1-(β-D-arabinofuranosyl)uracil has been used extensively as a key intermediate in nucleoside chemistry (A. Miah et al., 2',3'-Anhydrouridine. A useful synthetic intermediate, J. Chem. Soc.—Perkin Trans. 1. (1998) 3277-3283. https://doi.org/10.1039/a803563f.) and various routes towards its synthesis have been shown in the art (EP1992632A1). The nucleophilic ring opening of this intermediate allows for the attachment of many different functional groups, and it is particularly useful in the design and development of the universal nucleic acid nanoparticle. This reaction is highly inefficient and requires the use of harsh conditions (>120° C., multiple equivalents of strong Lewis acids).

To overcome these limitations, 2,2'-Anhydro-1-(β-n-arabinofuranosyl)uracil is treated with one or more of the following reagents: dimethylacetamide (DMA), dioxane, hexamethylphosphoramide (HMPA), DMF, dimethylsulfoxide (DMSO), N,N'-dimethylpropyleneurea (DMPU), 1,3-dimethyl-2-imidazolidinone (DMI), tetrahydrofuran (THF) and combinations thereof; temperature: room temperature to 160° C.; base (including and without limitation): barium tert-butoxide, benzyltrimethylammonium hydroxide, 2-tert-butylimino-2-diethylamino-1,3-dimethyl-perhydro-1,3,2-diazaphosphorine, n-butyllithium, sec-butyllithium, tert-butyllithium, Dabco®, N,N-diisopropylmethylamine, dimethylamine, 4-(dimethylamino)pyridine, ethylamine, N-ethyldiisopropylamine, lithium bis(trimethylsilyl)amide, lithium tert-butoxide, lithium dicyclohexylamide, lithium diethylamide, lithium diisopropylamide, lithium dimethylamide, lithium ethoxide, lithium isopropoxide, lithium methoxide, lithium 2,2,6,6-tetramethylpiperidide, magnesium bis(hexamethyldisilazide), methylamine, methyllithium, morpholine, piperidine, potassium bis(trimethylsilyl)amide, potassium tert-butoxide, potassium ethoxide, potassium methoxide, triethylamine; Lewis acid (including and without limitation): aluminium bromide, aluminium chloride, aluminium isopropoxide, boron trichloride (and its various complexes), boron trifluoride (and its various complexes), dicyclohexylboron, iron (III) bromide, iron (III) chloride, montmorillonite K10 & K30, tin (IV) chloride, titanium (IV) chloride, titanium (IV) isopropoxide, titanium tetrachloride.

FlICk Chemistry

The fluorescent isoindole crosslink (FlICk) reaction has recently emerged as a valuable tool to stabilise the secondary structure of peptides (M. Todorovic et al., Fluorescent Isoindole Crosslink (FlICk) Chemistry: A Rapid, User-friendly Stapling Reaction, Angew. Chemie Int. Ed. (2019) 14258-14262. https://doi.org/10.1002/anie.201909719.). In this reaction, ortho-phthalaldehyde is added to a macromolecule with free amine and thiol groups and the resultant condensation reaction affords a fluorescent isoindole. The isoindole group can then stabilise that peptide secondary structure and also generates a fluorescent signal that can be used for in vitro and in vivo studies.

Figure 11:
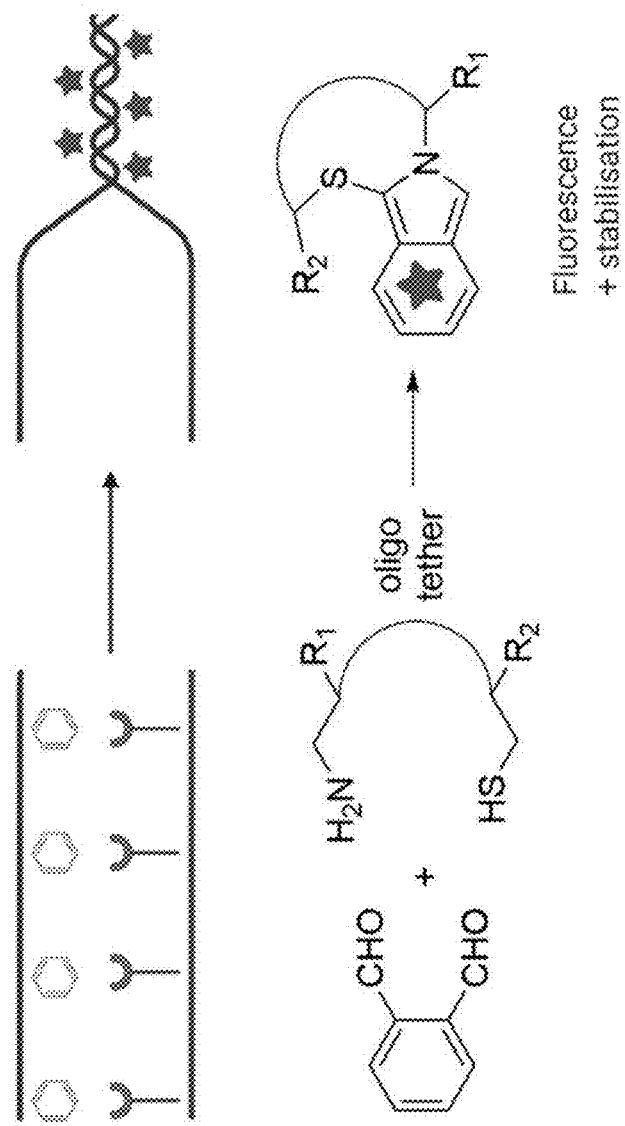
FIG. 11 is a schematic summarising fluorescent isoindole click (FlICk) chemistry as applied to nucleotide nanoparticles. Adjacent amines and thiols are treated with orthophthalaldehyde and the resultant condensation reaction generates a detectable fluorophore.

Such a reaction will allow for both stabilisation of the nucleic acid nanoparticle construct and will provide in-built fluorescence for biological studies (FIG. 11). Fluorescent isoindole dyes are known in the art and are described, for example, in U.S. Pat. No. 9,412,955B2 and WO 2012/022945. This methodology is advantageous over other stapling methods as a fluorophore is generated in addition to strand stabilisation. It also negates the use of attaching an additional fluorescent moiety.

Figure 12:
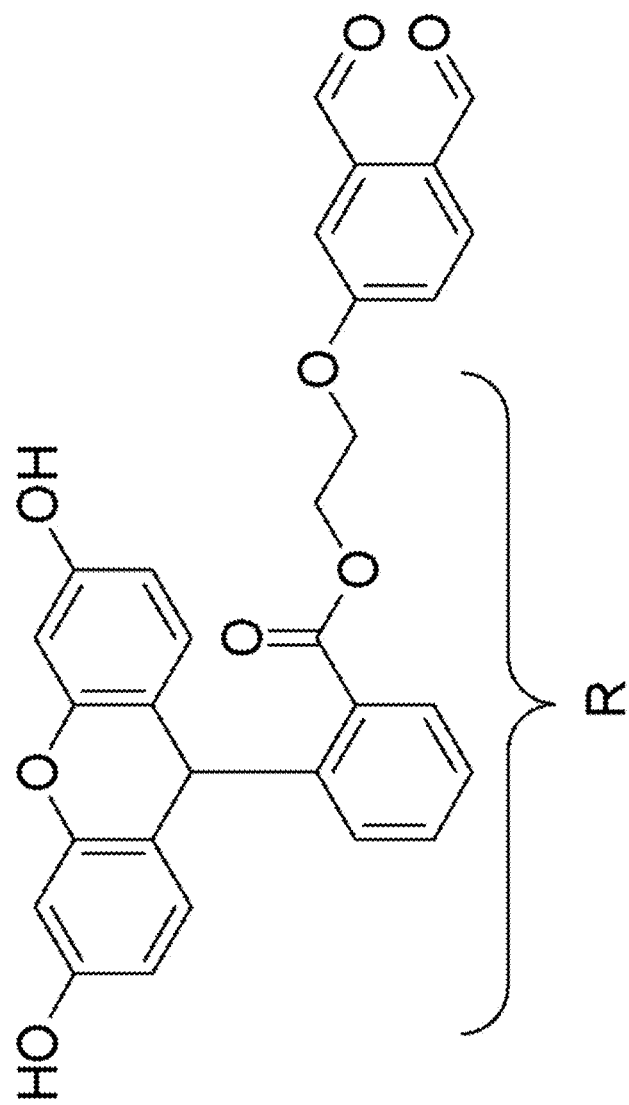
FIG. 12 is a schematic showing the conjugation of a fluorophore (rhodamine B) to ortho-phthalaldehyde to increase its fluorescent ability.
Figure 12:
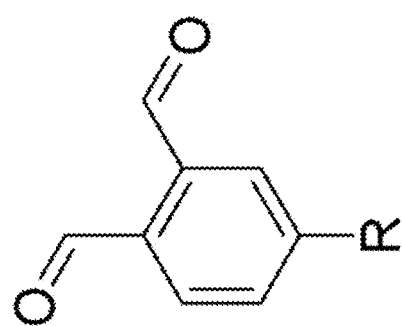

To generate the fluorescent moiety, a thiol-containing nucleotide needs to be placed near an adjacent nucleotide with an amine modification. These could be nucleotides on the same oligonucleotide strand, or on opposing stands in a duplex. These might also be part of a kissing stem-loop. Assembled nucleic acid nanoparticle construct will then be treated with ortho-phthalaldehyde or analogues thereof.

ortho-Phthalaldehyde analogues might include the dialdehyde conjugated to a known fluorescent dye. These could include, but are not limited to, fluorescein, Hoechst 33342, BODIPY-FL, Cascade Yellow, 4-MU, pyrene, BODIPY-TR, Cy3, Cy5, $SRh_{101}$, $Rh_{110}$, resofurin, DAPI, or NBD (FIG. 12).

FlICk stapling will utilise amine- and thiol-modified nucleotides. In addition, the composition may also incorporate fluorescent tag sites; novel thiol-amine based nucleotides whereby the thiol and amine groups are within 4-5 bonds apart on the same molecule. An example of which is given below as 1-((2R,3R,4R,5R)-3-(3-amino-2-(mercaptomethyl)propoxy)-4-hydroxy-5-(hydroxymethyl)tetrahydrofuran-2-yl)pyrimidine-2,4(1H,3H)-dione.

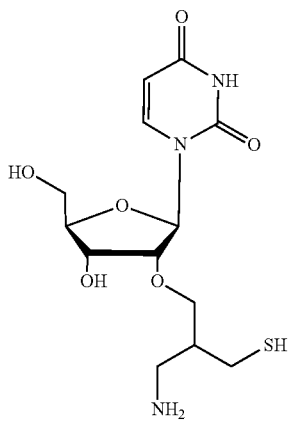

Functions of Attached Cargo

The modifications outlined above will allow for the attachment of various functionalities. These include, but are not limited to, cytotoxic drugs and other therapeutics, mRNA origami, mediators of endosomal escape and moieties to manipulate the protein corona. These entities might be small molecules, peptides, proteins, oligonucleotides, or combinations thereof.

Cellular Entry

Intracellular targeting of cargo molecules is a key challenge in developing compositions that use nucleic acid nanoparticles to deliver therapeutic cargo. The invention addresses this problem specifically by providing compositions that include nanoparticles that have one or more cell entry mechanisms to improve the therapeutic efficacy of cargo molecules and is an extension of the work carried out in USPTO 62/894,390.

Endocytosis involves the budding of vesicles from the plasma membrane and routing of the vesicles to the lysosome, where the endocytosed cargo is degraded. The pH within endosomes decreases en route to the lysosome, and the acidic environment of the lysosome supports degradation of macromolecules. Consequently, the use of pH-sensitive linkers to join cargo molecules to nucleic acid nanoparticles allows secure attachment in the neutral pH of the circulating blood or other extracellular milieus but release of the cargo from the nanoparticle in the vesicles endocytic pathway. See, e.g., Gujrati M, et al., Multifunctional pH-Sensitive Amino Lipids for siRNA Delivery, Bioconjug Chem. 2016 Jan. 20; 27(1):19-35, doi: 10.1021/acs.bioconjchem.5b00538, the contents of which are incorporated herein by reference.

One approach to promote endosomal escape is to modify nucleotides and/or conjugate small molecules having particular properties to nucleotides in an RNA nanoparticle. The modification or addition may be at the 2' position of a nucleotide, the base of nucleotide, or the phosphorus-containing backbone. For example and without limitations, the conjugates may be or include the following: 2'-O-imidazolacetyl modification, 2'-O—[N,N-dimethylaminoethoxy] ethyl modification, alkyl-phosphorothioates, amines (e.g., a combination of primary, secondary, tertiary, and imidazole amines with different pKa values), cholesterol lipids, endosomal enhancing domains, fluorinated alkyne chains, guanidinobutylphosphoramidate, hydrophobic groups, positively-charged moieties, triethylene glycol, and trifluormethylquinoline. Such modifications have been used to facilitate endosomal escape of other types of macromolecules. For example, hydrophobic amino acids such as tryptophan or phenylalanine can enhance endosomal escape due to the interaction and pore formation with the endosomal membrane. Amines, including combinations of primary, secondary, tertiary, and imidazole amines with different pKa values, are protonated at pH 5-7 and promote endosomal escape by rupturing the particle membrane and releasing the cargo into the cytosol. Many of the aforementioned strategies to promote endosomal escape are described in, for example, Liu D and Auguste D T, Cancer targeted therapeutics: From molecules to drug delivery vehicles, J Control Release. 2015 Dec. 10; 219:632-643. doi: 10.1016/j.jconrel.2015.08.041; Singh D D, et al., CRISPR/Cas9 guided genome and epigenome engineering and its therapeutic applications in immune mediated diseases, Semin Cell Dev Biol. 2019 Jun. 19. pii: S1084-9521(18)30111-3. doi: 10.1016/j.semcdb.2019.05.007; and Lonn P, et al., Enhancing Endosomal Escape for Intracellular Delivery of Macromolecular Biologic Therapeutics, Sci Rep. 2016 Sep. 8; 6:32301. doi: 10.1038/srep32301; Gujrati M, et al., Multifunctional pH-Sensitive Amino Lipids for siRNA Delivery, Bioconjug Chem. 2016 Jan. 20; 27(1):19-35, doi: 10.1021/acs.bioconjchem.5b00538; Deglane, G., et al., Impact of the guanidinium group on hybridization and cellular uptake of cationic oligonucleotides, Chembiochem, 2006 7(4): p. 684-92, DOI: 10.1002/cbic.200500433; Prhavc, M., et al., 2'-O-[2-[2-(N,N-dimethylamino)ethoxy]ethyl] modified oligonucleotides: symbiosis of charge interaction factors and stereoelectronic effects, Org Lett, 2003. 5(12): p. 2017-20, DOI: 10.1021/o10340991; Shen, W., et al., Journal of Materials Chemistry B, 2016. 4(39): p. 6468-6474; and Kurrikoff, K, et al., Recent in vivo advances in cell-penetrating peptide-assisted drug delivery, Expert Opin Drug Deliv, 2016, 13(3): p. 373-87, DOI: 10.1517/17425247.2016.1125879; Gilleron J, et al., Image-based analysis of lipid nanoparticle-mediated siRNA delivery, intracellular trafficking and endosomal escape, Nat Biotechnol. 2013 July; 31(7):638-46. doi: 10.1038/nbt.2612, the contents of each of which are incorporated herein by reference.

One or more of the following molecules, which facilitate cellular entry, either via endocytosis or otherwise, may be conjugated to a nucleic acid in the nanoparticle: UN 7938, trifluormethylquinoline, UN 2383, CPW1F10, CBN40D12, ADD41 D14, ADD29 F15, CBN40H10, CBN40 K7, BADGE, CBN35 C21, CBNO53 M19, CPW1-J18, methoxychlor, CPW097 A20, LOMATIN, guanabenz, UNC7938, CPM2, 3-(perfluorobut-1-yl)-1-hydroxypropyl, 3-(perfluorohex-1-yl)-1-hydroxypropyl, 3-deazapteridine, α-tocopherol, verapamil, nigericin, 3,3,4,4,5,5,6,6,7,7,8,8,9,9,9-pentadecafluorononan-2-one, or N1-ethyl-N1-methyl-N2-(7-(trifluoromethyl)quinolin-4-yl)ethane-1,2-diamine, TfR-T12, melittin, HA2, folate, octa-arginine conjugate stearyl-R8, a locked nucleic acid, a peptide transduction domain, and a fluorinated or perfluorinated compound.

In some embodiments, the nucleic acid nanoparticle has a guanidinobutylphosphoramidate, as shown below:

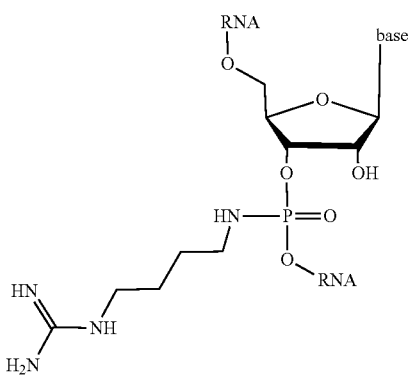

In some embodiments, the nucleic acid nanoparticle has a 2'-O-imidazolacetyl modification, as shown below:

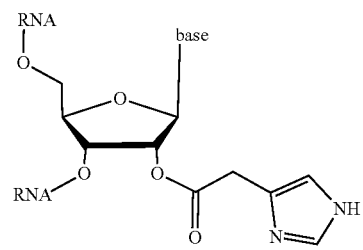

In some embodiments, the nucleic acid nanoparticle has a 2'-O—[N,N-dimethylamino)ethoxy]ethyl modification, as shown below:

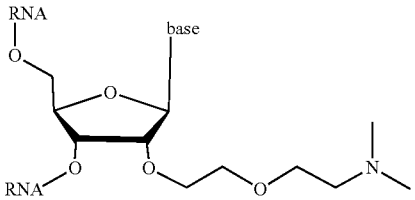

In some embodiments, the nucleic acid nanoparticle has a dsDNA with cholesterol lipid conjugated via a triethylene glycol (TEG) linker attached as an arm on the core NP.

In some embodiments, the nucleic acid nanoparticle has cholesterol attached directly to a molecule of RNA.

In some embodiments, the nucleic acid nanoparticle has a hydrophobic belt of alkyl-phosphorothioates (PPT) attached to a dsDNA or dsRNA.

In some embodiments, the nucleic acid nanoparticle has a component having a pKa of from about 5.0 to about 7.0.

In some embodiments, the nucleic acid nanoparticle has a hydrophobic component.

In some embodiments, the nucleic acid nanoparticle has a component that is positively-charged at a pH of about 7.0.

In some embodiments, the nucleic acid nanoparticle has a peptide. The peptide may include one or more of the sequences in Table 1.

TABLE 1 peptide sequences to mediate endosomal escape

| SEQ ID NO. | Sequence |
|---|---|
| 1 | GWWG |
| 2 | CHGWWG |
| 3 | CHGWWGLLL |
| 4 | GWWGLLL |
| 5 | CGWWGLLL |
| 6 | HCGWWGLLL |
| 7 | HGWWGLLL |
| 8 | CGWWG |
| 9 | HGWWG |
| 10 | CGFWFGLLL |
| 11 | GFWFGLLL |
| 12 | HCGFWFGLLL |
| 13 | HGFWFGLLL |
| 14 | CGFWFG |
| 15 | HGFWFG |
| 16 | GFWFG |
| 17 | HCGFWFG |
| 18 | HCGWWG |
| 19 | CLLL |
| 20 | LLL |
| 21 | HCLLL |
| 22 | HLL |
| 23 | CGFWFGLLL |
| 24 | HGFWFGLLL |
| 25 | CHGFWFGLLL |
| 26 | HCGFWFGLLL |
| 27 | GFWFGLLL |
| 28 | GFWFG |
| 29 | CGFWFG |
| 30 | CHGFWFG |
| 31 | HCGFWFG |
| 32 | HGFWFG |
| 33 | GWYWMDL |
| 34 | CGWYWMDL |
| 35 | HGWYWMDL |
| 36 | HCGWYWMDL |
| 37 | CHGWYWMDL |
| 38 | CGWYWMDLLL |

TABLE 1-continued peptide sequences to mediate endosomal escape

| SEQ ID NO. | Sequence |
|---|---|
| 39 | HCGWYWMDLLL |
| 40 | HGWYWMDLLL |
| 41 | CHGWYWMDLLL |
| 42 | GWYWMDLLL |
| 43 | FFLIPKG |
| 44 | CFFLIPKG |
| 45 | HCFFLIPKG |
| 46 | CHFFLIPKG |
| 47 | HFFLIPKG |
| 48 | FFLIPKGLLL |
| 49 | CFFLIPKGLLL |
| 50 | HCFFLIPKGLLL |
| 51 | CHFFLIPKGLLL |
| 52 | HFFLIPKGLLL |
| 53 | HYF |
| 54 | CHYF |
| 55 | HCHYF |
| 56 | CHHYF |
| 57 | HYFLLL |
| 58 | CHYFLLL |
| 59 | HHYFLLL |
| 60 | HCHYFLLL |

In some embodiments, the nucleic acid nanoparticle has a component that includes a hydrophobic moiety, a hydrophilic moiety, and a nucleotide attachment moiety. For example and without limitation, the component may have the following structure:

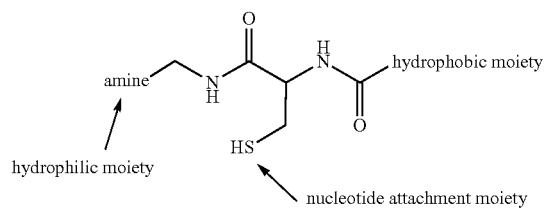

The hydrophilic moiety may include an amine. The hydrophilic moiety may be spermine, ethylenediamine, methylethylenediamine, ethylethylenediamine, imidazole, spermine-imidazole-4-imine, N-ethyl-N'-(3-dimethylaminopropyl)-guanidinyl ethylene imine, dimethylaminoethyl acrylate, amino vinyl ether, 4-imidazoleacetic acid, diethylaminopropylamide, sulfonamides (e.g. sulfadimethoxine sulfamethoxazole, sulfadiazine, sulfamethazine), amino ketals, N-2-hydroxylpropyltimehyl ammonium chloride, imidazole-4-imines, methyl-imidazoles, 2-(aminomethyl)imidazole, 4-(aminomethyl)imidazole, 4(5)-(Hydroxymethyl)imidazole, N-(2-aminoethyl)-3-((2-aminoethyl)(methyl)amino)propanamide, 2-(2-ethoxyethoxy)ethan-1-amine, bis(3-aminopropyl)amine, [N,N-dimethylamino)ethoxy]ethyl, N-(2-aminoethyl)-3-((2-aminoethyl)(ethyl)amino)propanamide, (N-(aminoethyl)carbamoyl)methyl, N-(2-((2-aminoethyl)amino)ethyl)acetamide 3,3'-((2-aminoethyl)azanediyl)bis(N-(2-aminoethyl)propanamide), guanidyl benzylamide, [3-(guanidinium)propyl], dimethylethanolamine, 1-(2,2-dimethyl-1,3-dioxolan-4-yl)-N,N-dimethylmethanamine, 2-(2,2-dimethyl-1,3-dioxolan-4-yl)-N,N-dimethylethan-1-amine, N-(2-((2-(2-aminoethoxy)propan-2-yl)oxy)ethyl)acetamide, aminobutyl, aminoethyl, 1-(2-aminoethyl)-3-(3-(dimethylamino)propyl)-2-ethylguanidine, 1-(3-amino-3-oxopropyl)-2,4,6-trimethylpyridin-1-ium, 1-(1,3-bis(carboxyoxy)propan-2-yl)-2,4,6-trimethylpyridin-1-ium, guanidinylethyl amine, ether hydroxyl triazole, or a β-aminoester.

The nucleotide attachment moiety may be cysteine.

The nucleic acid nanoparticle may promote cellular entry of the cargo molecule in a receptor independent-manner. The nucleic acid nanoparticle may promote endosomal escape of the cargo molecule in a receptor dependent-manner. The nucleic acid nanoparticle may contain a component that binds to a receptor in the cell. The component that binds to a receptor may be folate, TfR-T$_{12}$, or a hemagglutinin peptide.

The composition may contain any of the linkers described above.

Figure 13:
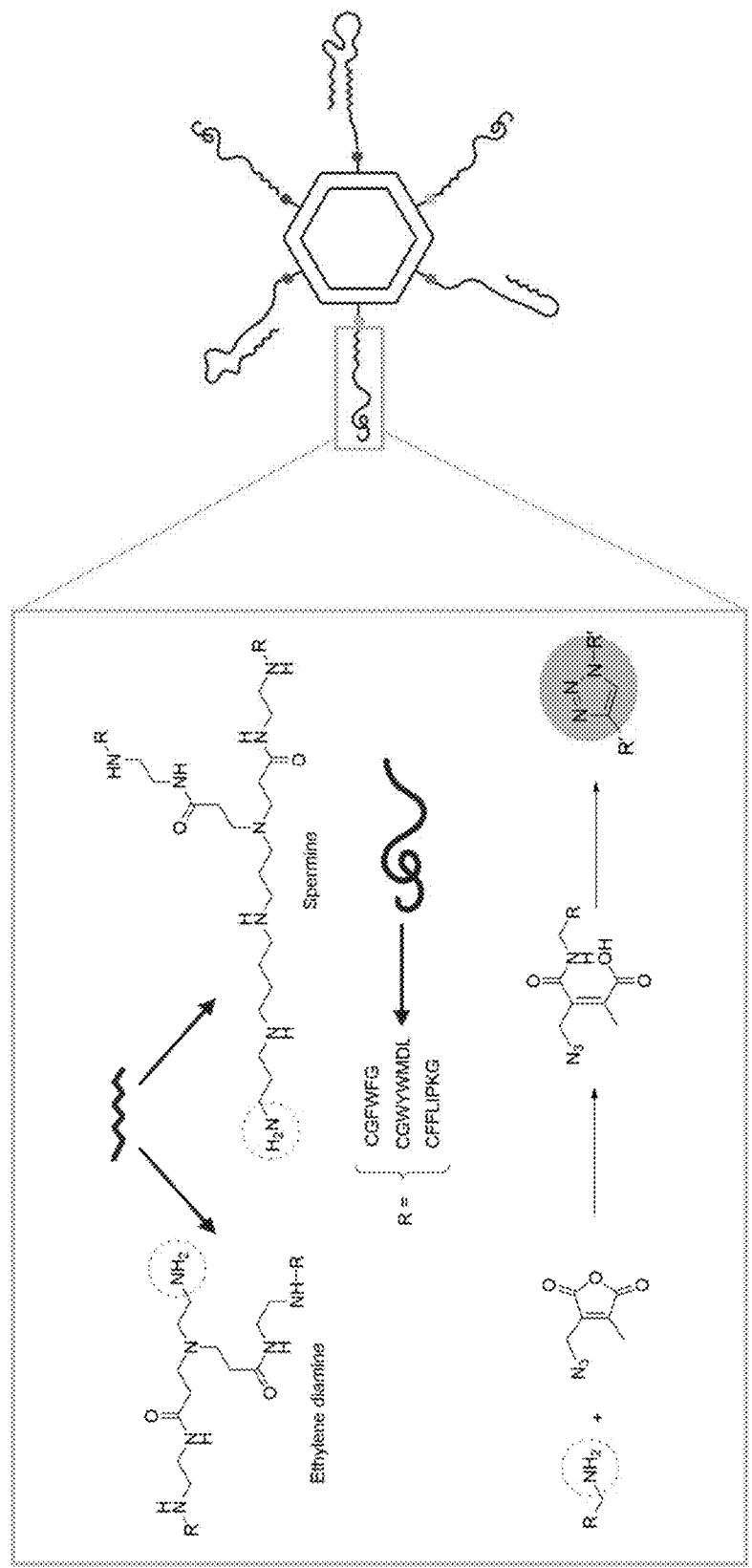
FIG. 13 is a schematic showing attachment of an endosomal escape-mediating peptide to a nucleic acid nanoparticle via an acid labile linker.

In some embodiments, the nucleic acid nanoparticle may be attached to a moiety that can increase cellular uptake via an azidomethyl-methylmaleic anhydride linker (FIG. 13) (K. Maier et al. J. Am. Chem. Soc. 134 (2012) 10169-10173. https://doi.org/10.1021/ja302705v.).

The composition may contain any of the nucleic acid nanoparticles described above. The nucleic acid nanoparticles may contain any of the modified nucleotides (and derivatives thereof) described above. Derivatives might include varied linker lengths at the 2' position, or various groups substituted on the bases.

In addition to the modifications described above, the following moieties (and derivatives thereof) might be attached to the nucleotide backbone directly:

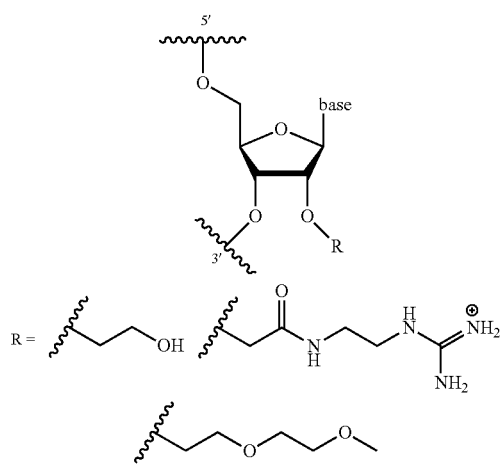

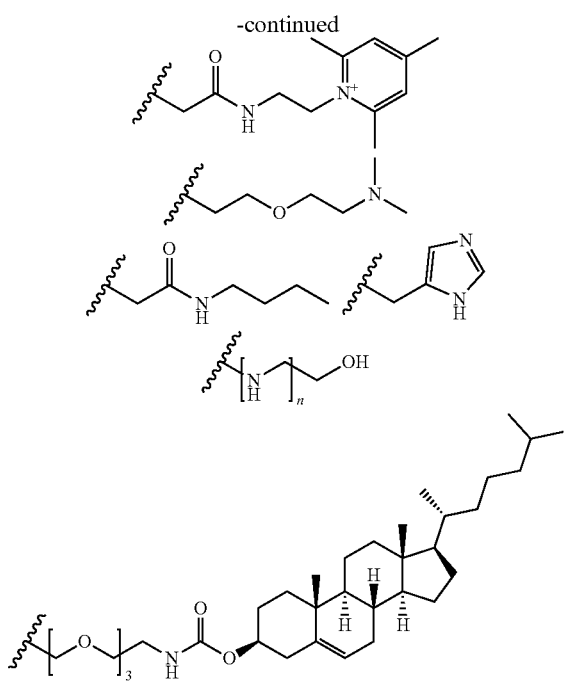

Derivatives might include varied linker lengths at the 2' position, or various groups substituted on the bases.

In addition to endosomal escape, the nucleic acid nanoparticle might be decorated with molecules that can dynamically interact with lipid bilayers. DNA nanopores have been shown to be able to perforate lipid bilayers and facilitate the transport of water-soluble molecules directly into cells (J. R. Burns et al., Membrane-spanning DNA nanopores with cytotoxic effect, Angew. Chemie—Int. Ed. 53 (2014) 12466-12470. https://doi.org/10.1002/anie.201405719.). These nanopores utilise anchored cholesterol groups; one cholesterol group per two DNA duplexes gives rise to high perforation activity (O. Birkholz et al., Multi-functional DNA nanostructures that puncture and remodel lipid membranes into hybrid materials, Nat. Commun. 9 (2018) 1521. https://doi.org/10.1038/s41467-018-02905-w.). The cholesterol moiety above could be conjugated to the nucleic acid nanoparticle and help mediate nanoparticle uptake.

Cytotoxic Nucleosides

Figure 14:
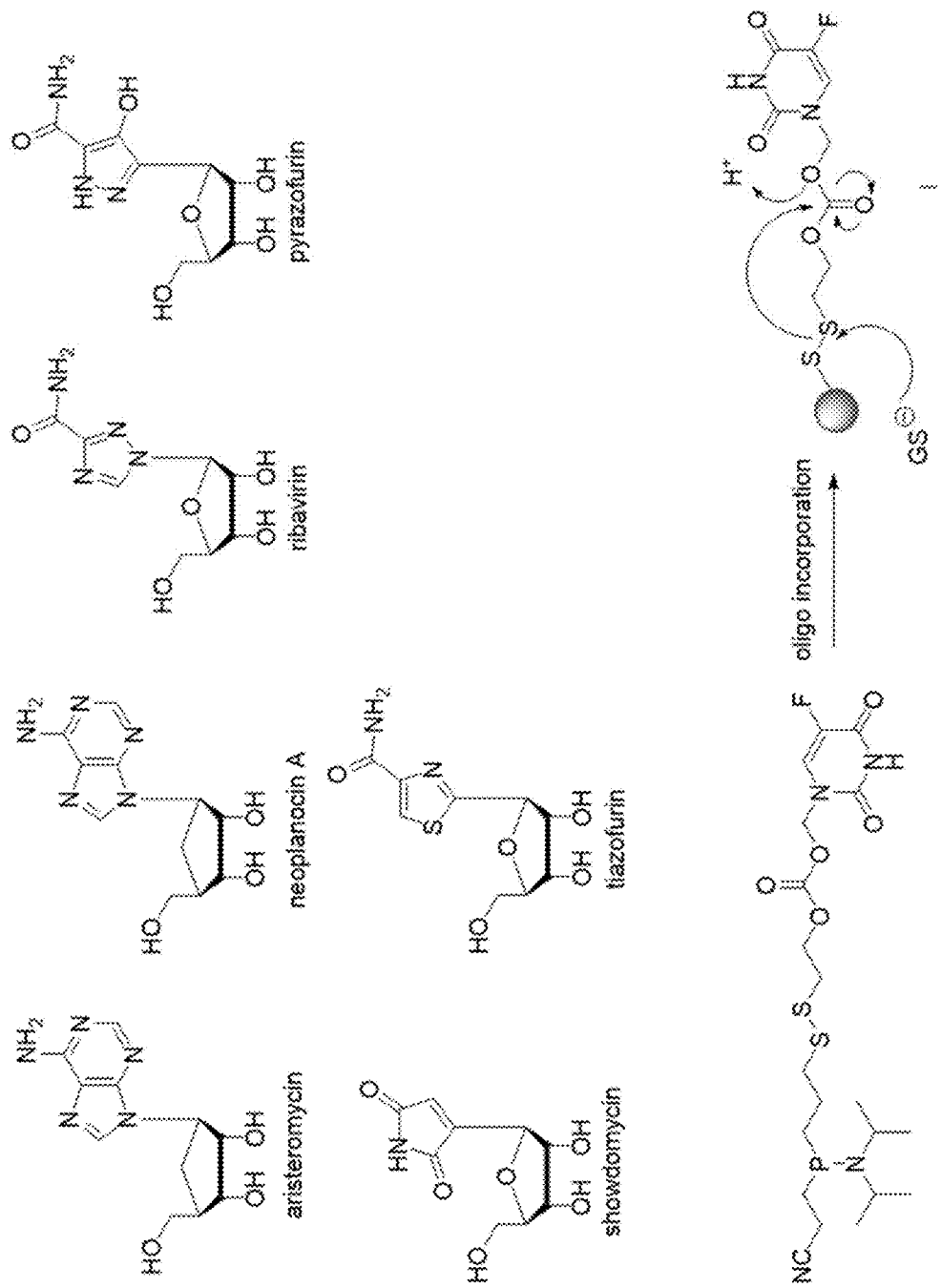
FIG. 14 is a schematic showing possible cytotoxic nucleotides to be incorporated into the nucleic acid nanoparticle. Stimuli-responsive properties can be incorporated through a disulphide linkage.

In addition to direct attachment of cytotoxic cargo, compositions of the present invention may include cytotoxic nucleosides embedded in the oligonucleotide chain or nucleic acid nanoparticle. These nucleosides may include, but are not limited to, aristomycin, neoplanocin A, ribavirin, pyrazofurin, cytarabine arabinoside (ara-C), gemcitabine, 2-CdA, showdomycin and tiazofurin and combinations thereof (FIG. 14). Currently used therapeutic nucleoside and nucleotide analogues exploit the same metabolic pathways as endogenous nucleosides or nucleotides and act as antimetabolites. Upon entering the cell the compounds are phosphorylated by a nucleoside kinase and/or a nucleoside monophosphate kinase, and then by further cellular kinases or phosphoribosyl transferases. This will often lead to compound activation. Many current cytotoxic nucleosides and nucleotides in the clinic are prone to resistance, therefore a combination approach within a nucleic acid delivery system may help circumvent this problem. These pronucleotide modifications are described in the art and are incorporated herein, by reference; B. Colin at al. Synthesis and biological evaluation of some phosphate triester derivatives of the anti-cancer drug AraC, Nucleic Acids Res. 17(18) (1989) 7195-7201. doi: 10.1093/nar/17.15.6065; C. McGuigan et al. Synthesis and biological evaluation of some phosphate triester derivatives of the anti-viral drug AraA, Nucleic Acids Res. 17(15) (1989) 6065-6075. doi: 10.1093/nar/17.15.6065; C. McGuigan et al. Aryl phosphate derivatives of AZT retain activity against HIV1 in cell lines which are resistant to the action of AZT, Antiviral Res. 17(4) (1992) 311-321. doi: 10.1016/0166-3542(92)90026-2; J. Balzarini et al. Mechanism of anti-HIV action of masked alaninyl d4T-MP derivatives, Proc. Natl. Acad. Sci. 93(14) (1996) 7295-7299. doi: 10.1073/pnas.93.14.7295; T.-F. Chou et al. Phosphoramidate pronucleotides: a comparison of the phosphoramidase substrate specificity of human and *Escherichia coli* histidine triad nucleotide binding proteins, Mol. Pharm. 4(2) (2007) 208-217. doi: 10.1021/mp060070y; T. W. Abraham et al. Synthesis and biological activity of aromatic amino acid phosphoramidates of 5-fluoro-2'-deoxyuridine and 1-β-arabinofuranosylcytosine: Evidence of phosphoramidase activity, J. Med. Chem. 39(23) (1996) 4569-4575. doi: 10.1021/jm9603680; J. Kim et al. Direct Measurement of Nucleoside Monophosphate Delivery from a Phosphoramidate Pronucleotide by Stable Isotope Labeling and LC—ESI-MS/MS, Mol. Pharm. 1(2) (2004) 102-1H. doi: 10.1021/mp0340338; C. Congiatu et al. Molecular modelling studies on the binding of some protides to the putative human phosphoramidase Hint1, Nucleosides Nucleotides Nucleic Acids 26(8-9) (2007) 1121-1124. doi: 10.1080/15257770701521656; P. Wipf et al. Synthesis of chemoreversible prodrugs of ara-C with variable time-release profiles. Biological evaluation of their apoptotic activity, Bioorg. Med. Chem. 4(10) (1996) 1585-1596. doi: 10.1016/0968-0896(96)00153-8; S. C. Tobias et al. Synthesis and biological evaluation of a cytarabine phosphoramidate prodrug, Mol. Pharm. 1(2) (2004) 112-116. doi: 10.1021/mp034019v.

The above modifications could be directly embedded within the oligonucleotides that form the nucleic acid nanoparticle.

The deoxycytidine analogue, ara-C, is prone to resistance mechanisms which reduce its efficacy. To counteract this, the elaidic acid ester of ara-C, known as elacytarabine, has been developed (A. C. Burke et al. Elacytarabine-lipid vector technology overcoming drug resistance in acute myeloid leukemia, Expert Opin. Invest. Drugs 20(12) (2011) 1707-1715. doi: 10.1517/13543784.2011.625009; S. O'brien, Elacytarabine has single-agent activity in patients with advanced acute myeloid leukaemia, Br. J. Haematol. 158(5) (2012) 581-588. doi: 10.1111/j.1365-2141.2012.09186.x). The present invention might include this modification either at the 5' terminus, 3' terminus or embedded within an oligonucleotide strand.

A common reason for the lack of cytotoxicity of many nucleoside compounds is their inability to be activated to the monophosphate level by a nucleoside kinase or other activating enzyme (J. D. Rose et al., Enhancement of nucleoside cytotoxicity through nucleotide prodrugs, J. Med. Chem. 45 (2002) 4505-4512. doi: 10.1021/jm020107s.). Thus, these nucleosides might be attached as pendant moieties as a monophosphate prodrug.

Cytotoxic nucleosides might be attached to a stimuli-responsive linker such as a glutathione-responsive disulphide linkage. Disulphide-containing phosphoramidites, such as 2-((3-((2-cyanoethyl)(diisopropylamino)phosphaneyl)propyl)disulfaneyl)ethyl methyl carbonate, may be incorporated at the 5' terminus, 3' terminus or embedded within an oligonucleotide strand. An example of a cytotoxic prodrug conjugated to this disulphide is 5-fluorouracil (FIG. 14).

Figure 15:
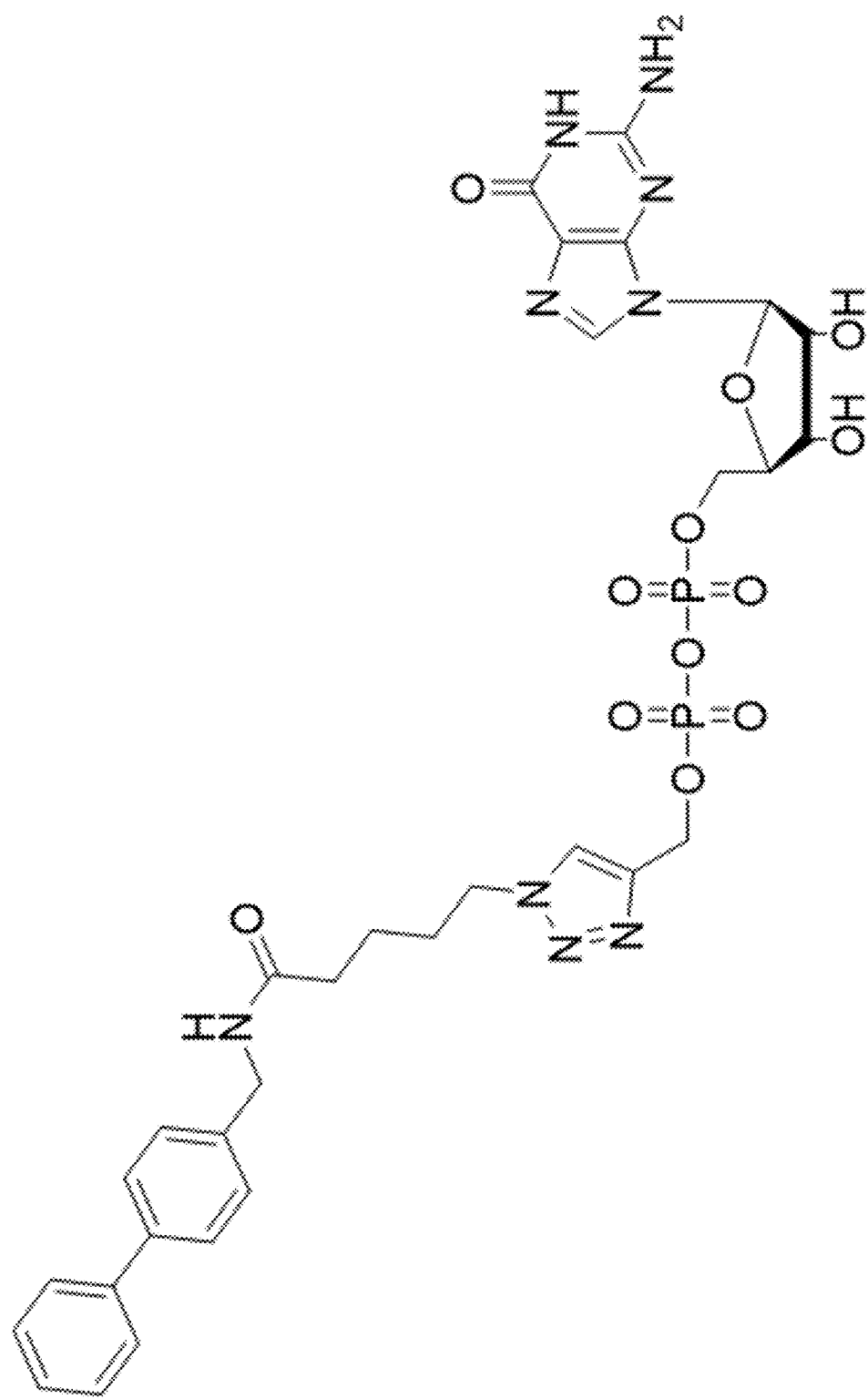
FIG. 15 is a schematic showing a cytotoxic nucleotide that can be generated via CuAAC.

Click chemistry might also be used to generate cytotoxic compounds. Fucosyltransferases (Fuc-T) are enzymes which catalyze the final glycosylation step in the biosynthesis and expression of many important saccharides. They have been associated with several pathologies, including cancer metastasis, and their inhibition with nucleotide-like compounds has been widely explored (L. V. Lee et al. A potent and highly selective inhibitor of human α-1,3-fucosyltransferase via click chemistry, J. Am. Chem. Soc. 125 (2003) 9588-9589. doi: 10.1021/ja0302836.). The present invention might include triazole-linked nucleic acids. An example of a cytotoxic compound generated via a triazole link includes N-([1,1'-biphenyl]-4-ylmethyl)-5-(4-(((3-(((2R,3S,4R,5R)-5-(2-amino-6-oxo-1,6-dihydro-9H-purin-9-yl)-3,4-dihydroxytetrahydrofuran-2-yl)methoxy)-1,1,3,3-tetraoxo-1$\lambda^6$,3$\lambda^6$-diphosphoxaneyl)oxy)methyl)-1H-1,2,3-triazol-1-yl)pentanamide (FIG. 15).

Figure 16:
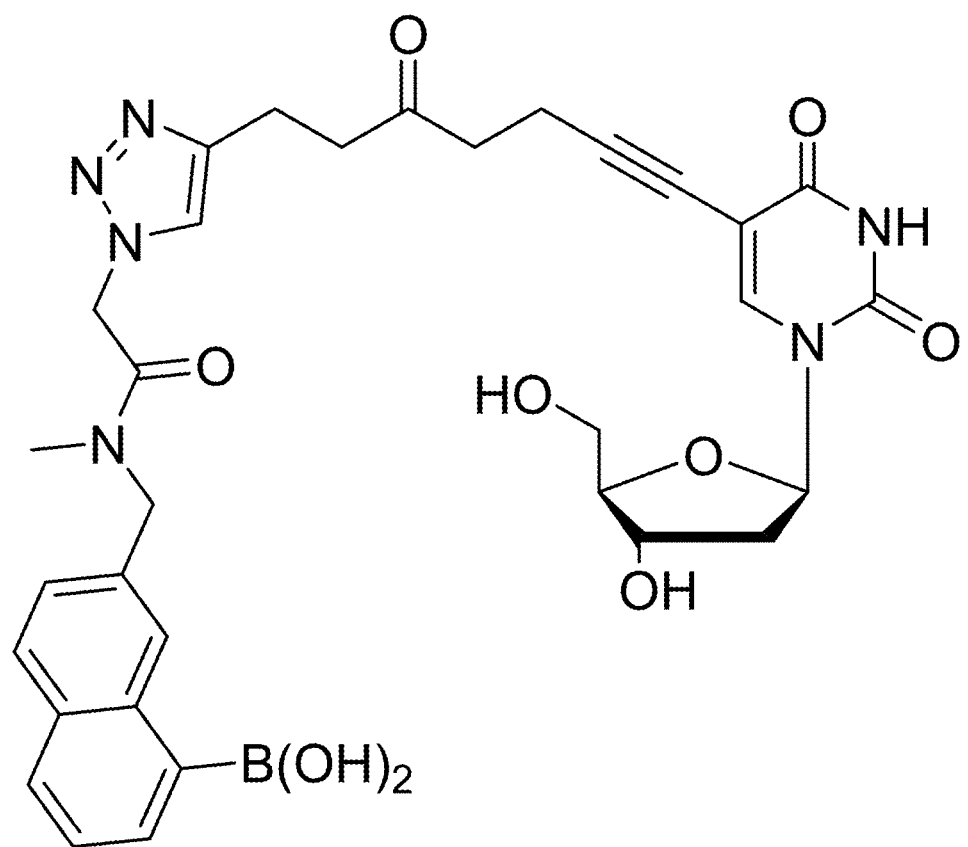
FIG. 16 is a boronic acid-based cytotoxic nucleotide.
Figure 17:
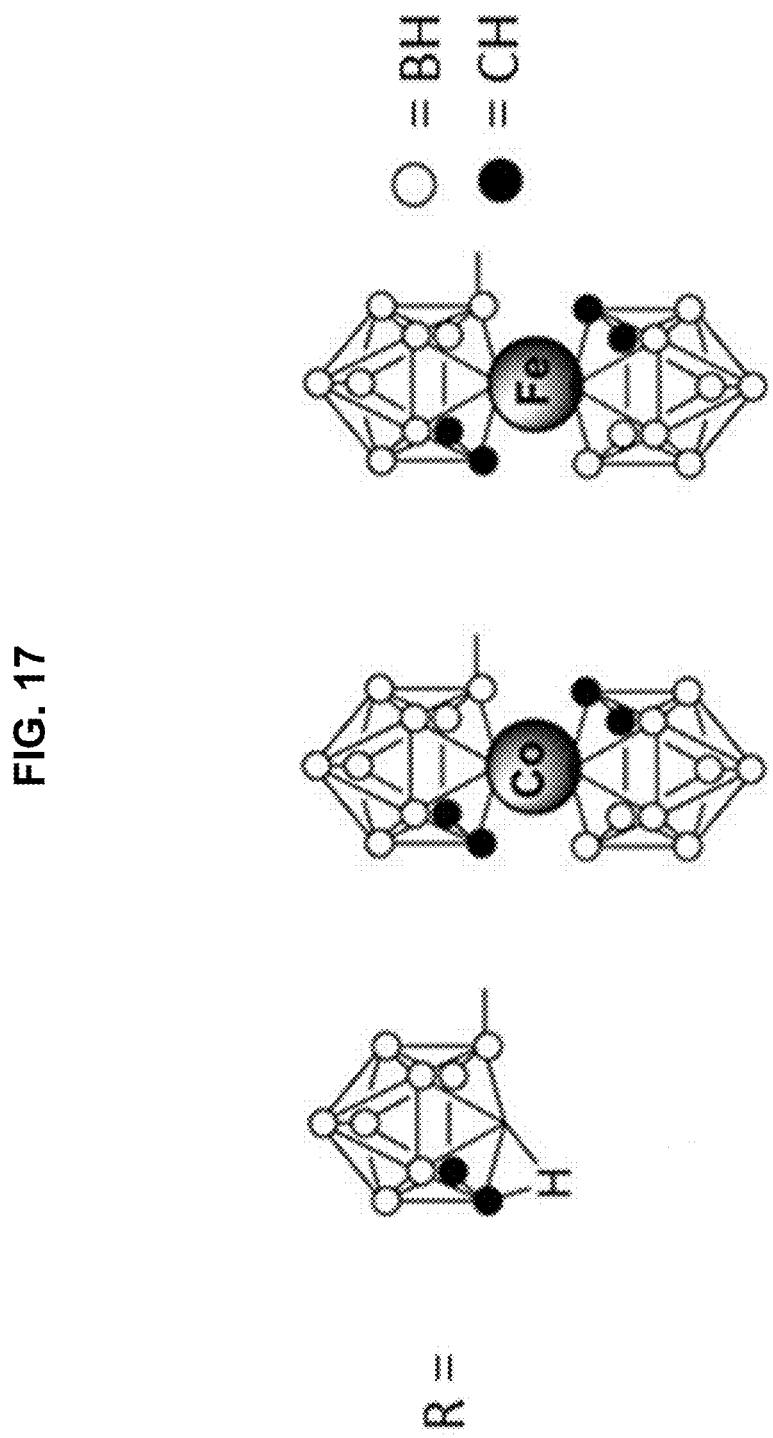
FIG. 17 is a schematic showing metal-based moieties that can be complexed to nucleic acids at the 5' terminus.

Nanoparticles may contain hybrids incorporated at the 5' or 3' end. These could include the boronic acid carrier described by Wang (FIG. 16) (N. Lin et al. Design and synthesis of boronic-acid-labeled thymidine triphosphate for incorporation into DNA, Nucleic Acids Res. 35(4) (2007) 1222-1229. doi:10.1093/nar/gkl1091; M. Li et al. Selecting aptamers for a glycoprotein through the incorporation of the boronic acid moiety, J. Am. Chem. Soc. 130(38) (2008) 12636-12638. doi:10.1021/ja801510d) and strand carborane or metal-carborane complexes (FIG. 17) (A. Olejniczak et al. 2'-deoxyadenosine bearing hydrophobic carborane pharmacophore, Nucleosides Nucleotides Nucleic Acids 26(10-12) (2007) 1611-1613. doi:10.1080/15257770701548733; B. A. Wojtczak et al. "Chemical Ligation": A versatile method for nucleoside modification with boron clusters, Chemistry 14(34) (2008) 10675-10682. doi:10.1002/chem.200801053).

Figure 19:
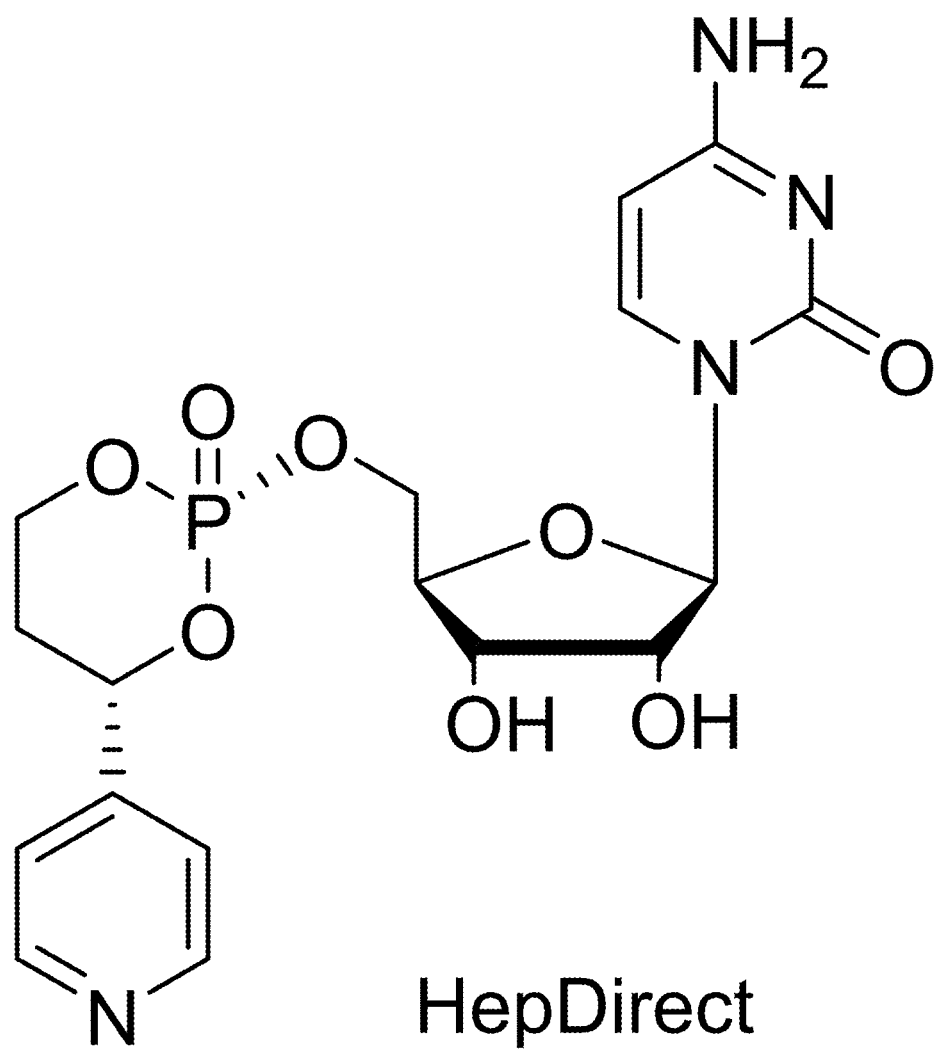
FIG. 19 is a schematic showing HepDirect, a cytotoxic compound that can be incorporated into a nucleic acid nanoparticle.
Figure 20:
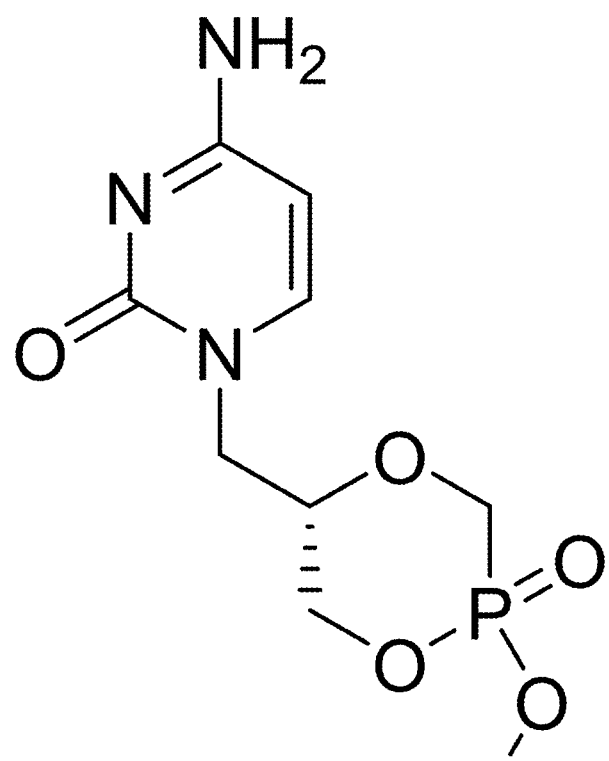
FIG. 20 is a schematic showing octadecyloxyethyl cyclic cidofovir, a cytotoxic compound that can be incorporated into a nucleic acid nanoparticle.

The nucleic acid nanoparticles may also bear any phosphate prodrugs incorporated either at the 5' terminus, 3' terminus or embedded within an oligonucleotide strand, or post-synthetically via click chemistry. Such modifications include bis(S-acyl-2-thioethyl) ester derivatives of 9-[2-(phosphonomethoxy)ethyl]adenine (PMEA) (FIG. 18) (S. Benzaria et al. Synthesis, in vitro antiviral evaluation, and stability studies of bis (S-acyl-2-thioethyl) ester derivatives of 9-[2-(phosphonomethoxy) ethyl] adenine (PMEA) as potential PMEA prodrugs with improved oral bioavailability, J. Med. Chem. 39(25) (1996) 4958-4965. doi:10.1021/jm9602890), cycloSal pro-nucleotides (C. Meier et al. Application of the cycloSal-prodrug approach for improving the biological potential of phosphorylated biomolecules, Antiviral Res. 71(2-3) (2006) 282-292. doi:10.1016/j.antiviral.2006.04.011; C. Meier et al. Chemistry and anti-herpes simplex virus type 1 evaluation of cyclo Sal-nucleotides of acyclic nucleoside analogues, Antivir. Chem. Chemother. 9(5) (1998) 389-402. doi:10.1177/095632029800900503; O. R. Ludek et al. Divergent synthesis and biological evaluation of carbocyclic α-, iso- and 3'-epi-nucleosides and their lipophilic nucleotide prodrugs, Synthesis 2006 (08) (2006) 1313-1324. doi: 10.1055/s-2006-926411). HepDirect prodrugs; phosphate and phosphonate prodrugs that result in direct liver-targeted delivery following a cytochrome P450-catalyzed oxidative cleavage reaction in hepatocytes (FIG. 19) (M. D. Erion, Liver-targeted drug delivery using HepDirect prodrugs, J. Pharmacol. Exp. Ther. 312(2) (2005) 554-560. doi: 10.1124/jpet.104.075903; S. H. Boyer, Synthesis and characterization of a novel liver-targeted prodrug of cytosine-1-β-D-arabinofuranoside monophosphate for the treatment of hepatocellular carcinoma, J. Med. Chem. 49(26) (2006) 7711-7720. doi:10.1021/jm0607449; M. D. Erion et al. Design, synthesis, and characterization of a series of cytochrome P450 3A-activated prodrugs (hepdirect prodrugs) useful for targeting phosph (on) ate-based drugs to the liver, J. Am. Chem. Soc. 126(16) (2004) 5154-5163. doi:10.1021/ja031818y; K. Y. Hostetler, Alkoxyalkyl prodrugs of acyclic nucleoside phosphonates enhance oral antiviral activity and reduce toxicity: current state of the art, Antiviral Res. 82(2) (2009) A84-A98. doi:10.1016/j.antiviral.2009.01.005), octadecyloxyethyl-cidofovir (ODE-CDV) (FIG. 20) (G. R. Painter et al. Design and development of oral drugs for the prophylaxis and treatment of smallpox infection, Trends Biotechnol. 22(8) (2004) 423-427. doi: 10.1016/j.tibtech.2004.06.008).

All of the therapeutic moieties mentioned in this section could be directly embedded within the oligonucleotides that form the nucleic acid nanoparticle.

Combinatorial Chains

Figure 21:
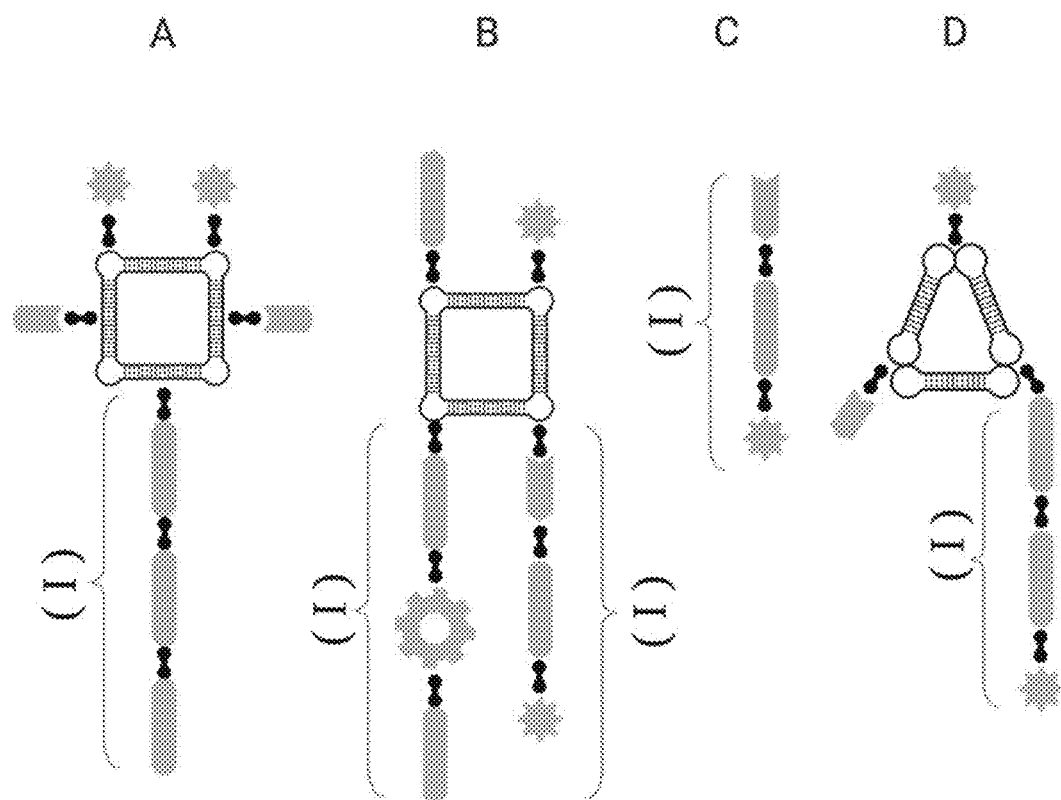
FIG. 21 is a schematic outlining the concept of combinatorial chains; a way of linking two or more cargo molecules together to increase therapeutic loading capacity. Non-exhaustive examples of compositions are given (A-D). Referenced in the schematic are: I) Combinatorial chains; II) Nanostructure; III) Linker; IV) Therapeutic cargo; V) Targeting cargo; VI) Cellular entry cargo; VII) Other functional cargo.
Figure 21:
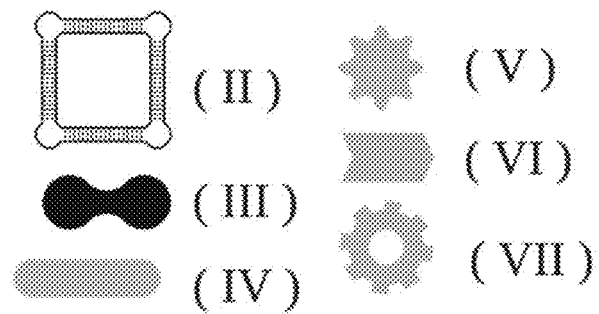

In addition to direct attachment of singular cargo molecules at each attachment point on a nanoparticle, compositions of the present invention may also include cargo molecules that are linked to other cargo molecules (FIG. 21). Cargo molecules may also be linked to other cargo molecules in the absence of a nanoparticle.

These linked cargo molecules, also referred to as 'Combinatorial chains' (FIG. 21), could include, but are not limited to, molecules that promote a function and/or biological effect inside or outside a cell (e.g. IRES, ribosomal recruitment, cytokine stimulation), molecules that promote entry into a cell (e.g. peptides, endosomal escape compounds), molecules that bind to target cells (e.g. aptamers, antibodies, ligands), cytotoxic compounds (e.g. cytotoxic nucleosides), molecules that express a gene product inside a cell (e.g. mRNA), chemotherapeutic compounds (e.g. alkylating agents, antimetabolites, topoisomerase inhibitors), molecules that silence or alter a gene inside a cell (e.g. siRNA, miRNA, antisense therapy, lncRNA), CRISPR molecules (e.g. gRNA, Cas9 protein, Cas9 mRNA), small molecule therapies (e.g. protein-tyrosine kinase inhibitors, proteasome inhibitors), proteins, peptides, and diagnostic agents.

The combinatorial chains can be any combination of cargo molecules and may be any length. In one embodiment they could include an siRNA, peptide, and aptamer combinatorial chain, which may or may not be linked to a nanostructure. In another embodiment, a combinatoria chain could be multiple siRNA therapies that are designed to silence different, or the same, target gene. A further embodiment could include multiple therapies such as chemotherapeutics and siRNA forming part of the same combinatorial chain. In another embodiment the cargo molecules could be arranged linearly or linked in a branched arrangement to form the combinatorial chains.

The combinatorial chains may or may not be linked to a nanoparticle. Multiple chains may also be linked to the same nanoparticle. Combinatorial chains can be linked to nucleic acid nanoparticles and nanoparticles that are not constructed from nucleic acids (e.g. lipid and polymer nanoparticles and antibody-drug conjugates).

Combinatorial chains can be joined to a nanoparticle by click chemistry. Briefly these include, but are not limited to, CuAAC, SPAAC, RuAAC, IEDDA, SuFEx, SPANC, hydrazone/oxime ether formation, thiol-ene radical reaction, thiol-yne radical reaction, thiol-Michael addition reaction, thiol-isocyanate reaction, thiol-epoxide click reaction, nucleophilic ring opening reactions (spring-loaded reactions), traceless Staudinger ligation.

Combinatorial chains can also be joined to a nucleic acid nanoparticle by toehold interactions (K. A. Afonin et al. The Use of Minimal RNA Toeholds to Trigger the Activation of Multiple Functionalities, Nano Lett. 16 (2016) 1746-1753. https://doi.org/10.1021/acs.nanolett.5b04676.).

Cargo molecules that form combinatorial chains may be linked to each other via linker molecules. Linker molecules include, but are not limited to thiol cleavable linkers such as dithiobismaleimidoethane, 1,4-bis[3-(2-pyridyldithio)propionamido]butane and 3-(2-pyridyldithio)propionyl hydrazide, base-cleavable linkers such as bis[2-(N-succinimidyl-oxycarbonyloxy)ethyl] sulfone or hydroxylamine-cleavable linkers such as (ethylene glycol bis(succinimidyl succinate)). Reversible click moieties, i.e. the Meldrum's acid derivative, 5-(bis(methylthio)methylene)-2,2-dimethyl-1,3-dioxane-4,6-dione might also be used to crosslink cargo molecules (K. L. Diehl et al. Click and chemically triggered declick reactions through reversible amine and thiol coupling via a conjugate acceptor, Nat. Chem. 8 (2016) 968-973. https://doi.org/10.1038/nchem.2601.). Dicer substrates may also be used, either on their own or in combination with the above. Non-cleavable linkers may also be employed where the therapeutic does not require cytosolic release; these include, but are not limited to, thiol-reactive maleimides (e.g., 1,8-bismaleimido-diethyleneglycol, 1,11-bismaleimido-triethyleneglycol, 1,4-bismaleimidobutane, bismaleimidohexane, bismaleimidoethane, tris(2-maleimidoethyl) amine), thiol/amine reactive linkers (e.g. N-α-maleimidoacet-oxysuccinimide ester, N-β-maleimidopropyl-oxysuccinimide ester, N-ε-maleimidocaproic acid, N-γ-maleimidobutyryl-oxysuccinimide ester, succinimidyl 4-(N-maleimidomethyl) cyclohexane-1-carboxy-(6-amidocaproate), succinimidyl 6-(3(2-pyridyldithio)propionamido)hexanoate, m-maleimidobenzoyl-N-hydroxysuccinimide ester, succinimidyl iodoacetate, succinimidyl (4-iodoacetyl)aminobenzoate, PEGylated, long-chain SMCC crosslinkers, succinimidyl 4-(p-maleimidophenyl)butyrate and sulfo-NHS equivalents), hydroxyl/thiol reactive linkers (e.g. p-maleimidophenyl isocyanate).

Embodiments

In embodiments, the invention provides compositions comprising an oligonucleotide covalently linked to one or more cargo molecules.

In embodiments, the compositions comprise oligonucleotides that are functionalized with reactive sites that allow for conjugation and assembled into a nucleic acid nanoparticle.

In embodiments, the nucleic acid nanoparticle is attached to a cargo molecule, wherein the nucleic acid nanoparticle is functionalized to promote a biological activity of the cargo molecule in a subject.

In embodiments, the nucleic acid nanoparticle is trimeric, tetrameric, pentameric or hexameric.

In embodiments, the invention provides methods comprising attaching a nucleic acid nanoparticle to at least one cargo molecule via at least one reaction that comprises at least one of the following features: the reaction occurs in one pot, the reaction is not disturbed by water, the reaction generates minimal byproducts, and the reaction comprises a high thermodynamic driving force that affords a single reaction product.

In embodiments, the method comprises attaching a first cargo molecule via a first reaction comprising at least one of the features and attaching a second cargo molecule via a second reaction comprising at least one of the features, wherein the first reaction and the second reaction are orthogonal.

In embodiments, the first reaction comprises modification on a strand of at least one oligonucleotide in the nucleic acid nanoparticle.

In embodiments, the nucleic acid nanoparticle is attached to the first cargo molecule via copper (I) azide-alkyne cycloaddition.

In embodiments, the nucleic acid nanoparticle is attached to the first cargo molecule via strain-promoted azide-alkyne cycloaddition.

In embodiments, the nucleic acid nanoparticle is attached to the first cargo molecule via an inverse electron demand Diels Alder reaction.

In embodiments, the nucleic acid nanoparticle is attached to the first cargo molecule via a disulphide linkage.

In embodiments, the nucleic acid nanoparticle is attached to the first cargo molecule via sulfur (VI) fluoride exchange.

In embodiments, the nucleic acid nanoparticle is attached to the first cargo molecule via hydrazone formation.

In embodiments, the nucleic acid nanoparticle is attached to the first cargo molecule via a thiol-ene radical addition.

In embodiments, the nucleic acid nanoparticle is attached to the first cargo molecule via a thiol-yne reaction.

In embodiments, the nucleic acid nanoparticle is attached to the first cargo molecule via thiol-Michael addition.

In embodiments, the nucleic acid nanoparticle is attached to the first cargo molecule via thiol-isocyanate chemistry.

In embodiments, the nucleic acid nanoparticle is attached to the first cargo molecule via thiol-epoxide chemistry.

In embodiments, the nucleic acid nanoparticle is attached to the first cargo molecule via a nucleophilic ring opening reaction.

In embodiments, the nucleic acid nanoparticle is attached to the first cargo molecule via a traceless Staudinger ligation.

In embodiments, one reactive functionality is attached to another via a spacer or linker.

In embodiments, the nucleic acid nanoparticle is attached to the first cargo via a linker responsive to a stimulus.

In embodiments, the stimulus is selected from the group consisting of pH, light, temperature, reduction potential or oxygen concentration.

In embodiments, the nucleic acid nanoparticle is covalently stabilized.

In embodiments, the invention provides compositions comprising a nucleic acid that complexes with an o-phthalaldehyde to generate an isoindole.

In embodiments, the invention provides compositions comprising an oligonucleotide functionalized with amine and thiol reactive sites and a nucleic acid nanoparticle self-assembled these functionalized oligonucleotides.

In embodiments, an amine and thiol simultaneously react with ortho-phthalaldehyde to generate a fluorescent isoindole.

In embodiments, the fluorescent moiety is conjugated to an additional fluorophore.

In embodiments, the nucleic acid nanoparticle is conjugated to a cargo via orthogonal click chemistry.

In embodiments, the invention provides compositions comprising a nucleic acid nanoparticle comprising a nucleic acid duplex comprising a reactive moiety that complexes with an external agent to form a fluorophore.

In embodiments, an amine and thiol simultaneously react with ortho-phthalaldehyde wherein the fluorophore is a fluorescent isoindole.

In embodiments, the fluorophore is conjugated to an additional fluorophore.

In embodiments, the nucleic acid nanoparticle is conjugated to a cargo molecule via orthogonal click chemistry.

In embodiments, the nucleic acid nanoparticle comprises a component comprising a hydrophobic moiety, a hydrophilic moiety, and a nucleotide attachment moiety.

In embodiments, the hydrophobic and hydrophilic moieties are attached to the nucleic acid nanoparticle covalently.

In embodiments, the hydrophobic and hydrophilic moieties are covalently attached to the nucleic acid via an amide, amine, or ether linkage.

In embodiments, the hydrophilic moiety comprises an amine.

In embodiments, the hydrophilic moiety is selected from the group consisting of spermine, ethylenediamine, methylethylenediamine, ethylethylenediamine, imidazole, spermine-imidazole-4-imine, N-ethyl-N-(3-dimethylaminopropyl)-guanidinyl ethylene imine, dimethylaminoethyl acrylate, amino vinyl ether, 4-imidazoleacetic acid, diethylaminopropylamide, sulfonamides (e.g. sulfadimethoxine sulfamethoxazole, sulfadiazine, sulfamethazine), amino ketals, N-2-hydroxylpropyltimehyl ammonium chloride, imidazole-4-imines, methyl-imidazoles, 2-(aminomethyl)imidazole, 4-(aminomethyl)imidazole, 4(5)-(Hydroxymethyl) imidazole, N-(2-aminoethyl)-3-((2-aminoethyl)(methyl) amino)propanamide, 2-(2-ethoxyethoxy)ethan-1-amine, bis (3-aminopropyl)amine, [N,N-dimethylamino)ethoxy]ethyl, N-(2-aminoethyl)-3-((2-aminoethyl)(ethyl)amino)propanamide, (N-(aminoethyl)carbamoyl)methyl, N-(2-((2-aminoethyl)amino)ethyl)acetamide 3,3'4(2-aminoethyl)azanediyl) bis(N-(2-aminoethyl)propanamide), guanidyl benzylamide, [3-(guanidinium)propyl], dimethylethanolamine, 1-(2,2-dimethyl-1,3-dioxolan-4-yl)-N,N-dimethylmethanamine, 2-(2,2-dimethyl-1,3-dioxolan-4-yl)-N,N-dimethylethan-1-amine, N-(2-((2-(2-aminoethoxy)propan-2-yl)oxy)ethyl)acetamide, aminobutyl, aminoethyl, 1-(2-aminoethyl)-3-(3-(dimethylamino)propyl)-2-ethylguanidine, 1-(3-amino-3-oxopropyl)-2,4,6-trimethylpyridin-1-ium, 1-(1,3-bis (carboxyoxy)propan-2-yl)-2,4,6-trimethylpyridin-1-ium, guanidinylethyl amine, ether hydroxyl triazole, and a β-aminoester.

In embodiments, the nucleotide is functionalized with a moiety selected from the group consisting of 2-(2-(dimethylamino)ethoxy)ethan-1-ol, N-butyl-2-hydroxyacetamide, (1H-imidazol-5-yl)methanol, amino((2-(2-hydroxyacetamido)ethyl)amino)methaniminium and 1-(2-(2-hydroxyacetamido)ethyl)-2,4,6-trimethylpyridin-1-ium.

In embodiments, the nucleotide attachment moiety is cysteine.

In embodiments, the nucleic acid nanoparticle promotes endosomal escape of the cargo molecule in a receptor independent-manner.

In embodiments, the nucleic acid nanoparticle comprises a component that binds to a receptor in a cell.

In embodiments, the component comprises one selected from the group consisting of folate, TfR-T12, and a hemagglutinin peptide.

In embodiments, the cargo molecule is attached to the nucleic acid nanoparticle via a linker that can be cleaved in the lysosome.

In embodiments, the cargo molecule is attached to a cathepsin B-cleavable linker.

In embodiments, the cargo molecule is attached to a protease-cleavable linker.

In embodiments, the cargo molecule is attached to a pyrophosphate diester.

In embodiments, the invention provides processes for synthesis of 2'-O substituted nucleosides, the processes comprising the treatment of anhydrouridine with alcohol-based nucleophiles.

In embodiments, the treatment comprises a base selected from the group consisting of barium tert-butoxide, benzyltrimethylammonium hydroxide, 2-tert-butylimino-2-diethylamino-1,3-dimethyl-perhydro-1,3,2-diazaphosphorine, n-butyllithium, sec-butyllithium, tert-butyllithium, Dabco®, N,N-diisopropylmethylamine, dimethylamine, 4-(dimethylamino)pyridine, ethylamine, N-ethyldiisopropylamine, lithium bis(trimethylsilyl)amide, lithium tert-butoxide, lithium dicyclohexylamide, lithium diethylamide, lithium diisopropylamide, lithium dimethylamide, lithium ethoxide, lithium isopropoxide, lithium methoxide, lithium 2,2,6,6-tetramethylpiperidide, magnesium bis(hexamethyldisilazide), methylamine, methyllithium, morpholine, piperidine, potassium bis(trimethylsilyl)amide, potassium tert-butoxide, potassium ethoxide, potassium methoxide, triethylamine.

In embodiments, the treatment comprises a base selected from the group consisting of aluminium bromide, aluminium chloride, aluminium isopropoxide, boron trichloride (and its various complexes), boron trifluoride (and its various complexes), dicyclohexylboron, iron (III) bromide, iron (III) chloride, montmorillonite K10 & K30, tin (IV) chloride, titanium (IV) chloride, titanium (IV) isopropoxide, titanium tetrachloride.

In embodiments, the invention provides compositions comprising a cargo molecule and a nucleic acid nanoparticle attached to the cargo molecule, wherein the nucleic acid nanoparticle is functionalized to promote a biological activity of the cargo molecule in a subject.

In embodiments, the nucleic acid nanoparticle is functionalized to promote internalisation into a cell.

In embodiments, the cargo molecule is functionalized to promote internalisation into a cell.

In embodiments, the cargo molecule is an anchored cholesterol molecule that promotes permeation through the lipid bilayer of the cell.

In embodiments, the functionalization promotes internalisation into the cell via clathrin-mediated endocytosis, non-clathrin/non-caveolae endocytosis, caveolae-mediated endocytosis, passive diffusion, simple diffusion, facilitated diffusion, transcytosis, macropinocytosis, phagocytosis, receptor mediated endocytosis, receptor diffusion, vesicle-mediated transport, active transport.

In embodiments, the nucleic acid nanoparticle may enter the cell, or be processed, via the endosome, lysosome, pinosome, or phagosome.

In embodiments, the nucleic acid nanoparticle may enter the cell across a biological membrane.

In embodiments, the functionalization may take effect in the cell cytoplasm, nucleus, mitochondria or other cellular compartment.

In embodiments, the cargo molecule is selected from the group consisting of mRNA, gRNA/CRISPR, siRNA, ASO, miRNA, lnRNA, shRNA, ribozymes, aptamers, peptides, proteins, antibodies and therapeutic small molecules.

In embodiments, the cytotoxic nucleotides are incorporated into the oligonucleotide backbone.

In embodiments, the cytotoxic nucleotides are selected from the group consisting of aristomycin, neoplanocin A, ribavirin, pyrazofurin, cytarabine arabinoside (ara-C), gemcitabine, cladribine (2-CdA), showdomycin, elacytarabine.

In embodiments, the phosphate prodrugs are incorporated into the nucleic acid backbone.

In embodiments, the phosphate prodrugs are bis(S-acyl-2-thioethyl) ester derivatives of 9-[2-(phosphonomethoxy) ethyl]adenine, cycloSal pro-nucleotides, HepDirect prodrugs or octadecyloxyethyl-cidofovir.

In embodiments, the oligonucleotides are assembled into a nucleic acid nanoparticle.

In embodiments, the invention provides compositions comprising a first cargo molecule and a second cargo molecule linked to the first cargo molecule.

In embodiments, the first cargo molecule has a biological function.

In embodiments, the first cargo molecule is selected from the group consisting of mRNA, gRNA/CRISPR, siRNA, ASO, miRNA, lnRNA, shRNA, ribozymes, aptamers, peptides, proteins, antibodies and therapeutic small molecules.

In embodiments, the first cargo molecule is a cell- or tissue-targeting ligand comprising an aptamer, lectin, glycoprotein, lipid, antibody, nanobody, or DARPIN.

In embodiments, at least one of the first and second cargo molecules comprises GalNAc or a GalNAc derivative that is linked via a monovalent, bivalent, or trivalent branched linker.

In embodiments, at least one of the first and second cargo molecules comprises cholesterol or a derivative thereof.

In embodiments, at least one of the first and second cargo molecules comprises a phospholipid.

In embodiments, at least one of the first and second cargo molecules comprises a cationic lipid, optionally comprising a quaternary ammonium ion.

In embodiments, at least one of the first and second cargo molecules comprises an anionic lipid, optionally comprising a phosphate group.

In embodiments, at least one of the first and second cargo molecules comprises an ionizable lipid.

In embodiments, at least one of the first and second cargo molecules comprises a branched lipid.

In embodiments, the first cargo molecule is linked to the second cargo molecule by a cleavable linker.

In embodiments, the first cargo molecule and the second cargo molecule are siRNAs.

In embodiments, the first cargo molecule and the second cargo molecule are linked via an oligonucleotide spacer from the group consisting of (dT)n, (dA)n, d(C)n, d(G)n, (rU)n, (rA)n, (rC)n, (rG)n, and combinations thereof, wherein n is 1-16.

In embodiments, at least one of the first and second cargo molecules is linked to a third cargo molecule.

In embodiments, at least one of the first and second cargo molecules is linked to the third cargo molecule by a thiol-cleavable linker comprising dithiobismaleimidoethane and 1,4-bis[3-(2-pyridyldithio)propionamido]butane.

In embodiments, the at least one of the first and second cargo molecules is linked to the third cargo molecule by a hydroxylamine-cleavable linker comprising ethylene glycol bis(succinimidyl succinate.

In embodiments, the at least one of the first and second cargo molecules is linked to the third cargo molecule by a base-cleavable linker comprising bis[2-(N-succinimidyl-oxycarbonyloxy)ethyl] sulfone.

In embodiments, the at least one of the first and second cargo molecules is linked to the third cargo molecule by a Meldrum's acid derivative comprising 5-(bis(methylthio) methylene)-2,2-dimethyl-1,3-dioxane-4,6-dione.

In embodiments, the at least one of the first and second cargo molecules is linked to the third cargo molecule via a covalent bond.

In embodiments, the at least one of the first and second cargo molecules is linked to the third cargo molecule by a dicer substrate.

In embodiments, the at least one of the first and second cargo molecules is linked to the third cargo molecule with a linker selected from the group consisting of 1,8-bismaleimido-diethyleneglycol, 1,11-bismaleimido-triethyleneglycol, 1,4-bismaleimidobutane, bismaleimidohexane, bismaleimidoethane, tris(2-maleimidoethyl)amine), N-α-maleimidoacet-oxysuccinimide ester, N-β-maleimidopropyl-oxysuccinimide ester, N-ε-maleimidocaproic acid, N-γ-maleimidobutyryl-oxysuccinimide ester, succinimidyl 4-(N-maleimidomethyl) cyclohexane-1-carboxy-(6-amidocaproate), succinimidyl 6-(3(2-pyridyldithio)propionamido)hexanoate, m-maleimidobenzoyl-N-hydroxysuccinimide ester, succinimidyl iodoacetate, succinimidyl (4-iodoacetyl)aminobenzoate, PEGylated, long-chain SMCC crosslinkers, succinimidyl 4-(p-maleimidophenyl)butyrate and sulfo-NHS equivalents), p-maleimidophenyl isocyanate.

In embodiments, the at least one of the first and second cargo molecules is linked to a nanoparticle.

In embodiments, the invention provides compositions comprising at least two cargo molecules and a nucleic acid nanoparticle attached to each of the at least two cargo molecules.

In embodiments, each of the at least two cargo molecules has a biological function.

In embodiments, each of the at least two cargo molecules is selected from the group consisting of mRNA, gRNA/CRISPR, siRNA, ASO, miRNA, lnRNA, shRNA, ribozymes, aptamers, peptides, proteins, antibodies and therapeutic small molecules.

In embodiments, more than one of the at least two cargo molecules are conjugated to the same nucleic acid nanoparticle.

In embodiments, the more than one of the at least two cargo molecules are different.

In embodiments, the more than one cargo molecules are the same.

In embodiments, the different cargo molecules are conjugated to the nanoparticle in unequal amounts.

In embodiments, the at least two cargo molecules are conjugated via a stable covalent bond.

In embodiments, the at least two molecules are conjugated via a stable covalent bond to a stimuli-responsive linker.

In embodiments, the invention provides compositions comprising an oligonucleotide covalently linked to one or more cargo molecules.

In embodiments, the oligonucleotides are functionalized with reactive sites that allow for conjugation and conjugated to a nucleic acid nanoparticle.

In embodiments, the nucleic acid nanoparticle is a tertiary structure of three or more junctions, said junctions are formed by at least two oligonucleotide strands of 3 to 200 nucleotides in length wherein each oligonucleotide strand partially interacts with at least one other oligonucleotide strand through either hydrogen bonding or base-stacking interactions or both.

In embodiments, each nucleotide optionally comprises a modification including, but not limited to, 2'-O-methyl, 2'-fluoro, 2'-F-arabinonucleic acid, 2'-O-methoxyethyl, locked nucleic acid, unlocked nucleic acid, 4'-thioribonucleoside, 4'-C-aminomethyl-2'-O-methyl, cyclohexenyl nucleic acid, hexitol nucleic acid, glycol nucleic acid, phosphorothioate, boranophosphate, 5'-C-methyl, 5'(E)-vinylphosphonate, and 2' thiouridine.

In embodiments, the nucleic acid nanoparticle is attached to a cargo molecule, wherein the cargo molecule promotes a biological activity of the cargo molecule in a subject.

In embodiments, the nucleic acid nanoparticle performs at least one biological activity selected from the group consisting of (i) binding to a serum protein in blood, or to a receptor in a cell or at the cell surface, (ii) promoting endosomal escape of the cargo molecule in a receptor-independent manner, (iii) targeting a tissue in an animal or subject, (iv) modulating biodistribution, (v) inducing or preventing an immunological response, (vi) enhancing cellular uptake, (vii) modulating gene expression, (viii) inducing cytotoxicity, and (ix) having a therapeutic effect, or combinations thereof.

In embodiments, the one or more cargo molecules are comprised of at least one of mRNA, gRNA/CRISPR, siRNA, shRNA, ASO, saRNA, miRNA, lnRNA, ribozyme, aptamer, peptide, protein, protein domain, antibody, antibody fragment, antibody mimetic, lectin, vitamin, lipid, carbohydrate, benzamides and therapeutic small molecules, or combinations thereof.

In embodiments, the functionalization promotes internalisation into the cell, wherein the internalisation mechanism comprises at least one of clathrin-mediated endocytosis, non-clathrin/non-caveolae endocytosis, caveolae-mediated endocytosis, passive diffusion, simple diffusion, facilitated diffusion, transcytosis, macropinocytosis, phagocytosis, receptor mediated endocytosis, receptor diffusion, vesicle-mediated transport, and active transport.

In embodiments, the attachment of the nucleic acid nanoparticle to at least one cargo molecule is obtainable by a method comprising at least one reaction that comprises at least one of the following features: (i) the reaction occurs in one pot, (ii) the reaction is not disturbed by water, (iii) the reaction generates minimal byproducts, and (iv) the reaction comprises a high thermodynamic driving force that affords a single reaction product.

In embodiments, the attachment reaction comprises: (i) attaching a first cargo molecule via a first reaction comprising at least one of the features described above and (ii) attaching a second cargo molecule via a second reaction comprising at least one of the features of described above, wherein the first reaction and the second reaction are orthogonal.

In embodiments, the oligonucleotide 5', 3' or internal position (at any given position on a nucleotide) is modified with a functionality that will allow for the formation of covalent bonds via reactions selected from the group consisting of CuAAC, SPAAC, RuAAC, IEDDA, SuFEx, SPANC, hydrazone/oxime ether formation, thiol-ene radical reaction, thiol-yne radical reaction, thiol-Michael addition reaction, thiol-isocyanate reaction, thiol-epoxide click reaction, nucleophilic ring opening reactions (spring-loaded reactions), traceless Staudinger ligation. These linkages may be formed by carrying out coupling reactions with any oligonucleotide or cargo molecule modified with a chemical moiety from the group consisting of, but not limited to, ADIBO-PEG4, N-[(1R,8S,9s)-bicyclo[6.1.0]non-4-yn-9-yl-methyloxycarbonyl]-1,8-diamino-3,6-dioxaoctane, (1R,8S, 9s)-bicyclo[6.1.0]non-4-yn-9-ylmethanol, bromoacetamido-dPEG®4-amido-DBCO, bromoacetamido-dPEG®12-amido-DBCO, bromoacetamido-dPEG®24-amido-DBCO, dibenzocyclooctyne-acid, dibenzocyclooctyne-N-hydroxysuccinimidyl ester, dibenzocyclooctyne-PEG4-acid, dibenzocyclooctyne-PEG4-alcohol, dibenzocyclooctyne-PEG4-N-hydroxysuccinimidyl ester, (4-(1,2,4,5-tetrazin-3-yl)phenyl)methanamine hydrochloride, (E)-cyclooct-4-enol, (E)-cyclooct-4-enyl 2,5-dioxo-1-pyrrolidinyl carbonate, 2,5-Dioxo-1-pyrrolidinyl 5-[4-(1,2,4,5-tetrazin-3-yl)benzylamino]-5-oxopentanoate, 5-[4-(1,2,4,5-tetrazin-3-yl)benzylamino]-5-oxopentanoic acid, 5-norbornene-2-acetic acid succinimidyl ester, 5-norbornene-2-endo-acetic acid, methyltetrazine-NHS ester, methyltetrazine-PEG4-NHS ester, TCO PEG4 succinimidyl ester, TCO-amine, tetrazine-PEG5-NHS ester, alkyne-PEG5-acid, (R)-3-amino-5-hexynoic acid hydrochloride, (S)-3-amino-5-hexynoic acid hydrochloride, (S)-3-(boc-amino)-5-hexynoic acid, N-boc-4-pentyne-1-amine, boc-propargyl-Gly-OH, 3-ethynylaniline, 4-ethynylaniline, propargylamine hydrochloride, propargyl chloroformate, propargyl-N-hydroxysuccinimidyl ester, propargyl-PEG2-acid, 3-(4-azidophenyl)propionic acid, 3-azido-1-propanamine, 3-azido-1-propanol, 4-carboxybenzenesulfonazide, O-(2-aminoethyl)-O'-(2-azidoethyl)heptaethylene glycol, O-(2-aminoethyl)-O'-(2-azidoethyl)nonaethylene glycol, O-(2-aminoethyl)-O'-(2-azidoethyl)pentaethylene glycol, azido-dPEG®4(n)acid (where n could be 4, 8, 12, 24), azido-dPEG®(n)-amine (where n could be 7, 11, 23, 35), azido-dPEG®4(n) NHS ester (where n could be 4, 8, 12, 24), azido-dPEG®(n)-TFP ester (where n could be 4, 8, 12, 24, 36), 2-[2-(2-azidoethoxy)ethoxy]ethanol, O-(2-azidoethyl)-O-[2-(diglycolyl-amino)ethyl]heptaethylene glycol, O-(2-azidoethyl)heptaethylene glycol, O-(2-azidoethyl)-O'-methyl-triethylene glycol, O-(2-azidoethyl)-O'-methyl-undecaethylene glycol, 17-azido-3,6,9,12,15-pentaoxaheptadecan-1-amine, 14-azido-3,6,9,12-tetraoxatetradecanoic acid, 11-azido-3,6,9-trioxaundecan-1-amine, bromoacetamido-dPEG®(n)azide (where n could be 3, 11, 23) and combinations thereof.

In embodiments, the nucleic acid nanoparticle is attached to a first cargo molecule, a second cargo molecule linked to the first cargo molecule, and optionally, further cargo molecules linked to the second or first cargo molecule.

In embodiments, the first cargo molecule is selected from the group consisting of at least one of mRNA, gRNA/CRISPR, siRNA, shRNA, ASO, saRNA, miRNA, lnRNA, ribozyme, aptamer, peptide, protein, protein domain, antibody, antibody fragment, antibody mimetic, lectin, vitamin, lipid, carbohydrate, benzamides and therapeutic small molecules, or combinations thereof.

In embodiments, the first cargo molecule is linked to the second cargo molecule by a cleavable linker.

In embodiments, at least one of the first and second cargo molecules is linked to a third cargo molecule by either a thiol-cleavable linker comprising dithiobismaleimidoethane and 1,4-bis[3-(2-pyridyldithio)propionamido]butane, a hydroxylamine-cleavable linker comprising ethylene glycol bis(succinimidyl) succinate, a base-cleavable linker comprising bis[2-(N-succinimidyl-oxycarbonyloxy)ethyl] sulfone or a Meldrum's acid derivative comprising 5-(bis(methylthio)methylene)-2,2-dimethyl-1,3-dioxane-4,6-dione.

In embodiments, at least one of the first and second cargo molecules is linked to a third cargo molecule by a dicer substrate or extended nucleic acid spacer region that is amenable to cleavage, including, but not limited to, the sequences (T)k, (A)l, (G)m, (C)n, and combinations thereof, where k, l m, and n are positive integers.

In embodiments, at least one of the first and second cargo molecules is linked to a third cargo molecule with a linker selected from the group consisting of 1,8-bismaleimido-diethyleneglycol, 1,11-bismaleimido-triethyleneglycol, 1,4-bismaleimidobutane, bismaleimidohexane, bismaleimido-ethane, tris(2-maleimidoethyl)amine), N-α-maleimidoacet-oxysuccinimide ester, N-β-maleimidopropyl-oxysuccinimide ester, N-ε-maleimidocaproic acid, N-γ-maleimidobutyryl-oxysuccinimide ester, succinimidyl 4-(N-maleimidomethyl)cyclohexane-1-carboxy-(6-amidocaproate), succinimidyl 6-(3(2-pyridyldithio)propionamido)hexanoate, m-maleimidobenzoyl-N-hydroxysuccinimide ester, succinimidyl iodoacetate, succinimidyl (4-iodoacetyl)aminobenzoate, PEGylated, long-chain SMCC crosslinkers, succinimidyl 4-(p-maleimi-dophenyl)butyrate and sulfo-NHS equivalents), and p-ma-leimidophenyl isocyanate.

In embodiments, the second cargo molecule is linked to any given number of cargo molecules in a polymeric fashion.

In embodiments, the first cargo molecule is linked to the nucleic acid nanoparticle via reactions selected from the group consisting of CuAAC, SPAAC, RuAAC, IEDDA, SuFEx, SPANC, hydrazone/oxime ether formation, thiol-ene radical reaction, thiol-yne radical reaction, thiol-Michael addition reaction, thiol-isocyanate reaction, thiol-ep-oxide click reaction, nucleophilic ring opening reactions (spring-loaded reactions), traceless Staudinger ligation. These linkages may be formed by carrying out coupling reactions with any oligonucleotide or cargo molecule modified with a chemical moiety from the group consisting of, but not limited to, ADIBO-PEG4, N-[(1R,8S,9s)-bicyclo[6.1.0]non-4-yn-9-ylmethyloxycarbonyl]-1,8-diamino-3,6-dioxaoctane, (1R,8S,9s)-bicyclo[6.1.0]non-4-yn-9-ylmetha-nol, bromoacetamido-dPEG®4-amido-DBCO, bromoacetamido-dPEG®12-amido-DBCO, bromoacet-amido-dPEG®24-amido-DBCO, dibenzocyclooctyne-acid, dibenzocyclooctyne-N-hydroxysuccinimidyl ester, dibenzo-cyclooctyne-PEG4-acid, dibenzocyclooctyne-PEG4-alco-hol, dibenzocyclooctyne-PEG4-N-hydroxysuccinimidyl ester, (4-(1,2,4,5-tetrazin-3-yl)phenyl)methanamine hydro-chloride, (E)-cyclooct-4-enol, (E)-cyclooct-4-enyl 2,5-di-oxo-1-pyrrolidinyl carbonate, 2,5-Dioxo-1-pyrrolidinyl 5-[4-(1,2,4,5-tetrazin-3-yl)benzylamino]-5-oxopentanoate, 5-[4-(1,2,4,5-tetrazin-3-yl)benzylamino]-5-oxopentanoic acid, 5-norbornene-2-acetic acid succinimidyl ester, 5-nor-bornene-2-endo-acetic acid, methyltetrazine-NHS ester, methyltetrazine-PEG4-NHS ester, TCO PEG4 succinimidyl ester, TCO-amine, tetrazine-PEG5-NHS ester, alkyne-PEG5-acid, (R)-3-amino-5-hexynoic acid hydrochloride, (S)-3-amino-5-hexynoic acid hydrochloride, (S)-3-(boc-amino)-5-hexynoic acid, N-boc-4-pentyne-1-amine, boc-propargyl-Gly-OH, 3-ethynylaniline, 4-ethynylaniline, propargylamine hydrochloride, propargyl chloroformate, propargyl-N-hydroxysuccinimidyl ester, propargyl-PEG2-acid, 3-(4-azidophenyl)propionic acid, 3-azido-1-propan-amine, 3-azido-1-propanol, 4-carboxybenzenesulfonazide, O-(2-aminoethyl)-O'-(2-azidoethyl)heptaethylene glycol, O-(2-aminoethyl)-O'-(2-azidoethyl)nonaethylene glycol, O-(2-aminoethyl)-O'-(2-azidoethyl)pentaethylene glycol, azido-dPEG®4(n)acid (where n could be 4, 8, 12, 24), azido-dPEG®(n)-amine (where n could be 7, 11, 23, 35), azido-dPEG®4(n) NHS ester (where n could be 4, 8, 12, 24), azido-dPEG®(n)-TFP ester (where n could be 4, 8, 12, 24, 36), 2-[2-(2-azidoethoxy)ethoxy]ethanol, O-(2-azidoethyl)-O-[2-(diglycolyl-amino)ethyl]heptaethylene glycol, O-(2-azidoethyl)heptaethylene glycol, O-(2-azidoethyl)-O'-methyl-triethylene glycol, O-(2-azidoethyl)-O'-methyl-undecaethylene glycol, 17-azido-3,6,9,12,15-pentaoxaheptadecan-1-amine, 14-azido-3,6,9,12-tetraoxatetradecanoic acid, 11-azido-3,6,9-trioxaundecan-1-amine, bromoacetamido-dPEG®(n)azide (where n could be 3, 11, 23) and combinations thereof.

In embodiments, each of at least two cargo molecules has a biological function.

In embodiments, the invention provides compositions comprising an oligonucleotide covalently linked to one or more cargo molecules.

In embodiments, the composition comprises oligonucleotides that are functionalized with reactive sites that allow for conjugation and assembled into a nucleic acid nanoparticle.

In embodiments, the nucleic acid nanoparticle is attached to a cargo molecule, wherein the nucleic acid nanoparticle is functionalized to promote a biological activity of the cargo molecule in a subject.

In embodiments, the nucleic acid nanoparticle is trimeric, tetrameric, pentameric or hexameric.

In embodiments, the invention provides methods comprising attaching a nucleic acid nanoparticle to at least one cargo molecule via at least one reaction that comprises at least one of the following features: the reaction occurs in one pot, the reaction is not disturbed by water, the reaction generates minimal byproducts, and the reaction comprises a high thermodynamic driving force that affords a single reaction product.

In embodiments, the method comprises attaching a first cargo molecule via a first reaction comprising at least one of the features and attaching a second cargo molecule via a second reaction comprising at least one of the features, wherein the first reaction and the second reaction are orthogonal.

In embodiments, the first reaction comprises modification on a strand of at least one oligonucleotide in the nucleic acid nanoparticle.

In embodiments, the nucleic acid nanoparticle is attached to the first cargo molecule via copper (I) azide-alkyne cycloaddition.

In embodiments, the nucleic acid nanoparticle is attached to first the cargo molecule via strain-promoted azide-alkyne cycloaddition.

In embodiments, the nucleic acid nanoparticle is attached to the first cargo molecule via an inverse electron demand Diels Alder reaction.

In embodiments, the nucleic acid nanoparticle is attached to the first cargo molecule via a disulphide linkage.

In embodiments, the nucleic acid nanoparticle is attached to the first cargo molecule via sulfur (VI) fluoride exchange.

In embodiments, the nucleic acid nanoparticle is attached to the first cargo molecule via hydrazone formation.

In embodiments, the nucleic acid nanoparticle is attached to the first cargo molecule via a thiol-ene radical addition.

In embodiments, the nucleic acid nanoparticle is attached to the first cargo molecule via a thiol-yne reaction.

In embodiments, the nucleic acid nanoparticle is attached to the first cargo molecule via thiol-Michael addition.

In embodiments, the nucleic acid nanoparticle is attached to the first cargo molecule via thiol-isocyanate chemistry.

In embodiments, the nucleic acid nanoparticle is attached to the first cargo molecule via thiol-epoxide chemistry.

In embodiments, the nucleic acid nanoparticle is attached to the first cargo molecule via a nucleophilic ring opening reaction.

In embodiments, the nucleic acid nanoparticle is attached to the first cargo molecule via a traceless Staudinger ligation.

In embodiments, the oligonucleotide 5', 3' or internal position (at any given position on a nucleotide) is modified with a functionality that will allow for the formation of covalent bonds outlined via these methods. These linkages may be formed by carrying out coupling reactions with any oligonucleotide or cargo molecule modified with a chemical moiety from the group consisting of, but not limited to, ADIBO-PEG4, N-[(1R,8S,9s)-bicyclo[6.1.0]non-4-yn-9-yl-methyloxycarbonyl]-1,8-diamino-3,6-dioxaoctane, (1R,8S,9s)-bicyclo[6.1.0]non-4-yn-9-ylmethanol, bromoacetamido-dPEG®4-amido-DBCO, bromoacetamido-dPEG®$_{12}$-amido-DBCO, bromoacetamido-dPEG®24-amido-DBCO, dibenzocyclooctyne-acid, dibenzocyclooctyne-N-hydroxysuccinimidyl ester, dibenzocyclooctyne-PEG4-acid, dibenzocyclooctyne-PEG4-alcohol, dibenzocyclooctyne-PEG4-N-hydroxysuccinimidyl ester, (4-(1,2,4,5-tetrazin-3-yl)phenyl)methanamine hydrochloride, (E)-cyclooct-4-enol, (E)-cyclooct-4-enyl 2,5-dioxo-1-pyrrolidinyl carbonate, 2,5-Dioxo-1-pyrrolidinyl 5-[4-(1,2,4,5-tetrazin-3-yl)benzylamino]-5-oxopentanoate, 5-[4-(1,2,4,5-tetrazin-3-yl)benzylamino]-5-oxopentanoic acid, 5-norbornene-2-acetic acid succinimidyl ester, 5-norbornene-2-endo-acetic acid, methyltetrazine-NHS ester, methyltetrazine-PEG4-NHS ester, TCO PEG4 succinimidyl ester, TCO-amine, tetrazine-PEG5-NHS ester, alkyne-PEG5-acid, (R)-3-amino-5-hexynoic acid hydrochloride, (S)-3-amino-5-hexynoic acid hydrochloride, (S)-3-(boc-amino)-5-hexynoic acid, N-boc-4-pentyne-1-amine, boc-propargyl-Gly-OH, 3-ethynylaniline, 4-ethynylaniline, propargylamine hydrochloride, propargyl chloroformate, propargyl-N-hydroxysuccinimidyl ester, propargyl-PEG2-acid, 3-(4-azidophenyl)propionic acid, 3-azido-1-propanamine, 3-azido-1-propanol, 4-carboxybenzenesulfonazide, O-(2-aminoethyl)-O'-(2-azidoethyl)heptaethylene glycol, O-(2-aminoethyl)-O'-(2-azidoethyl)nonaethylene glycol, O-(2-aminoethyl)-O'-(2-azidoethyl)pentaethylene glycol, azido-dPEG®4(n)acid (where n could be 4, 8, 12, 24), azido-dPEG®(n)-amine (where n could be 7, 11, 23, 35), azido-dPEG®4(n) NHS ester (where n could be 4, 8, 12, 24), azido-dPEG®(n)-TFP ester (where n could be 4, 8, 12, 24, 36), 2-[2-(2-azidoethoxy)ethoxy]ethanol, O-(2-azidoethyl)-O-[2-(diglycolylamino)ethyl]heptaethylene glycol, O-(2-azidoethyl)heptaethylene glycol, O-(2-azidoethyl)-O'-methyl-triethylene glycol, O-(2-azidoethyl)-O'-methyl-undecaethylene glycol, 17-azido-3,6,9,12,15-pentaoxaheptadecan-1-amine, 14-azido-3,6,9,12-tetraoxatetradecanoic acid, 11-azido-3,6,9-trioxaundecan-1-amine, bromoacetamido-dPEG®(n)azide (where n could be 3, 11, 23) and combinations thereof.

In embodiments, the nucleic acid nanoparticle is attached to the first cargo via a linker responsive to a stimulus.

In embodiments, the stimulus is selected from the group consisting of pH, light, temperature, reduction potential or oxygen concentration.

In embodiments, the nucleic acid nanoparticle is covalently stabilized.

In embodiments, the invention provides compositions comprising a nucleic acid that complexes with an o-phthalaldehyde to generate an isoindole.

In embodiments, the invention provides compositions comprising an oligonucleotide functionalized with amine and thiol reactive sites and a nucleic acid nanoparticle self-assembled these functionalized oligonucleotides.

In embodiments, an amine and thiol simultaneously react with ortho-phthalaldehyde to generate a fluorescent isoindole.

In embodiments, the fluorescent moiety is conjugated to an additional fluorophore.

In embodiments, the nucleic acid nanoparticle is conjugated to a cargo via orthogonal click chemistry, as outlined in claim 7.

In embodiments, the invention provides compositions comprising a nucleic acid nanoparticle comprising a nucleic acid duplex comprising a reactive moiety that complexes with an external agent to form a fluorophore.

In embodiments, an amine and thiol simultaneously react with ortho-phthalaldehyde wherein the fluorophore is a fluorescent isoindole.

In embodiments, the fluorophore is conjugated to an additional fluorophore.

In embodiments, the nucleic acid nanoparticle is conjugated to a cargo molecule via orthogonal click chemistry.

In embodiments, the nucleic acid nanoparticle comprises a component comprising a hydrophobic moiety, a hydrophilic moiety, and a nucleotide attachment moiety.

In embodiments, the hydrophobic and hydrophilic moieties are attached to the nucleic acid nanoparticle covalently.

In embodiments, the hydrophobic and hydrophilic moieties are covalently attached to the nucleic acid via an amide, amine, or ether linkage.

In embodiments, the hydrophilic moiety comprises an amine.

In embodiments, the hydrophilic moiety is selected from the group consisting of spermine, ethylenediamine, methylethylenediamine, ethylethylenediamine, imidazole, spermine-imidazole-4-imine, N-ethyl-N-(3-dimethylaminopropyl)-guanidinyl ethylene imine, dimethylaminoethyl acrylate, amino vinyl ether, 4-imidazoleacetic acid, diethylaminopropylamide, sulfonamides (e.g. sulfadimethoxine sulfamethoxazole, sulfadiazine, sulfamethazine), amino ketals, N-2-hydroxylpropyltimehyl ammonium chloride, imidazole-4-imines, methyl-imidazoles, 2-(aminomethyl)imidazole, 4-(aminomethyl)imidazole, 4(5)-(Hydroxymethyl)imidazole, N-(2-aminoethyl)-3-((2-aminoethyl)(methyl)amino)propanamide, 2-(2-ethoxyethoxy)ethan-1-amine, bis(3-aminopropyl)amine, [N,N-dimethylamino)ethoxy]ethyl, N-(2-aminoethyl)-3-((2-aminoethyl)(ethyl)amino)propanamide, (N-(aminoethyl)carbamoyl)methyl, N-(2-((2-aminoethyl)amino)ethyl)acetamide 3,3'-((2-aminoethyl)azanediyl)bis(N-(2-aminoethyl)propanamide), guanidyl benzylamide, [3-(guanidinium)propyl], dimethylethanolamine, 1-(2,2-dimethyl-1,3-dioxolan-4-yl)-N,N-dimethylmethanamine, 2-(2,2-dimethyl-1,3-dioxolan-4-yl)-N,N-dimethylethan-1-amine, N-(2-((2-(2-aminoethoxy)propan-2-yl)oxy)ethyl)acetamide, aminobutyl, aminoethyl, 1-(2-aminoethyl)-3-(3-(dimethylamino)propyl)-2-ethylguanidine, 1-(3-amino-3-oxopropyl)-2,4,6-trimethylpyridin-1-ium, 1-(1,3-bis(carboxyoxy)propan-2-yl)-2,4,6-trimethylpyridin-1-ium, guanidinylethyl amine, ether hydroxyl triazole, and a β-aminoester.

In embodiments, the nucleotide is functionalized with a moiety selected from the group consisting of 2-(2-(dimethylamino)ethoxy)ethan-1-ol, N-butyl-2-hydroxyacetamide, (1H-imidazol-5-yl)methanol, amino((2-(2-hydroxyacetamido)ethyl)amino)methaniminium and 1-(2-(2-hydroxyacetamido)ethyl)-2,4,6-trimethylpyridin-1-ium.

In embodiments, the nucleotide attachment moiety is cysteine.

In embodiments, the nucleic acid nanoparticle promotes endosomal escape of the cargo molecule in a receptor independent-manner.

In embodiments, the nucleic acid nanoparticle comprises a component that binds to a receptor in a cell.

In embodiments, the component comprises one selected from the group consisting of folate, TfR-T12, and a hemagglutinin peptide.

In embodiments, the cargo molecule is attached to the nucleic acid nanoparticle via a linker that can be cleaved in the lysosome.

In embodiments, the cargo molecule is attached to a cathepsin B-cleavable linker.

In embodiments, the cargo molecule is attached to a protease-cleavable linker.

In embodiments, the cargo molecule is attached to a pyrophosphate diester.

In embodiments, the invention provides a process for synthesis of 2'-O substituted nucleosides, the process comprising the treatment of anhydrouridine with alcohol-based nucleophiles.

In embodiments, the treatment comprises a base selected from the group consisting of barium tert-butoxide, benzyltrimethylammonium hydroxide, 2-tert-butylimino-2-diethyl-amino-1,3-dimethyl-perhydro-1,3,2-diazaphosphorine, n-butyllithium, sec-butyllithium, tert-butyllithium, Dabco®, N,N-diisopropylmethylamine, dimethylamine, 4-(dimethylamino)pyridine, ethylamine, N-ethyldiisopropylamine, lithium bis(trimethylsilyl)amide, lithium tert-butoxide, lithium dicyclohexylamide, lithium diethylamide, lithium di isopropylamide, lithium dimethylamide, lithium ethoxide, lithium isopropoxide, lithium methoxide, lithium 2,2,6,6-tetramethylpiperidide, magnesium bis(hexamethyldisilazide), methylamine, methyllithium, morpholine, piperidine, potassium bis(trimethylsilyl)amide, potassium tert-butoxide, potassium ethoxide, potassium methoxide, triethylamine.

In embodiments, the treatment comprises a base selected from the group consisting of aluminium bromide, aluminium chloride, aluminium isopropoxide, boron trichloride (and its various complexes), boron trifluoride (and its various complexes), dicyclohexylboron, iron (III) bromide, iron (III) chloride, montmorillonite K10 & K30, tin (IV) chloride, titanium (IV) chloride, titanium (IV) isopropoxide, titanium tetrachloride.

In embodiments, the invention provides compositions comprising a cargo molecule and a nucleic acid nanoparticle attached to the cargo molecule, wherein the nucleic acid nanoparticle is functionalized to promote a biological activity of the cargo molecule in a subject.

In embodiments, the nucleic acid nanoparticle is functionalized to promote internalisation into a cell.

In embodiments, the cargo molecule is functionalized to promote internalisation into a cell.

In embodiments, the cargo molecule is an anchored cholesterol molecule that promotes permeation through the lipid bilayer of the cell.

In embodiments, the functionalization promotes internalisation into the cell via clathrin-mediated endocytosis, non-clathrin/non-caveolae endocytosis, caveolae-mediated endocytosis, passive diffusion, simple diffusion, facilitated diffusion, transcytosis, macropinocytosis, phagocytosis, receptor mediated endocytosis, receptor diffusion, vesicle-mediated transport, active transport.

In embodiments, the nucleic acid nanoparticle may enter the cell, or be processed, via the endosome, lysosome, pinosome, or phagosome.

In embodiments, the nucleic acid nanoparticle may enter the cell across a biological membrane.

In embodiments, the functionalization may take effect in the cell cytoplasm, nucleus, mitochondria or other cellular compartment.

In embodiments, the cargo molecule is selected from the group consisting of mRNA, gRNA/CRISPR, siRNA, ASO, miRNA, lnRNA, shRNA, ribozymes, aptamers, peptides, proteins, antibodies and therapeutic small molecules.

In embodiments, cytotoxic nucleotides are incorporated into the oligonucleotide backbone.

In embodiments, the cytotoxic nucleotides are selected from the group consisting of aristomycin, neoplanocin A, ribavirin, pyrazofurin, cytarabine arabinoside (ara-C), gemcitabine, cladribine (2-CdA), showdomycin, elacytarabine.

In embodiments, the phosphate prodrugs are incorporated into the nucleic acid backbone.

In embodiments, the phosphate prodrugs are bis(S-acyl-2-thioethyl) ester derivatives of 9-[2-(phosphonomethoxy)ethyl]adenine, cycloSal pro-nucleotides, HepDirect prodrugs or octadecyloxyethyl-cidofovir.

In embodiments, the oligonucleotides are assembled into a nucleic acid nanoparticle.

In embodiments, the invention provides compositions comprising two or more cargo molecules that are covalently linked.

In embodiments, the chain of cargo molecules has the general formula

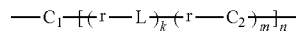

wherein C1 and C2 are cargo molecules, r is a bioconjugation linkage formed as product of a bioorthogonal reaction, L is either a linear or a branched linker, k is 0 or 1, m is 1 or any positive integer greater than 1, n is 1 or any positive integer greater than 1, and for any m>1, or n>1, or both m>1 and n>1, the following applies: (i) each r is the same or a mixture of at least two different bioconjugation linkages, (ii) each L is the same or a mixture of at least two different linker molecules, and (iii) each C2 is the same or a mixture of at least two different cargo molecules.

In embodiments, at least one of the cargo molecules has a biological function.

In embodiments, one or more cargo molecules are nucleic acids, peptides, proteins, lipids, carbohydrates, alkaloids, polyketides, tetrapyrroles, terpenes/terpenoids, phenylpropanoids, pharmaceutical compounds or combinations thereof.

In embodiments, at least one of the cargo molecules is mRNA, gRNA/CRISPR, siRNA, ASO, saRNA, miRNA, lnRNA, shRNA, ribozyme, aptamer, peptide, protein, protein domain, antibody, antibody fragment, antibody mimetic, lectin, lipid, vitamin, benzamide, small molecule, or combinations thereof.

In embodiments, at least two of the cargo molecules are siRNAs linked via an oligonucleotide spacer from the group consisting of (dT)n, (dA)n, d(C)n, d(G)n, (rU)n, (rA)n, (rC)n, (rG)n, or combinations thereof, wherein n is any positive integer between 1 and 50.

In embodiments, the two or more siRNAs are attached to each other in 5' to 5', 3' to 3' or 5' to 3' direction.

In embodiments, at least one of the cargo molecules target the asialoglycoprotein receptor expressed by hepatocytes, whereby one or more targeting moieties comprise N-acetylgalactosamine or a N-acetylgalactosamine derivative that is linked via a monovalent, bivalent, or trivalent branched linker.

In embodiments, the at least one N-acetylgalactosamine moiety is attached to an oligonucleotide cargo molecule during solid-phase synthesis or post-synthetically, whereby the attachment occurs at the 5' terminus, 3' terminus or one or more sequential internal positions of said oligonucleotide cargo molecule.

In embodiments, one or more of the cargo molecules comprise at least one of the following lipids: (i) cholesterol or a derivative thereof, (ii) a phospholipid, (iii) a cationic lipid, optionally comprising a quaternary ammonium ion, (iv) an anionic lipid, optionally comprising a phosphate group, (v) an ionizable lipid, and (vi) a branched lipid.

In embodiments, at least one of the cargo molecules is linked to a further cargo molecule by a cleavable linker.

In embodiments, at least one of the cargo molecules is linked to a further cargo molecule by a thiol-cleavable linker comprising dithiobismaleimidoethane and 1,4-bis[3-(2-pyridyldithio)propionamido]butane.

In embodiments, at least one of the cargo molecules is linked to a further cargo molecule by a hydroxylamine-cleavable linker comprising ethylene glycol bis(succinimidyl succinate).

In embodiments, at least one of the cargo molecules is linked to a further cargo molecule by a base-cleavable linker comprising bis[2-(N-succinimidyl-oxycarbonyloxy)ethyl] sulfone.

In embodiments, at least one of the cargo molecules is linked to a further cargo molecule by a Meldrum's acid derivative comprising 5-(bis(methylthio)methylene)-2,2-dimethyl-1,3-dioxane-4,6-dione.

In embodiments, at least one of the cargo molecules is linked to a further cargo molecule via a covalent bond.

In embodiments, at least one of the cargo molecules is linked to a further cargo molecule by a dicer substrate.

In embodiments, at least one of the cargo molecules is linked to a further cargo molecule with a linker selected from the group consisting of 1,8-bismaleimido-diethyleneglycol, 1,11-bismaleimido-triethyleneglycol, 1,4-bismaleimidobutane, bismaleimidohexane, bismaleimidoethane, tris(2-maleimidoethyl)amine), N-α-maleimidoacet-oxysuccinimide ester, N-β-maleimidopropyl-oxysuccinimide ester, N-ε-maleimidocaproic acid, N-γ-maleimidobutyryl-oxysuccinimide ester, succinimidyl 4-(N-maleimidomethyl)cyclohexane-1-carboxy-(6-amidocaproate), succinimidyl 6-(3(2-pyridyldithio)propionamido)hexanoate, m-maleimidobenzoyl-N-hydroxysuccinimide ester, succinimidyl iodoacetate, succinimidyl (4-iodoacetyl)aminobenzoate, PEGylated, long-chain SMCC crosslinkers, succinimidyl 4-(p-maleimidophenyl)butyrate and sulfo-NHS equivalents), p-maleimidophenyl isocyanate.

In embodiments, at least one of the cargo molecules is linked to a further cargo molecule via reactions selected from the group consisting of CuAAC, SPAAC, RuAAC, IEDDA, SuFEx, SPANC, hydrazone/oxime ether formation, thiol-ene radical reaction, thiol-yne radical reaction, thiol-Michael addition reaction, thiol-isocyanate reaction, thiol-epoxide click reaction, nucleophilic ring opening reactions (spring-loaded reactions), traceless Staudinger ligation. These linkages may be formed by carrying out coupling reactions with any cargo molecule modified with a chemical moiety from the group consisting of, but not limited to, ADIBO-PEG4, N-[(1R,8S,9s)-bicyclo[6.1.0]non-4-yn-9-yl-methyloxycarbonyl]-1,8-diamino-3,6-dioxaoctane, (1R,8S,9s)-bicyclo[6.1.0]non-4-yn-9-ylmethanol, bromoacetamido-dPEG®4-amido-DBCO, bromoacetamido-dPEG®12-amido-DBCO, bromoacetamido-dPEG®24-amido-DBCO, dibenzocyclooctyne-acid, dibenzocyclooctyne-N-hydroxysuccinimidyl ester, dibenzocyclooctyne-PEG4-acid, dibenzocyclooctyne-PEG4-alcohol, dibenzocyclooctyne-PEG4-N-hydroxysuccinimidyl ester, (4-(1,2,4,5-tetrazin-3-yl)phenyl)methanamine hydrochloride, (E)-cyclooct-4-enol, (E)-cyclooct-4-enyl 2,5-dioxo-1-pyrrolidinyl carbonate, 2,5-Dioxo-1-pyrrolidinyl 5-[4-(1,2,4,5-tetrazin-3-yl)benzylamino]-5-oxopentanoate, 5-[4-(1,2,4,5-tetrazin-3-yl)benzylamino]-5-oxopentanoic acid, 5-norbornene-2-acetic acid succinimidyl ester, 5-norbornene-2-endo-acetic acid, methyltetrazine-NHS ester, methyltetrazine-PEG4-NHS ester, TCO PEG4 succinimidyl ester, TCO-amine, tetrazine-PEG5-NHS ester, alkyne-PEG5-acid, (R)-3-amino-5-hexynoic acid hydrochloride, (S)-3-amino-5-hexynoic acid hydrochloride, (S)-3-(boc-amino)-5-hexynoic acid, N-boc-4-pentyne-1-amine, boc-propargyl-Gly-OH, 3-ethynylaniline, 4-ethynylaniline, propargylamine hydrochloride, propargyl chloroformate, propargyl-N-hydroxysuccinimidyl ester, propargyl-PEG2-acid, 3-(4-azidophenyl)propionic acid, 3-azido-1-propanamine, 3-azido-1-propanol, 4-carboxybenzenesulfonazide, O-(2-aminoethyl)-O'-(2-azidoethyl)heptaethylene glycol, O-(2-aminoethyl)-O'-(2-azidoethyl)nonaethylene glycol, O-(2-aminoethyl)-O'-(2-azidoethyl)pentaethylene glycol, azido-dPEG®4(n)acid (where n could be 4, 8, 12, 24), azido-dPEG®(n)-amine (where n could be 7, 11, 23, 35), azido-dPEG®4(n) NHS ester (where n could be 4, 8, 12, 24), azido-dPEG®(n)-TFP ester (where n could be 4, 8, 12, 24, 36), 2-[2-(2-azidoethoxy)ethoxy]ethanol, O-(2-azidoethyl)-O-[2-(diglycolyl-amino)ethyl]heptaethylene glycol, O-(2-azidoethyl)heptaethylene glycol, O-(2-azidoethyl)-O'-methyl-triethylene glycol, O-(2-azidoethyl)-O'-methyl-undecaethylene glycol, 17-azido-3,6,9,12,15-pentaoxaheptadecan-1-amine, 14-azido-3,6,9,12-tetraoxatetradecanoic acid, 11-azido-3,6,9-trioxaundecan-1-amine, bromoacetamido-dPEG®(n)azide (where n could be 3, 11, 23) and combinations thereof.

In embodiments, the chain of cargo molecules is conjugated to a nucleic acid nanoparticle, wherein the conjugate has the general formula structure of

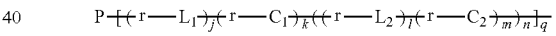

wherein P is a RNA nanoparticle, r is a bioconjugation linkage formed as product of a bioorthogonal conjugation reaction, L1 and L2 are either linear or branched linker molecules, j is 0 or 1, C1 and C2 are cargo molecules, k is 1 or any positive integer greater than 1, l is 0 or 1, m is 1 or any positive integer greater than 1, n is 1 or any positive integer greater than 1, q is 1 or any positive integer greater than 1, and for any k>1 or m>1 or n>1 or q>1 or combinations thereof, the following applies: (i) r is the same or a mixture of at least two different bioconjugation linkages, (ii) L1 is the same or a mixture of at least two different linker molecules, (iii) L2 is the same or a mixture of at least two different linker molecules, (iv) L1 and L2 are the same or different linker molecules, (v) C1 is the same or a mixture of at least two different cargo molecules, (vi) C2 is the same or a mixture of at least two different cargo molecules, and (vii) C1 and C2 are the same or different linker molecules.

In embodiments, the invention provides compositions comprising at least two cargo molecules and a nucleic acid nanoparticle attached to each of the at least two cargo molecules.

In embodiments, each of the at least two cargo molecules has a biological function.

In embodiments, each of the at least two cargo molecules is selected from the group consisting of mRNA, gRNA/

CRISPR, siRNA, ASO, miRNA, lnRNA, shRNA, ribozymes, aptamers, peptides, proteins, antibodies and therapeutic small molecules.

In embodiments, more than one of the at least two cargo molecules are conjugated to the same nucleic acid nanoparticle.

In embodiments, the more than one of the at least two cargo molecules are different.

In embodiments, the more than one cargo molecules are the same.

In embodiments, the different cargo molecules are conjugated to the nanoparticle in unequal amounts.

In embodiments, the at least two cargo molecules are conjugated via a stable covalent bond.

In embodiments, the at least two molecules are conjugated via a stable covalent bond to a stimuli-responsive linker.

In embodiments, at least one of the cargo molecules is linked to a further cargo molecule via reactions selected from the group consisting of CuAAC, SPAAC, RuAAC, IEDDA, SuFEx, SPANC, hydrazone/oxime ether formation, thiol-ene radical reaction, thiol-yne radical reaction, thiol-Michael addition reaction, thiol-isocyanate reaction, thiol-epoxide click reaction, nucleophilic ring opening reactions (spring-loaded reactions), traceless Staudinger ligation. These linkages may be formed by carrying out coupling reactions with any cargo molecule modified with a chemical moiety from the group consisting of, but not limited to, ADIBO-PEG4, N-[(1R,8S,9s)-bicyclo[6.1.0]non-4-yn-9-yl-methyloxycarbonyl]-1,8-diamino-3,6-dioxaoctane, (1R,8S,9s)-bicyclo[6.1.0]non-4-yn-9-ylmethanol, bromoacetamido-dPEG®4-amido-DBCO, bromoacetamido-dPEG®$_{12}$-amido-DBCO, bromoacetamido-dPEG®$_{24}$-amido-DBCO, dibenzocyclooctyne-acid, dibenzocyclooctyne-N-hydroxysuccinimidyl ester, dibenzocyclooctyne-PEG4-acid, dibenzocyclooctyne-PEG4-alcohol, dibenzocyclooctyne-PEG4-N-hydroxysuccinimidyl ester, (4-(1,2,4,5-tetrazin-3-yl)phenyl)methanamine hydrochloride, (E)-cyclooct-4-enol, (E)-cyclooct-4-enyl 2,5-dioxo-1-pyrrolidinyl carbonate, 2,5-Dioxo-1-pyrrolidinyl 5-[4-(1,2,4,5-tetrazin-3-yl)benzylamino]-5-oxopentanoate, 5-[4-(1,2,4,5-tetrazin-3-yl)benzylamino]-5-oxopentanoic acid, 5-norbornene-2-acetic acid succinimidyl ester, 5-norbornene-2-endo-acetic acid, methyltetrazine-NHS ester, methyltetrazine-PEG4-NHS ester, TCO PEG4 succinimidyl ester, TCO-amine, tetrazine-PEG5-NHS ester, alkyne-PEG5-acid, (R)-3-amino-5-hexynoic acid hydrochloride, (S)-3-amino-5-hexynoic acid hydrochloride, (S)-3-(boc-amino)-5-hexynoic acid, N-boc-4-pentyne-1-amine, boc-propargyl-Gly-OH, 3-ethynylaniline, 4-ethynylaniline, propargylamine hydrochloride, propargyl chloroformate, propargyl-N-hydroxysuccinimidyl ester, propargyl-PEG2-acid, 3-(4-azidophenyl)propionic acid, 3-azido-1-propanamine, 3-azido-1-propanol, 4-carboxybenzenesulfonazide, O-(2-aminoethyl)-O'-(2-azidoethyl)heptaethylene glycol, O-(2-aminoethyl)-O'-(2-azidoethyl)nonaethylene glycol, O-(2-aminoethyl)-O'-(2-azidoethyl)pentaethylene glycol, azido-dPEG®4(n)acid (where n could be 4, 8, 12, 24), azido-dPEG®(n)-amine (where n could be 7, 11, 23, 35), azido-dPEG®4(n) NHS ester (where n could be 4, 8, 12, 24), azido-dPEG®(n)-TFP ester (where n could be 4, 8, 12, 24, 36), 2-[2-(2-azidoethoxy)ethoxy]ethanol, O-(2-azidoethyl)-O-[2-(diglycolylamino)ethyl]heptaethylene glycol, O-(2-azidoethyl)heptaethylene glycol, O-(2-azidoethyl)-O'-methyl-triethylene glycol, O-(2-azidoethyl)-O'-methyl-undecaethylene glycol, 17-azido-3,6,9,12,15-pentaoxaheptadecan-1-amine, 14-azido-3,6,9,12-tetraoxatetradecanoic acid, 11-azido-3,6,9-trioxaundecan-1-amine, bromoacetamido-dPEG®(n)azide (where n could be 3, 11, 23) and combinations thereof.

EXAMPLES

Example 1—Nomenclature of Molecules

Table 2 provides the naming format for the constructs used in this invention. Tables 4 and 5 provide the sequences of exemplary RNA monomers used to form RNA nanoparticles and functionality of each RNA monomer. Table 6 outlines the peptides used in this invention.

TABLE 2

| S1- | TTUO- | 001 |
|---|---|---|
| S = construct shape<br>1 = design iteration | T = targeting<br>T = therapy<br>U = uptake<br>O = other<br>A number is assigned to outline how many of these modifications are present | Version (specific attachments listed in a separate key) |

RNA strands covered in this invention are described in Table 3.

TABLE 3 construct strands

| Identifier | SEQ ID NO. | Sequence | Modifications/comments |
|---|---|---|---|
| C-1.0 | 84 | GGGAAAcucuGucGuGGGAcGGuc AGAcuGuucAAccAcuccucuuc | 2'F U, C |
| C-1.1 | 85 | [Thiol C6 S-S] GGGAAAcucuGucGuGGGAcGGuc AGAcuGuucAAccAcuccucuuc | 2'F U, C<br>5' Thiol C6 S-S modifier |
| C-1.2 | 86 | [5' Norbornene] GGGAAAcucuGucGuGGGAcGGuc AGAcuGuucAAccAcuccucuuc | 2'F U, C<br>5' Norbornene modifier |
| C-1.3 | 87 | cAGuGuccGAuAuAcGcucGGGGA AAcucuGucGuGGGAcGGucAGAc uGuucAAccAcuccucuuc | 2'F U, C<br>Strand C-1.0 with 5' hybridisation arm for aptamer attachment |

TABLE 3-continued construct strands

| Identifier | SEQ ID NO. | Sequence | Modifications/comments |
|---|---|---|---|
| C-2.0 | 88 | GGGAAAGAAGAGGAGuGGAcGGuA cuGuGuuucAAccuGucucuGAc | 2'F U, C |
| C-2.1 | 89 | [Thiol C6 S-S] GGGAAAGAAGAGGAGuGGAcGGuA cuGuGuuucAAccuGucucuGAc | 2'F U, C 5' Thiol C6 S-S modifier |
| C-2.2 | 90 | [5' DBCO] GGGAAAGAAGAGGAGuGGAcGGuA cuGuGuuucAAccuGucucuGAc | 2'F U, C 5' DBCO-Serinol modifier |
| C-2.3 | 91 | cAGuGuccGAuAuAcGcucGGGGA AAGAAGAGGAGuGGAcGGuAcuGu GuuucAAccuGucucuGAc | 2'F U, C Strand C-2.0 with 5' hybridisation arm for aptamer attachment |
| C-3.0 | 92 | GGGAAAGcAGuGuAGcGGAcGGuG uGucAGuucAAcccAcGAcAGAG | 2'F U, C |
| C-3.1 | 93 | cAGuGuccGAuAuAcGcucGGGGA AAGcAGuGuAGcGGAcGGuGuGuc AGuucAAcccAcGAcAGAG | 2'F U, C [additional region for hybridization] |
| C-3.2 | 94 | cAGuGuccGAuAuAcGcucGGGGA AAGcAGuGuAGcGGAcGGuGuGuc AGuucAAcccAcGAcAGAG | 2'F U, C Strand C-3.0 with 5' hybridisation arm for aptamer attachment |
| C-4.0 | 95 | GGGAAAGucAGAGAcAGGAcGGuc uAGGucuucAAccGcuAcAcuGc | 2'F U, C |
| C-4.1 | 96 | [Thiol C6 S-S] GGGAAAGucAGAGAcAGGAcGGuc uAGGucuucAAccGcuAcAcuGc | 2'F U, C 5' Thiol C6 S-S modifier |
| C-4.2 | 97 | [5' Amino modifier C6] GGGAAAGucAGAGAcAGGAcGGuc uAGGucuucAAccGcuAcAcuGc | 2'F U, C 5' Amino modifier C6 |
| C-4.3 | 98 | [5' DBCO] GGGAAAGucAGAGAcAGGAcGGuc uAGGucuucAAccGcuAcAcuGc | 2'F U, C 5' DBCO-Serinol modifier |
| C-4.4 | 99 | [5' Norbornene] GGGAAAGucAGAGAcAGGAcGGuc uAGGucuucAAccGcuAcAcuGc | 2'F U, C 5' Norbornene modifier |
| C-4.5 | 100 | cAGuGuccGAuAuAcGcucGGGGA AAGucAGAGAcAGGAcGGucuAGG ucuucAAccGcuAcAcuGc | 2'F U, C Strand C-4.0 with 5' hybridisation arm for aptamer attachment |
| C-5.0 | 101 | GGGAAAcuAGAuuGGAAcAcAGuA uuGGAcAGucuGAuuGGAcuGAcA cAuuGGAGAc | 2'F U, C |
| C-5.1 | 102 | [Cy3] GGGAAAcuAGAuuGGAAcAcAGuA uuGGAcAGucuGAuuGGAcuGAcA cAuuGGAGAc | 2'F U, C 5' Cy3 |
| C-5.2 | 103 | [Cy7] GGGAAAcuAGAuuGGAAcAcAGuA uuGGAcAGucuGAuuGGAcuGAcA cAuuGGAGAc | 2'F U, C 5' Cy7 |
| C-5.3 | 104 | [5' Amino modifier C6] GGGAAAcuAGAuuGGAAcAcAGuA uuGGAcAGucuGAuuGGAcuGAcA cAuuGGAGA | 2'F U, C 5' Amino modifier C6 |
| C-5.4 | 105 | GGGAAAcuAGAuuGGAAcAcAGuA uuGGAcAGucuGAuuGGAcuGAcA cAuuGGAGAc | 2'F U, C 2'O propargyl A (bold) |

TABLE 3-continued construct strands

| Identifier | SEQ ID NO. | Sequence | Modifications/comments |
|---|---|---|---|
| C-5.5 | 106 | GGGAAAcuAGAuuGGAAcAcAGuAuuGGAcAGucuGAuuGGAcuGAcAcAuuGGAGAc | 2'F U, C<br>2'O propargyl A (bold) | siRNA strands covered in this invention are described in Table 4.

TABLE 4 siRNA strands

| Identifier | SEQ ID NO. | Sequence | Modifications/comments |
|---|---|---|---|
| S-1.0 | 61 | GcAAuuAcAuGAGcGAGcATT | 2'F U, C<br>[sense strand, PLK1-targeting canonical siRNA] |
| S-1.1 | 62 | [5' Thiol C6 S-S]<br>GcAAuuAcAuGAGcGAGcATT | 2'F U, C<br>5' Thiol C6 S-S modifier<br>[sense strand, PLK1-targeting canonical siRNA] |
| S-1.2 | 63 | [5' Amino modifier C6]<br>GcAAuuAcAuGAGcGAGcATT | 2'F U, C<br>5' Amino modifier C6<br>[sense strand, PLK1-targeting canonical siRNA] |
| S-1.3 | 64 | [Cy3]<br>GcAAuuAcAuGAGcGAGcATT | 2'F U, C<br>5' Cy3<br>[sense strand, PLK1-targeting canonical siRNA] |
| S-1.4 | 65 | [Cy7]<br>GcAAuuAcAuGAGcGAGcATT | 2'F U, C<br>5' Cy7<br>[sense strand, PLK1-targeting canonical siRNA] |
| S-1.5 | 66 | [5' PEGS-tetrazine]<br>GcAAuuAcAuGAGcGAGcATT | 2'F U, C<br>5' PEGS-tetrazine (from NHS coupling) [sense strand, PLK1-targeting canonical siRNA] |
| S-1.6 | 67 | [5' PEG4-azide]<br>GcAAuuAcAuGAGcGAGcATT | 2'F U, C<br>5' PEG4-azide (from NHS coupling) [sense strand, PLK1-targeting canonical siRNA] |
| S-1.7 | 68 | GcAAuuAcAuGAGcGAGcATT<br>Thiol C6 S-S] | [3' 2'F U, C<br>3' Thiol C6 S-S modifier<br>[sense strand, PLK1-targeting canonical siRNA] |
| S-2.0 | 69 | UGCUCGCUCAUGUAAUUGCGG | N/A<br>[antisense strand, PLK1-targeting canonical siRNA] |
| S-2.1 | 70 | uGcucGcucAuGuAAuuGcGG | 2'F U, C<br>[antisense strand, PLK1-targeting canonical siRNA] |
| S-3.0 | 71 | [5' Amino modifier C6]<br>GcAAuuAcAuGAGcGAGcATT<br>TTGcAAuuAcAuGAGcGAGcA | 2'F U, C<br>5' Amino modifier C6<br>[antisense strand, PLK1-targeting canonical siRNA]- combinatorial chain with TTTT spacer |
| S-3.1 | 72 | [5' PEG5-tetrazine]<br>GcAAuuAcAuGAGcGAGcATTT<br>TGcAAuuAcAuGAGcGAGcA | 2'F U, C<br>5' PEGS-tetrazine<br>[antisense strand, PLK1-targeting canonical siRNA]- combinatorial chain with TTTT spacer |

TABLE 4-continued siRNA strands

| Identifier | SEQ ID NO. | Sequence | Modifications/comments |
|---|---|---|---|
| S-4.0 | 73 | [5' Amino modifier C6] GcAAuuAcAuGAGcGAGcATTS-STTGcAAuuAcAuGAGcGAGcA | 2'F U, C 5' Amino modifier C6 [antisense strand, PLK1-targeting canonical siRNA]- combinatorial chain with disulfide linkage |
| S-4.1 | 74 | [5' PEGS-tetrazine] GcAAuuAcAuGAGcGAGcATTS-STTGcAAuuAcAuGAGcGAGcA | 2'F U, C 5' PEG5-tetrazine [antisense strand, PLK1-targeting canonical siRNA]- combinatorial chain with disulfide linkage |

TABLE 5 aptamer strands

| Identifier | SEQ ID NO. | Sequence | Modifications/comments |
|---|---|---|---|
| A-1.0 | 75 | [Cy5] GGAcGGAuuuAAucGccGu AGAAAAGCAuGucAAAGcc GGAccGucc | 2'F U, C 5' Cy5 E07min aptamer |
| A-1.1 | 76 | cGAGcGuAuAucGGAcAcu GuuuuuuGGAcGGAuuuAA ucGccGuAGAAAAGcAuGu cAAAGccGGAAccGucc | 2'F U, C E07min aptamer [additional region for hybridization] |
| A-1.2 | 77 | [5' Amino modifier C6] cGAGcGuAuAucGGAcAcu GuuuuuuGGAcGGAuuuAA ucGccGuAGAAAAGcAuGu cAAAGccGGAAccGucc | 2'F U, C 5' Amino modifier C6 E07min (SXFFX1) aptamer |
| A-1.3 | 78 | [5' PEGS-tetrazine] cGAGcGuAuAucGGAcAcu GuuuuuuGGAcGGAuuuAA ucGccGuAGAAAAGcAuGu cAAAGccGGAAccGucc | 2'F U, C 5' PEG5-tetrazine E07min (SXFFX1) aptamer |

Peptides used herein are described in Table 6.

TABLE 6 peptides used in this invention

| Identifier | SEQ ID NO. | Description | Sequence | Modifications/comments |
|---|---|---|---|---|
| P-1.0 | 16 | Linear peptide | GFWFG | None |
| P-1.1 | 79 | Linear peptide | GFWFG | Maleimide functionalized (via) 6-maleimidohexanoic acid (N terminus) |
| P-2.0 | 80 | HA2 | GLFGAIAGFIEN GWEGMIDGWYG | Maleimide functionalized (via) 6-maleimidohexanoic acid (N terminus) |
| P-3.0 | 81 | INF7 | GLFEAIEGFIEN GWEGMIDGWYG | Maleimide functionalized (via) 6-maleimidohexanoic acid (N terminus) |
| P-4.0 | 82 | GALA3 | LAEALAEALEAL AA | Maleimide functionalized (via) 6-maleimidohexanoic acid (N terminus) |
| P-5.0 | 83 | KALA | WEAKLAKALAKA LAKHLAKALAKA LKACEA | Maleimide functionalized (via) 6-maleimidohexanoic acid (N terminus) |

Example 2—RNA Synthesis

RNA strands were synthesized using a H-16 synthesizer (K&A). Syntheses were performed on a 1 μmol column in a DMT-OFF mode, using a standard RNA coupling protocol (720 s for 2'-tert-butyldimethylsilyl (TBDSM)-protected amidites and all other modifications. The solutions of amidites, tetrazole and acetonitrile were dried over activated molecular sieves (4 Å) overnight. After synthesis the RNA was deprotected with 1:1 methylamine/ammonium hydroxide (AMA) for 3 h at rt. The solid support was then filtered and washed twice with EtOH:water (1:1). The resultant RNA solution was then evaporated to dryness and dissolved in 200 μl dry DMSO. Then 275 μl TEA*3HF (TREAT-HF) was added and incubated either at 65° C. for 3 h. The RNA was then subjected to EtOH precipitation.

Crude RNA strands were purified either by IEX-HPLC or by IP-RP HPLC. IEX was carried out with a semi-preparative DNAPac PA100 (ThermoFisher), 22×250 mm column at 75° C. with a flow rate of 4.5 mL/min and UV detection at 260 nm. Usually, 100-250 μL of crude RNA solution was injected per run. Elution was performed with a linear gradient of approximately Δ10% B over 2 to 2.5 column volumes, with the starting concentration adjusted to the length of the oligonucleotide. Buffer A: 25 mM Tris-HCl, pH 8.0, 20% acetonitrile, 10 mM sodium perchlorate; buffer B: 25 mM Tris·HCl, pH 8.0, 20% acetonitrile, 600 mM sodium perchlorate.

RP-HPLC was carried out with a Hypersil Gold (ThermoFisher) C18 column (10×150 mm) at 60° C., with a flow rate of 5 mL/min and UV detection at 260 nm. Usually, 100-250 μL of crude RNA solution was injected per run. Buffer A: TEAA (0.1 M, pH=7); buffer B: MeCN. Fractions containing RNA were pooled and acetonitrile was removed in vacuo. The purified oligos were then desalted with Gel-Pak desalting columns (Glen). The solution was evaporated, and the RNA dissolved in nuclease-free water for concentration determination by UV absorbance and quality assessment via denaturing PAGE.

Adaptation to Synthesis Procedure for Modified Strands

5' amino—10% DEA solution in MeCN was applied onto the oligonucleotide while still on CPG. After 5 min treatment the column was rinsed with MeCN and processed further.

5' Cy3-MMTr group at 5'-end of Cy3 containing sequences was removed during RPC MMT-ON purification.

Example 3—Optimised Assembly Protocol

The key scaffold in this work, square SQ1, was assembled according to a standard protocol. Equimolar amounts of the 5 different strands (A, B, C, D, E—FIG. 22; these correspond to C-1.0, C-2.0, C-3.0, C-4.0 and C-5.0 and sub-variants) were combined in PBS+MgCl$_2$ (2 mM) buffer, with a final concentration of 10 μM. The 5 strands were annealed to each other at 95° C. for 5 min then slowly cooled down to 15° C. The scaffold was then analyzed by native polyacrylamide gel electrophoresis (PAGE) and dynamic light scattering (DLS) (vide infra).

Figure 22:
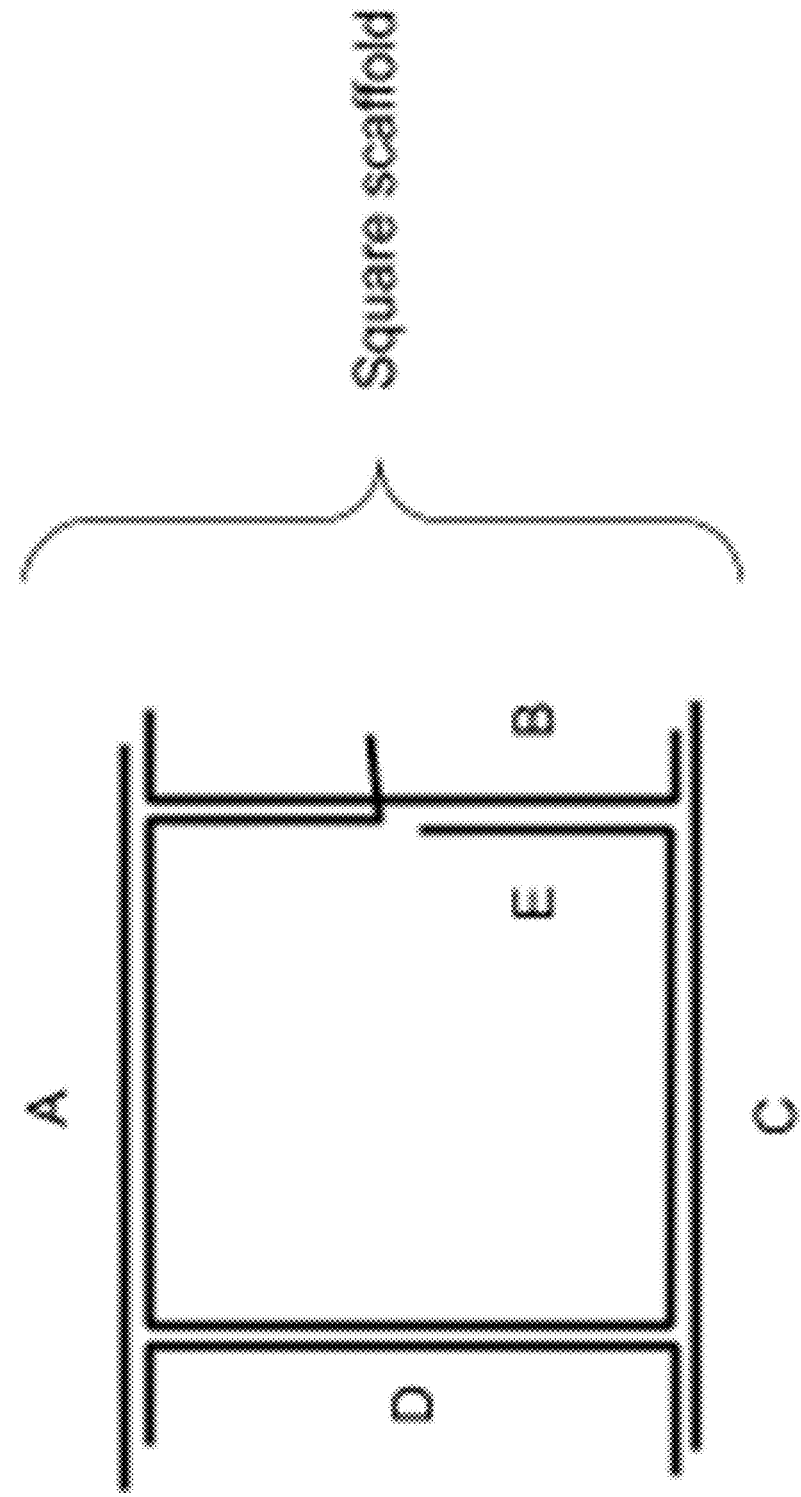
FIG. 22 is Schematic outlining the core scaffold of a composition in an embodiment of the invention (SQ-0000-001).

FIG. 22 is Schematic outlining the core scaffold of a composition in an embodiment of the invention (SQ-0000-001).

For PAGE, the assembled scaffold was electrophoresed on native PAGE (6%) in 1×TBMg (890 mM Tris Borate+20 mM Mg(OAc)$_2$, pH=8.3) at a constant voltage of 100 V. Gel bands were visualized using GelRed™. 10 μmol of structures was loaded. 2 μL of glycerin (70% in H$_2$O) was added to samples before loading.

For DLS, the assembled scaffold was analyzed using a Malvern Zetasizer Nano S ZEN 1600 Nano Particle Size Analysis—20 μL of samples were used, and intensity was recorded. Average of three trials was calculated. All measurements were carried out at 25° C. Samples were centrifuged at 12000 rpm for 5 minutes before analysis in order to remove dust and debris.

Example 4—Synthesis of Modifiers to Enable Conjugation Chemistries

General Experimental $^1$H NMR spectra were recorded at 400 MHz. $^{13}$C NMR spectra were recorded at 100 MHz. Chemical shifts (δ) are quoted in units of parts per million (ppm) downfield from tetramethylsilane and are referenced to a residual solvent peak. (CDCl$_3$ (δ$_H$: 7.26, δ$_C$: 77.0)). Coupling constants (J) are quoted in units of Hertz (Hz). The following abbreviations are used within $^1$H NMR analysis: s=singlet, d=doublet, t=triplet, q=quartet, pent=pentet, m=multiplet, dd=doublet of doublets, dt=doublet of triplets. Spectra recorded at 400 ($^1$H NMR) and 100 ($^{13}$C NMR) were carried out by the Imperial College London Department of Chemistry NMR Service.

Low- and high-resolution mass spectrometry (EI, CI, FAB) were recorded at Imperial College London. Measurements carried out by the Imperial College Department of Chemistry Mass Spectrometry Service used a Micromass Platform II and Micromass AutoSpec-Q spectrometer.

Flash column chromatography was carried out on BDH silica gel 60, particle size 0.040-0.063 mm. Thin layer chromatography (TLC) was performed on pre-coated aluminium backed or glass backed plates (Merck Kieselgel 60 F254), and visualised with ultraviolet light (254 nm) or potassium permanganate (KMnO$_4$), vanillin or phosphomolybdic acid (PMA) stains.

5' C6 S—S Norbornene Modifier

Figure 23:
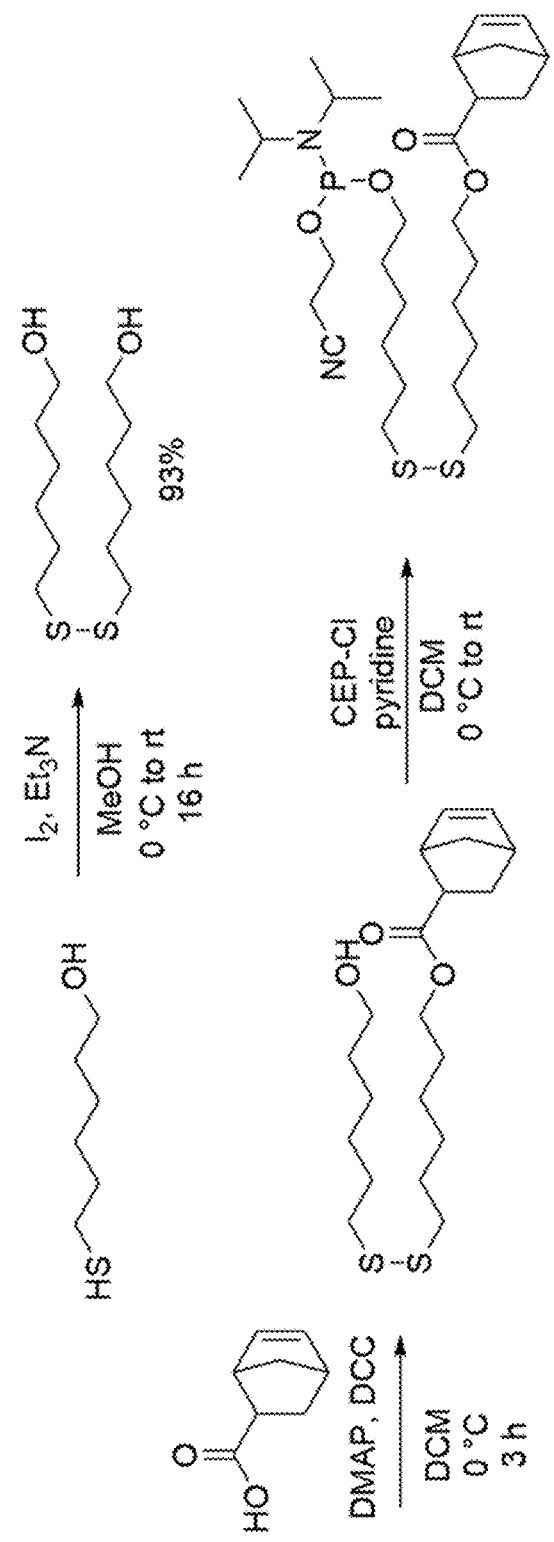
FIG. 23 is schematic of the synthesis of a disulfide-norbornene 5' modifier according to an embodiment of the invention.

FIG. 23 is schematic of the synthesis of a disulfide-norbornene 5' modifier according to an embodiment of the invention.

6,6'-Disulfanediylbis(hexan-1-ol)

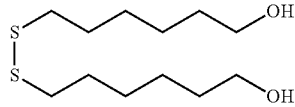 [SMILES: OCCCCCCSSCCCCCCO]

Synthesized according to a procedure outlined by Varenikov and co-workers (A. Varenikov, M. Gandelman, Organotitanium Nucleophiles in Asymmetric Cross-Coupling Reaction: Stereoconvergent Synthesis of Chiral α-CF3 Thioethers, J. Am. Chem. Soc. 141 (2019) 10994-10999. https://doi.org/10.1021/jacs.9b05671.). Colorless oil obtained (18.2 g, 92%). NMR (400 MHz, Chloroform-d) δ 3.65 (t, J=6.6 Hz, 4H), 2.70 (dd, J=7.9, 6.8 Hz, 4H), 1.81-1.77 (m, 2H), 1.76-1.65 (m, 4H), 1.59 (dq, J=7.9, 6.6 Hz, 4H), 1.51-1.32 (m, 8H).

6-((6-Hydroxyhexyl)disulfaneyl)hexyl bicyclo[2.2.1]hept-5-ene-2-carboxylate

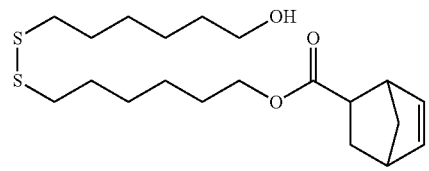 [SMILES: O=C(OCCCCCCSSCCCCCCO)C1CC2C=CC1C2]

Synthesized according to a modified procedure found in the art (US2011/263526). A solution of DCC (1.15 g in 5 mL anhydrous DCM, 5.61 mmol) was added dropwise to a stirred solution of 5-norbornene-2-carboxylic acid (500 mg, 3.62 mmol), 6,6'-disulfanediylbis(hexan-1-ol) (1.93 g, 7.25 mmol) and DMAP (89 mg, 0.72 mmol) in anhydrous DCM (20 mL) over 5 min at 0° C. The reaction mixture was then stirred at 0° C. for 3 h. Upon completion (TLC: 25% EtOAc/pentane), the reaction mixture was filtered. The filtrate was then washed with water (3×20 mL) and brine (3×20 mL). The organic layer was then dried (MgSO$_4$) and concentrated in vacuo. The crude residue was then purified by column chromatography (20 to 30% EtOAc/pentane), affording the title compound as a colorless oil (469 mg, 34%). $^1$H NMR (400 MHz, Chloroform-d) δ 6.22 (dd, J=5.7, 3.1 Hz, 1H), 5.94 (dd, J=5.7, 2.9 Hz, 1H), 4.04 (td, J=6.6, 4.2 Hz, 2H), 3.23 (dq, J=3.4, 1.8 Hz, 1H), 2.95 (ddd, J=12.6, 4.7, 3.0 Hz, 2H), 2.71 (td, J=7.3, 2.2 Hz, 5H), 1.93 (ddd, J=12.6, 9.3, 3.7 Hz, 1H), 1.72 (dt, J=7.2, 4.0 Hz, 4H), 1.51-1.37 (m, 14H), 1.36-1.26 (m, 1H); HRMS ES+(m/z): [M]$^+$ calc'd for C$_{20}$H$_{34}$O$_3$: 386.6090; found: 386.6097.

6-((6-(((2-cyanoethoxy)(diisopropylamino)phosphaneyl)oxy)hexyl)disulfaneyl)hexyl bicyclo[2.2.1]hept-5-ene-2-carboxylate

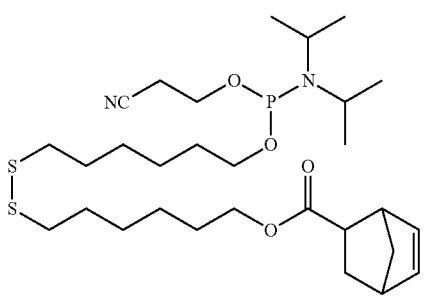 [SMILES: CC(C)N(C(C)C)P(OCCC#N)OCCCCCCSSCCCCCCOC(=O)C1CC2C=CC1C2]

6-((6-Hydroxyhexyl)disulfaneyl)hexyl bicyclo[2.2.1]hept-5-ene-2-carboxylate (496 mg, 0.87 mmol) and N,N-diisopropylethylamine (451 mg, 609 μL, 3.49 mmol) were dissolved in anhydrous DCM (15 mL) and stirred over activated molecular sieves for 1 h at 0° C. 2-Cyanoethyl N,N-diisopropylchlorophosphoramidite (413 mg, 1.74 mmol) was added and the reaction mixture was stirred for 30 min at 0° C., and was then slowly warmed to rt over 1.5 h. Upon completion (TLC: 25% EtOAc/pentane), the reaction mixture was washed with sat. NaHCO$_3$ (3×20 mL). The organic layer was then dried (MgSO$_4$) and concentrated in vacuo, and the crude product was purified by column chromatography (10% EtOAc/pentane+1% Et$_3$N), affording the title compound was a colourless oil (341 mg, 67%). $^1$H NMR (400 MHz, Chloroform-d) δ 6.21 (dd, J=5.7, 3.1 Hz, 1H), 5.94 (dd, J=5.7, 2.9 Hz, 1H), 4.04 (td, J=6.6, 4.0 Hz, 2H), 3.92-3.78 (m, 2H), 3.75-3.54 (m, 4H), 3.23 (dd, J=4.1, 2.3 Hz, 1H), 3.03-2.88 (m, 2H), 2.73-2.67 (m, 6H), 2.07 (s, 1H), 1.92 (ddd, J=11.8, 9.3, 3.7 Hz, 1H), 1.70 (d, 0.1=7.2 Hz, 3H), 1.66-1.61 (m, 4H), 1.45-1.39 (m, 8H), 1.30 (t, J=4.4 Hz, 1H), 1.21 (dd, J=6.8, 4.1 Hz, 14H); $^{31}$P NMR (162 MHz, Chloroform-d) δ 147.26; HRMS ES+(m/z): [M]$^+$ calc'd for C$_{29}$H$_{51}$O$_4$PS$_2$: 586.3028; found: 586.8304.

5' Norbornene Modifier

Bicyclo[2.2.1]hept-5-en-2-ylmethyl (2-cyanoethyl) diisopropylphosphoramidite

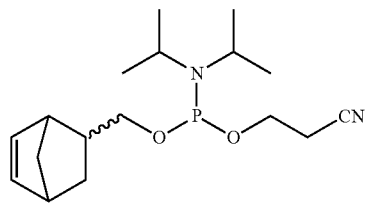 [SMILES: CC(C)N(C(C)C)P(OCCC#N)OCC1CC2C=CC1C2]

Synthesized according to a procedure outlined by Schoch and co-workers. (J. Schoch, M. Wiessler, A. Jäschke, Post-Synthetic Modification of DNA by Inverse-Electron-Demand Diels-Alder Reaction, J. Am. Chem. Soc. 132 (2010) 8846-8847. https://doi.org/10.1021/ja102871p.). $^1$H NMR (400 MHz, Chloroform-d) δ 6.16 (dd, J=5.7, 3.1 Hz, 1H), 5.98 (ddd, J=8.2, 5.8, 2.9 Hz, 1H), 3.94-3.76 (m, 3H), 3.62 (dpd, J=10.1, 6.8, 1.4 Hz, 2H), 3.40 (ddt, J=38.5, 10.1, 7.0 Hz, 1H), 3.30-3.14 (m, 1H), 2.96-2.92 (m, 1H), 2.82 (q, J=1.8 Hz, 1H), 2.72-2.62 (m, 2H), 1.82 (dddd, J=11.7, 9.2, 3.8, 1.1 Hz, 1H), 1.50-1.43 (m, 1H), 1.20 (dd, J=6.8, 5.6 Hz, 15H), 0.59-0.49 (m, 1H); $^{31}$P NMR (162 MHz, Chloroform-d) δ 147.18 (dd, J=37.8, 10.4 Hz).

4-(2-azidoethyl)-1H-imidazole

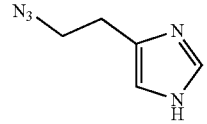

Synthesized according to a procedure outlined by Yang and co-workers. (A Luo.ng, T. Issarapanichkit, S. D. Kong, R. Fong and J. Yang pH-Sensitive, N-ethoxybenzylimidazole (NEBI) bifunctional crosslinkers enable triggered release of therapeutics from drug delivery carriers, Org. Biomol. Chem., 2010, 8, 5105-5109, doi.org/10.1039/C0OB00228C). Light brown oil obtained (360 mg, 95%). $^1$H NMR (400 MHz, Chloroform-d) δ 7.64 (s, 1H), 6.92 (s, 1H), 3.61 (t, J=6.7 Hz, 2H), 2.97-2.88 (m, 2H); LRMS ES+(m/z): [M]+ calc'd for C$_5$H$_7$N$_5$; 137.1 found: 138.1 [M+H]$^+$.

Guanidine Azide

Tert-butyl (4-azidobutyl)carbamate

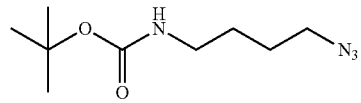

Synthesized according to a procedure outlined by Ramos and co-workers. (R. Swider, M. Maslyk, J. M. Zapico, C. Coderch, R. Panchuk, N. Skorokhyd, A. Schnitzler, K. Niefind, B. de Pascual-Teresa and A. Ramos, Synthesis, biological activity and structural study of new benzotriazole-based protein kinase CK2 inhibitors, RSC Adv., 2015, 5, 72482, doi.org/10.1039/C5RA12114K). Colorless sticky solid obtained (361 mg, 88%). $^1$H NMR (400 MHz, Chloroform-d) δ 4.59 (br. s, 1H), 3.33 (t, J=6 Hz, 2H), 3.18-3.15 (m, 2H), 1.67-1.56 (m, 4H), 1.46 (s, 9H).

1-(4-azidobutyl)guanidine

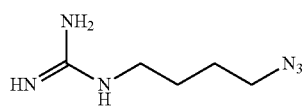 [SMILES: [N-]=[N+]=NCCCCNC(=N)N]

Tert-butyl (4-azidobutyl)carbamate (360 mg, 1.0 mmol) was dissolved in DCM/TFA (9:1, 16.6 mL) and stirred at room temperature overnight. The organic solvents were evaporated, redissolved in DCM (10 mL) quenched with $K_2CO_{3(s)}$, filtered and evaporated. Obtained oily product was directly used for the following step.

Half of the amount of crude mixture (186 mg, 1.0 eq, 1.61 mmol) was dissolved in DCM (15.5 mL), followed by N,N'-Bis(benzyloxycarbonyl)-1H-pyrazole-1-carboxamidine (561 mg, 1.1 eq, 1.7 nmol), TEA (0.6 mL). The reaction mixture was stirred overnight at rt. DCM (15 mL) was added to the reaction mixture, which was then subsequently washed with water (2×15 mL), saturated $NaHCO_3$ (10 mL), brine (10 mL). The organic phase was then dried over $MgSO_4$ and concentrated in vacuo. The obtained oil was dissolved in DCM/TFA (2:8, 5 mL) and stirred overnight at rt. The reaction was quenched with solid $K_2CO_3$, filtered, washed with $H_2O$ (2×10 mL). The water phase was evaporated and desalted on the C18 column resulting in the title compound. LRMS ES+(m/z): [M]$^+$ calc'd for $C_5H_{12}N_6$; 156.1 found: 157.1 [M+H]+.

Example 5-5' Modification of Amine Modified Strands with NHS-Ester-Based Linkers To install the appropriate reactive groups to enable conjugation chemistry, 5' amino modified RNA strands were treated with heterobifunctional NHS-linkers containing the same.

Figure 24:
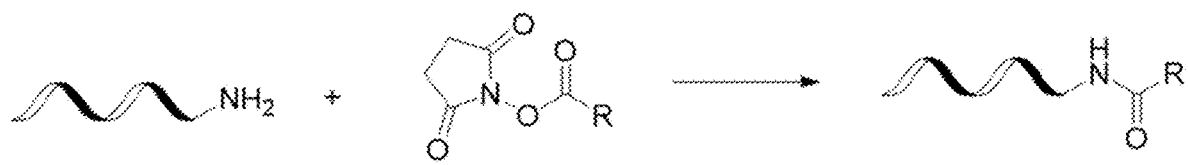
FIG. 24 is a schematic outlining the procedure used for modification of 5' amino-modified RNA with NHS-ester linkers.
Figure 24:
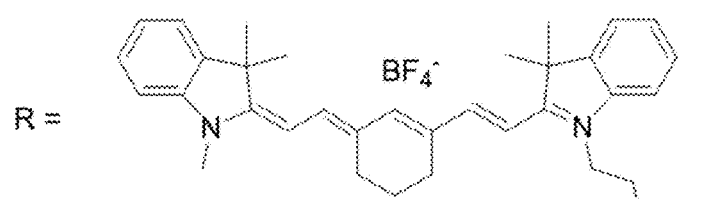
Figure 24:
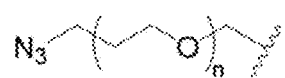
Figure 24:
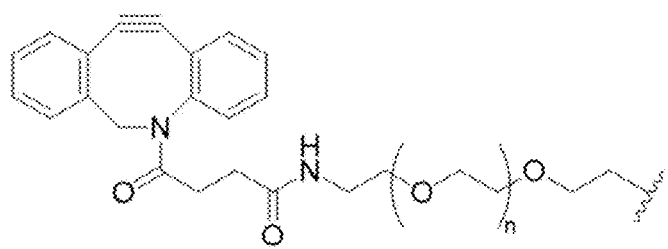
Figure 24:
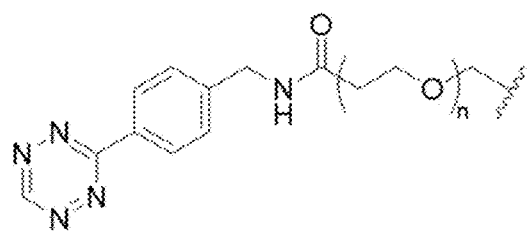

FIG. 24 is a schematic outlining the procedure used for modification of 5' amino-modified RNA with NHS-ester linkers. Modifications include tetrazine, azides and dibenzocyclooctynes (DBCO)

General Coupling Procedure

The amino-modified oligonucleotide was prepared as a stock solution or dry aliquot. The heterobifunctional NHS-ester (NHS-SM) was dissolved at a concentration of 100 mM in anhydrous DMSO.

Amino-modified oligonucleotide was diluted to a final concentration of 100-200 μM, followed by the addition of DMSO (50% total volume), bicarbonate buffer (0.5 M, pH=8.4, 20% total volume) and NHS-SM (5-20 eq). The reaction mixture was agitated at 30° C. for 1-3 h and was then purified by RP-HPLC. With higher volumes, EtOH precipitation and resuspension in $H_2O$ is recommended.

Modified Coupling Procedure for Tetrazine NHS

The amino-modified oligonucleotide was prepared as a stock solution or dry aliquot. The heterobifunctional NHS-ester (NHS-SM) was dissolved at a concentration of 100 mM in anhydrous DMF.

Amino-modified oligonucleotide was diluted to a final concentration of 100-200 μM, followed by sodium chloride/bicarbonate buffer (100 mM NaCl, 0.05 M, pH=8.4) and NHS-Tetrazine (5-20 eq). The reaction mixture was agitated at 30° C. for 1 h and was then purified by RP-HPLC. With higher volumes, EtOH precipitation and resuspension in $H_2O$ is recommended.

Figure 25:
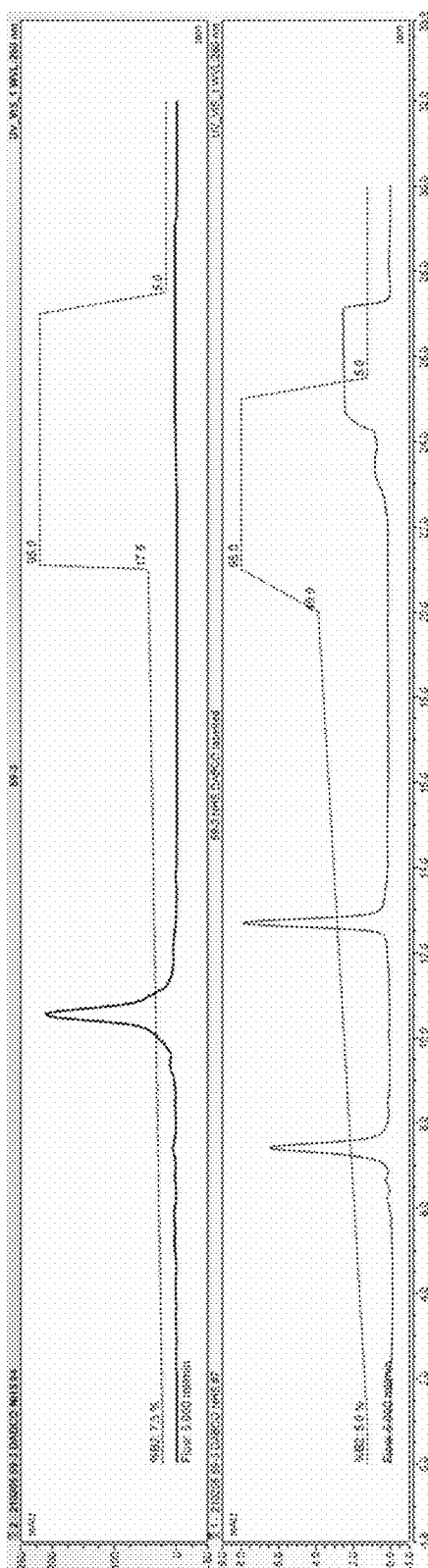
FIG. 25 shows RP-HPLC traces of the reaction of a 5' amino modified RNA with NHS-PEG-DBCO.

FIG. 25 shows RP-HPLC traces of the reaction of a 5' amino modified RNA with NHS-PEG-DBCO. Upper panel shows the entire trace C-4.2, and lower panel shows the peak at 13 min, which contains the product C-4.3.

Figure 26:
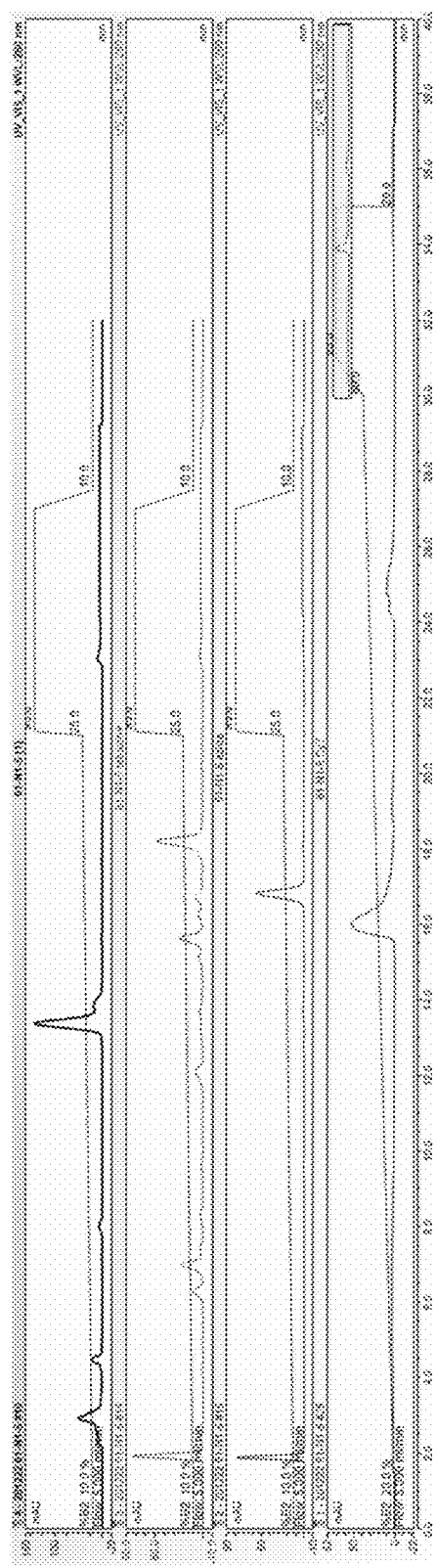
FIG. 26 shows a preparative RP-HPLC traces of a 5' amino modified siRNA.

FIG. 26 shows a preparative RP-HPLC traces of a 5' amino modified siRNA. Upper panel shows the starting material S-1.2, second panel shows material treated with NHS-PEG5-tetrazine, third panel shows material treated with NHS-PEG4-azide, and bottom panel shows material treated with NHS-Cy7.

Example 6—IEDDA and SPAAC Conjugation of siRNA and Aptamers to RNA

Example of IEDDA Click Procedure

Norbornene modified core strand C-4.4 (5 nmol, 1.0 eq, 50 uM final concentration) was mixed with siRNA functionalized via tetrazine-NHS (S-1.5, 15 nmol, 3.0 eq) in PBS buffer. The reaction mixture was agitated at rt for 12 h, followed by purification with reverse phase HPLC using a Hypersil Gold C18 preoperative column at a flow rate of 5 mL/min. 5% to 25% B in 20 min (A: 0.1 M TEAA buffer pH 7, B: MeCN), fractions containing product were concentrated and desalted, resulting in 44% isolated yield.

Example of SPAAC Click Procedure

DBCO modified core strand (C-4.3, 1 nmol, 1.0 eq, 50 uM final concentration) was mixed with azide functionalized siRNA S-1.6 (2 nmol, 2.0 eq) in PBS buffer. The reaction mixture was agitated at rt for 24 h, followed by direct PAGE analysis.

IEDDA on Assembled NA Nanoparticle

Figure 35:
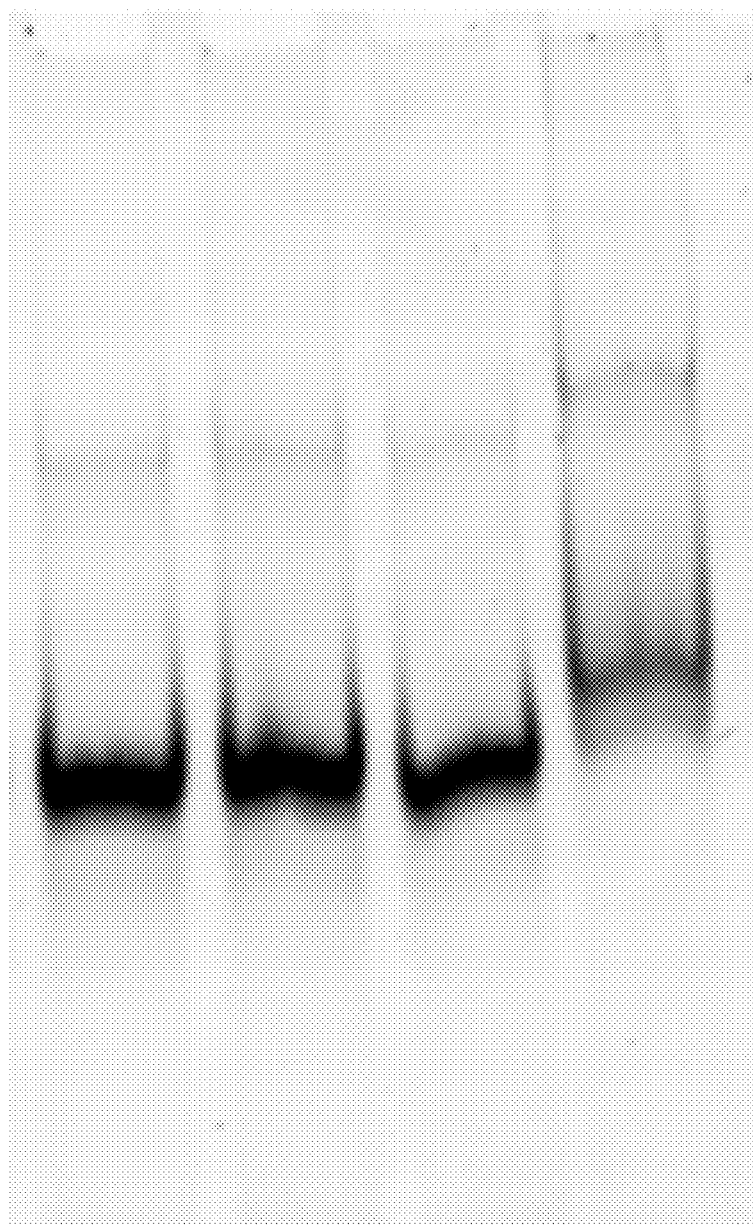
FIG. 35 shows native PAGE (8%, 150 V, 1 h) showing representative IEDDA conjugations with a fully assembled NA nanoparticle (SQ1-0000-005).

The NA nanoparticle (SQ1-0000-005) was assembled according to the standard assembly protocol to afford a construct at a concentration of 10 μM, with one strand (C-4.4) having a reactive norbornene moiety at the 5' position. This was then treated with tetrazine-labelled siRNA S-1.5 in 1, 2 and 4 molar equivalents, respectively, in PBS. The resultant solution was agitated at 30° C., followed by direct analysis by 8% native PAGE (FIG. 35).

Figure 27:
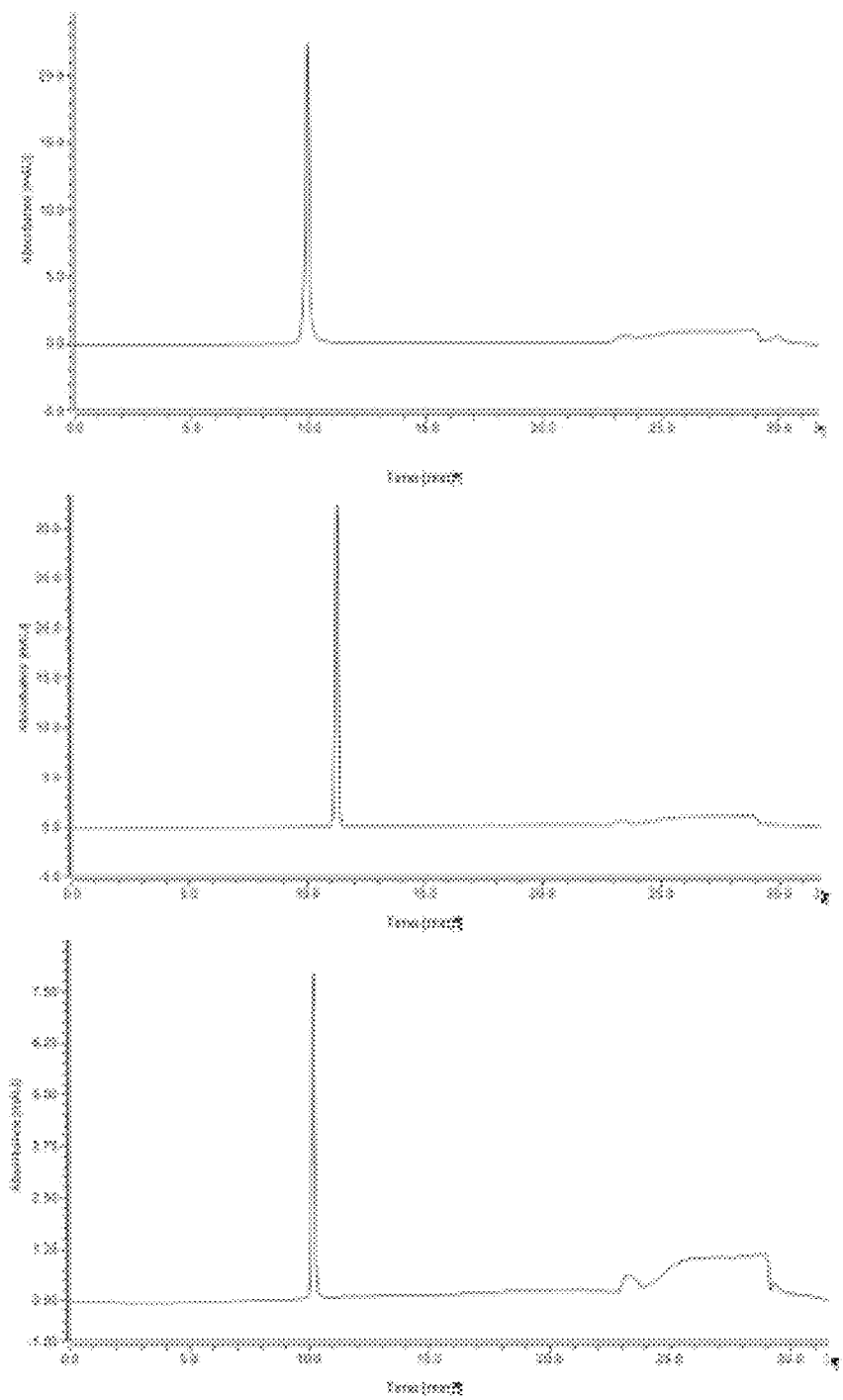
FIG. 27 shows analytical RP-HPLC traces of RNA strands.

FIG. 27 shows analytical RP-HPLC traces of RNA strands. Upper panel shows unmodified strand C-4.0, middle panel is analogous strand modified with norbornene C-4.4, and bottom panel show analogous strand modified with tetrazine C-4.3.

Figure 28:
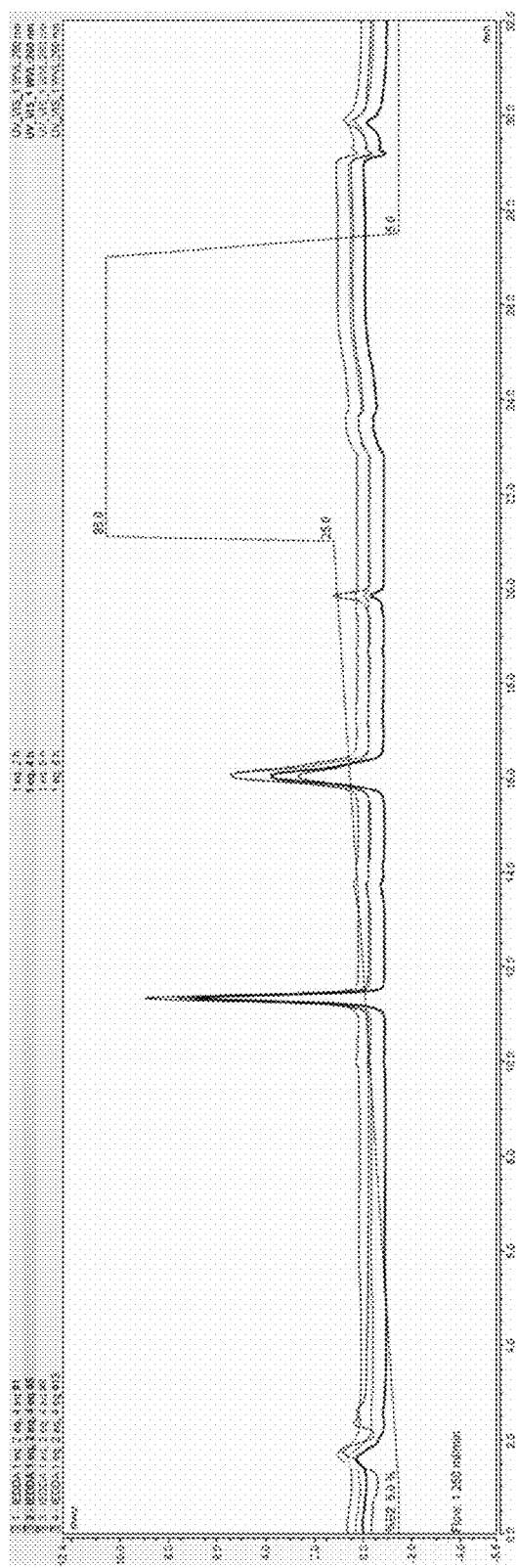
FIG. 28 shows overlaid analytical RP-HPLC traces of a time-course experiment following the coupling of a 5' norbornene modified C-4.4 RNA with 5' tetrazine modified siRNA S-1.5 (1:1 molar equivalents).

FIG. 28 shows overlaid analytical RP-HPLC traces of a time-course experiment following the coupling of a 5' norbornene modified C-4.4 RNA with 5' tetrazine modified siRNA S-1.5 (1:1 molar equivalents).

Figure 29:
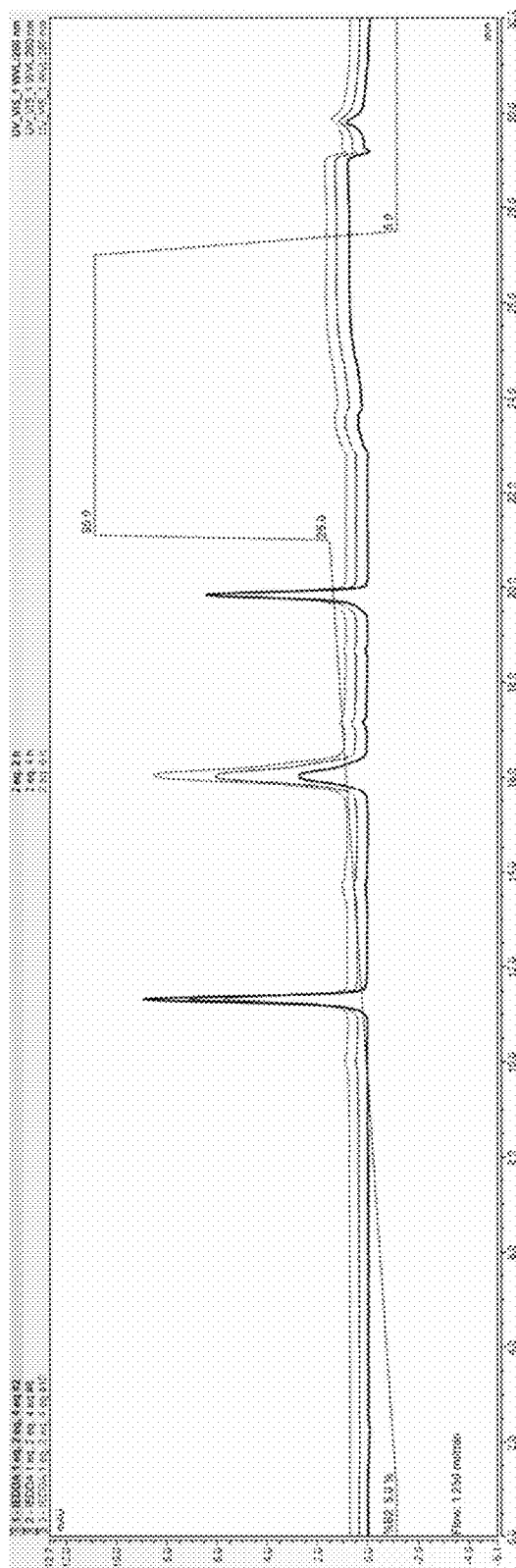
FIG. 29 shows overlaid analytical RP-HPLC of a time-course experiment following the coupling of a 5' norbornene modified RNA C-4.4 with 5' tetrazine modified siRNA S-1.5 (1:2 molar equivalents).

FIG. 29 shows overlaid analytical RP-HPLC of a time-course experiment following the coupling of a 5' norbornene modified RNA C-4.4 with 5' tetrazine modified siRNA S-1.5 (1:2 molar equivalents).

Figure 30:
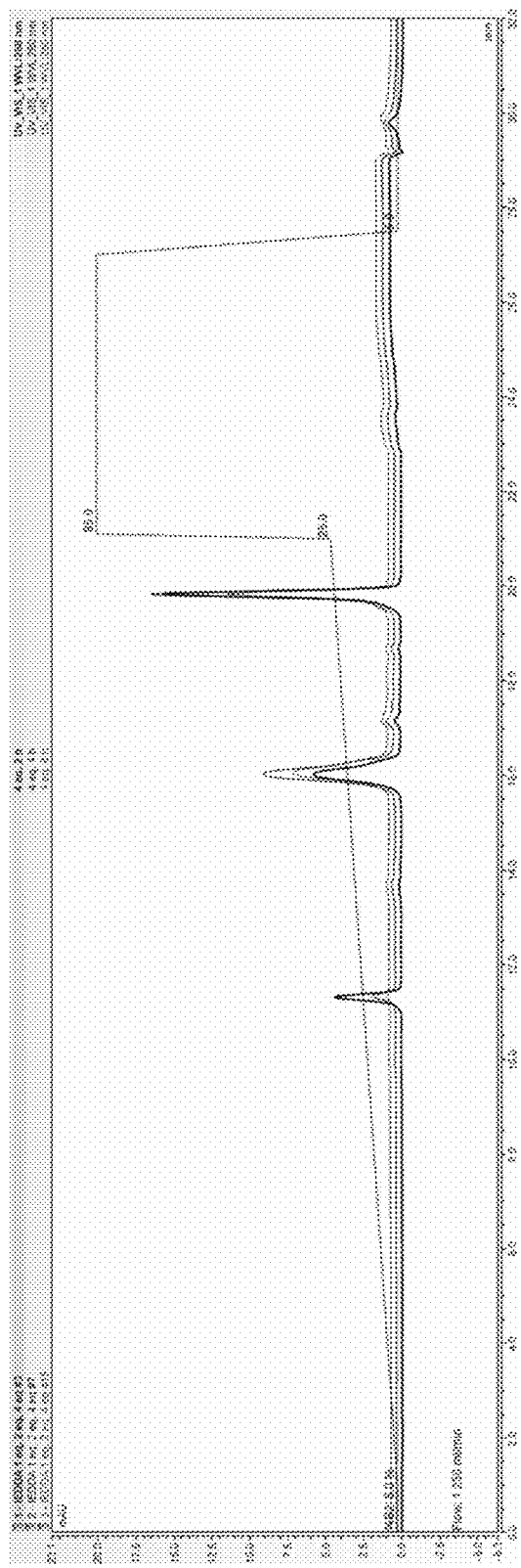
FIG. 30 shows overlaid analytical RP-HPLC traces from a time-course experiment following the coupling of a 5' norbornene modified RNA C-4.4 with 5' tetrazine modified siRNA S-1.5 (1:4 molar equivalents).

FIG. 30 shows overlaid analytical RP-HPLC traces from a time-course experiment following the coupling of a 5' norbornene modified RNA C-4.4 with 5' tetrazine modified siRNA S-1.5 (1:4 molar equivalents).

Figure 31:
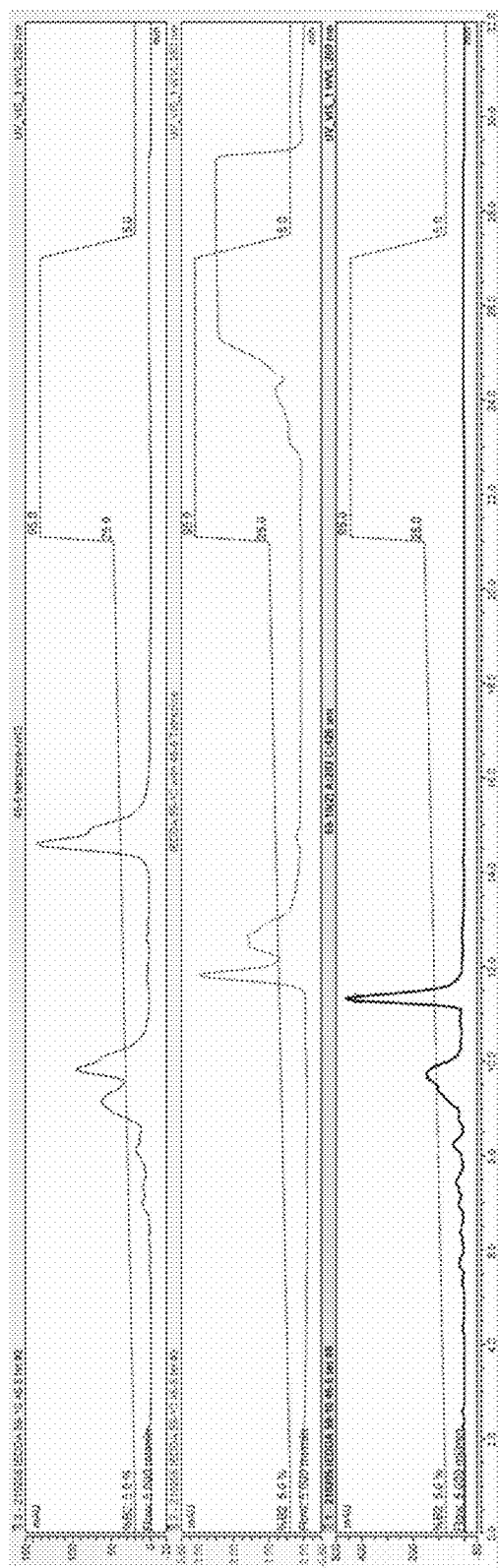
FIG. 31 shows analytical RP-HPLC traces of coupling of 5' norbornene modified RNA C-4.4 with 5' tetrazine modified aptamer A-1.3.

FIG. 31 shows analytical RP-HPLC traces of coupling of 5' norbornene modified RNA C-4.4 with 5' tetrazine modified aptamer A-1.3. Upper panel shows trace to 14.2 min of tetrazine modified aptamer, middle panel shows trace to 12.2 min of IEDDA conjugate, and bottom panel shows trace to 11.5 min of 5' norbornene modified RNA.

Figure 32:
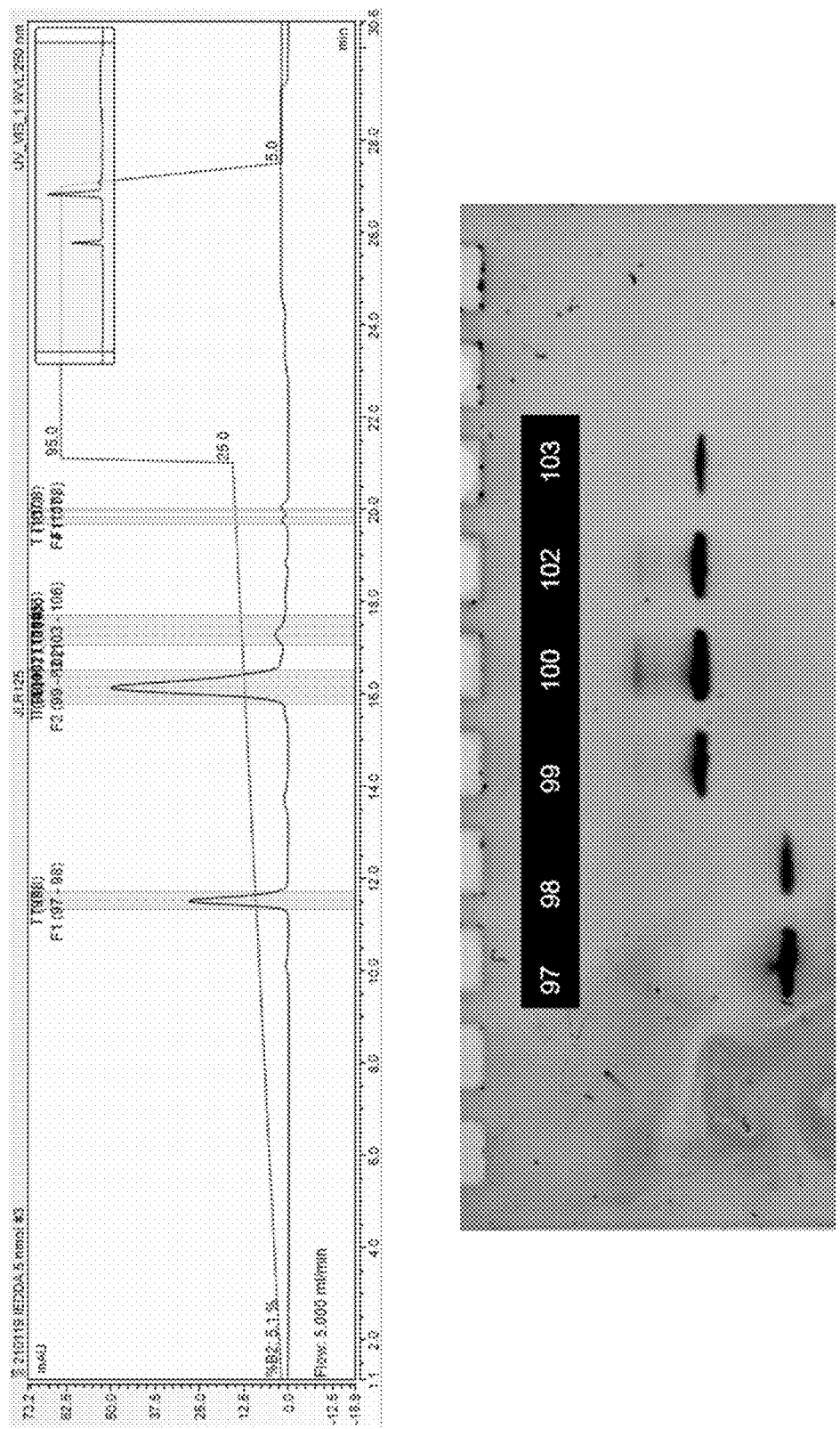
FIG. 32 shows HPLC traces showing purification of an IEDDA coupled strand (NA nanoparticle core strand C-4.4+ siRNA S-1.5) with corresponding PAGE (15% denaturing, 250 V) showing purified fractions.

FIG. 32 shows HPLC traces showing purification of an IEDDA coupled strand (NA nanoparticle core strand C-4.4+ siRNA S-1.5) with corresponding PAGE (15% denaturing, 250 V) showing purified fractions.

Figure 33:
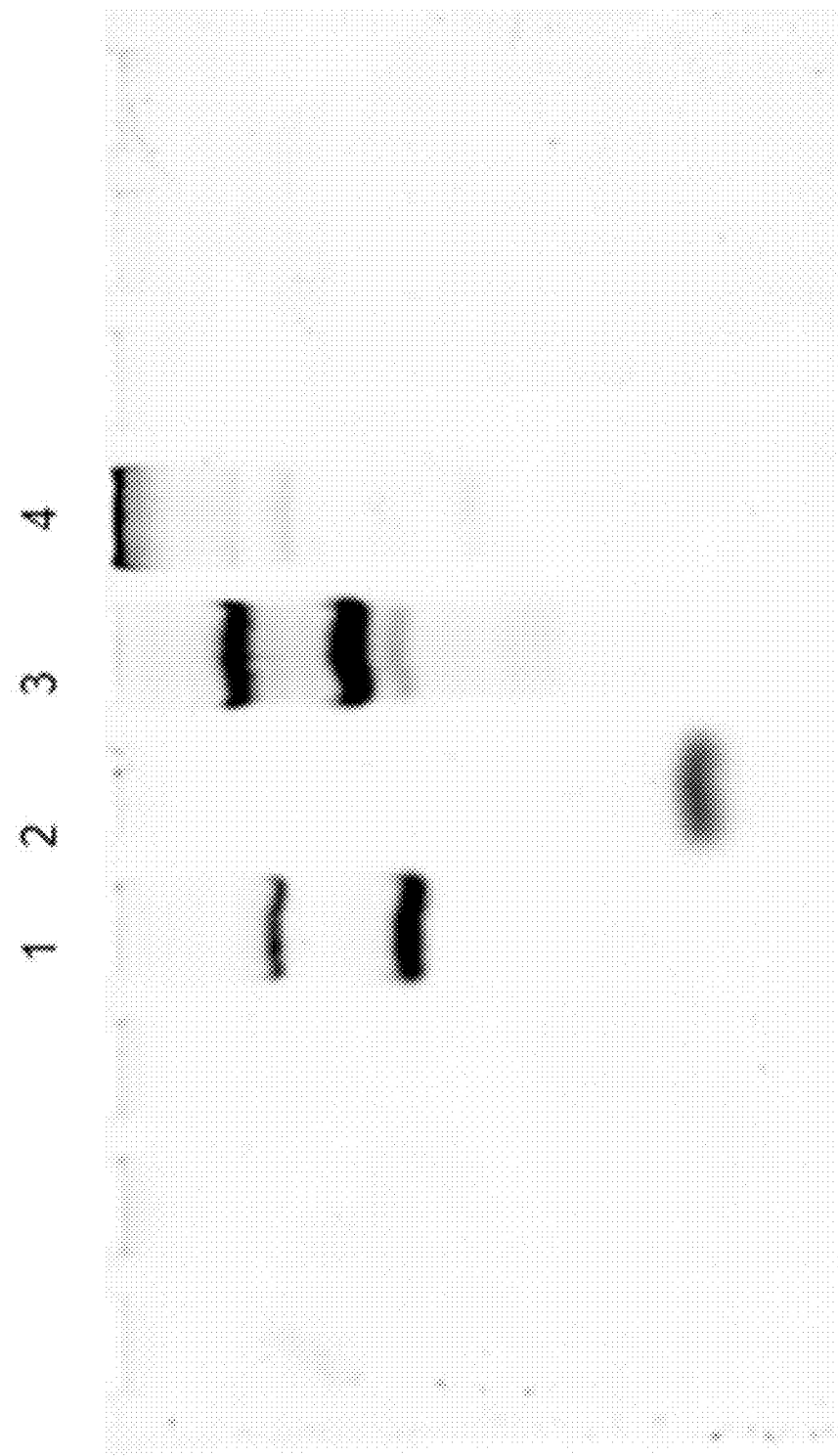
FIG. 33 shows 18% MOPS PAGE (150 V, 2.5 h, gel red stain) showing siRNA sense and antisense strands annealed. T

FIG. 33 shows 18% MOPS PAGE (150 V, 2.5 h, gel red stain) showing siRNA sense and antisense strands annealed. The sense strand is conjugated to a core NA nanoparticle strand via IEDDA (C-4.4+S-1.5). Lane 1, core strand-IEDDA-sense strand (C-4.4+S-1.5); lane 2, antisense strand (S-2.1); lane 3, annealed product (C-4.4+S-1.5+S-2.1); lane 4, low range ssRNA ladder.

Figure 34:
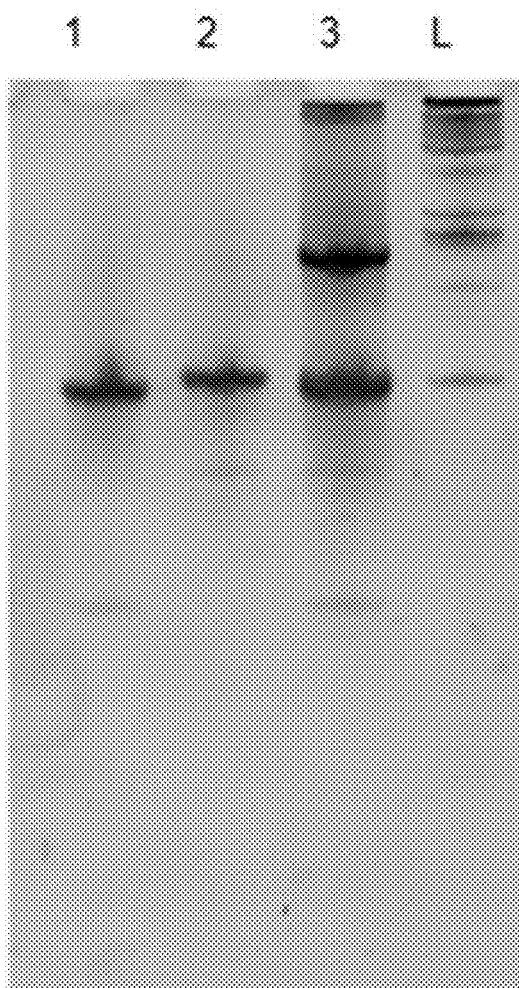
FIG. 34 shows 15% denaturing PAGE (250 V, 1 h, gel red stain) showing the conjugation core NA nanoparticle strand C-4.4 to aptamer A-1.3 via IEDDA using 1:1 molar equivalents of core:aptamer at 30° C.
Figure 34:
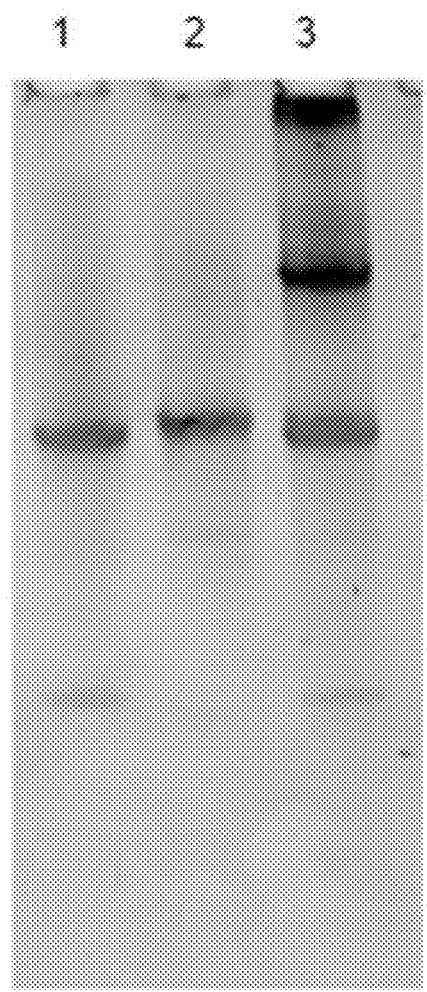

FIG. 34 shows 15% denaturing PAGE (250 V, 1 h, gel red stain) showing the conjugation core NA nanoparticle strand C-4.4 to aptamer A-1.3 via IEDDA using 1:1 molar equivalents of core:aptamer at 30° C. Left panel shows PAGE following a 6-hour reaction time, and right panel shows PAGE following 12-hour reaction time. Lane 1, core NA nanoparticle strand C-4.4; lane 2, aptamer A-1.3; lane 3, IEDDA reaction mixture; lane L, low range ssRNA ladder.

FIG. 35 shows native PAGE (8%, 150 V, 1 h) showing representative IEDDA conjugations with a fully assembled NA nanoparticle (SQ1-0000-005). Lane 1, starting material; lane 2, 1 molar equivalent siRNA (S-1.5); lane 3, 2 molar equivalents siRNA (S-1.5); lane 4, 4 molar equivalents siRNA (S-1.5).

Figure 36:
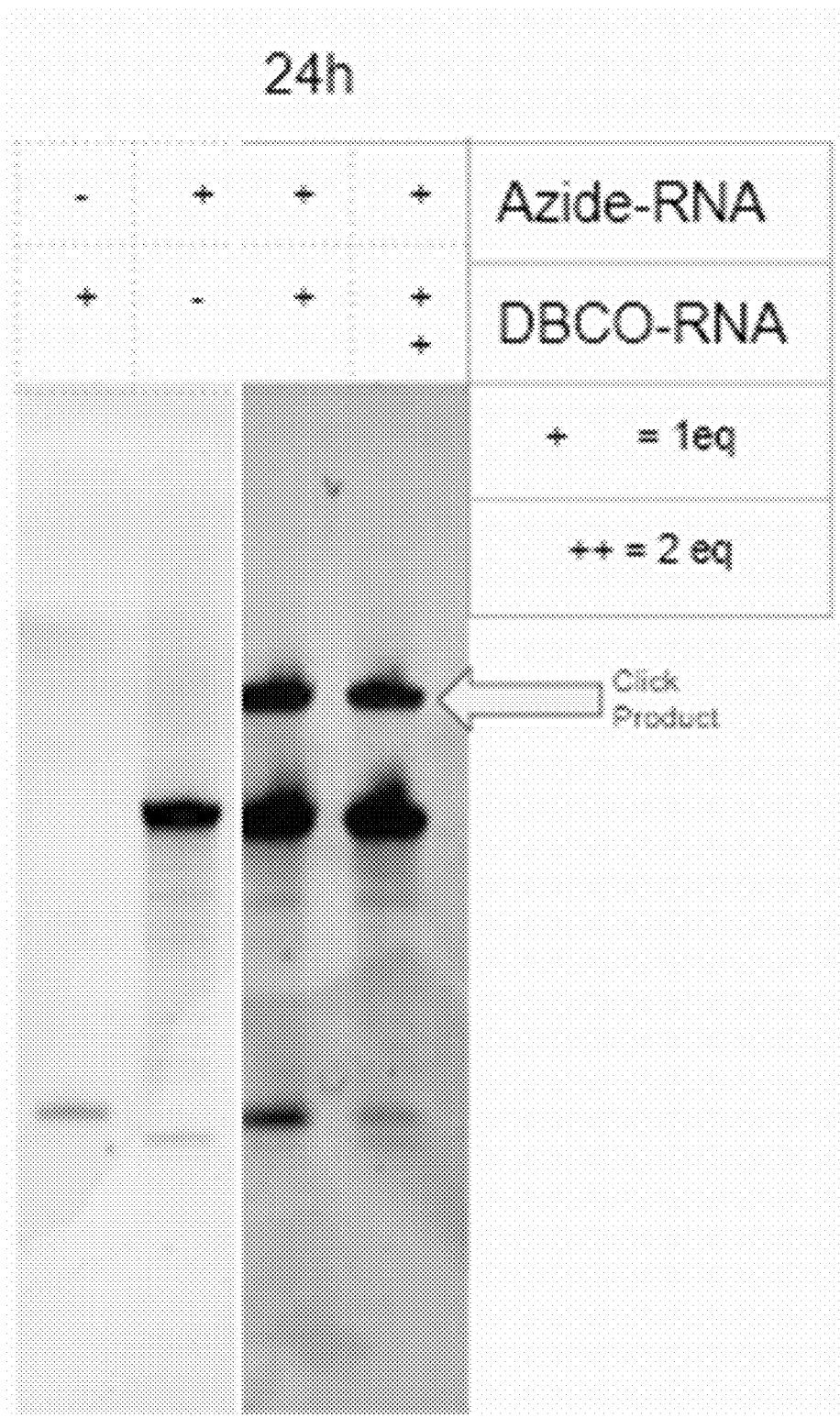
FIG. 36 shows a denaturing PAGE (15%, 250V, 1 h) of SPAAC conjugation with core strand C-4.3 with azide-functionalized siRNA S-1.6.

FIG. 36 shows a denaturing PAGE (15%, 250V, 1 h) of SPAAC conjugation with core strand C-4.3 with azide-functionalized siRNA S-1.6.

Figure 37:
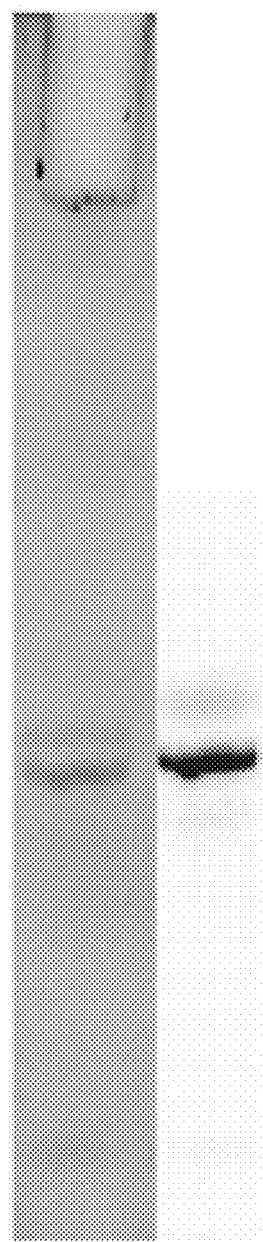
FIG. 37 shows a denaturing PAGE (15%, 250V, 1 h) of Cy7-NHS labelling of C-5.3 to form C-5.2 (302 nm GelRed/Cy7 channel).

FIG. 37 shows a denaturing PAGE (15%, 250V, 1 h) of Cy7-NHS labelling of C-5.3 to form C-5.2 (302 nm GelRed/Cy7 channel).

Example 7—CuAAC on 5' Modified RNA

Copper azide-alkyne cycloaddition (CuAAC) was carried out according to two protocols; (1) To a 0.6 ml Eppendorf, previously flushed with $N_2$, for a 20 μl reaction, were added azide containing RNA (3 μM), alkyne containing RNA (9 μM), PBS (10×, 2 ul), 0.6 μL of a 20% (v/v) acetonitrile/water solution. After degassing the reaction mixture, 0.3 μL of a degassed 10 mM sodium ascorbate solution (freshly prepared) was added, followed by the freshly prepared copper sulfate (0.1 μl, 5 mM stock solution). The reaction mixture was once again degassed and was incubated for 1 h at rt or in a heat block at 40° C. Then, an additional 0.1 μl of degassed sodium ascorbate solution was added to the reaction mixture. The reaction mixture was once again degassed and was incubated for 1 h at rt or in a heat block at 40° C. Clicked products were analyzed by denaturing PAGE. (2) To a 0.6 ml Eppendorf, previously flushed with $N_2$, were added azide containing RNA (1 nmol, 1 μl), alkyne containing RNA (1.5 nmol, 1 μl), $MgCl_2$ (20 mM, 0.5 TEAA (0.4 M, 1 μl, pH=7), DMSO (5 μl) and fresh ascorbic acid (25 mM, 1 μl). After degassing the reaction mixture, the freshly prepared CuBr-TBTA solution (50 mM CuBr/50 mM TBTA 1:2 (v/v) in DMSO/t-BuOH 3:1 (v/v), 0.5 μl) was added. The reaction mixture was once again degassed and left on a shaker at rt for 1-2 hours. Clicked products were analyzed by denaturing PAGE. An RNA-RNA coupling efficiency of ~10-50% was observed.

Example 8—CuAAC on Internally Modified RNA

CuAAC was attempted on RNA that was modified with propargyl groups at internal positions (C-5.4, C-5.5).
General Procedure for Internal Click Modifications
A 100 μL solution was prepared with 20 μL of the alkyne-modified RNA (100 μM in TEAA 2 M, pH=7.0), 4 μL heptaethylene glycol (5 mM, in DMSO), 20 μL sodium ascorbate 10 mM (in TEAA 2 M, pH=7.0) and 20 μL of a 10 mM 1:1 solution of $Cu_2SO_4$ (in DMSO) and THPTA (in TEAA 2 M, pH=7.0). The reaction mixture was agitated overnight at room temperature. After this time, the mixture was filtered through a Discovery® DSC-SAX SPE Tube (Merck) previously conditioned with 1.5 mL of 250 mM Tris pH 8, 10 mM sodium perchlorate, 20% MeCN. Eluted using 0.75 mL of 250 mM Tris pH 8, 600 mM sodium perchlorate, 20% MeCN. The sample was desalted using a Gel-Pak™ 1.0 Desalting Column (Glen) before LCMS analysis.

Figure 38:
FIG. 38 shows a denaturing gel (15%, 250V, 1 h) of clicked strands (PEG and cholesterol at one position (strand C-5.4), or eight positions (strand C-5.5).

FIG. 38 shows a denaturing gel (15%, 250V, 1 h) of clicked strands (PEG and cholesterol at one position (strand C-5.4), or eight positions (strand C-5.5)). A shift revealed that the product was coupled to one or more cholesterol units. Lane 1, strand C-5.4 (unconjugated, starting material); lane 2, strand C-5.4*cholesterol-clicked (C18 purification); lane 3, strand C-5.4*cholesterol-clicked (EtOH precipitation); lane 4, strand C-5.4*PEG7-clicked (C18 purification); lane 5, strand C-5.4*PEG7-clicked (EtOH precipitation); lane 6, strand C-5.5 (unconjugated, starting material); lane 7, strand C-5.5*cholesterol-clicked (C18 purification); lane 8, strand C-5.5*cholesterol-clicked (EtOH precipitation); lane 9, strand C-5.5*PEG7-clicked (C18 purification); and lane 10, strand C-5.5*PEG7-clicked (EtOH precipitation).

Figure 39:
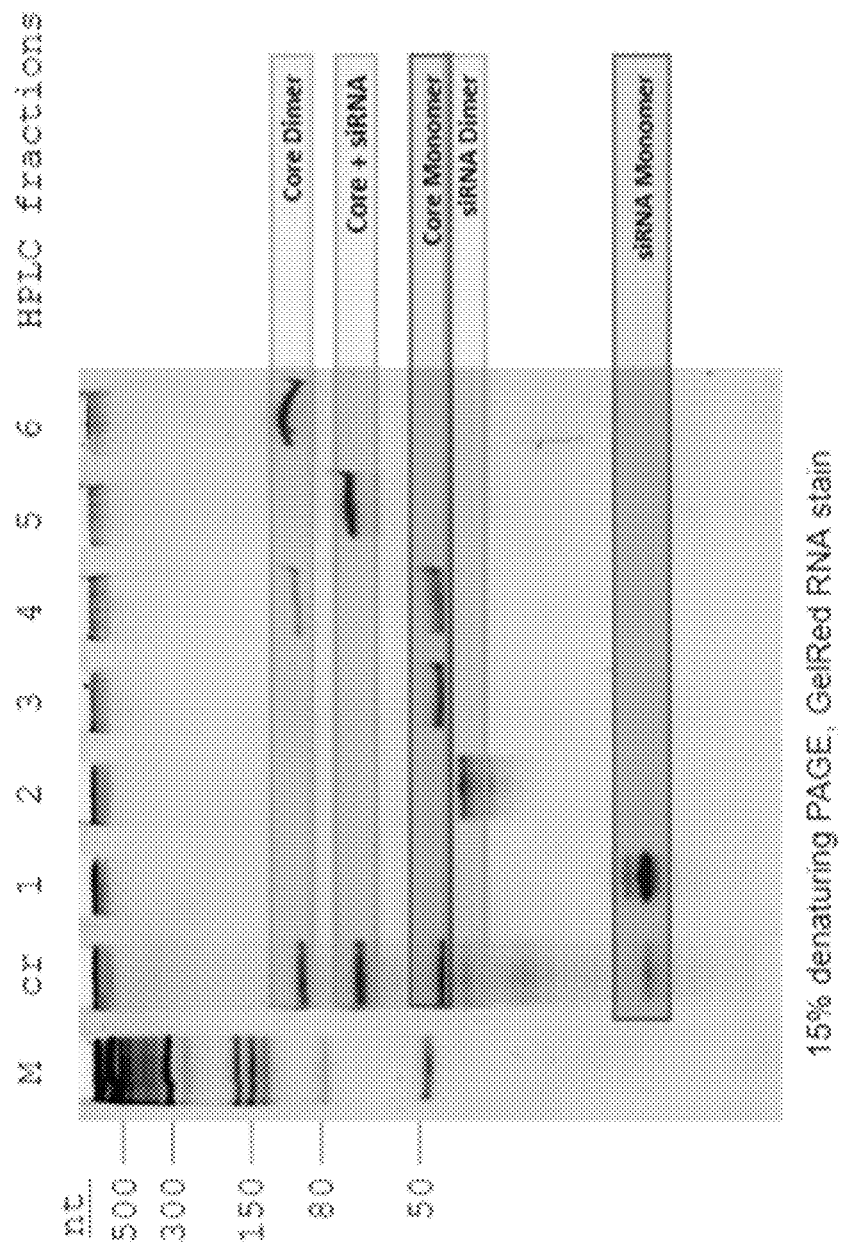
FIG. 39 shows denaturing PAGE (15%, 250V, 1 h) showing functionalization of nanoparticle core strand C-1.1 with 5'-thiol-modified siRNA sense strand S-1.1 via reversible disulfide crosslinking.

FIG. 39 shows denaturing PAGE (15%, 250V, 1 h) showing functionalization of nanoparticle core strand C-1.1 with 5'-thiol-modified siRNA sense strand S-1.1 via reversible disulfide crosslinking. Lane M, Low Range ssRNA Ladder (NEB, #N0364S); lane cr, crude coupling mixture; lanes 1-6, Fractions 1-6 obtained after IEX-HPLC purification of the crude coupling mixture.

Example 9—Solution-Phase Conjugation of Thiol-Containing RNAs Via Disulfide Formation siRNA molecules were attached to the core construct via disulfide bond formation. Thiol-containing RNA sense strand (S-1.1) and core strand (C-1.1 or C-4.1) were mixed with DTT (4 mg DTT per 20 A260 units/mL of RNA in a total volume of 250 uL), the pH of the solution was adjusted to pH>8 with triethylamine, and the reduction was carried out at room temperature for 30 mins to 2.5 hours. The reduced RNA was subjected to desalting with Gel-Pak desalting columns (Glen) and the RNA concentration in the desalted fractions was determined by UV absorbance on a nanodrop. Thereupon, the coupling partners (siRNA sense and core strand) were mixed together so that one of the strands, preferably the siRNA sense strand, was used in 2-5-fold molar excess. A volume of 1 M $KCO_3/K(CO_3)_2$ buffer (pH 10) equivalent to 10% of the final volume, and a volume of formamide equivalent to 20% of the final volume were added to the strand mixture and the mixture was incubated overnight at room temperature on a thermoshaker. Coupling products were then purified by IEX-HPLC and the purified products were loaded on denaturing PAGE (15%) in 1×TBE at a constant voltage of 250 V. Gel bands were visualized using GelRed™ (FIG. 39).

Example 10—Peptide Synthesis and Attachment

Solid Phase Peptide Synthesis—Example Procedure
The following solutions were prepared: Deprotection solution: 20% piperidine in DMF; Activator solution: 0.25 M HATU in DMF; Basic solution: 2,6-lutidine (2.05 mL)+DIPEA (1.96 mL) in DMF (5.54 mL) Capping solution: $Ac_2O$ (0.92 mL)+2,6-lutidine (1.3 mL) in DMF (18 mL); Amino acid solution: 0.2 M in DMF.

Pre-loaded amino-based resin (as described above) (50 mg) was swelled in DMF (3 mL) at rt for 30 min. The DMF was then drained and the resin was immersed in 20% piperidine in DMF (this step was repeated). The resin was then washed with DMF (3×3 mL), DCM (3×3 mL) and again with DMF (3×3 mL). In a separate vessel, the desired amino acid solution (1.29 mL), HATU (452 µL, 4.5 equiv.) and base solution (110 µL) were mixed and then added to the resin. The resultant suspension was then agitated at rt for 30 min, the syringe was flushed and the coupling step was repeated. Coupling success was monitored with the Kaiser test. Following successful coupling, the resin was washed with DMF (3×3 mL), DCM (3×3 mL) and DMF (3×3 mL). The resin was then immersed in capping solution (vide supra) for 5 min. The syringe was flushed and the resin was washed with DMF (3×3 mL), DCM (3×3 mL) and DMF (3×3 mL). The process was then repeated (from the deprotection step) until the desired sequence was obtained.

Cleavage from the resin was achieved by submerging it in a mixture of TFA/phenol/water/TIPS (88/5/5/2) and agitating for 3 h, followed by dropwise precipitation into ice cold diethyl ether. The resultant precipitate was then dissolved in acetic acid and lyophilised, affording the desired peptide as the acetate salt.

Purification

HPLC analysis and purification of the peptides and peptide conjugates was performed on a Thermo Fisher Vanquish Core with a RESOURCE™ RPC 3 column (3 mL, 6.4 mm×100 mm). Samples were dissolved in DMSO and injected. Flow rate 3 mL/min; eluent A: H$_2$O (0.1% TFA); eluent B: MeCN (0.1% TFA).

A gradient of 0-100% B in 15 min was utilised, followed by 100% B for 5 min.

Mass Analysis of Synthesized Peptides

Peptides used herein are described in Table 7.

Figure 40:
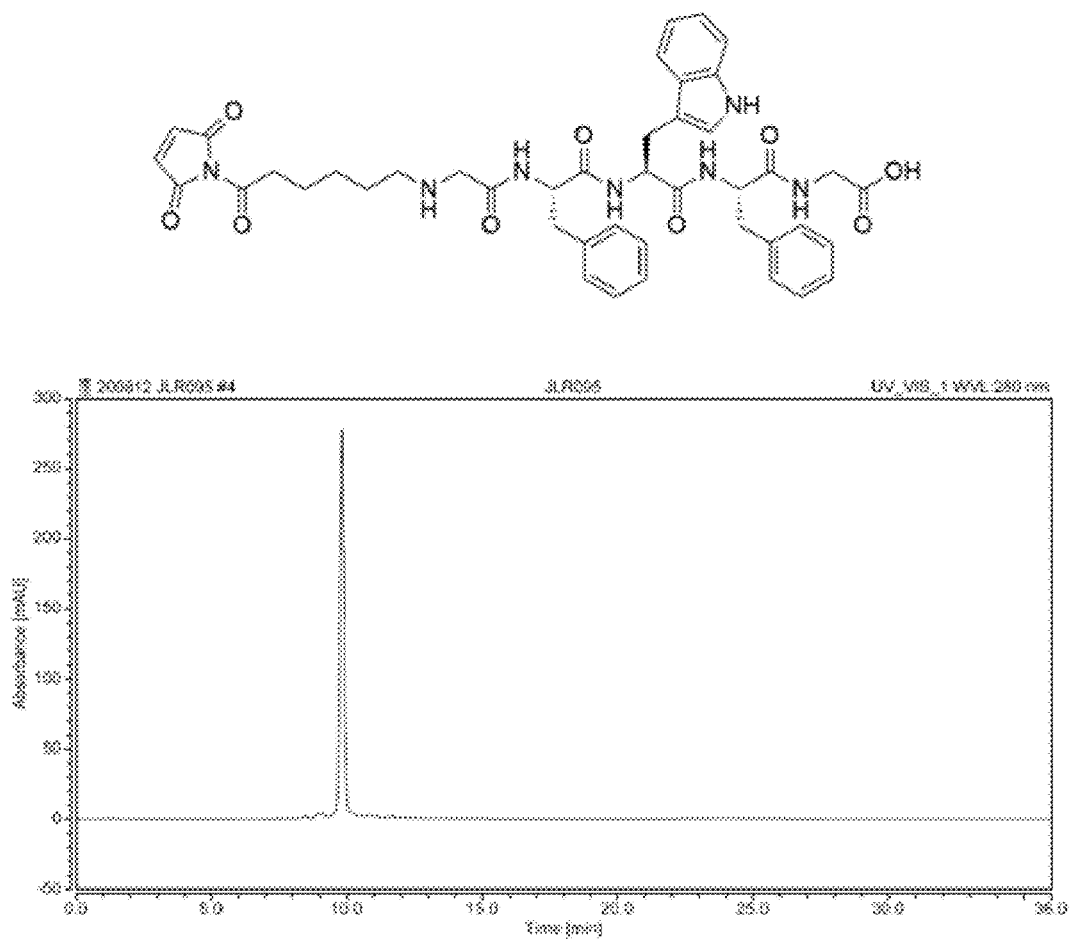
FIG. 40 shows a RP HPLC trace of maleimide-modified GFWFG. 0 to 100% B in 15 min (A=H2O+0.1% TFA; B=MeCN+0.1% TFA).

FIG. 40 shows a RP HPLC trace of maleimide-modified GFWFG. 0 to 100% B in 15 min (A=H$_2$O+0.1% TFA; B=MeCN+0.1% TFA).

Figure 41:
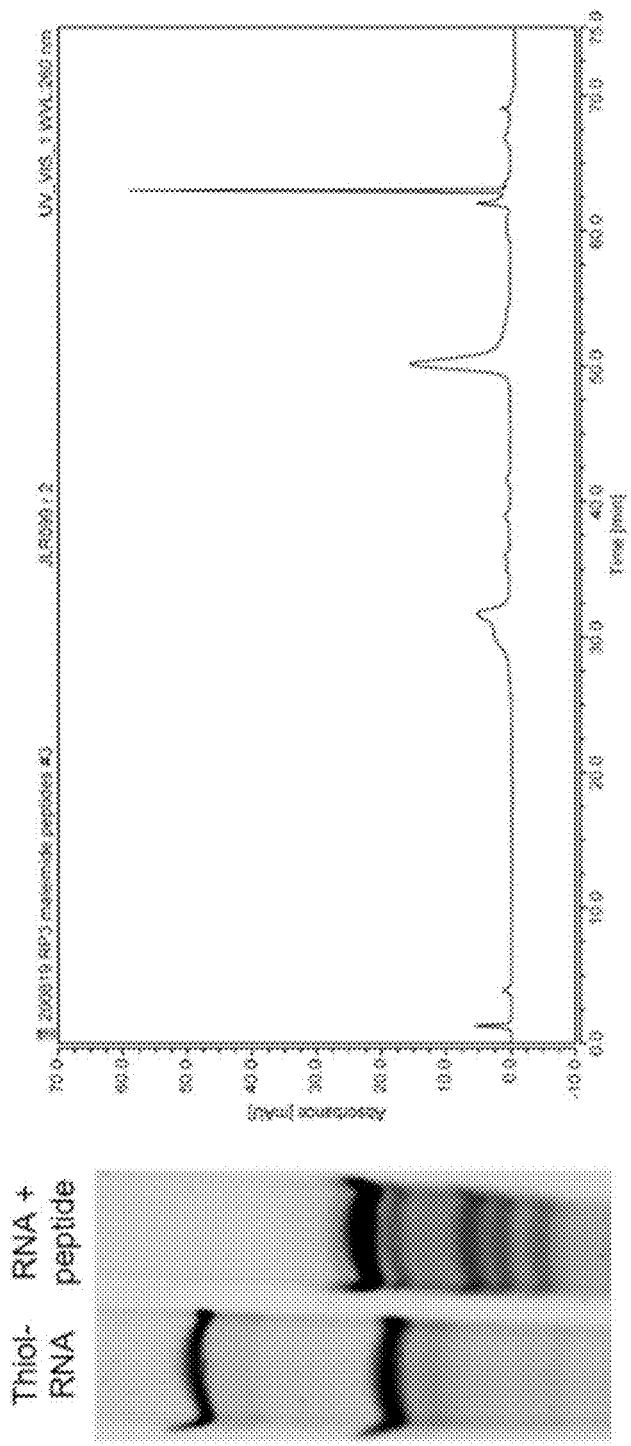
FIG. 41 shows denaturing PAGE of the thiol-RNA C-2.1 vs. the peptide-conjugated RNA of the same strand in the left panel and crude RP HPLC trace of the conjugation reaction mixture in the right panel.

FIG. 41 shows denaturing PAGE of the thiol-RNA C-2.1 vs. the peptide-conjugated RNA of the same strand in the left panel and crude RP HPLC trace of the conjugation reaction mixture in the right panel. The peak at 30 minutes corresponds to the thiol-RNA. The peak at 50 minutes is the peptide-RNA product.

Example 11—Solution-Phase Conjugation of Maleimide-Functionalized Peptide to Thiol-Containing RNA Example Procedure Lyophilized oligonucleotide C-2.1 (234 nmol) was dissolved in water (1 mL) and split into two separate vials. To each vial was added Et$_3$N (10 µL) and 50 µL of a 1 M solution of DTT. The resultant solution was then agitated at rt for 2.5 h. Excess DTT was then removed with a GelPak desalting column (Glen Research) and the RNA concentration was measured. 96 nmol of fully desalted RNA was recovered. The two desalted oligos were pooled together to give a total volume in H$_2$O of 3.6 mL. To this, TEAA (100 mM, pH=7, 0.8 mL) was added. The peptide (10 equiv. relative to RNA) was dissolved, in a separate vial, in 20% formamide in MeCN to give a concentration of 50 mM. This was added to the freshly desalted oligo solution, which led to noticeable precipitation. DMSO (4.4 mL) was added to give a 1:1 (v/v) mixture of TEAA/DMSO to solubilise the peptide and assist in denaturation of the oligo. The reaction mixture was agitated at rt for 16 h. This can be purified directly by RP HPLC as the difference in RNA retention time vs. RNA-peptide conjugate is approximately 20 min.

Example 12—FlICk Chemistry

To enable successful RNA-cargo conjugation via FlICk chemistry, two key functionalities are required: ortho-pthalaldehyde and a "pincer" arrangement with a terminal amine and thiol. The 5' end of oligonucleotides may be modified with any Cys-Lys containing peptides, including, but not limited to, the Cys-Lys dipeptide shown below. This modification will allow a stapling reaction to occur with an ortho-pthalaldehyde bearing molecule.

TABLE 7

| Identifier | SEQ ID NO. | Sequence | Modifications/comments | Expected mass | Mass found |
|---|---|---|---|---|---|
| P-1.0 | 16 | GFWFG | None | 612.3 | 612.3 |
| P-1.1 | 79 | GFWFG | Maleimide functionalized (via) 6-maleimidohexanoic acid (N terminus) | 1779.8 | 1779.8 |
| P-2.0 | 80 | GLFGAIAGFIEN GWEGMIDGWYG | Maleimide functionalized (via) 6-maleimidohexanoic acid (N terminus) | 2655.0 | 2655.0 |
| P-3.0 | 81 | GLFEAIEGFIEN GWEGMIDGWYG | Maleimide functionalized (via) 6-maleimidohexanoic acid (N terminus) | 2786.4 | 2786.4 |
| P-4.0 | 82 | LAEALAEALEAL AA | Maleimide functionalized (via) 6-maleimidohexanoic acid (N terminus) | 1549.0 | 1549.0 |

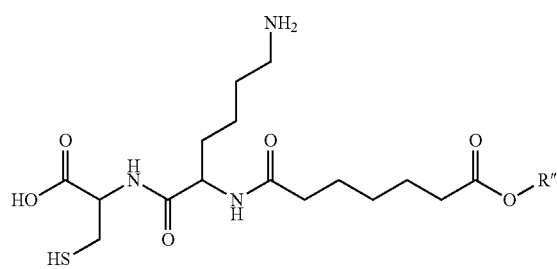

R' = reactive site to enable click conjugation ortho-Pthalaldehyde modified oligonucleotides have been used in the literature to couple DNA to proteins (Y. Ma, Z. Lv, T. Li, T. Tian, L. Lu, W. Liu, Z. Zhu, C. Yang, Design and synthesis of ortho-phthalaldehyde phosphoramidite for single-step, rapid, efficient and chemoselective coupling of DNA with proteins under physiological conditions, Chem. Commun. 54 (2018) 9434-9437. https://doi.org/10.1039/c8cc05037f.). This methodology may be applied here to functionalise RNA cargo with the desired functionality to elicit FlICk chemistry. The intermediate used in this synthesis (below) may also be used to functionalise alternative cargo, including, but not limited to, peptides, proteins, antibodies, lipids and therapeutic small molecules.

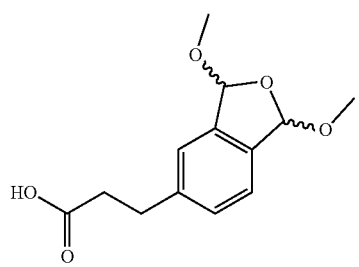 [SMILES: COC1OC(OC)c2cc(CCC(=O)O)ccc21]

Figure 42:
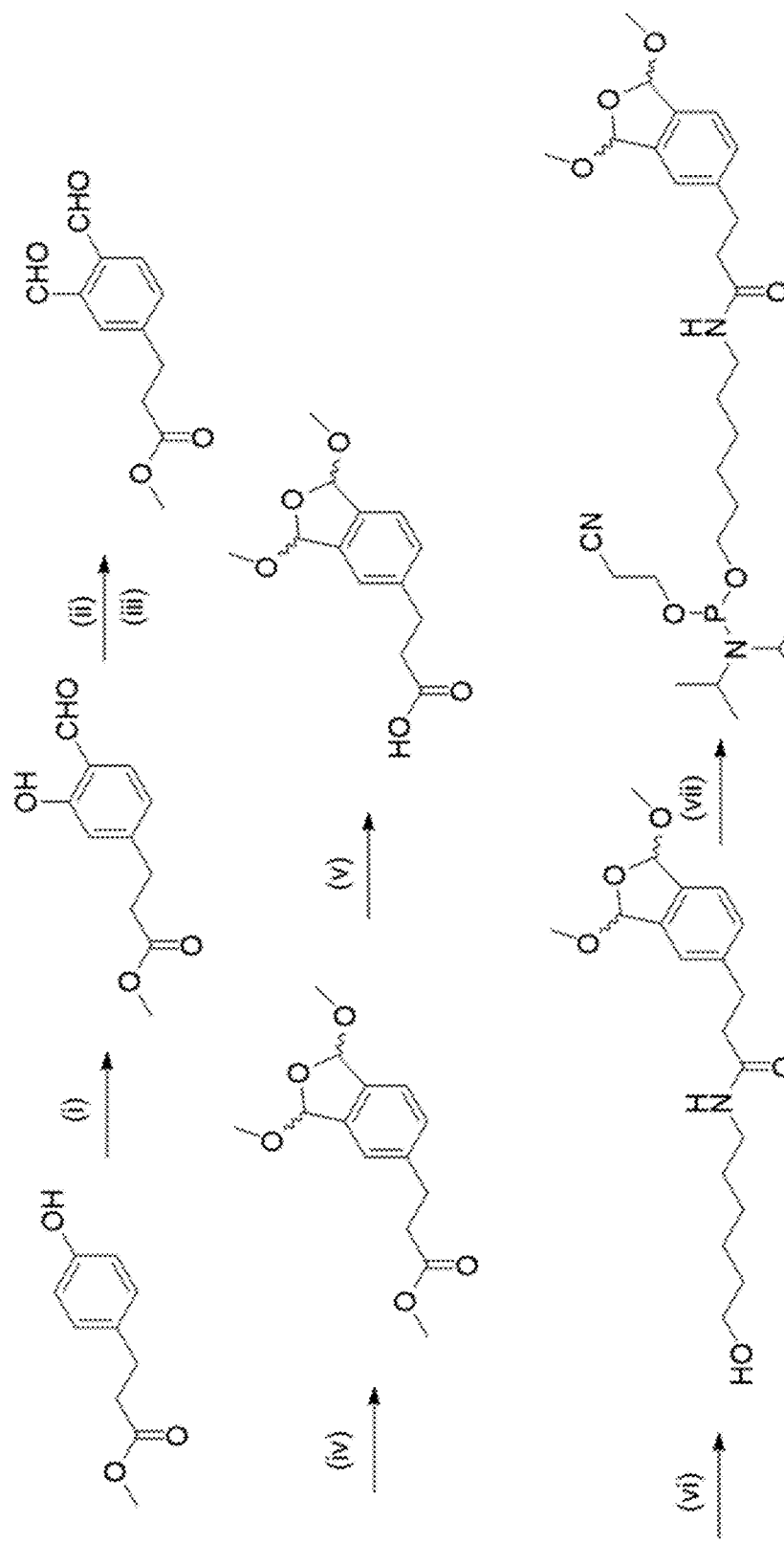
FIG. 42 shows a scheme for synthesis of an ortho-phthalaldehyde-containing phosphoramidite for use in FlICk chemistry.

FIG. 42 shows a scheme for synthesis of an ortho-phthalaldehyde-containing phosphoramidite for use in FlICk chemistry. Based on a literature method outlined by Ma and co-workers (Y. Ma, Z. Lv, T. Li, T. Tian, L. Lu, W. Liu, Z. Zhu, C. Yang, Design and synthesis of ortho-phthalaldehyde phosphoramidite for single-step, rapid, efficient and chemoselective coupling of DNA with proteins under physiological conditions, Chem. Commun. 54 (2018) 9434-9437. https://doi.org/10.1039/c8cc05037f).

Example 13—Cytotoxic Nucleotides

Cytotoxic nucleosides, including, but not limited to aristomycin, neoplanocin A, ribavirin, pyrazofurin, cytarabine arabinoside (ara-C), gemcitabine, cladribine (2-CdA), showdomycin, elacytarabine, may be attached to the nucleic acid nanoparticle via a stimuli-responsive linker such an oxime. These could be linked to any given OH on the nucleoside, and would be joined via a pthalimide-oxy modified oligonucleotide, utilising methodology outlined by Meyer and co-workers (structures shown below). (Y. Ma, Z. Lv, T. Li, T. Tian, L. Lu, W. Liu, Z. Zhu, C. Yang, Design and synthesis of ortho-phthalaldehyde phosphoramidite for single-step, rapid, efficient and chemoselective coupling of DNA with proteins under physiological conditions, Chem. Commun. 54 (2018) 9434-9437. https://doi.org/10.1039/c8cc05037f.).

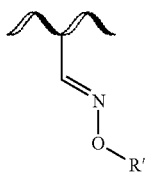

R' = cytotoxic nucleoside (3¢ and/or 5¢ or internal modification)

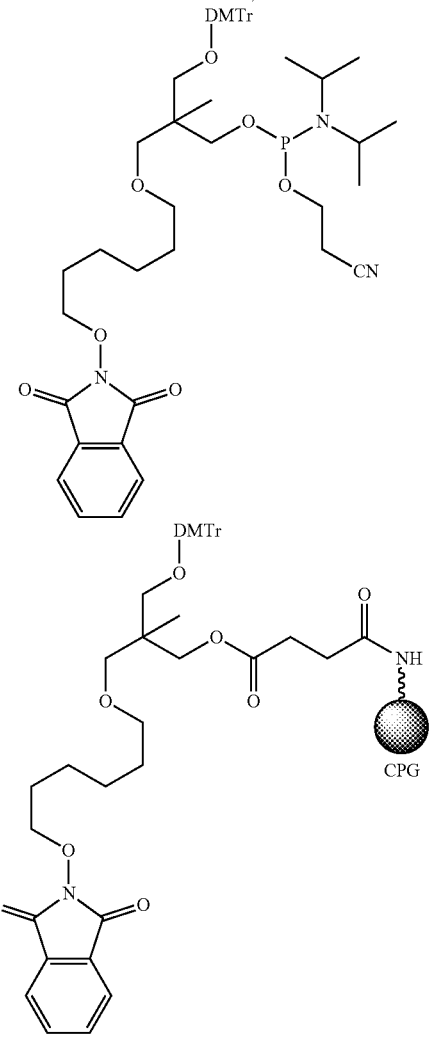

Alternatively, these compounds might be incorporated into the nucleic acid backbone via phosphoramidite chemistry, surrounded by sequences that are prone to cleavage or attached directly to self-immolative linkers (C. A. Blencowe, A. T. Russell, F. Greco, W. Hayes, D. W. Thornthwaite, Self-immolative linkers in polymeric delivery systems, Polym. Chem. 2 (2011) 773-790. https://doi.org/10.1039/c0py00324g.). Ribavirin, for example, could be incorporated at any internal within an oligo utilising this chemistry. This compound (below) is known in the art (I. Dawson, A. N. Jina, S. Torkelson, S. Rhee, M. Moore, D. A. Zarling, P. D. Hobbs, Synthesis and characterization of a ribavirin-3', 5'-phosphate pentadecamer homoribopolymer bearing a 5'-amino tether group and a 3'-thymidine, Nucleic Acids Res. 18 (1990) 1099-1102. https://doi.org/10.1093/nar/18.5.1099.).

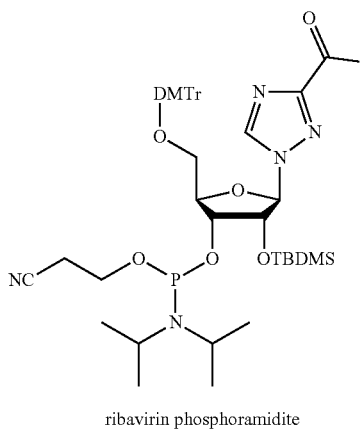

ribavirin phosphoramidite

A compound with the general formula could be incorporated throughout the component oligonucleotide strands:

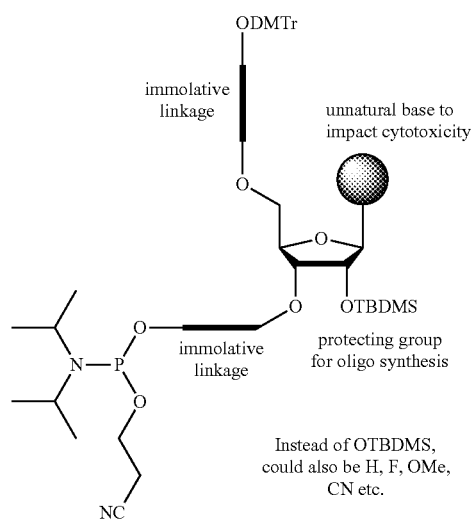

An example of a ribavirin phosphoramidite with an immolative linker is given below. Disulfides adjacent to carbonates have long been used as macromolecular prodrugs (A. Kock, K. Zuwala, A. A. A. Smith, P. Ruiz-Sanchis, B. M. Wohl, M. Tolstrup, A. N. Zelikin, Disulfide reshuffling triggers the release of a thiol-free anti-HIV agent to make up fast-acting, potent macromolecular prodrugs, Chem. Commun. 50 (2014) 14498-14500. https://doi.org/10.1039/c4cc04280h.; X. Hu, J. Hu, J. Tian, Z. Ge, G. Zhang, K. Luo, S. Liu, Polyprodrug amphiphiles: Hierarchical assemblies for shape-regulated cellular internalization, trafficking, and drug delivery, J. Am. Chem. Soc. 135 (2013) 17617-17629. https://doi.org/10.1021/ja409686x.; S. Bhuniya, S. Maiti, E. J. Kim, H. Lee, J. L. Sessler, K. S. Hong, J. S. Kim, An activatable theranostic for targeted cancer therapy and imaging, Angew. Chemie—Int. Ed. 53 (2014) 4469-4474. https://doi.org/10.1002/anie.201311133.). The proposed synthesis of this compound is outlined in FIG. 49.

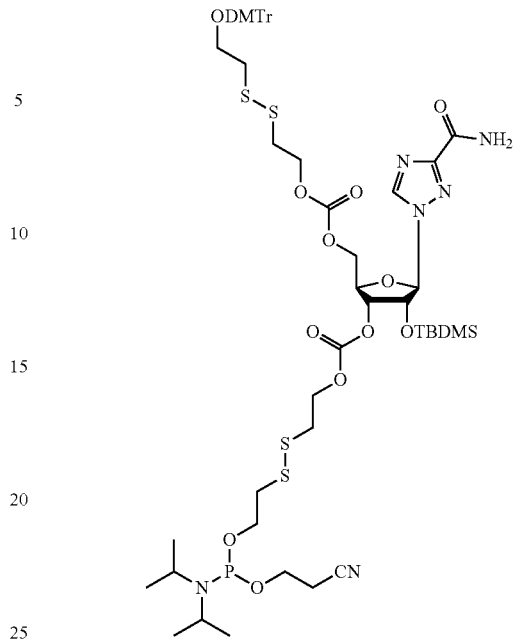

Figure 49:
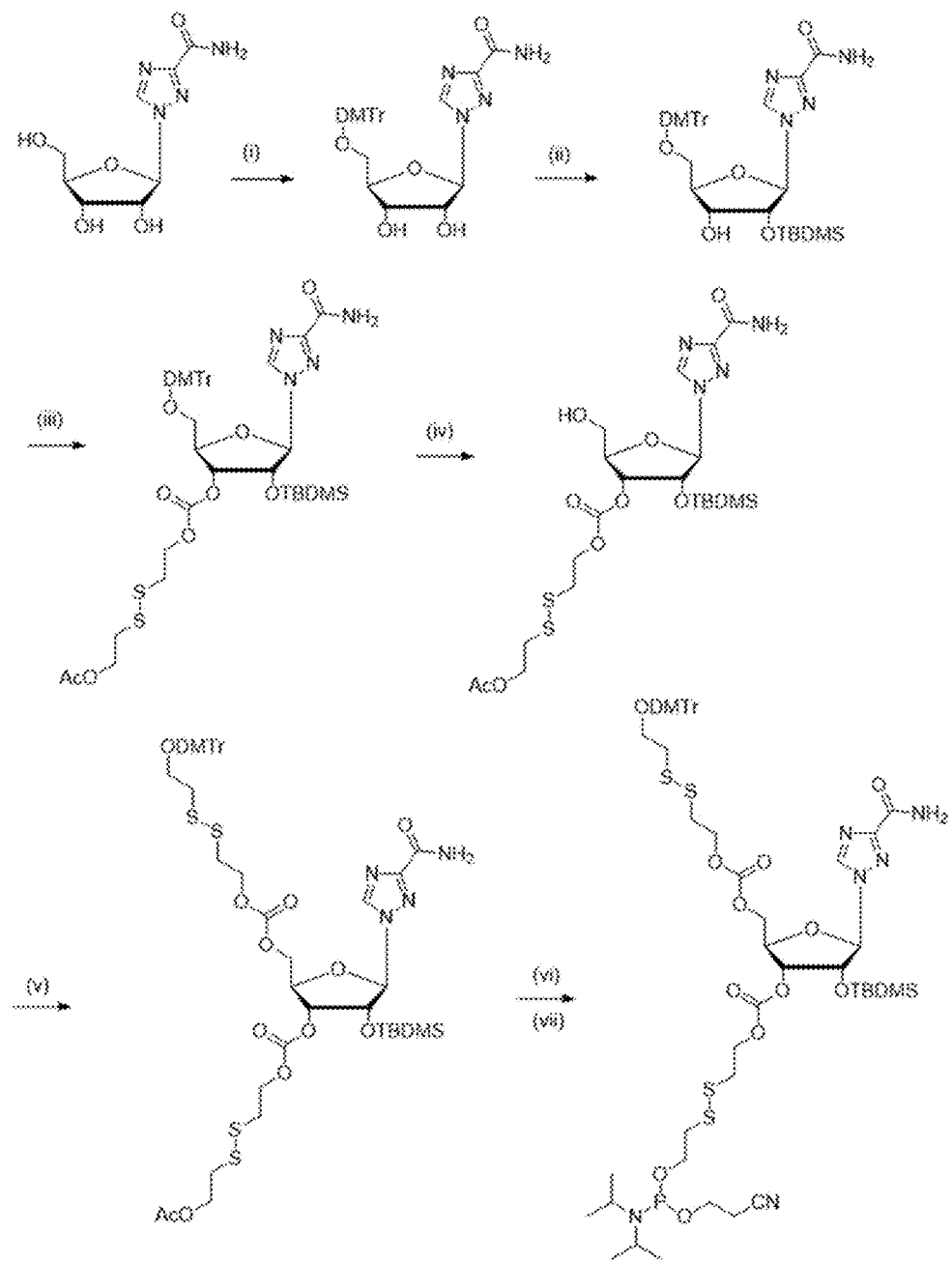
FIG. 49 shows a synthesis scheme of a self-immolative ribavirin phosphoramidite. (i) DMTrCl, pyridine (ii) TBDMSCl, AgNO$_3$, pyridine (iii) 2-((2-(((4-nitrophenoxy)carbonyl)oxy)ethyl)disulfaneyl)ethyl acetate, TEA, DCM, (iv) AcOH (v) 2-((2-(bis(4-methoxyphenyl)(phenyl)methoxy)ethyl)disulfaneyl)ethyl (4-nitrophenyl) carbonate, TEA, DCM (vi) K$_2$CO$_3$, MeOH (vii) CEP-Cl, pyridine, DCM.

FIG. 49 shows a synthesis scheme of a self-immolative ribavirin phosphoramidite. (i) DMTrCl, pyridine (ii) TBDMSCl, AgNO$_3$, pyridine (iii) 2-((2-(((4-nitrophenoxy)carbonyl)oxy)ethyl)disulfaneyl)ethyl acetate, TEA, DCM, (iv) AcOH (v) 2-((2-(bis(4-methoxyphenyl)(phenyl)methoxy)ethyl)disulfaneyl)ethyl (4-nitrophenyl) carbonate, TEA, DCM (vi) K$_2$CO$_3$, MeOH (vii) CEP-Cl, pyridine, DCM.

Example 14—Biological Activity of Conjugated siRNA

Annealment of Antisense Strand

Figure 18:
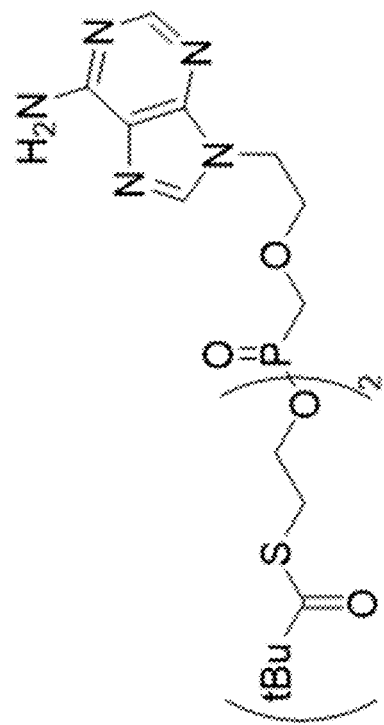
FIG. 18 is a schematic showing an (S-acyl-2-thioethyl) ester derivative of 9-[2-(phosphonomethoxy) ethyl adenine, a cytotoxic compound that can be incorporated into a nucleic acid nanoparticle.

Equimolar amounts of (i) siRNA antisense strand (S-2.1) and (ii) sense strand or sense strand conjugate, respectively, were mixed at a final concentration of 20 µM in nuclease-free water. The mixture was heated to 95° C. for 5 min followed by a temperature ramp-down to 20° C. at a rate of 0.1° C. per second in a thermocycler. Annealing was confirmed by native PAGE in MOPS buffer (20 mM MOPS, 5 mM NaOAc, 2.25 mM MgCl$_2$, pH 7.0) (FIG. 33 –18% MOPS PAGE).

Transfection, Reverse Transcription and qPCR

Human MDA-MB-231 breast cancer cells were split, counted, diluted in DMEM (supplemented with 10% FBS and 1% Penicillin/Streptomycin) and plated in 24-well plates at a density of 7×10$^4$ cells/well. 24 hours after plating, at a confluence of 30-50%, cells were transfected with 20 nM of siRNA, or siRNA conjugates, directed against polo-like kinase 1 (PLK1). Transfections of siRNA were compared to both control transfections with non-targeting siRNA (siGENOME RISC-Free Control siRNA, Horizon Discovery #D-001220-01-20) and untransfected cells. The transfection mixture was prepared as follows: siRNA was diluted to a concentration of 120 nM in Opti-MEM®. Then, a 1:100 dilution of Lipofectamine™ 2000 transfection reagent was prepared in Opti-MEM® and incubated for 5 minutes at room temperature. Equal volumes of the diluted siRNA and the diluted lipofectamine were mixed gently and incubated for 20 min at room temperature, during which the growth medium of the cells was aspirated and replaced by 200 μl complete growth medium. After that, 100 μl/well of the siRNA-lipofectamine mixture were added onto the cells to give a final concentration of 20 nM siRNA. The plate was gently rocked and placed at 37° C. in a CO2 incubator. 24 hours later, the growth medium was replaced with 500 μl of complete medium. 48 h post-transfection, the cells were washed twice with PBS and the plates were frozen at −70° C.

RNA was isolated from frozen transfected cells using the RNeasy Plus Mini Kit (Qiagen) according to manufacturer's instructions. First-strand cDNA was synthesized from 200 ng RNA in a 20 μl reaction containing 200 U of SuperScript III reverse transcriptase (Thermo Fisher Scientific) and 0.5 μl random primers, following the supplier's protocol. For each gene of interest, a qPCR master mix was prepared by combining 7.5 μL PowerUp SYBR Green Master Mix (Thermo Fisher Scientific) with 1 μL of 5 μM combined forward and reverse primers and 1.5 μL RNAse free water (for a single reaction). Then, 10 μL of the master mix were aliquoted into wells of a 96-well plate and 5 μL of 1:30 diluted cDNA were added. Each condition was pipetted in triplicate. The plate was sealed with an optical adhesive cover and loaded in a Quantstudio 5 Real Time PCR instrument. The cycling conditions were: 2 min at 50° C. (1 cycle); 2 min at 95° C., 1 s at 95° C. and 30 s at 60° C. (40 cycles); followed by melt curve analysis (1 s at 95° C., 30 s at 60° C., and a ramp-up from 60° C. to 90° C. with continuous fluorescence measurements).

Figure 43:
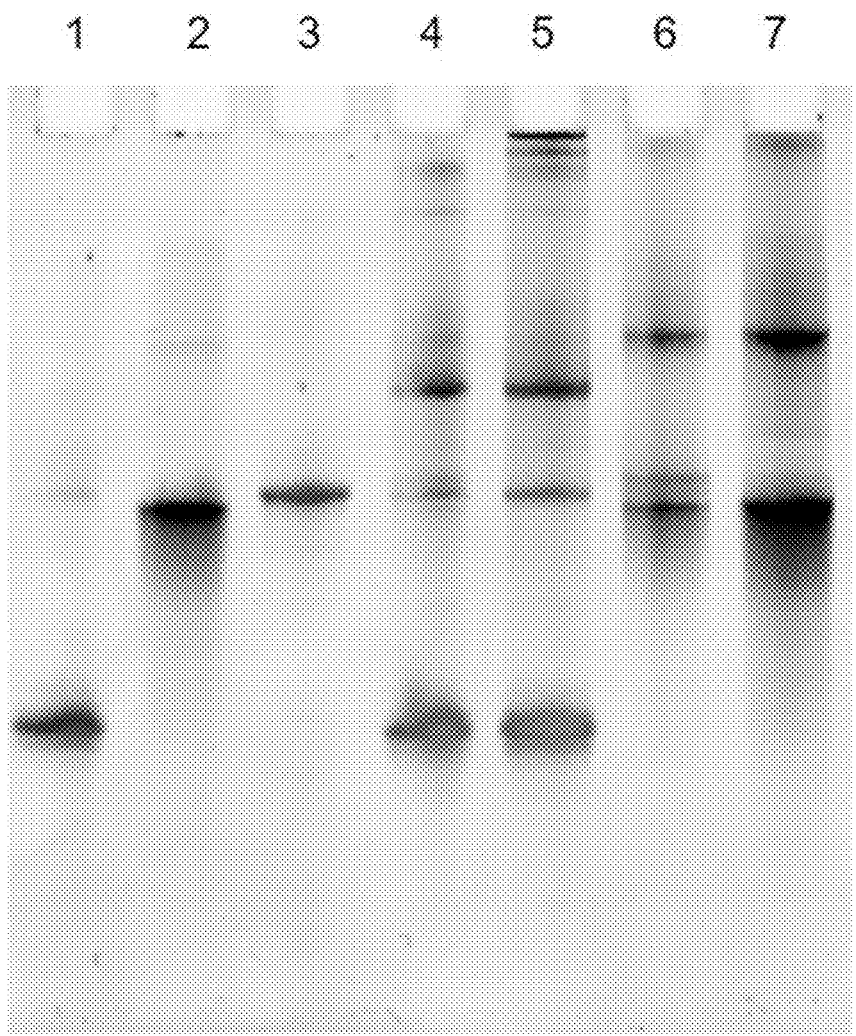
FIG. 43 is a graph showing the expression levels of PLK1 mRNA in MDA-MB-231 breast cancer cells 48 hours after transfection with 20 nM of RNA strands conjugated to PLK1-targeting siRNA via disulfide or IEDDA coupling, as obtained by qPCR.

FIG. 43 is a graph showing the expression levels of PLK1 mRNA in MDA-MB-231 breast cancer cells 48 hours after transfection with 20 nM of RNA strands conjugated to PLK1-targeting siRNA via disulfide or IEDDA coupling, as obtained by qPCR. Column 1, no RNA control (cells treated with lipofectamine 2000 only); column 2, no lipofectamine control (cells treated with siRNA); column 3, sense strand only control (cells transfected with core strand C-4.1 conjugated to sense strand S-1.1 via 5'-to-5' disulfide bond formation, no antisense strand added); column 4, 5'-to-5' disulfide-bridged conjugate of core strand and siRNA duplex (C-4.1+S-1.1+S-2.1); column 5, siRNA duplex (with 5' thiol, S-1.1+S-2.1); column 6, 5'-to-5' IEDDA-coupled conjugate of core strand and siRNA duplex (C-4.4+S-1.5+S-2.1); column 7, siRNA duplex (with 3' thiol, S-1.7+S-2.1); column 8, 5'-to-3' disulfide-bridged conjugate of core strand and siRNA duplex (C-4.1+S-1.7+S-2.1).

As shown in FIG. 43, all siRNA conjugates tested in this work remained biologically active and resulted in a 60-90% reduction in PLK1 mRNA levels in MDA-MB-231 breast cancer cells.

Example 15—Combinatorial Cargo—siRNA

To increase the loading capacity of the nucleic acid nanoparticles, two PLK1 siRNAs (sense strands) were conjugated directly to each other using the combinatorial linker design. Two conjugation strategies were used; a TTTT spacer and disulfide. The sequences are provided in Table 8.

TABLE 8

| Identifier | SEQ ID NO. | Sequence | Modifications/comments |
|---|---|---|---|
| S-3.0 | 71 | [5' Amino GcAAuuAcAuGAGcGAGcATTT TGcAAuuAcAuGAGcGAGcA | modifier C6] 2'F U, C 5' Amino modifier C6 [antisense strand, PLK 1-targeting canonical siRNA]-combinatorial chain with TTTT spacer |
| S-3.1 | 72 | [5' PEG5-tetrazine] GcAAuuAcAuGAGcGAGcATTT TGcAAuuAcAuGAGcGAGcA | 2'F U, C 5' PEG5-tetrazine [antisense strand, PLK 1-targeting canonical siRNA]-combinatorial chain with TITT spacer |
| S-4.0 | 73 | [5' Amino modifier C6] GcAAuuAcAuGAGcGAGcATTS-STTGcAAuuAcAuGAGcGAGcA | 2'F U, C 5' Amino modifier C6 [antisense strand, PLK 1-targeting canonical siRNA]-combinatorial chain with disulfide linkage S-S |
| S-4.1 | 74 | [5' PEG5-tetrazine] GcAAuuAcAuGAGcGAGcATTS-STTGcAAuuAcAuGAGcGAGcA | 2'F U, C 5' PEG5-tetrazine [antisense strand, PLK 1-targeting canonical siRNA]-combinatorial chain with disulfide linkage S-S |

Synthesis of the combinatorial siRNAs was carried out using the conventional solid phase techniques outlined in Example 2. For the disulfide-linked chain, the 5' thiol C6 modifier (Glen) was added at the 5' end of the first siRNA sequence. The DMT group was then removed and the chain was extended as usual.

RT-qPCR analysis of cells transfected with combinatorial siRNAs following the protocols outlined in Example 14 showed that both combinatorial design strategies (4. and 5.) lead to higher knockdown activity in MDA-MB-231 cells compared to the classic single siRNA design (3).

Figure 44:
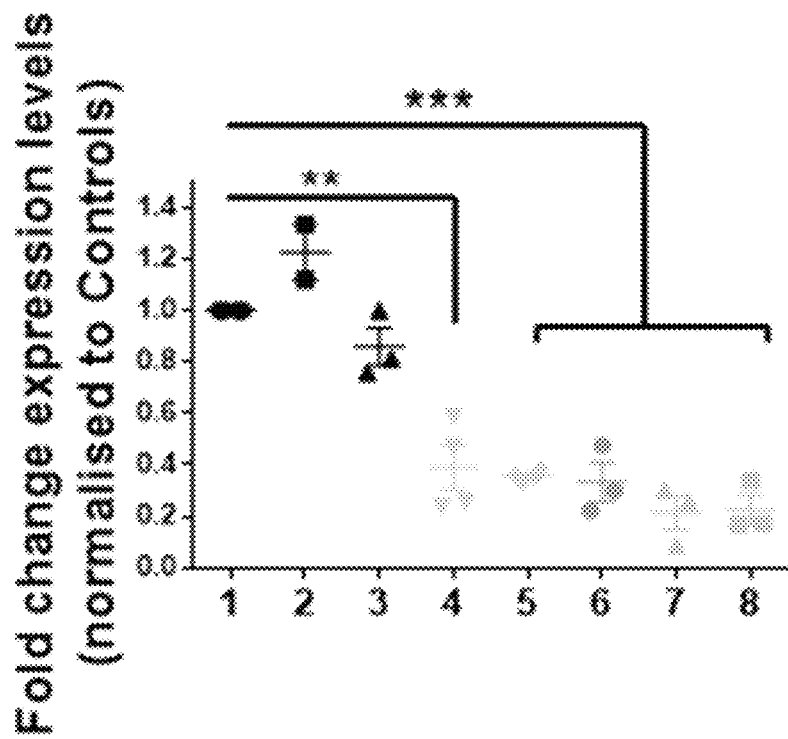
FIG. 44 shows an analytical denaturing PAGE (250 V, 1 h, gelred stain) of IEDDA coupling reaction mixtures.

FIG. 44 shows an analytical denaturing PAGE (250 V, 1 h, gelred stain) of IEDDA coupling reaction mixtures. Lane 1, RNA S-1.5 (starting material); lane 2, S-3.1 (starting material); lane 3, C-4.4 (starting material); lane 4, C-4.4 conjugated to S-1.5 (IEDDA), desalted; lane 5, C-4.4 conjugated to S-1.5 (IEDDA), EtOH precipitated; lane 6, C-4.4 conjugated to S-3.1, desalted; and lane 7, C-4.4 conjugated to S-3.1, EtOH precipitated.

Figure 45:
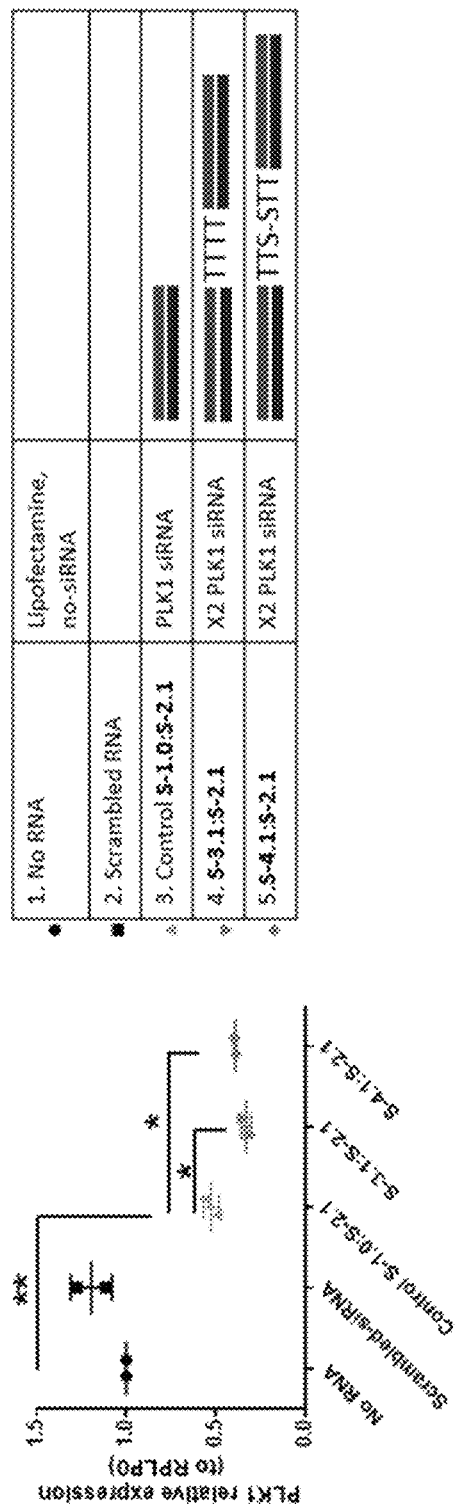
FIG. 45 is a graph showing the expression levels of PLK1 mRNA in MDA-MB-231 breast cancer cells 48 hours after transfection with 20 nM of the indicated siRNA, as obtained by qPCR.

FIG. 45 is a graph showing the expression levels of PLK1 mRNA in MDA-MB-231 breast cancer cells 48 hours after transfection with 20 nM of the indicated siRNA, as obtained by qPCR. Data shown were obtained from 2 biological replicates. Scrambled siRNA denotes a commercial non-targeting siRNA with impaired ability for RISC interaction (siGENOME RISC-Free Control siRNA, Horizon Discovery, D-001220-01-20).

Figure 50:
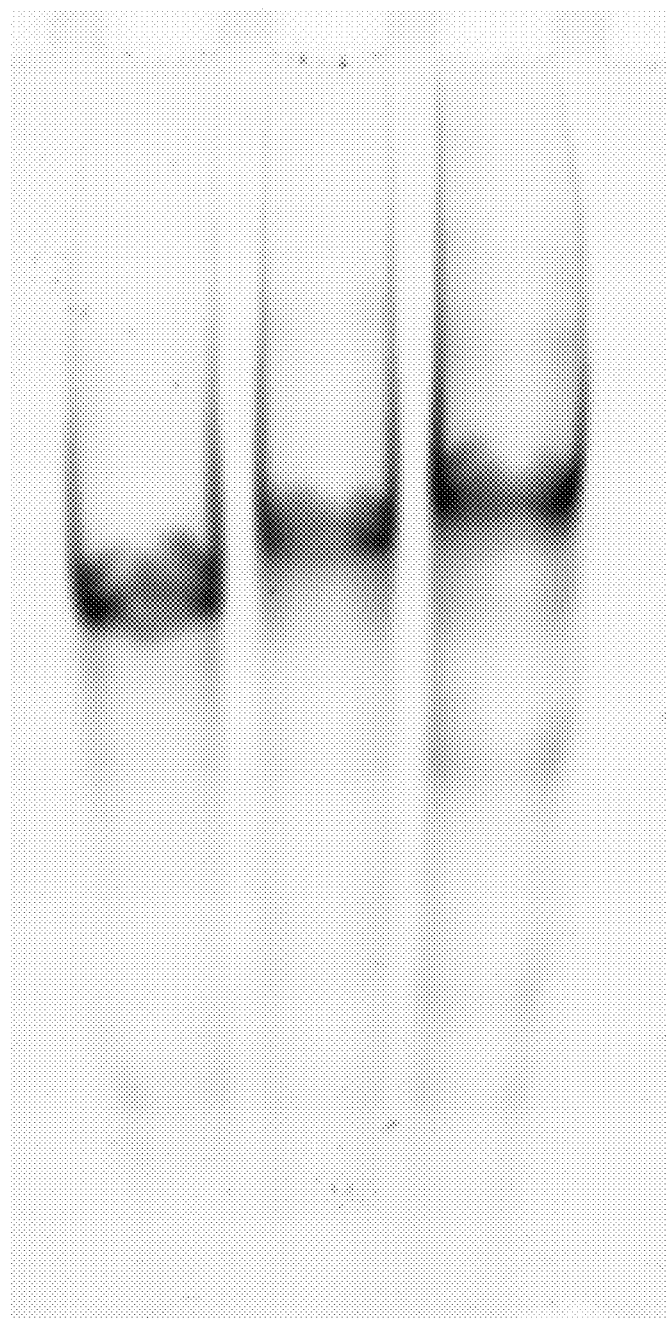
FIG. 50 shows three different versions of the assembly via non denaturing PAGE.

FIG. 50 shows three different versions of the assembly via non denaturing PAGE. The characterization of the increased loading of the assemblies was done on a 6% non-denaturing PAGE at 100V with a 75 mins run time. The constructs formed were (i) S-AO construct with no aptamer (also named SQ1-0000-001, comprised of strands C-1.0, C-2.0, C-3.0, C-4.0, C-5.0), (ii) SQ-0100-001 construct with one siRNA (also named SQ16, comprised of strands C-1.0, C-2.0, C-3.0, C-4.4, C-5.0, S-1.5, S-2.0), (iii) SQ-0200-001 construct with two siRNAs (also named SQ-17, comprised of strands C-1.0, C-2.0, C-3.0, C-4.4, C-5.0, S-3.1, S-2.0), were combined in equimolar amounts in PBS supplemented with 2 mM MgCl2, at a final concentration of 10 µM. The strands were heated to 95° C. for 5 min and slowly cooled down to room temperature. For each version of the assembly, 1 pmol was loaded in the gel. The post run staining of the gel was done with GelRed stain. It can be seen that with increase in the number of siRNAs on the assembly, there is a gel shift.

Example 16—Combinatorial Cargo—GalNAc/siRNA

N-acetylgalactosamine (GalNAc)-siRNA conjugates have been widely explored to overcome the challenges associated with naked siRNA delivery. The prototypical siRNA conjugate is a trimer of GalNAc, which binds to the Asialoglycoprotein receptor (ASGPR) (Springer, A. D.; Dowdy, S. F. GalNAc-SiRNA Conjugates: Leading the Way for Delivery of RNAi Therapeutics. Nucleic Acid Ther. 2018, 28 (3), 109-118.). This motif may be used as part of the combinatorial cargo design. This could be attached via phosphoramidite chemistry as an extension of, for example, S-3.0 to S-4.1 at the 5' end. This modification would be incorporated via standard solid phase synthesis with (4-(Trimethoxytritytyloxymethyl)-1-(6-(4-(3,4,6-O-triacetyl-2-acetylamino-2-deoxy-β-D-galactopyranosyl)butanamido)hexanoyl)piperidin-4-yl)methyl-O-[(2-cyanoethyl)-(N,N-diisopropyl)] phosphoramidite (Glen Research).

Figure 51:
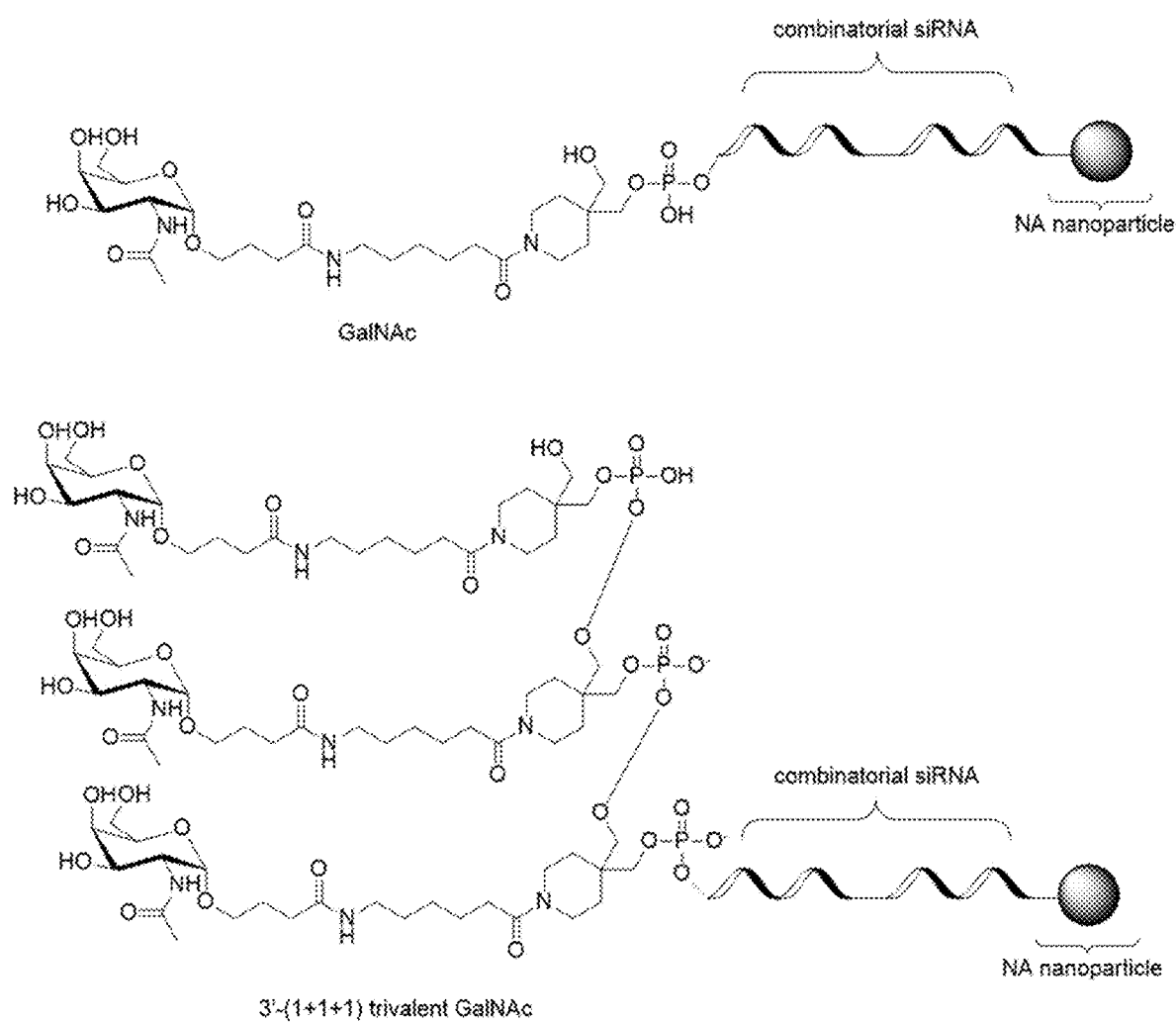
FIG. 51 is a schematic of combinatorial cargo (siRNA) coupled to mono- and trivalent GalNAc via GalNAc C3 5' phosphoramidite (Glen).

FIG. 51 is a schematic of combinatorial cargo (siRNA) coupled to mono- and trivalent GalNAc via GalNAc C3 5' phosphoramidite (Glen).

Figure 52:
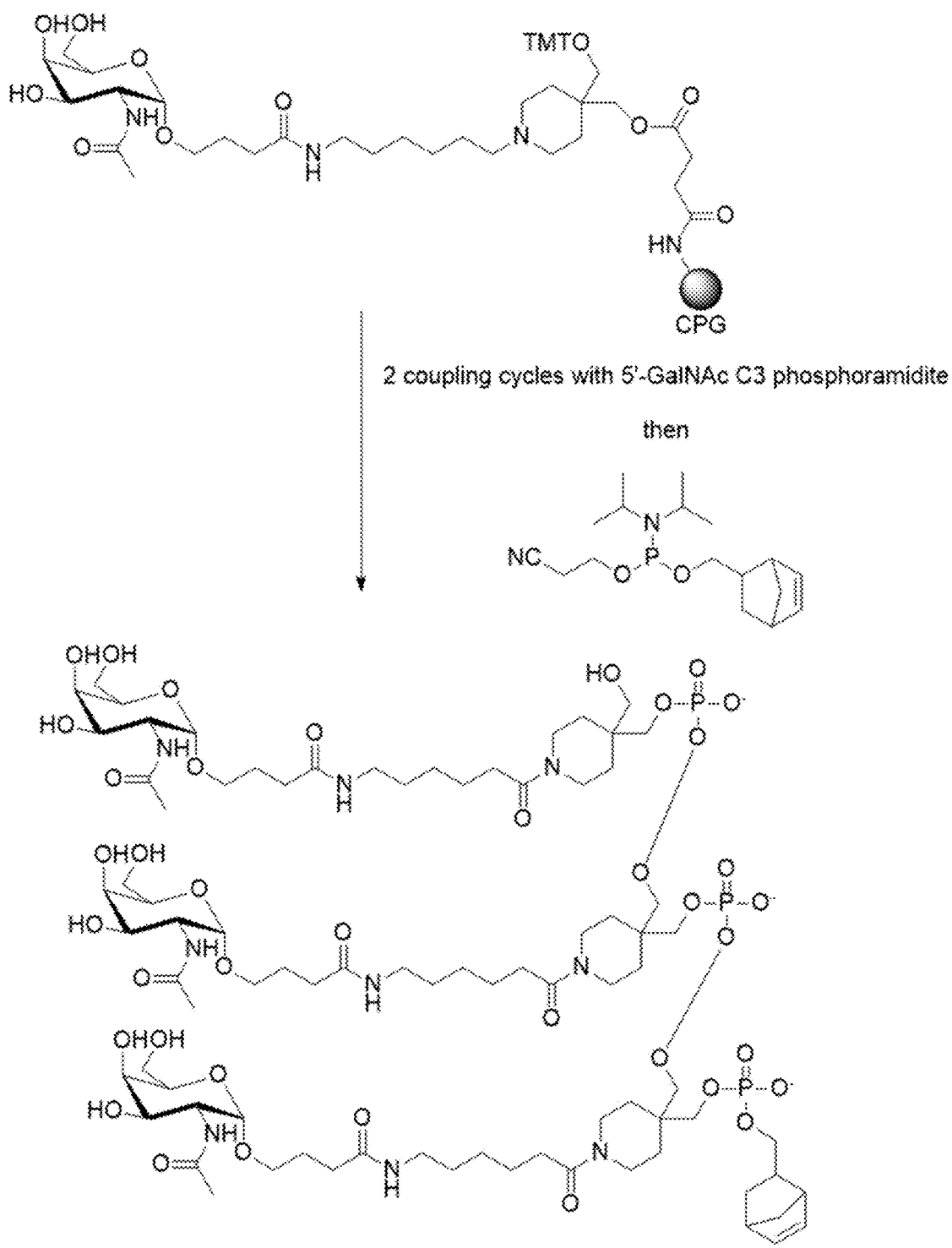
FIG. 52 is a schematic of synthesis of a 5' GalNAc modifier for post-synthetic IEDDA conjugation. GalNAc C3 CPG (Glen) to be chain extended with GalNAc C3 5' phosphoramidite (Glen) and the 5' norbornene phosphoramidite, followed by standard RNA deprotection conditions (AMA/HF).

FIG. 52 is a schematic of synthesis of a 5' GalNAc modifier for post-synthetic IEDDA conjugation. GalNAc C3 CPG (Glen) to be chain extended with GalNAc C3 5' phosphoramidite (Glen) and the 5' norbornene phosphoramidite, followed by standard RNA deprotection conditions (AMA/HF).

A post-synthetic approach could also be taken. Trivalent GalNAc could be synthesized cheaply and readily via solid-phase synthesis, followed by direct extension with bicyclo [2.2.1]hept-5-en-2-ylmethyl (2-cyanoethyl) diisopropylphosphoramidite.

Example 17—Combinatorial Cargo—Dual Conjugation to Cholesterol and GalNAc

Most strategies to improve the efficacy of siRNA conjugates either focus on enhancing the potency of the conjugated ligand—for example by optimising ligand valency, spacing, charge, linker length and linker hydrophobicity—or aim to augment the chemical stability of the therapeutic siRNA. A different approach would be to combine multiple ligands and multiple siRNA molecules in a single conjugate.

Figure 53:
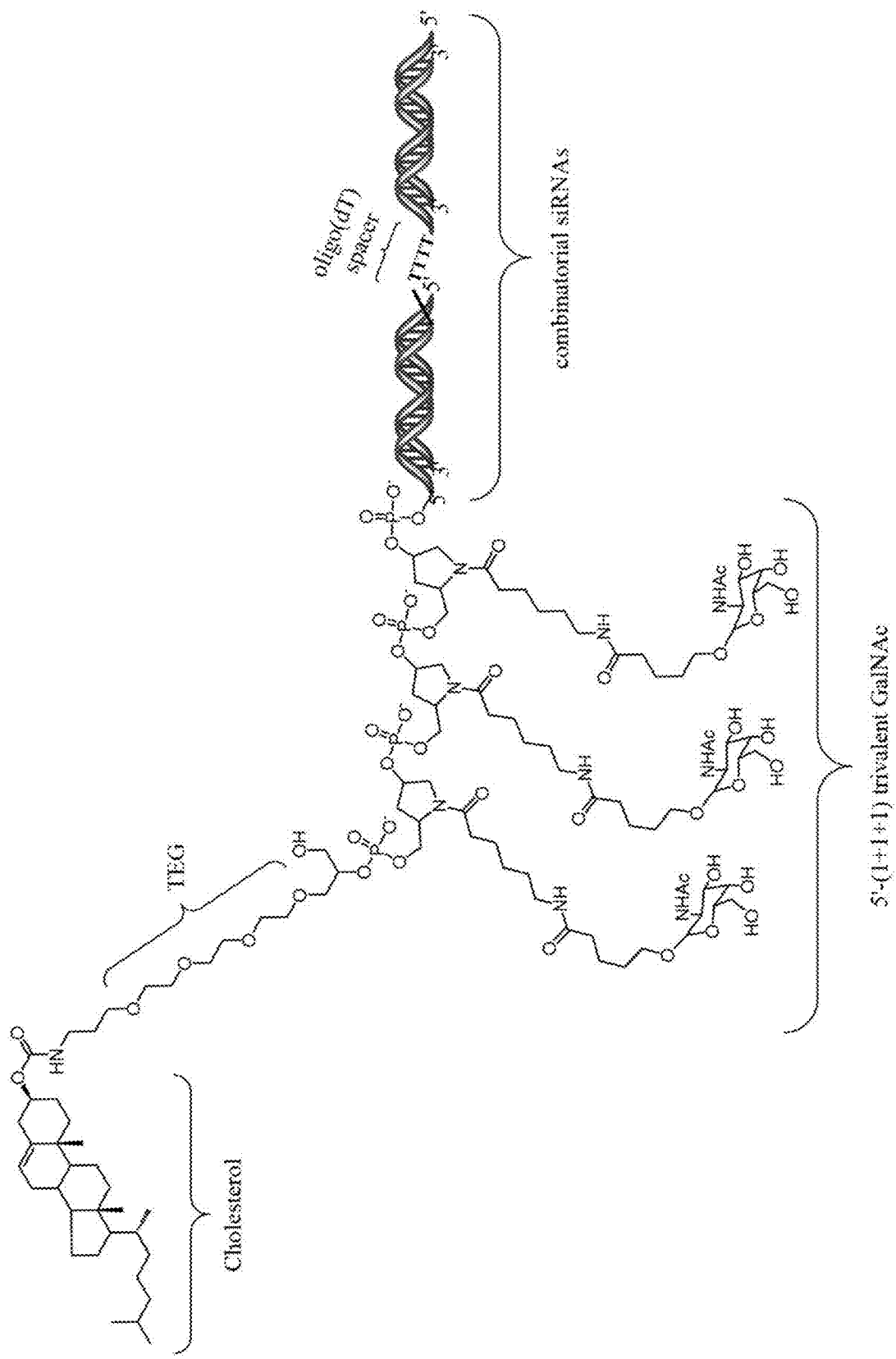
FIG. 53 is a schematic of combinatorial cargo (siRNA) double-conjugated to cholesterol and trivalent GalNAc via modified phosphoramidites.

FIG. 53 is a schematic of combinatorial cargo (siRNA) double-conjugated to cholesterol and trivalent GalNAc via modified phosphoramidites.

Such a strategy would increase the therapeutic payload, enable multi-gene silencing and at the same time allow to finetune the pharmacokinetic properties of the conjugate. The attachment of cholesterol and a tri- or tetravalent GalNAc moiety to a double siRNA during solid-phase synthesis of oligonucleotides could be used to target two mRNAs, whereby the delivery of the conjugate would be restricted to hepatocytes thanks to GalNAc and potential nephrotoxicity could be limited owing to cholesterol which reduces renal accumulation (F. Wada, T. Yamamoto, T. Ueda, M. Sawamura, S. Wada, M. Harada-Shiba, S. Obika, Cholesterol—GalNAc Dual Conjugation Strategy for Reducing Renal Distribution of Antisense Oligonucleotides, Nucleic Acid Ther. 28 (2018) 50-57. https://doi.org/10.1089/nat.2017.0698). The cholesterol and GalNAc ligands would be incorporated via standard solid phase synthesis from phosphoramidites with a single GalNAc moiety as described previously (K. G. Rajeev, J. K. Nair, M. Jayaraman, K. Charisse, N. Taneja, J. O'Shea, J. L. S. Willoughby, K. Yucius, T. Nguyen, S. Shulga-Morskaya, S. Milstein, A. Liebow, W. Querbes, A. Borodovsky, K. Fitzgerald, M. A. Maier, M. Manoharan, Hepatocyte-Specific Delivery of siRNAs Conjugated to Novel Non-nucleosidic Trivalent N-Acetylgalactosamine Elicits Robust Gene Silencing in Vivo, ChemBioChem. 16 (2015) 903-908. https://doi.org/https://doi.org/10.1002/cbic.201500023) and a 5'-Cholesterol-TEG-CE phosphoramidite. The double-ligand double-siRNA could further be attached to a RNA nanoparticle scaffold strand in a post-synthetic click reaction, for example via IEDDA-mediated conjugation to strand C-4.4.

Example 18—Assessment of Aptamer Binding

Attachment of Aptamers by Hybridization

The 5 square scaffold RNA strands designed to assemble into (i) Cy3-labelled S-AO construct with no aptamer (also named SQ1-0000-001, comprised of strands C-1.0, C-2.0, C-3.0, C-4.0, C-5.1), (ii) S-A1 construct with one aptamer (also named SQ1-1000-001, comprised of strands C-1.3, C-2.0, C-3.0, C-4.0, C-5.1), (iii) S-A2 construct with two aptamers (also named SQ-2000-001, comprised of strands C-1.3, C-2.0, C-3.2, C-4.0, C-5.1), and (iv) S-A4 construct with four aptamers (also named S-4000-001, comprised of strands C-1.3, C-2.3, C-3.2, C-4.5, C-5.1) were combined in equimolar amounts in PBS supplemented with 2 mM MgCl2, at a final concentration of 10 µM. The 5 strands were heated to 95° C. for 5 min and slowly cooled down to room temperature. The aptamer (A-1.1) was heated to 75° C. for 3 minutes and was then mixed into the core strand assembly with 0, equimolar, twice molar or quadruple molar equivalents, respectively. Next, the mixture was incubated at 55° C. for 10 minutes to hybridize the aptamer strands to the construct. The quality of the nanoparticle was assessed by native PAGE.

Aptamer Binding Assay

A431 epidermoid carcinoma cells, a cell line that expresses high levels of epidermal growth factor receptor (EGFR), were plated at a concentration of $0.75 \times 10^5$ cells in a 24-well plate 48 hours before treatment with aptamer constructs. The media was refreshed once after 24 hours. On day 2 after plating, the cells were washed with 1 mL of DPBS and were treated with 200 µL of 200 nM of constructs (S-A0/SQ1-0000-001, S-A1/SQ-1000-001, SQ-A2/S-2000-001, SQ-A4/S-4000-001) in DMEM supplemented with 10% FBS. The cells were incubated at 37° C. for 2 hours. Media was then aspirated and the cells were trypsinized with 200 μL of 0.25% (w/v) Trypsin at 37° C. for 5 mins. After neutralisation with complete growth medium, the cells were aliquoted into Eppendorf tubes and centrifuged at 300×g for 4 mins at 4° C. The media was aspirated, the cells were resuspended in 1 mL of MACS buffer and were then transferred through a meshed FACS tube. This washing procedure was repeated 2 times. The cells were finally resuspended in 200 μL of MACS buffer and were kept on ice prior to flow cytometric analysis.

Flow Cytometry

Aptamer binding to cells was studied on a BD LSR-Fortessa™ Flow Cytometer with FACS Diva software. About 5 minutes prior to flow cytometric measurements, the cells were stained with 2 μl of 1:10 diluted DAPI solution to allow for discrimination between live and dead cells. DAPI signal was detected with a 405 nm laser and a 450/50 nm filter, and Cy3 fluorescence was collected with a 561 nm laser and 586/15 nm filter. Gating, data analysis and plotting were performed with FlowJo™ software v.10.7.1 for macOS. The histogram enumerating the amount of Cy3+ cells and the geometric mean of fluorescence intensity were extracted and statistical analysis was performed using Tukey one-way analysis of variance in GraphPad Prism.

Figure 46:
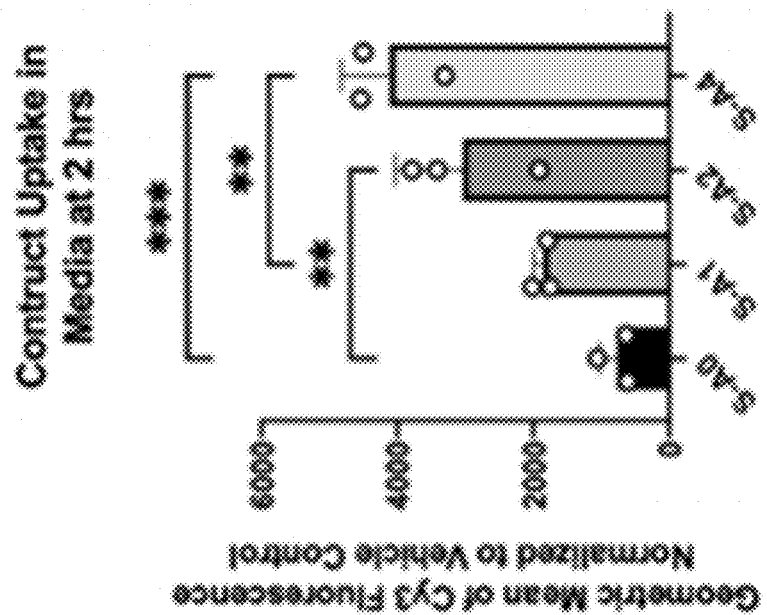
FIG. 46 shows graphs showing binding of Cy3-labelled constructs bearing 0, 1, 2 or 4 EGFR-targeting aptamers (A-1.1) to EGFR-overexpressing A431 cancer cells after incubation for 2 hours in cell culture media with 10% heat-inactivated FBS at a concentration of 200 nM.
Figure 46:
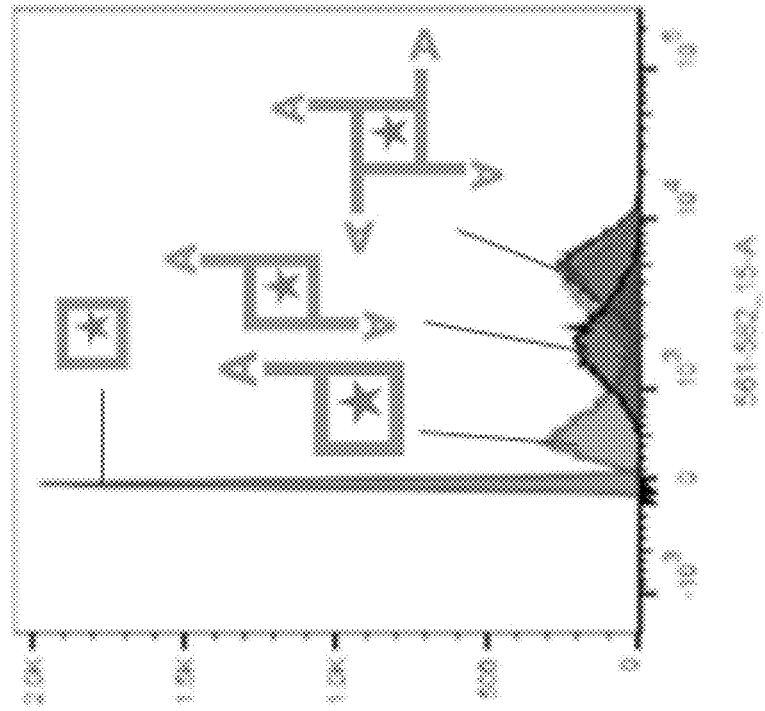

FIG. 46 shows graphs showing binding of Cy3-labelled constructs bearing 0, 1, 2 or 4 EGFR-targeting aptamers (A-1.1) to EGFR-overexpressing A431 cancer cells after incubation for 2 hours in cell culture media with 10% heat-inactivated FBS at a concentration of 200 nM. A, aptamer A-1.1; (*), Cy3 label; (), p≤0.01; (*), p≤0.001; (****), p≤0.0001; not significant if not denoted.

Example 19—Assessment of RNA Nanoparticle Uptake

Cells were imaged by confocal microscopy after treatment with 200 nM Cy5-labelled E07 min A-1.0 aptamer (A-1.0) or 200 nM Cy5-labelled constructs (SQ1-1000-001). For aptamer uptake experiments, 1×10$^4$ cells were plated in each well of a μ-Slide 8 well ibiditreat chamber (IBIDI), in 300 μL DMEM containing 10% v/v FBS. For uptake experiments, 3.4×10$^3$ cells (HeLa, MDA-MB-231 and A549 cells) or 6.8×10$^3$ cells (Mcf-7) were plated in each well of a μ-Slide 18 well ibiditreat chamber (IBIDI), in 100 μL DMEM containing 10% v/v FBS. 5 hours after cells had adhered and 48 hours before imaging, media was replaced with 50 particles per cell (PPC) CellLight early endosome-GFP (Thermo Fisher Scientific) for overnight incubation at 37° C. Additionally, 200 μL DMEM aliquots containing 200 nM aptamer were added to cells at corresponding incubation time points. Subsequently, media was removed and replaced with 60 nM LysoTracker Red DND-99 (Thermo Fisher Scientific) in 100-200 μL DMEM for 1 hour at 37° C. Cells were then washed once with Hank's Balanced Salt Solution (HBSS) (Gibco). Finally, 100-200 μL imaging media (HBSS buffered with 20 mM 4-(2-hydroxyethyl)-1-piperazineethanesulfonic acid (HEPES), adjusted to pH 7.4) was added to cells. Confocal images were captured with an EVOS microscope or a Zeiss LSM510 laser scanning microscope using 60× oil objective lens. Images were produced using ImageJ software.

Figure 47:
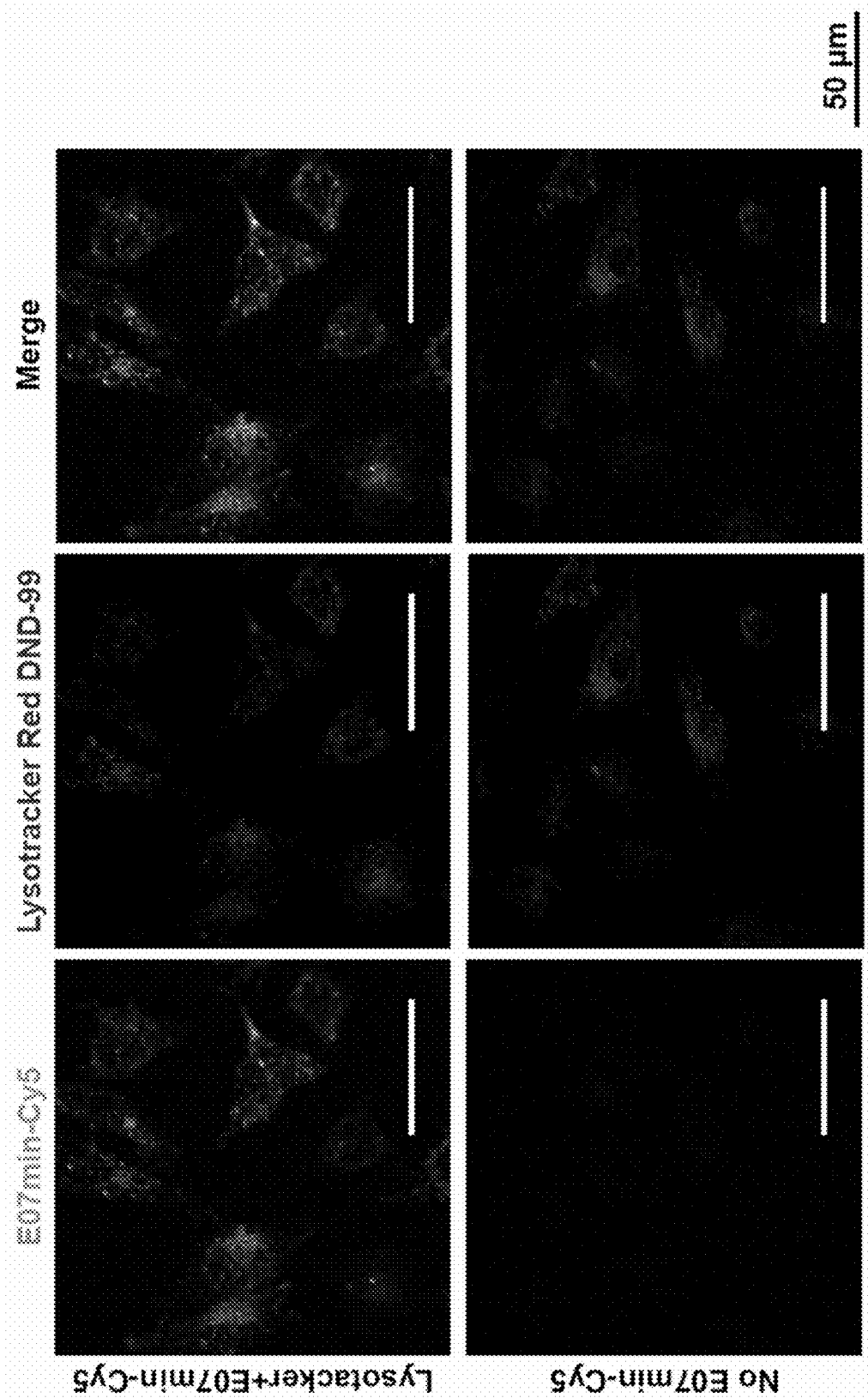
FIG. 47 shows microscopic images showing that aptamers accumulate in lysosomes after internalisation.

FIG. 47 shows microscopic images showing that aptamers accumulate in lysosomes after internalisation. Representative confocal fluorescent microscopy images of live HeLa cells after treatment with E07 min aptamer (A-1.0) for increasing lengths of time, at ×60 magnification. Lysotracker and early endosome GFP stains were used to identify each compartment. Scale bar, 50 μm.

Confocal data demonstrated that Cy5-labelled constructs with E0O7 min aptamer (SQ1-1000-001) were specifically uptaken by cancer cells expressing EGFR (FIG. 47).

For further uptake experiments, MDA-MB-231 cells were counted and seeded at a cell density of 3.4×10$^3$ cells/well in an 18-well IBIDI chamber. After 24 hours, the cells were washed and treated with 200 nM Cy5-labelled constructs (SQ1-1000-001) bearing a single EGFR-targeting E07 min aptamer in Opti-MEM™ for 4, 8 and 24 hours. Nuclear double-stranded DNA was stained with Hoechst 33342 prior to imaging. Fluorescence microscopy images were captured with an Olympus IX81 microscope using the 60× oil objective lens (NA 1.35). Images were analyzed using ImageJ software.

Figure 48:
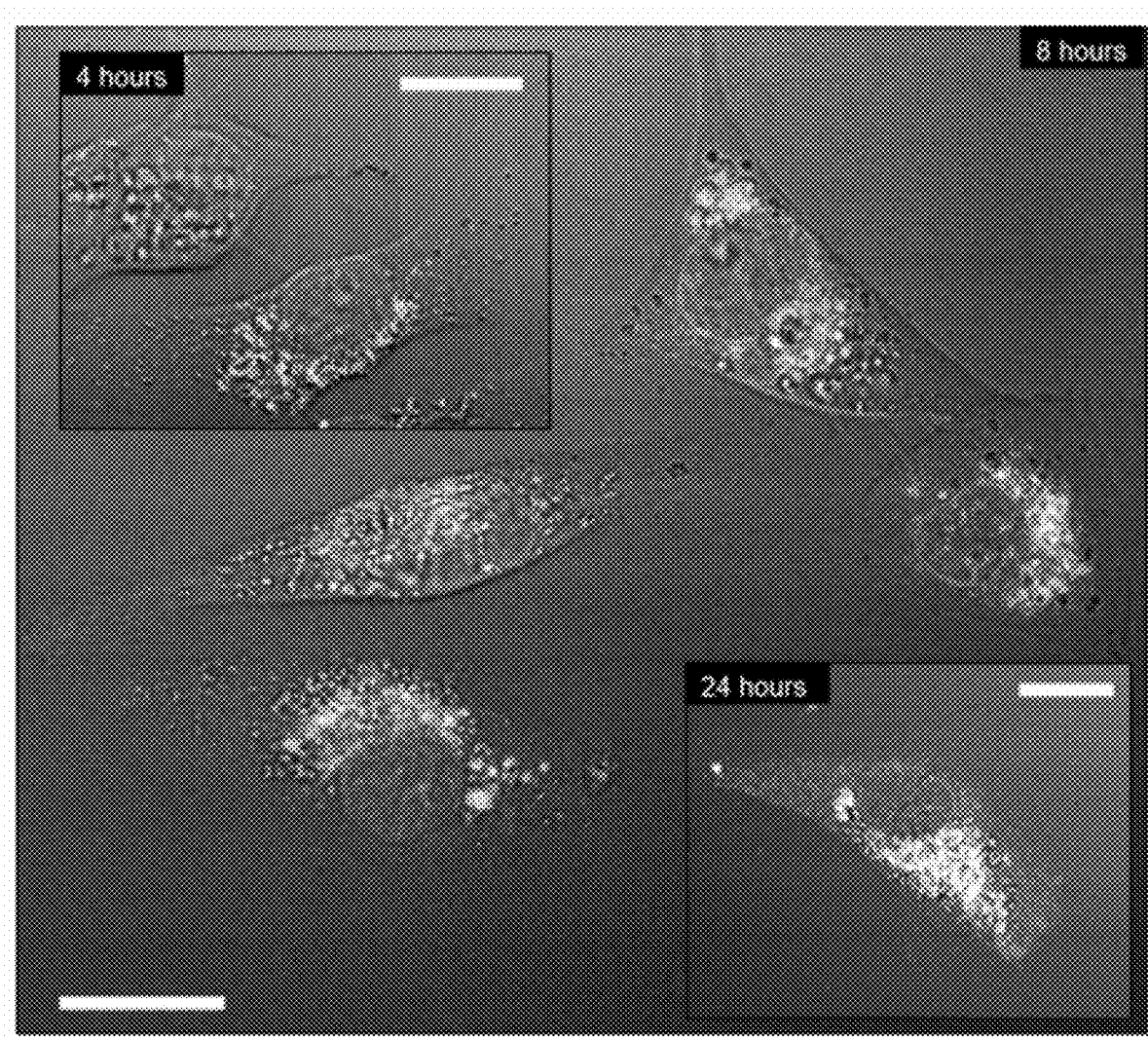
FIG. 48 shows microscopic images showing that RNA nanoparticles accumulate in the perinuclear space after internalisation in cells, suggesting endosomal uptake.

FIG. 48 shows microscopic images showing that RNA nanoparticles accumulate in the perinuclear space after internalisation in cells, suggesting endosomal uptake. Representative fluorescence microscopy images of live MDA-MB-231 cells after treatment with 200 nM Cy3-labelled constructs bearing a single aptamer (S-A1/S-1000-001) for 4 h, 8 h and 24 h, at ×60 magnification. Nuclei were stained with Hoechst 33342 and constructs were labelled with Cy5 (appearing as bright white spots). Scale bar, 20 μm.

The microscopy data shown in FIG. 48 demonstrate that Cy5-labelled constructs with E0O7 min aptamer (SQ1-1000-001) are uptaken by cancer cells and concentrate in the perinuclear area. The skilled artisan will recognise that the perinuclear space is a region known to be enriched in endosomal vesicles and lysosomes, and that methods such as colocalization assays can be used to demonstrate uptake into endosomes and lysosomes.

What is claimed is:

1. A composition comprising:
   a self-assembled RNA nanoparticle, said nanoparticle comprising:
   at least four oligonucleotide strands of 3 to 200 nucleotides in length, wherein at least one of the oligonucleotides strands is functionalized with one or more reactive sites that allow for conjugation allowing for the formation of a covalent bond via reactions selected from the group consisting of CuAAC, SPAAC, RuAAC, IEDDA, SuFEx, SPANC, hydrazone/oxime ether formation, thiol-ene radical reaction, thiol-yne radical reaction, thiol-Michael addition reaction, thiol-isocyanate reaction, thiol-epoxide click reaction, nucleophilic ring opening reactions (spring-loaded reactions), and traceless Staudinger ligation;
   a four-sided polygonal tertiary structure of four or more junctions, each of said junctions formed by at least two of the oligonucleotide strands;

wherein one or more cargo molecules are conjugated to the self-assembled RNA nanoparticle at the one or more reactive sites.

2. The composition of claim 1, wherein each oligonucleotide strand partially interacts with at least one other oligonucleotide strand through hydrogen bonding, base-stacking interactions, or both.

3. The composition of claim 2, wherein at least one of the oligonucleotide strands comprises at least one nucleotide modification selected from the group consisting of 2'-O-methyl, 2'-fluoro, 2'-F-arabinonucleic acid, 2'-O-methoxyethyl, locked nucleic acid, unlocked nucleic acid, 4'-thioribonucleoside, 4'-C-aminomethyl-2'-O-methyl, cyclohexenyl nucleic acid, hexitol nucleic acid, glycol nucleic acid, phosphorothioate, boranophosphate, 5'-C-methyl, 5'(E)-vinylphosphonate, and 2' thiouridine.

4. The composition of claim 1, wherein the RNA nanoparticle promotes a biological activity of the cargo molecule in a subject.

5. The composition of claim 1, wherein the RNA nanoparticle performs at least one biological activity selected from the group:
  (i) binding to a serum protein in blood, or to a receptor in a cell or at the cell surface;
  (ii) promoting endosomal escape of the cargo molecule in a receptor-independent manner;
  (iii) targeting a tissue in an animal or subject;
  (iv) modulating biodistribution;
  (v) inducing or preventing an immunological response;
  (vi) enhancing cellular uptake;
  (vii) modulating gene expression;
  (viii) inducing cytotoxicity; and
  (ix) having a therapeutic effect;
or combinations thereof.

6. The composition of claim 1, wherein the one or more cargo molecules comprise at least one of mRNA, gRNA/CRISPR, siRNA, shRNA, ASO, saRNA, miRNA, lnRNA, ribozyme, aptamer, peptide, protein, protein domain, antibody, antibody fragment, antibody mimetic, lectin, vitamin, lipid, carbohydrate, benzamides and therapeutic small molecules, or combinations thereof.

7. The composition of claim 1, wherein the functionalization promotes internalization into the cell, wherein the internalization mechanism comprises at least one of clathrin-mediated endocytosis, non-clathrin/non-caveolae endocytosis, caveolae-mediated endocytosis, passive diffusion, simple diffusion, facilitated diffusion, transcytosis, macropinocytosis, phagocytosis, receptor mediated endocytosis, receptor diffusion, vesicle-mediated transport, and active transport.

8. The composition of claim 1, wherein the attachment of the RNA nanoparticle to at least one cargo molecule is obtainable by a method comprising at least one reaction that comprises at least one of the following features:
  (i) the reaction occurs in one pot;
  (ii) the reaction is not disturbed by water;
  (iii) the reaction generates minimal byproducts; and
  (iv) the reaction comprises a high thermodynamic driving force that affords a single reaction product.

9. The composition of claim 8, wherein the attachment reaction comprises:
  (i) attaching a first cargo molecule via a first reaction comprising at least one of the features of claim 8; and
  (ii) attaching a second cargo molecule via a second reaction comprising at least one of the features of claim 8;

wherein the first reaction and the second reaction are orthogonal.

10. The composition of claim 9, wherein at least one of the oligonucleotide strands is functionalized at an internal position.

11. The composition of claim 9, wherein the RNA nanoparticle is attached to:
  a first cargo molecule; and
  a second cargo molecule linked to the first cargo molecule; and
  optionally, further cargo molecules linked to the second or first cargo molecule.

12. The composition of claim 11, wherein the first cargo molecule is selected from the group consisting of at least one of mRNA, gRNA/CRISPR, siRNA, shRNA, ASO, saRNA, miRNA, lnRNA, ribozyme, aptamer, peptide, protein, protein domain, antibody, antibody fragment, antibody mimetic, lectin, vitamin, lipid, carbohydrate, benzamides and therapeutic small molecules, or combinations thereof.

13. The composition of claim 11, wherein the first cargo molecule is linked to the second cargo molecule by a cleavable linker.

14. The composition of claim 13, wherein at least one of the first and second cargo molecules is linked to a third cargo molecule by either a thiol-cleavable linker comprising dithiobismaleimidoethane and 1,4-bis[3-(2-pyridyldithio)propionamido]butane, a hydroxylamine-cleavable linker comprising ethylene glycol bis(succinimidyl) succinate, a base-cleavable linker comprising bis[2-(N-succinimidyl-oxycarbonyloxy)ethyl] sulfone or a Meldrum's acid derivative comprising 5-(bis(methylthio)methylene)-2,2-dimethyl-1,3-dioxane-4,6-dione.

15. The composition of claim 11, wherein at least one of the first and second cargo molecules is linked to a third cargo molecule by a dicer substrate or extended nucleic acid spacer region that is amenable to cleavage, including, but not limited to, the sequences (T)k, (A)l, (G)m, (C)n, and combinations thereof, where k, l, m and n are positive integers.

16. The composition of claim 11, wherein at least one of the first and second cargo molecules is linked to a third cargo molecule with a linker selected from the group consisting of 1,8-bismaleimido-diethyleneglycol, 1,11-bismaleimido-triethyleneglycol, 1,4-bismaleimidobutane, bismaleimidohexane, bismaleimidoethane, tris(2-maleimidoethyl)amine), N-α-maleimidoacet-oxysuccinimide ester, N-β-maleimidopropyl-oxysuccinimide ester, N-ε-maleimidocaproic acid, N-γ-maleimidobutyryl-oxysuccinimide ester, succinimidyl 4-(N-maleimidomethyl)cyclohexane-1-carboxy-(6-amidocaproate), succinimidyl 6-(3(2-pyridyldithio)propionamido)hexanoate, m-maleimidobenzoyl-N-hydroxysuccinimide ester, succinimidyl iodoacetate, succinimidyl (4-iodoacetyl) aminobenzoate, PEGylated, long-chain SMCC crosslinkers, succinimidyl 4-(p-maleimidophenyl)butyrate and sulfo-NHS equivalents), and p-maleimidophenyl isocyanate.

17. The composition of claim 11, wherein the second cargo molecule is linked to any given number of cargo molecules in a polymeric fashion.

18. The composition of claim 11, wherein the first cargo molecule is linked to the RNA nanoparticle via reactions selected from the group consisting of CuAAC, SPAAC, RuAAC, IEDDA, SuFEx, SPANC, hydrazone/oxime ether formation, thiol-ene radical reaction, thiol-yne radical reaction, thiol-Michael addition reaction, thiol-isocyanate reaction, thiol-epoxide click reaction, nucleophilic ring opening reactions (spring-loaded reactions), traceless Staudinger ligation.

19. The composition of claim 12, wherein each of at least two cargo molecules has a biological function.

20. The composition of claim 10, wherein at least one of the oligonucleotide strands is conjugated to one or more cargo molecules at the one or more reactive sites, wherein the oligonucleotide strand or cargo molecule are conjugated via a reaction with a modified nucleotide of the oligonucleotide strand or cargo molecule, said modified nucleotide modified with a chemical moiety from the group consisting of ADIBO-PEG4, N-[(1R,8S,9s)-bicyclo[6.1.0]non-4-yn-9-ylmethyloxycarbonyl]-1,8-diamino-3,6-dioxaoctane, (1R,8S,9s)-bicyclo[6.1.0]non-4-yn-9-ylmethanol, bromoacetamido-dPEG 4-amido-DBCO, bromoacetamido-dPEG 12-amido-DBCO, bromoacetamido-dPEG 24-amido-DBCO, dibenzocyclooctyne-acid, dibenzocyclooctyne-N-hydroxysuccinimidyl ester, dibenzocyclooctyne-PEG4-acid, dibenzocyclooctyne-PEG4-alcohol, dibenzocyclooctyne-PEG4-N-hydroxysuccinimidyl ester, (4-(1,2,4,5-tetrazin-3-yl)phenyl)methanamine hydrochloride, (E)-cyclooct-4-enol, (E)-cyclooct-4-enyl 2,5-dioxo-1-pyrrolidinyl carbonate, 2,5-Dioxo-1-pyrrolidinyl 5-[4-(1,2,4,5-tetrazin-3-yl)benzylamino]-5-oxopentanoate, 5-[4-(1,2,4,5-tetrazin-3-yl)benzylamino]-5-oxopentanoic acid, 5-norbornene-2-acetic acid succinimidyl ester, 5-norbornene-2-endo-acetic acid, methyltetrazine-NHS ester, methyltetrazine-PEG4-NHS ester, TCO PEG4 succinimidyl ester, TCO-amine, tetrazine-PEGS-NHS ester, alkyne-PEGS-acid, (R)-3-amino-5-hexynoic acid hydrochloride, (S)-3-amino-5-hexynoic acid hydrochloride, (S)-3-(boc-amino)-5-hexynoic acid, N-boc-4-pentyne-1-amine, boc-propargyl-Gly-OH, 3-ethynylaniline, 4-ethynylaniline, propargylamine hydrochloride, propargyl chloroformate, propargyl-N-hydroxysuccinimidyl ester, propargyl-PEG2-acid, 3-(4-azidophenyl)propionic acid, 3-azido-1-propanamine, 3-azido-1-propanol, 4-carboxybenzenesulfonazide, O-(2-aminoethyl)-O'-(2-azidoethyl)heptaethylene glycol, O-(2-aminoethyl)-O'-(2-azidoethyl)nonaethylene glycol, O-(2-aminoethyl)-O'-(2-azidoethyl)pentaethylene glycol, azido-dPEG 4(n)acid (where n is 4, 8, 12, or 24), azido-dPEG (n)-amine (where n is 7, 11, 23, or 35), azido-dPEG 4(n) NHS ester (where n could be 4, 8, 12, 24), azido-dPEG (n)-TFP ester (where n is 4, 8, 12, 24, or 36), 2-[2-(2-azidoethoxy)ethoxy] ethanol, O-(2-azidoethyl)-O-[2-(diglycolyl-amino)ethyl]heptaethylene glycol, O-(2-azidoethyl)heptaethylene glycol, O-(2-azidoethyl)-O'-methyl-triethylene glycol, O-(2-azidoethyl)-O'-methyl-undecaethylene glycol, 17-azido-3,6,9,12,15-pentaoxaheptadecan-1-amine, 14-azido-3,6,9,12-tetraoxatetradecanoic acid, 11-azido-3,6,9-trioxaundecan-1-amine, bromoacetamido-dPEG (n)azide (where n is 3, 11, or 23) and combinations thereof.

* * * * *